US008962660B2

(12) United States Patent
Zhang et al.

(10) Patent No.: US 8,962,660 B2
(45) Date of Patent: Feb. 24, 2015

(54) OXABICYCLO [2.2.2] ACID GPR120 MODULATORS

(71) Applicant: Bristol-Myers Squibb Company, Princeton, NJ (US)

(72) Inventors: Hao Zhang, Belle Mead, NJ (US); Peter T. W. Cheng, Princeton, NJ (US); Sean Chen, Princeton, NJ (US); Shiwei Tao, Hillsborough, NJ (US); Shung C. Wu, Princeton, NJ (US); Lidet A Negash, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/205,421

(22) Filed: Mar. 12, 2014

(65) Prior Publication Data
US 2014/0275173 A1 Sep. 18, 2014

Related U.S. Application Data

(60) Provisional application No. 61/782,339, filed on Mar. 14, 2013.

(51) Int. Cl.
*A61K 45/06* (2006.01)
*A61K 31/4433* (2006.01)
*A61K 31/427* (2006.01)
*A61K 31/4245* (2006.01)
*A61K 31/4196* (2006.01)
*C07D 493/08* (2006.01)
*A61K 31/35* (2006.01)

(52) U.S. Cl.
CPC .............. *C07D 493/08* (2013.01); *A61K 31/35* (2013.01); *A61K 31/4196* (2013.01); *A61K 31/4245* (2013.01); *A61K 31/427* (2013.01); *A61K 31/4433* (2013.01); *A61K 45/06* (2013.01)
USPC ........................................ 514/337; 546/268.1

(58) Field of Classification Search
USPC ........................................ 514/337; 546/268.1
See application file for complete search history.

(56) References Cited

U.S. PATENT DOCUMENTS

| 7,834,013 | B2 | 11/2010 | Corbett et al. | |
|---|---|---|---|---|
| 8,153,694 | B2 | 4/2012 | Yasuma et al. | |
| 8,288,404 | B2 | 10/2012 | Ellsworth et al. | |
| 2013/0289058 | A1* | 10/2013 | Patel et al. | 514/275 |

FOREIGN PATENT DOCUMENTS

| WO | WO2009/081195 A1 | 7/2009 |
|---|---|---|
| WO | WO2013/160873 A1 | 10/2013 |
| WO | WO2014/022253 A1 | 2/2014 |
| WO | WO2014/078609 A1 | 5/2014 |
| WO | WO2014/078611 A1 | 5/2014 |

OTHER PUBLICATIONS

Arbeeny, C. et al., "The Metabolic Syndrome: From Pathophysiology to Novel Treatment Strategies", Curr. Med. Chem.—Imm.Endoc. & Metab. Agents, vol. 1, pp. 1-24 (2001).
Ford. E. et al., "Prevalence of the Metabolic Syndrome Among US Adults", JAMA, vol. 287(3), pp. 356-359 (2002).
Ichimura, A. et al., "Dysfunction of lipid sensor GPR120 leads to obesity in both mouse and human", Nature, vol. 483, pp. 350-354 (2012).
Im, Dong-Soon, "Omega-3 fatty acids in anti-inflammation (pro-resolution) and GPCRs", Progress in Lipid Research, vol. 51, pp. 232-237 (2012).
Miyauchi, S. et al., "Distribution and regulation of protein expression of the free fatty acid receptor GPR120", Naunyn-Schmied Arch Pharmacol, vol. 379, pp. 427-434 (2009).
Oh, D.Y. et al., "GPR120 is an Omega-3 Fatty Acid Receptor Mediating Potent Anti-inflammatory and Insulin-Sensitizing Effects", Cell, vol. 142, pp. 687-698 (2010).

* cited by examiner

*Primary Examiner* — Niloofar Rahmani
(74) *Attorney, Agent, or Firm* — Elliott Korsen

(57) ABSTRACT

The present invention provides compounds of Formula (I):

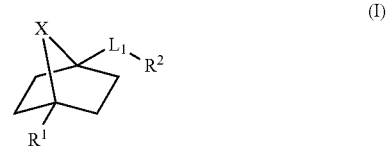

or a stereoisomer, or a pharmaceutically acceptable salt thereof, wherein all of the variables are as defined herein. These compounds are GPR120 G protein-coupled receptor modulators which may be used as medicaments.

12 Claims, No Drawings

OXABICYCLO [2.2.2] ACID GPR120 MODULATORS

CROSS-REFERENCE TO RELATED APPLICATIONS

This application claims priority to U.S. Provisional Application Ser. No. 61/782,339, filed Mar. 14, 2013; the entire content of which is incorporated herein by reference.

FIELD OF THE INVENTION

The present invention provides novel oxabicyclo [2.2.2] compounds, and their analogues thereof, which are GPR120 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Polyunsaturated fatty acids (PUFAs) such as omega-3 fatty acids are known to improve sensitivity to insulin. Insulin sensitivity can be improved by exerting anti-inflammatory effects in monocytes and/or macrophages and/or by enhancing glucose uptake in adipose and muscle. GPR120 is a membrane-bound receptor responsive to PUFAs which is preferentially expressed in adipose tissue and monocytes/macrophages. To decrease the medical burden of type 2 diabetes through enhanced glycemic control, GPR120 modulator compounds hold the promise of exerting a sensitizing effect to insulin as well as potential combination with a broad range of antidiabetic drugs.

The present invention relates to novel substituted bicyclic acid compounds which have the ability to modulate GPR120. Such compounds are therefore potentially useful for the treatment of diabetes and related conditions.

SUMMARY OF THE INVENTION

The present invention provides substituted oxabicyclo [2.2.2] compounds, and their analogues thereof, which are useful as GPR120 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment of multiple diseases or disorders associated with GPR120, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR120.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. COMPOUNDS OF THE INVENTION

In a first aspect, the present disclosure provides, inter alia, a compound of Formula (I):

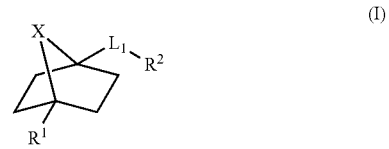

(I)

or a stereoisomer, a tautomer, a pharmaceutically acceptable salt, or a solvate thereof, wherein:

X is independently $CH_2O$ or $OCH_2$;

$L_1$ is independently a hydrocarbon linker substituted with 0-2 $R^c$, a hydrocarbon-heteroatom linker substituted with 0-2 $R^c$, or —$(O)_{0-1}$—$(CH_2)_{1-3}$—$(C_{3-4}$ cycloalkyl substituted with 0-2 $R^c$)—$(CH_2)_{0-2}$—; wherein said hydrocarbon linker has one to six carbon atoms and may be straight or branched, saturated or unsaturated; and said hydrocarbon-heteroatom linker has one to four carbon atoms and one group selected from O, CO, $S(O)_p$, NH, $N(C_{1-4}$ alkyl), CONH, NHCO and $NHCO_2$;

$R^1$ is independently selected from: $C_{6-10}$ carbocycle and a 5- to 10-membered heterocycle comprising carbon atoms and 1-4 heteroatoms selected from N, $NR^b$, O, and $S(O)_p$; wherein said carbocycle and heterocycle are substituted with 0-4 $R^3$ and 0-1 $R^4$;

$R^2$ independently selected from: OH, $CO_2H$, —CONH$(C_{1-4}$ alkyl), —CONHOH, —CONHSO$_2R^e$, and —CONH—$(CH_2)_{0-3}$-(5-membered heteroaryl comprising carbon atoms and 1-4 heteroatoms selected from N, $NR^b$, O, and $S(O)_p$);

$R^3$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-6}$ haloalkoxy, $C_{1-4}$ haloalkylthio, and $NO_2$;

$R^4$ is independently -$L_2$-$R^5$;

$L_2$ is independently selected from: a bond, O, S, $CH_2$, C(=O), and —$OSO_2$;

$R^5$ is independently selected from: $C_{1-6}$ alkyl, $C_{2-6}$ alkenyl, $C_{1-6}$ haloalkyl, —$(CH_2)_n$—$C_{3-6}$ carbocycle and a 5- to 6-membered heterocycle comprising carbon atoms and 1-4 heteroatoms selected from N, $NR^b$, O, and $S(O)_p$; wherein each ring moiety is substituted with 0-4 $R^a$;

$R^a$, at each occurrence, is independently selected from: OH, CN, halogen, $C_{1-4}$ alkyl substituted with 0-1 OH, $C_{1-4}$ alkoxy, and $C_{1-4}$ haloalkyl;

$R^b$, at each occurrence, is independently selected from: H, $C_{1-4}$ alkyl, and —$(CH_2)_{0-2}$-(phenyl substituted with 0-3 $R^d$);

$R^c$, at each occurrence, is independently selected from: halogen, OH, $C_{1-4}$ alkyl, $C_{1-4}$ haloalkyl, and $C_{1-4}$ alkoxy;

$R^d$, at each occurrence, is independently selected from: halogen, $C_{1-4}$ alkyl, $C_{1-4}$ alkoxy, and $C_{1-4}$ haloalkyl;

$R^e$ is independently selected from: $C_{1-4}$ alkyl and phenyl;

p is, independently at each occurrence, selected from 0, 1, and 2; and n is, independently at each occurrence, selected from 0, 1, and 2.

In a second aspect, the present disclosure includes a compound of Formula (I) or a stereoisomer, a tautomer, a pharmaceutically acceptable salt, or a solvate thereof, within the scope of the first aspect, wherein:

$L_1$ is independently a hydrocarbon linker substituted with 0-1 $R^c$, a hydrocarbon-heteroatom linker substituted with 0-1 $R^c$, or —$(O)_{0-1}$—$(CH_2)_{1-3}$—$(C_{3-4}$ cycloalkyl substituted with 0-1 $R^c$)—$(CH_2)_{0-1}$—; wherein said hydrocarbon linker has one to six carbon atoms and may be straight or branched, saturated or unsaturated; and said hydrocarbon-heteroatom linker has one to four carbon atoms and one group selected from O, CO, $S(O)_p$, CONH, and $NHCO_2$;

$R^1$ is independently selected from: phenyl, indanyl, naphthyl, and a 5- to 6-membered heterocycle comprising carbon atoms and 1-4 heteroatoms selected from N, $NR^b$, O, and $S(O)_p$; wherein each ring moiety substituted with 0-4 $R^3$ and 0-1 $R^4$;

$L_2$ is independently selected from: a bond, O, S, $CH_2$, and —$OSO_2$; and $R^5$ is independently selected from: $C_{1-6}$ alkyl, $C_{2-6}$ alkenyl, $C_{1-4}$ haloalkyl, tetrahydropyranyl, —$(CH_2)_n$—$(C_{3-6}$ carbocycle substituted with 0-2 $R^a$), and pyridyl substituted with 0-1 $R^a$.

In a third aspect, the present disclosure includes a compound of Formula (II):

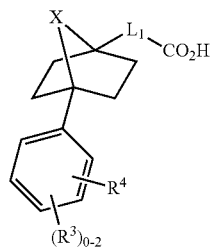

(II)

or a stereoisomer, a tautomer, a pharmaceutically acceptable salt, or a solvate thereof, within the scope of the first or second aspect, wherein:

X is independently $CH_2O$ or $OCH_2$;

$L_1$ is independently a hydrocarbon linker substituted with 0-1 OH, a hydrocarbon-heteroatom linker or —$(O)_{0-1}$—$(CH_2)_{1-3}$-(cyclopropyl)-$(CH_2)_{0-1}$—; wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and one group selected from O, CONH and $NHCO_2$;

$R^3$, at each occurrence, is independently selected from: halogen, $CF_3$, $OCF_3$, $SCF_3$, $NO_2$, $C_{1-4}$ alkyl, $C_{1-4}$ alkoxy, and $C_{1-4}$ alkylthio;

$R^4$ is independently -$L_2$-$R^5$;

$L_2$ is independently a bond, O or S;

$R^5$ is independently selected from: —$(CH_2)_{0-1}$—$C_{4-6}$ cycloalkyl, $C_{5-6}$ cycloalkenyl, tetrahydropyranyl, pyridyl substituted with 0-2 $R^a$, and —$(CH_2)_n$-(phenyl substituted with 0-2 $R^a$); and $R^a$, at each occurrence, is independently selected from: OH, CN, halogen, $C_{1-4}$ alkyl substituted with 0-1 OH, and $C_{1-4}$ alkoxy.

In a fourth aspect, the present disclosure includes a compound of Formula (I) or (II), or a stereoisomer, a tautomer, a pharmaceutically acceptable salt, or a solvate thereof, within the scope of any of the above aspects, wherein:

$L_1$ is independently selected from: $(CH_2)_{3-4}$, $CH_2CH_2OCH_2$, $CH_2OCH_2CH_2$, $CH_2CH_2CH_2OCH_2$, $CH_2CH_2CH=CH$, $CH_2CH=CHCH_2$, $CH_2CONHCH_2$, $CH_2NHCO_2CH_2$,

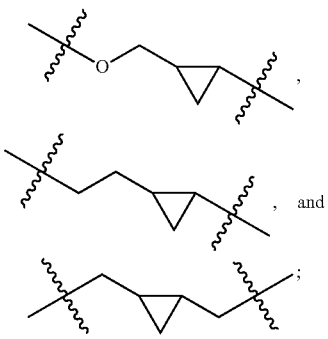

and $R^4$ is independently selected from: cyclopentenyl, —O—$CH_2$-cyclobutyl, —O—$(CH_2)_{0-1}$-cyclohexyl, —O-tetrahydropyranyl, —O-pyridyl, and -$L_3$-$(CH_2)_{0-4}$-(phenyl substituted with 0-2 $R^a$).

In a fifth aspect, the present disclosure includes a compound of Formula (III):

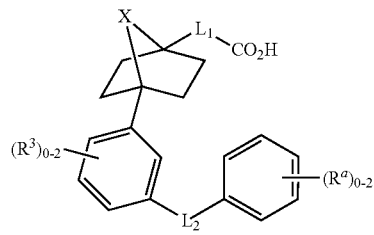

(III)

or a stereoisomer, a tautomer, a pharmaceutically acceptable salt, or a solvate thereof, within the scope of any of the above aspects, wherein:

X is independently $CH_2O$ or $OCH_2$;

$L_1$ is independently selected from: $(CH_2)_{3-4}$, $CH_2CH_2OCH_2$, $CH_2OCH_2CH_2$, $CH_2CH_2CH_2OCH_2$, $CH_2CH_2CH=CH$, $CH_2CH=CHCH_2$, $CH_2CONHCH_2$, $CH_2NHCO_2CH_2$,

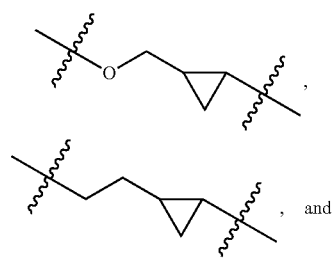

-continued

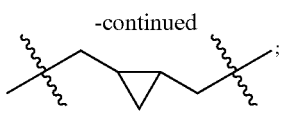

$L_2$ is independently O or S;

$R^3$, at each occurrence, is independently halogen or $C_{1-4}$ alkoxy; and $R^a$, at each occurrence, is independently selected from: CN, halogen, $C_{1-4}$ alkyl, and $C_{1-4}$ alkoxy.

In a sixth aspect, the present disclosure includes a compound of Formula (I), (II) or (III), or a stereoisomer, a tautomer, a pharmaceutically acceptable salt, or a solvate thereof, within the scope of any of the above aspects, wherein:

$L_1$ is independently selected from: $(CH_2)_4$, $CH_2CH_2OCH_2$, $CH_2OCH_2CH_2$, $CH_2CH_2CH_2OCH_2$, $CH_2CH_2CH=CH$, $CH_2CH=CHCH_2$,

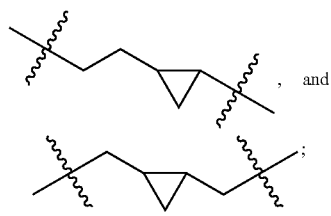

and $L_2$ is O.

In another aspect, the present disclosure provides, inter alia, a compound of Formula (I), or a stereoisomer, a tautomer, a pharmaceutically acceptable salt, or a solvate thereof, within the scope of the first aspect, wherein:

X is independently $CH_2O$ or $OCH_2$;

$L_1$ is independently a hydrocarbon linker substituted with 0-2 $R^c$, a hydrocarbon-heteroatom linker substituted with 0-2 $R^c$, or $-(CH_2)_{1-3}-(C_{3-4}$ cycloalkyl substituted with 0-2 $R^c)-(CH_2)_{0-2}-$; wherein said hydrocarbon linker has one to six carbon atoms and may be straight or branched, saturated or unsaturated; and said hydrocarbon-heteroatom linker has one to four carbon atoms and one group selected from O, CO, $S(O)_p$, NH, $N(C_{1-4}$ alkyl), CONH, NHCO and $NHCO_2$;

$R^1$ is independently selected from: $C_{6-10}$ carbocycle and a 5- to 10-membered heterocycle comprising carbon atoms and 1-4 heteroatoms selected from N, $NR^b$, O, and $S(O)_p$; wherein said carbocycle and heterocycle are substituted with 0-4 $R^3$ and 0-1 $R^4$;

$R^2$ independently selected from: OH, $CO_2H$, $-CONHSO_2R^e$, and $-CONH-(CH_2)_{0-3}-(5$-membered heteroaryl comprising carbon atoms and 1-4 heteroatoms selected from N, $NR^b$, O, and $S(O)_p$);

$R^3$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, and $NO_2$;

$R^4$ is independently $-L_2-R^5$;

$L_2$ is independently selected from: a bond, O, S, $CH_2$, $C(=O)$, and $-OSO_2$;

$R^5$ is independently selected from: $C_{1-6}$ alkyl, $C_{2-6}$ alkenyl, $C_{1-6}$ haloalkyl, $-(CH_2)_p-C_{3-6}$ carbocycle and a 5- to 6-membered heterocycle comprising carbon atoms and 1-4 heteroatoms selected from N, $NR^b$, O, and $S(O)_p$; wherein each ring moiety is substituted with 0-2 $R^a$;

$R^a$, at each occurrence, is independently selected from: halogen, $C_{1-4}$ alkyl, $C_{1-4}$ alkoxy, and $C_{1-4}$ haloalkyl;

$R^b$, at each occurrence, is independently selected from: H, $C_{1-4}$ alkyl, and $-(CH_2)_{0-2}$-(phenyl substituted with 0-3 $R^d$);

$R^c$, at each occurrence, is independently selected from: halogen, OH, $C_{1-4}$ alkyl, $C_{1-4}$ haloalkyl, and $C_{1-4}$ alkoxy;

$R^d$, at each occurrence, is independently selected from: halogen, $C_{1-4}$ alkyl, $C_{1-4}$ alkoxy, and $C_{1-4}$ haloalkyl;

$R^e$ is independently selected from: $C_{1-4}$ alkyl and phenyl;

p is, independently at each occurrence, selected from 0, 1, and 2; and n is, independently at each occurrence, selected from 0, 1, and 2.

In another aspect, the present disclosure includes a compound of Formula (I) or a stereoisomer, a tautomer, a pharmaceutically acceptable salt, or a solvate thereof, within the scope of the first aspect, wherein:

$L_1$ is independently a hydrocarbon linker substituted with 0-1 $R^c$, a hydrocarbon-heteroatom linker substituted with 0-1 $R^c$, or $-(CH_2)_{1-2}-(C_{3-4}$ cycloalkyl substituted with 0-1 $R^c)-(CH_2)_{0-1}-$; wherein said hydrocarbon linker has one to six carbon atoms and may be straight or branched, saturated or unsaturated; and said hydrocarbon-heteroatom linker has one to four carbon atoms and one group selected from O, CO, $S(O)_p$, CONH, and $NHCO_2$;

$R^1$ is independently selected from: phenyl, indanyl, naphthyl, and a 5- to 6-membered heterocycle comprising carbon atoms and 1-4 heteroatoms selected from N, $NR^b$, O, and $S(O)_p$; wherein each ring moiety substituted with 0-4 $R^3$ and 0-1 $R^4$;

$L_2$ is independently selected from: a bond, O, S, $CH_2$, and $-OSO_2$; and $R^5$ is independently selected from: $C_{1-6}$ alkyl, $C_{2-6}$ alkenyl, $C_{1-4}$ haloalkyl, tetrahydropyranyl, $-(CH_2)_n-(C_{3-6}$ carbocycle substituted with 0-2 $R^a$), and pyridyl substituted with 0-1 $R^a$.

In another aspect, the present disclosure includes a compound of Formula (II), or a stereoisomer, a tautomer, a pharmaceutically acceptable salt, or a solvate thereof, within the scope of the first or second aspect, wherein:

X is independently $CH_2O$ or $OCH_2$;

$L_1$ is independently a hydrocarbon linker substituted with 0-1 OH, a hydrocarbon-heteroatom linker or $-(CH_2)_{1-2}-$(cyclopropyl)-$(CH_2)_{0-1}-$; wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and one group selected from O, CONH and $NHCO_2$;

$R^3$, at each occurrence, is independently selected from: halogen, $CF_3$, $OCF_3$, $SCF_3$, $NO_2$, $C_{1-4}$ alkyl, $C_{1-4}$ alkoxy, and $C_{1-4}$ alkylthio;

$R^4$ is independently $-L_2-R^5$;

$L_2$ is independently a bond, O or S;

$R^5$ is independently selected from: $-(CH_2)_{0-1}-C_{4-6}$ cycloalkyl, $C_{5-6}$ cycloalkenyl, tetrahydropyranyl, pyridyl substituted with 0-2 $R^a$, and $-(CH_2)_n$-(phenyl substituted with 0-2 $R^a$); and $R^a$, at each occurrence, is independently selected from: halogen, $C_{1-4}$ alkyl and $C_{1-4}$ alkoxy.

In another aspect, the present disclosure includes a compound of Formula (I) or (II), or a stereoisomer, a tautomer, a pharmaceutically acceptable salt, or a solvate thereof, within the scope of any of the above aspects, wherein:

$L_1$ is independently selected from: $(CH_2)_4$, $CH_2CH_2OCH_2$, $CH_2OCH_2CH_2$, $CH_2CH_2CH_2OCH_2$, $CH_2CH_2CH=CH$, $CH_2CH=CHCH_2$, $CH_2CONHCH_2$, $CH_2NHCO_2CH_2$,

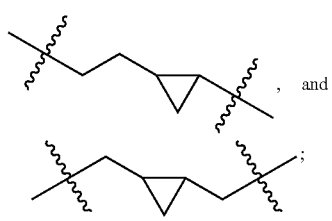

and $R^4$ is independently selected from: cyclopentenyl, —O—CH$_2$-cyclobutyl, —O—(CH$_2$)$_{0-1}$-cyclohexyl, —O-tetrahydropyranyl, —O-pyridyl, and -L$_3$-(CH$_2$)$_{0-1}$-(phenyl substituted with 0-2 R$^a$).

In another aspect, the present disclosure includes a compound of Formula (IIIa), or a stereoisomer, a tautomer, a pharmaceutically acceptable salt, or a solvate thereof, within the scope of any of the above aspects, wherein:

X is independently CH$_2$O or OCH$_2$;

L$_1$ is independently selected from: (CH$_2$)$_4$, CH$_2$CH$_2$OCH$_2$, CH$_2$OCH$_2$CH$_2$, CH$_2$CH$_2$CH$_2$OCH$_2$, CH$_2$CH$_2$CH=CH, CH$_2$CH=CHCH$_2$, CH$_2$CONHCH$_2$, CH$_2$NHCO$_2$CH$_2$,

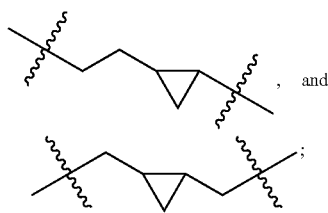

L$_2$ is independently O or S;

R$^3$ is independently halogen; and

R$^a$, at each occurrence, is independently selected from: halogen, C$_{1-4}$ alkyl and C$_{1-4}$ alkoxy.

In seventh aspect, the present disclosure provides a compound selected from the exemplified examples within the scope of the first aspect, or a stereoisomer, a tautomer, a pharmaceutically acceptable salt, or a solvate thereof.

In another aspect, the present invention provides a compound selected from any subset list of compounds within the scope of any of the above aspects.

In another aspect, within the scope of any of the above aspects, wherein: X is CH$_2$O.

In another aspect, within the scope of any of the above aspects, wherein: X is OCH$_2$.

In another aspect, within the scope of any of the above aspects, wherein: L$_2$ is O.

In another aspect, within the scope of any of the above aspects, wherein: L$_2$ is S.

In another embodiment, the compounds of the present invention have hGPR120 EC$_{50}$ values≤10 μM.

In another embodiment, the compounds of the present invention have hGPR120 EC$_{50}$ values≤5 μM.

In another embodiment, the compounds of the present invention have hGPR120 EC$_{50}$ values≤5 μM.

In another embodiment, the compounds of the present invention have hGPR120 EC$_{50}$ values≤1 μM.

In another embodiment, the compounds of the present invention have hGPR120 EC$_{50}$ values≤0.5 μM.

II. OTHER EMBODIMENTS OF THE INVENTION

In another embodiment, the present invention provides a composition comprising at least one of the compounds of the present invention or a stereoisomer, a tautomer, a pharmaceutically acceptable salt, or a solvate thereof In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin and alogliptin), a sodium-glucose transporter-2 (SGLT2) inhibitor (for example a member selected from dapagliflozin, canagliflozin, empagliflozin and remagliflozin), a GPR40/FFAR1 (Free fatty acid receptor 1) agonist (for example, TAK-875), and/or an MGAT2 (monoacylglycerol transferase 2) inhibitor (for example, compounds from WO 2012/124744, or compound (S)-10 from *Bioorg. Med. Chem. Lett.* (2013), doi: http://dx.doi.org/10.1016/j.bmcl.2013.02.084).

In a preferred embodiment, the present invention provides pharmaceutical composition, wherein the additional therapeutic agents are, for example, a dipeptidyl peptidase-IV inhibitor, a sodium-glucose transporter-2 inhibitor and a 11b-HSD-1 inhibitor.

In another embodiment, the present invention provides a method for the treatment of multiple diseases or disorders associated with GPR120, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR120 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis.

In another embodiment, the present invention provides a method for the treatment of diabetes, hyperglycemia, gestational diabetes, obesity, dyslipidemia and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR120.

In another embodiment, the present invention also provides the use of a compound of the present invention for the manufacture of a medicament for the treatment of multiple diseases or disorders associated with GPR120.

In another embodiment, the present invention provides a method for the treatment of multiple diseases or disorders associated with GPR120, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, linagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR120.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR120 receptor modulator of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, peliglitazar, tesaglitazar and aleglitazar), glucokinase activators (for example, PF-04937319 and AMG-151), GPR119 receptor modulators (for example, MBX-2952, PSN821, and APD597), sodium-glucose transporter-2 (SGLT2) inhibitors (for example, dapagliflozin, canagliflozin, empagliflozin and remagliflozin), GPR40 receptor agonists (e.g., TAK-875), amylin analogs such as pramlintide, and/or insulin.

The GPR120 receptor modulator of the present invention may also be optionally employed in combination with agents for treating complication of diabetes. These agents include PKC inhibitors and/or AGE inhibitors.

The GPR120 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 inhibitors and the like. The GPR120 receptor modulator of the present invention may also be employed in combination with an agonist of the glucagon-like peptide-1 receptor (GLP-1 R), such as exenatide, liraglutide, GLP-1(1-36) amide, GLP-1(7-36) amide, GLP-1(7-

37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. CHEMISTRY

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997) "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_P$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$) ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology, Vol.* 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984);

f) Rautio, J. et al., *Nature Rev. Drug Discovery*, 7:255-270 (2008); and g) Rautio, J., ed., *Prodrugs and Targeted Delivery (Methods and Principles in Medicinal Chemistry)*, Vol 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography and mass spectrometry, "HPLC" for high pressure liquid chromatography, "[M–H]" for parent mass minus a proton, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Hex Hexanes
MeOH Methanol
EtOH Ethanol
i-PrOH or IPA Isopropanol
AcOH or HOAc acetic acid
n-BuLi n-butyllithium
s-BuLi sec-butyllithium
t-BuLi tert-butyllithium
n-Bu$_4$NI tetra-n-butylammonium iodide
BH$_3$.THF borane-tetrahydrofuran complex
DIBALH or DIBAL-H diisobutylaluminum hydride
CDCl$_3$ deutero-chloroform
CHCl$_3$ Chloroform
(COCl)$_2$ oxalyl chloride
cDNA complimentary DNA
DMAP 4-dimethylaminopyridine
DMF N,N-dimethylformamide
DMSO dimethyl sulfoxide
DMSO-d$_6$ hexadeutero-dimethyl sulfoxide
EDC 1-ethyl-3-(3-dimethylaminopropyl)carbodiimide
EDTA ethylenediaminetetraacetic acid
EtOAc ethyl acetate
Et$_2$O diethyl ether
Boc tert-butyloxycarbonyl
CH$_2$Cl$_2$ or DCM Dichloromethane
CH$_3$CN or MeCN Acetonitrile
HCl hydrochloric acid
HOBT Hydroxybenzotriazole
H$_2$SO$_4$ sulfuric acid
K$_2$CO$_3$ potassium carbonate
KCN potassium cyanide
KOH potassium hydroxide
KO-t-Bu potassium tert-butoxide
LiOH lithium hydroxide
LiCl lithium chloride
LiAlH$_4$ or LAH lithium aluminum hydride
mCPBA or m-CPBA meta-chloroperbenzoic acid
MgSO$_4$ magnesium sulfate
Ms Methanesulfonate
MsCl methanesulfonyl chloride
MsOH or MSA methylsulfonic acid
NaCl sodium chloride
NaCN sodium cyanide
NaH sodium hydride
NaHCO$_3$ sodium bicarbonate
NaI sodium iodide
NaN$_3$ sodium azide
NaOH sodium hydroxide
NaOEt NaOEt=sodium ethoxide
Na$_2$SO$_3$ sodium sulfite
Na$_2$S$_2$O$_3$ sodium thiosulphate
Na$_2$SO$_4$ sodium sulfate
NH$_3$ ammonia
NH$_4$OAc ammonium acetate
NH$_4$Cl ammonium chloride
NH$_4$OH ammonium hydroxide
NiCl$_2$.6H$_2$O nickel (II) chloride hexahydrate
Pd/C palladium on carbon
i-Pr$_2$NEt diisopropylethylamine
Ph$_3$P triphenylphosphine
PPTS pyridinium 4-toluenesulfonate
SEMO trimethylsilylethoxymethoxy
SiO$_2$ silica oxide/silica gel
TEA or Et$_3$N triethylamine
Tf trifluoromethanesulfonate
TFA trifluoroacetic acid
THF tetrahydrofuran
TMSCHN$_2$ (diazomethyl)trimethylsilane
p-TsOH p-toluenesulfonic acid
TsCl 4-toluenesulfonyl chloride
Ts 4-toluenesulfonate
Triton B benzyltrimethylammonium hydroxide
LG leaving group
PG protecting group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure.* 6th Edition, Wiley & Sons, New York, N.Y. (2007); Katritzky, A. R. et al., eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Scheme 1 describes synthesis of 3-(1-aryl/heteroaryl)-2-oxabicyclo[2.2.2] octan-2-yl)propanoic acid analogs 5. An appropriately substituted aryl or heteroaryl bromide is metalated with an appropriate lithium reagent (e.g., n-butyllithium) and reacted with cyclohexanone bis-tosylate 2 (following a literature synthesis in 6 steps from diethyl malonate and ethyl acrylate, e.g., as described in WO 2001/034610 A1) to give the intermediate cyclohexyl alcohol 3, which is treated with base (e.g., aq. NaOH) and undergoes intramolecular alkylation with one of the two equivalent tosylate groups to give the oxabicyclo[2.2.2]tosylate 3. The intermediate tosylate 3 is then reacted with a malonate ester under standard basic conditions to give the alkylated malonate ester 4. Hydrolysis of both ester groups gives the intermediate diacid, which upon heating, undergoes spontaneous decarboxylation to provide carboxylic acid analogs 5.

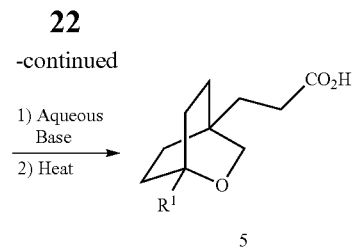

Scheme 2 shows the synthesis of 5-(1-aryl/heteroaryl)-2-oxabicyclo[2.2.2]octan-4-yl)pentanoic acid analogs 7. 3-(1-Aryl/heteroaryl)-2-oxabicyclo[2.2.2]octan-2-yl)propanoic acid analogs 5 is homologated using a standard 3-step Arndt-Eistert homologation sequence (acid chloride formation with e.g., oxalyl chloride, reaction of the acid chloride with TMSCHN$_2$ to provide the α-diazoketone, and subsequent silver-mediated Wolff rearrangement to give the homologated acid, as in Aoyama, T. et al., *Tetrahedron Lett.*, 21:4461 (1980)) to furnish the homologated acid 6. The 4-(1-Aryl/heteroaryl)-2-oxabicyclo[2.2.2]octan-3-yl)butanoic acid intermediates 6 then undergoes another Arndt-Eistert homologation sequence to provide the corresponding 5-(1-aryl/heteroaryl)-2-oxabicyclo[2.2.2]octan-4-yl)pentanoic acid analogs 7.

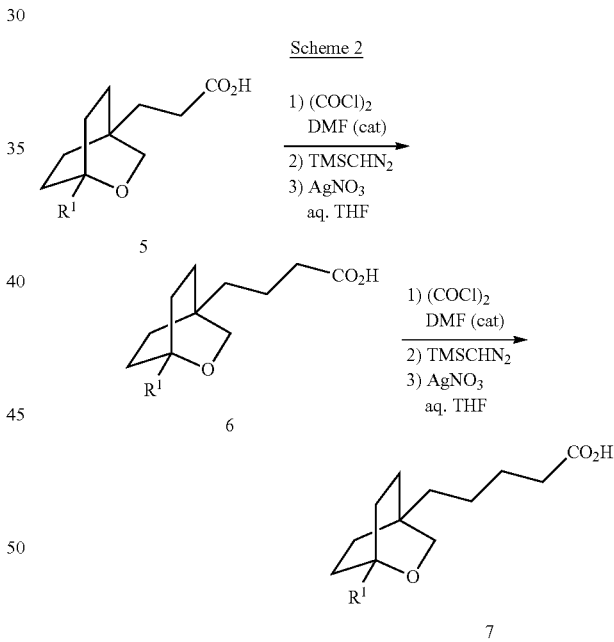

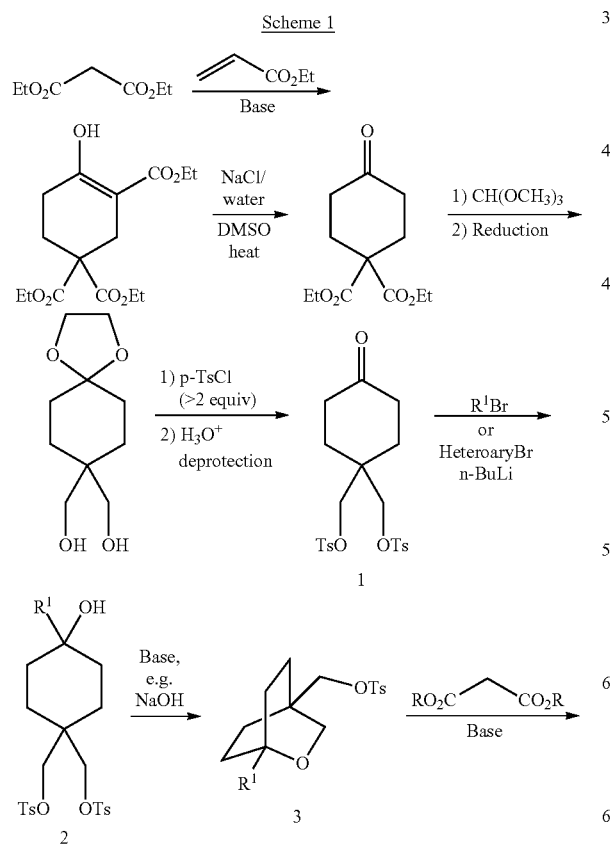

Scheme 3 shows the synthesis of 3-oxy-substituted 5-(1-aryl/heteroaryl)-2-oxabicyclo[2.2.2]octan-4-yl)pentanoic acid analogs 9. The oxabicyclic tosylate 3 is first converted to the corresponding acetate (e.g., NaOAc in DMSO with heating), which is then hydrolyzed under standard basic conditions to give the alcohol 8. Alcohol 8 then undergoes a conjugate 1,4-addition with an appropriate acrylate ester followed by deprotection of the ester to provide the desired 3-oxy-substituted acid analogs 9.

Scheme 3

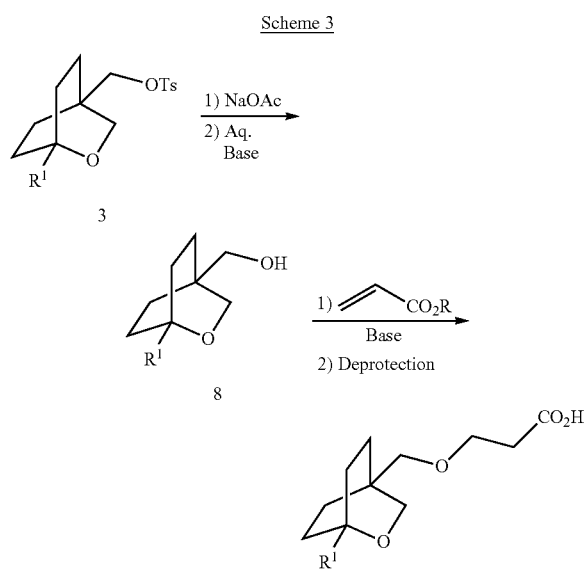

Scheme 4 shows the synthesis of 2-oxy-substituted 5-(1-aryl/heteroaryl)-2-oxabicyclo[2.2.2]octan-4-yl)pentanoic acid analogs 13. Tosylate 3 is converted to the corresponding nitrile 10 (e.g., NaCN/heat), which is then subjected to reduction conditions (e.g., DIBAL-H) which converts it to the corresponding aldehyde 11, which is further reduced to the alcohol 12. Alcohol 12 is alkylated under basic conditions with an α-bromoacetate ester, followed by appropriate deprotection conditions to provide the desired 2-oxy-substituted carboxylic acid analogs 13.

Scheme 4

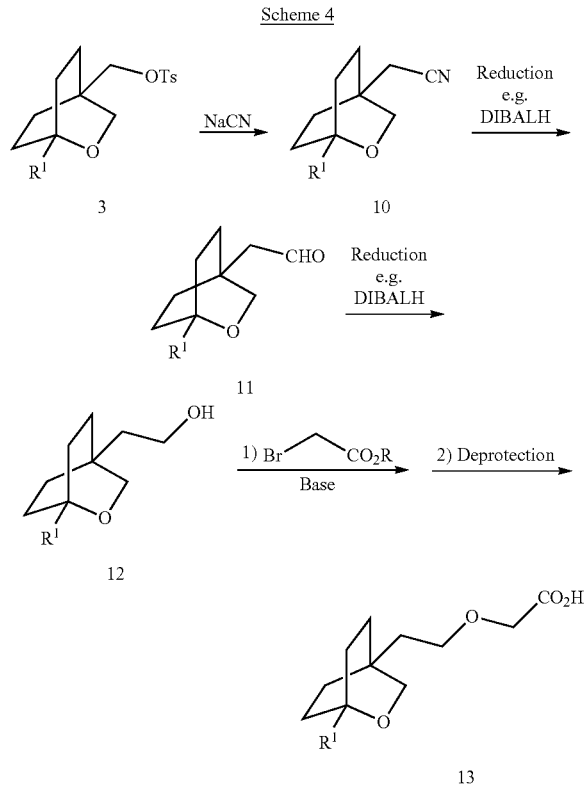

Scheme 5 shows the synthesis of more highly substituted aryl analogs 19. A suitably protected hydroxy aryl bromide (e.g., as an acid-labile tetrahydropyranyl ether that can be deprotected selectively in the presence of an ester) is lithiated (e.g., n-BuLi) and reacted with cyclohexanone bis-tosylate 1 to give the corresponding cyclohexanol bis-tosylate 14. Base-mediated intramolecular reaction of the alcohol with a tosylate of 26 provides the oxabicyclo[2.2.2]tosylate 15 (same 2 steps as in Scheme 1). The tosylate 15 is then converted in the same 3 step sequence as described in Scheme 4 to give the 2-oxy-substituted ester 16. Selective deprotection of the phenol is then achieved under mild acid conditions to give phenol ester 17. The phenol intermediate 17 is then subjected to an O-arylation reaction (e.g., Chan-Lam coupling reaction with aryl boronic acids; examples in Qiao, J. et al., *Synthesis*, 829 (2011)) to give the aryl ethers 18, followed by ester deprotection to give the corresponding 2-oxy-substituted carboxylic acid analogs 19.

Scheme 5

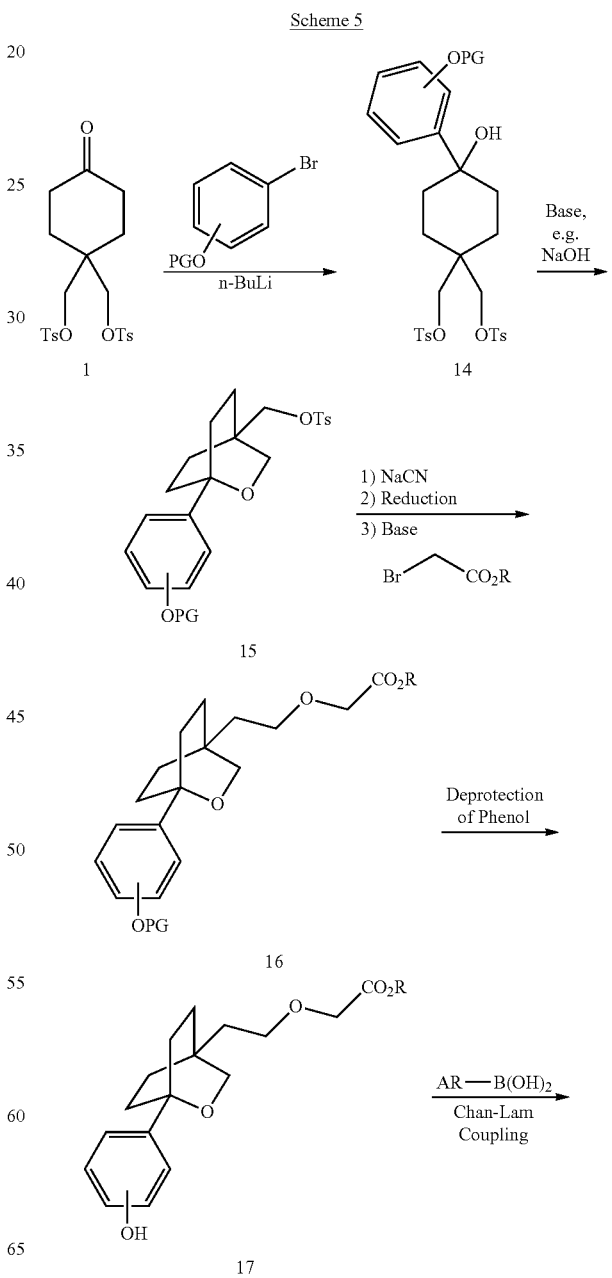

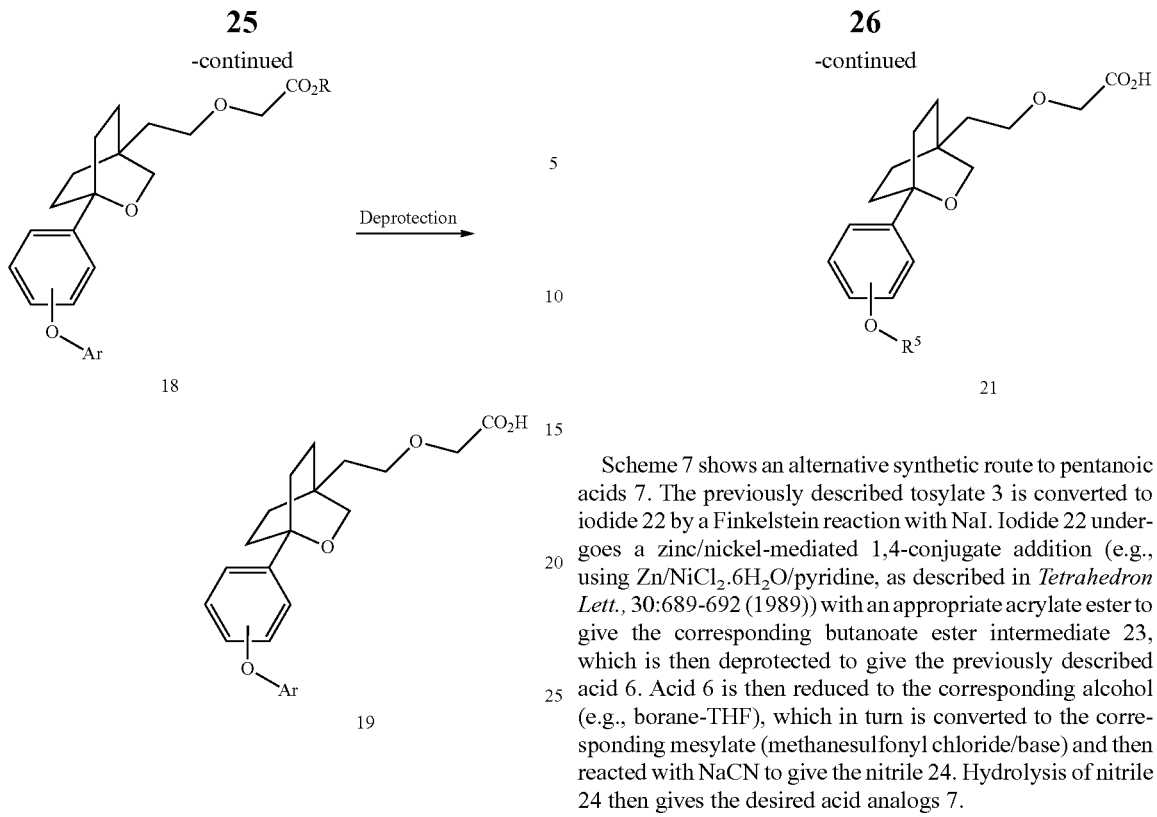

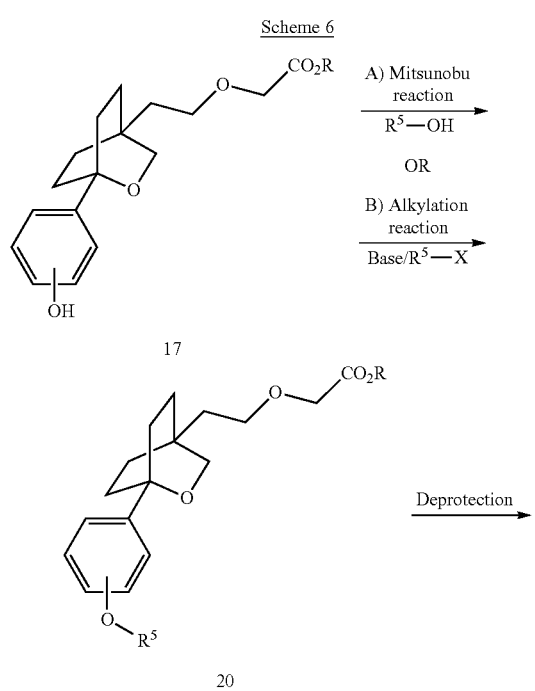

Alternatively, as shown in Scheme 6, the phenol intermediate 17 also undergoes reactions with alcohols R⁵—OH (e.g., Mitsunobu reaction), or reactions with alkyl halides R⁵—X under standard basic conditions, to give the corresponding alkyl ether intermediates 20 which are deprotected to give the desired corresponding 2-oxy-substituted carboxylic acid analogs 21.

Scheme 7 shows an alternative synthetic route to pentanoic acids 7. The previously described tosylate 3 is converted to iodide 22 by a Finkelstein reaction with NaI. Iodide 22 undergoes a zinc/nickel-mediated 1,4-conjugate addition (e.g., using Zn/NiCl₂.6H₂O/pyridine, as described in *Tetrahedron Lett.*, 30:689-692 (1989)) with an appropriate acrylate ester to give the corresponding butanoate ester intermediate 23, which is then deprotected to give the previously described acid 6. Acid 6 is then reduced to the corresponding alcohol (e.g., borane-THF), which in turn is converted to the corresponding mesylate (methanesulfonyl chloride/base) and then reacted with NaCN to give the nitrile 24. Hydrolysis of nitrile 24 then gives the desired acid analogs 7.

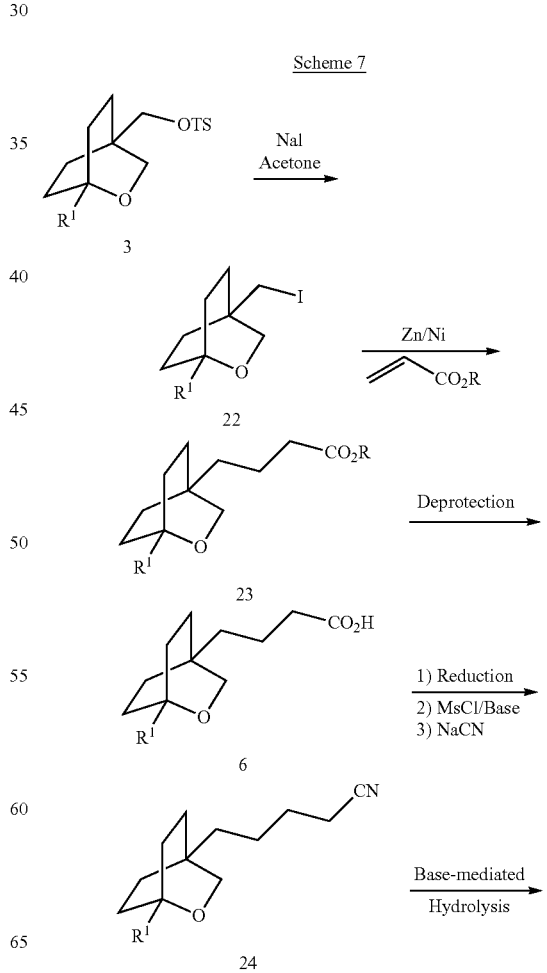

27

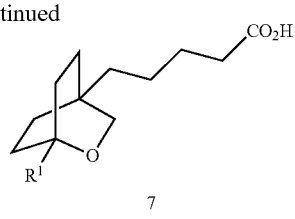

28

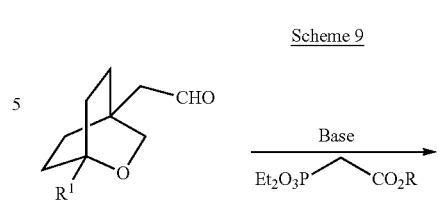

Scheme 9

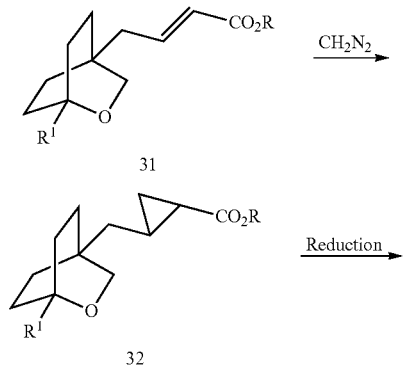

Scheme 8 shows the synthesis of the α,β-unsaturated carboxylic acid analogs 28 and the α,β-cyclopropyl carboxylic acid analogs 30. Alcohol 12 is converted to the corresponding nitrile 25 by a standard 2 step sequence as described for Scheme 7 (conversion to mesylate, followed by NaCN displacement of the mesylate). Nitrile 25 is reduced (e.g., DIBAL-H) to the corresponding aldehyde 26, which then undergoes a Horner-Emmons reaction with an appropriate phosphonate-ester to give the α,β-unsaturated ester 27. Deprotection of ester 27 provides the desired α,β-unsaturated carboxylic acid analogs 28. Alternatively, the α,β-unsaturated ester 27 is reacted with diazomethane (e.g., procedure of Mende, U. et al., *Tetrahedron Lett.*, 629 (1975)) to give the α,β-cyclopropyl ester 29, which is then deprotected to give the corresponding α,β-cyclopropyl acid analogs 30.

Scheme 8

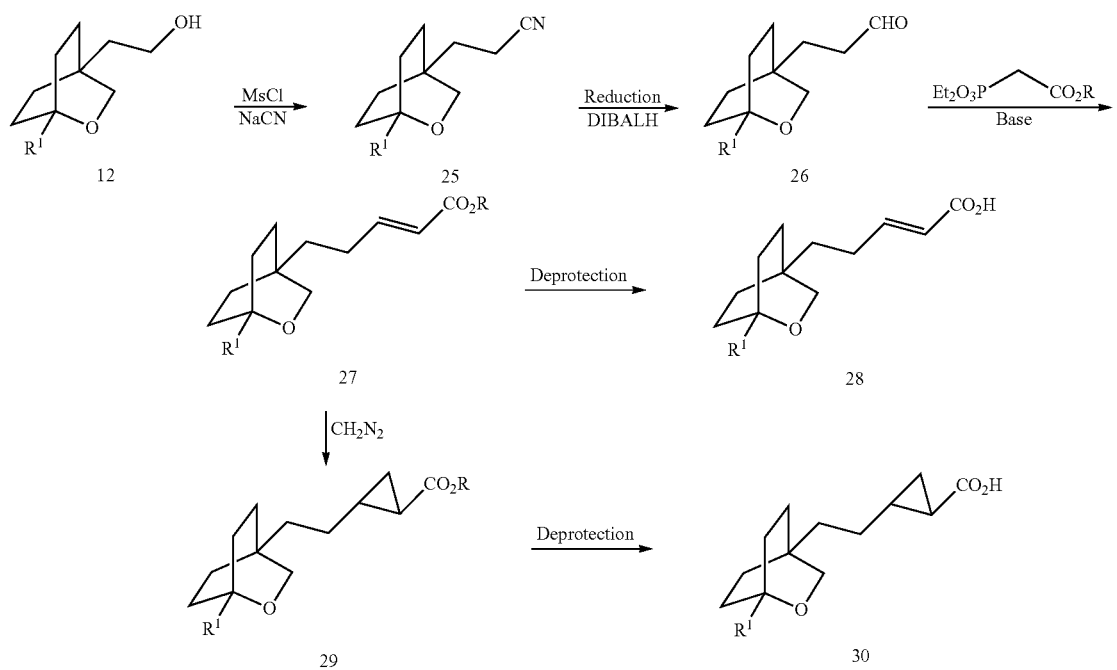

Scheme 9 shows the synthesis of β,γ-cyclopropyl carboxylic acid analogs 36. Aldehyde 26 is subjected to a Horner-Emmons reaction with an appropriate phosphonate ester to provide the α,β-unsaturated ester 31. Cyclopropanation of α,β-unsaturated ester 31 with diazomethane (e.g., procedure of Mende, U. et al., *Tetrahedron Lett.*, 629 (1975)) furnishes the α,β-cyclopropyl ester 32. Reduction of the α,β-cyclopropyl ester 21 (e.g., LiAlH$_4$) provides the cyclopropyl alcohol 33, which is converted to the corresponding nitrile 34 (via the mesylate and subsequent reaction with NaCN); base-mediated hydrolysis of 34 then provides the desired β,γ-cyclopropyl carboxylic acid analogs 35.

-continued

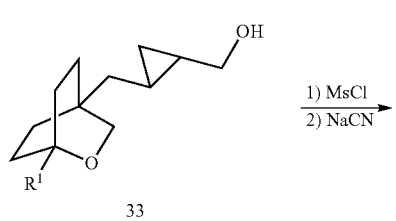

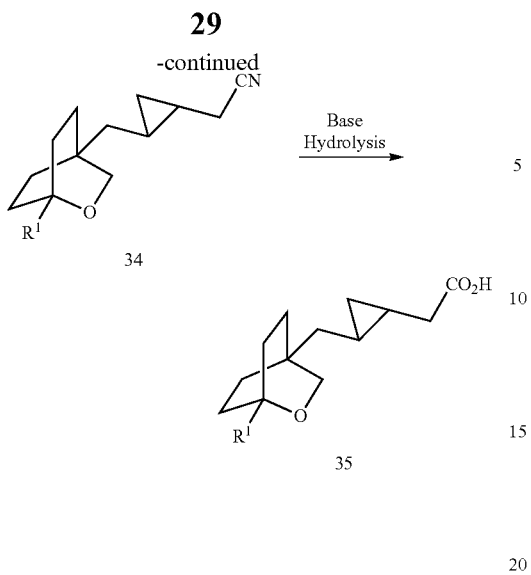

Scheme 10 shows a general scheme for the synthesis of acylsulfonamide analogs 36 from the corresponding carboxylic acid analogs, in this particular case 7. This is achieved through an EDCI-mediated coupling reaction. It is understood that, in addition to acids 7, this acylsulfonamide synthesis is also applicable to any of the other previously described carboxylic acid analogs, e.g., 13, 19, 21, 30 and 35.

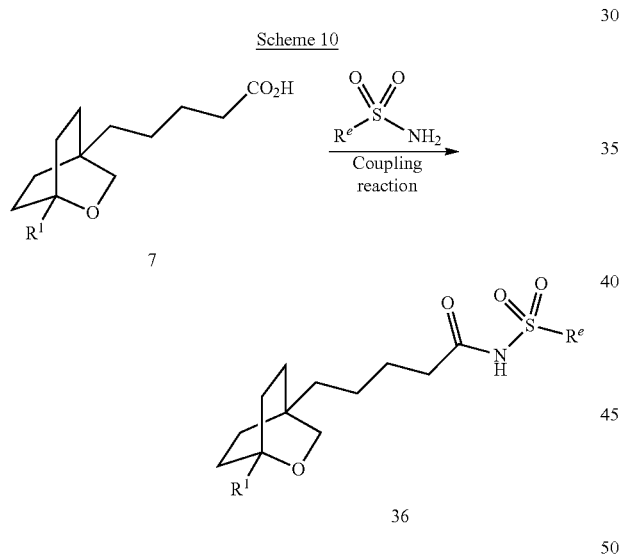

Scheme 11 shows the synthesis of another series of oxabicyclo[2.2.2] acid analogs 44. Wittig reaction of cyclohexanone-ester 37 provides the alkene-ester 38, which is subjected to palladium-mediated α-arylation of the ester with an appropriate aryl or heteroaryl halide (e.g., Johansson, C. et al., *Angew. Chem. Int. Ed.*, 49:676 (2010)) to furnish the α-aryl ester 39. Reduction of the ester 39 (e.g., LiAlH$_4$) provided the alkene-alcohol 40, which then undergoes epoxidation (e.g., m-chloroperbenzoic acid) to give the epoxide-alcohol 41. Acid-mediated intramolecular epoxide ring-opening with the alcohol provides the oxabicyclo[2.2.2] alcohol intermediate 42, which is then subjected to a 1,4-conjugate addition to an appropriate acrylate ester as described in Scheme 3 to give the 3-oxy-ester 43, which is then deprotected to provide the desired 3-oxy-carboxylic acid analogs 44.

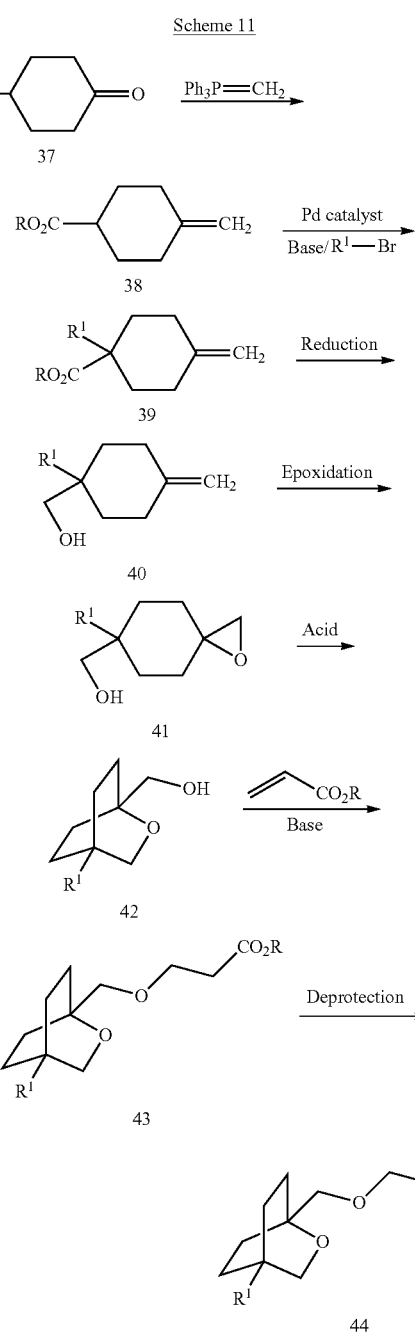

The synthesis of the corresponding 2-oxyacetic carboxylic acid analogs 47 is shown in Scheme 12. Oxidation of the intermediate alcohol 42 provides the aldehyde 43, which successively undergoes a Wittig reaction to give alkene 44, followed by hydroboration of the alkene 44 to give the alcohol 45. Reaction of alcohol 45 with an appropriate α-haloacetate ester in the presence of base (as described above in Scheme 4) provides the 2-oxy-ester 46. Deprotection of ester 46 then provides the desired 2-oxyacetic carboxylic acid analogs 47.

Scheme 12

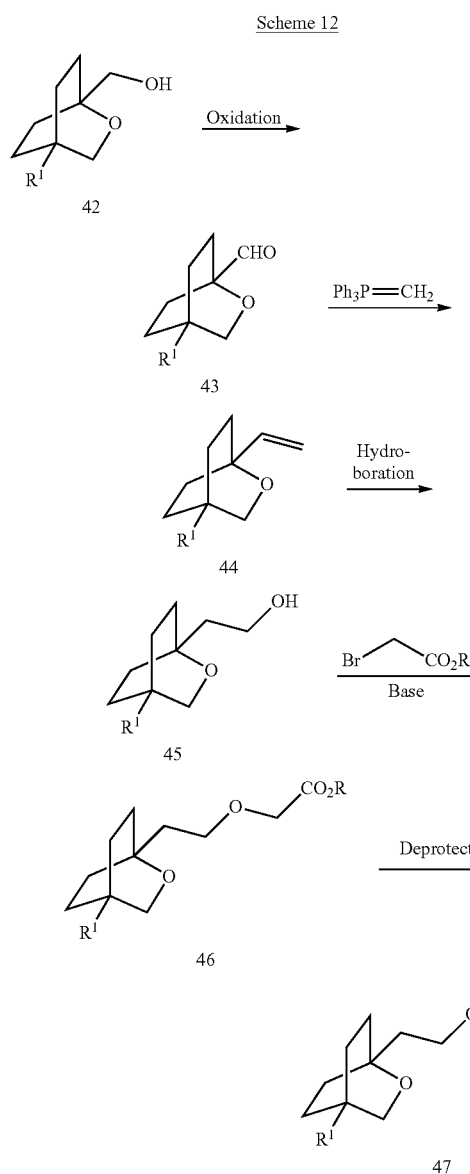

Scheme 13

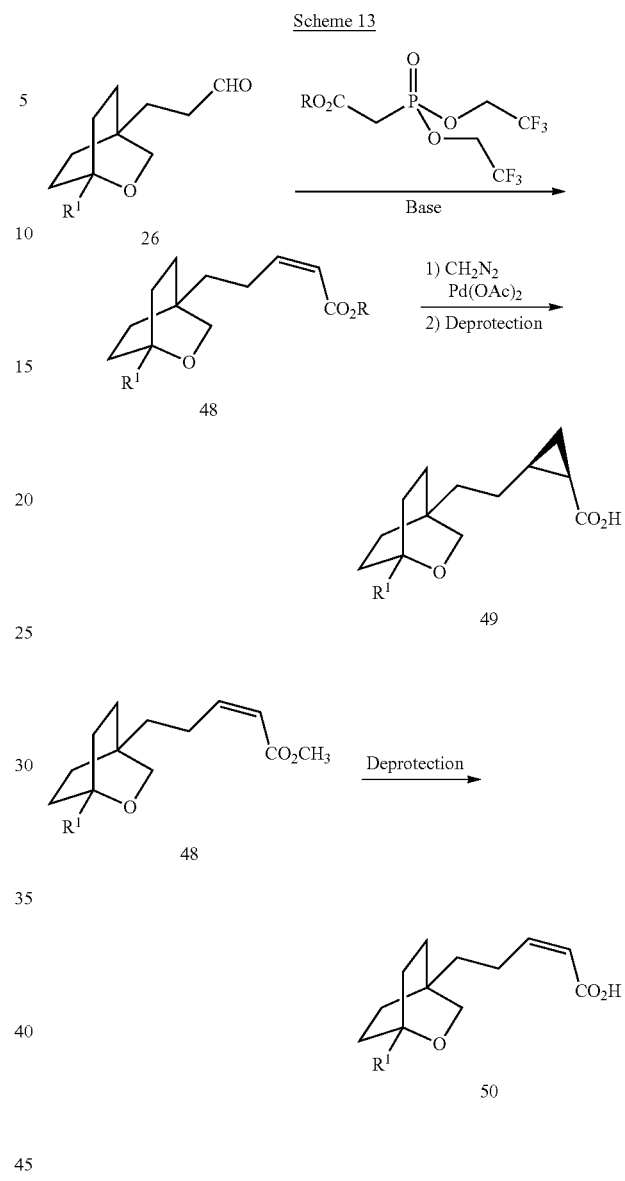

Scheme 13 shows the synthesis of α,β-cyclopropyl carboxylic acid analogs 49 and the corresponding Z-α,β-unsaturated carboxylic acid analogs 50. Aldehyde 26 is treated with the bis-trifluoroethyl phosphonate Horner-Emmons reagent (Reference: Still, W. C. et al., *Tetrahedron Lett.*, 24:4405 (1983)) under standard basic conditions to provide selectively the Z-α,β-unsaturated esters 48. The α,β-unsaturated ester 48 is reacted with diazomethane (in the same manner as described in Schemes 8-10) to give the α,β-cyclopropyl ester, which is then deprotected to give the corresponding α,β-cyclopropyl acid analogs 49. Alternatively, deprotection of ester 48 provides the desired Z-α,β-unsaturated carboxylic acid analogs 50.

Scheme 14 shows the synthesis of functionalized aryl α,β-cyclopropyl carboxylic acid analogs 55 and 56. The protected hydroxyaryl tosylate 15 is reacted with cyanide, after which the resulting nitrile product is reduced to the corresponding primary alcohol 51. Alcohol 51 is converted to the aldehyde 52 using the same sequence as described in Scheme 8 (for the conversion of 12 to 26). Horner-Emmons reaction of aldehyde 52 with a standard diethyl phosphonate provides the E-α,β-unsaturated ester 53, which is converted to the corresponding α,β-cyclopropyl ester with diazomethane, followed by deprotection to give the phenol-ester 54. Phenol 54 then undergoes an O-arylation reaction (e.g., Chan-Lam coupling with aryl boronic acids) followed by ester deprotection to give the O-aryl α,β-cyclopropyl carboxylic acids 55. Alternatively, phenol 54 is alkylated with appropriate alkyl halides ($R^5X$) under basic conditions followed by ester deprotection to give the O-alkyl α,β-cyclopropyl carboxylic acids 56.

Scheme 14

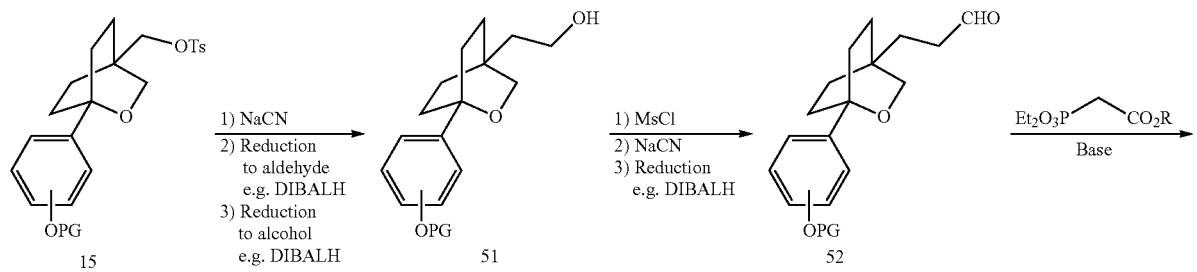

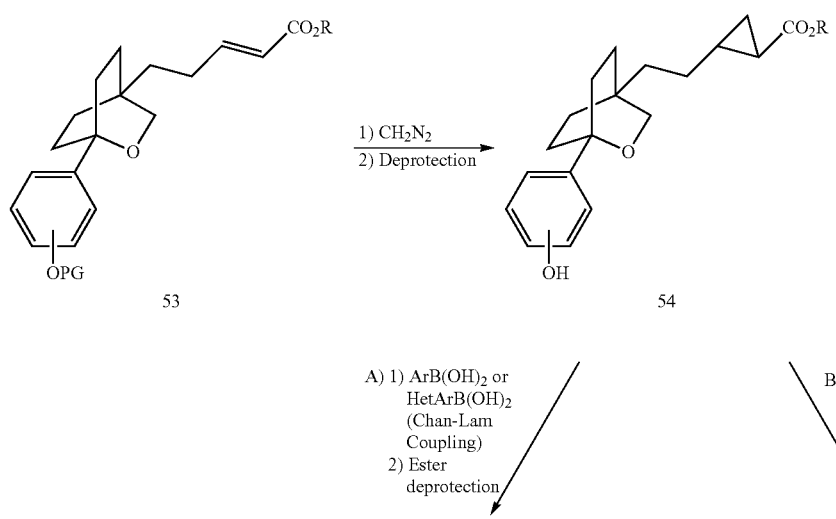

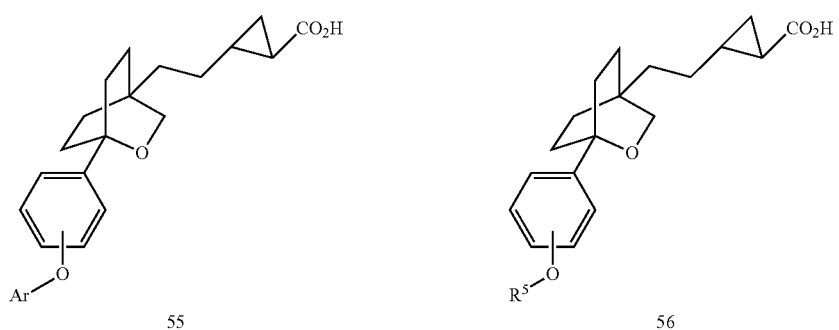

Scheme 15 shows the synthesis of diol analogs 58 and 60. Copper-catalyzed coupling of allyl Grignard reagent with iodide 22 (reference: Sai, M., *Bull. Chem. Soc. Jpn.*, 82:1194 (2009)) provides the terminal alkene 57, which is reacted with osmium tetroxide to give the diol analogs 58. Alternatively, ester 23 is reduced to the corresponding alcohol, then oxidized to the aldehyde and reacted with a standard Wittig reagent to give alkenes 59. Osmylation of alkenes 59 provides the diol analogs 60.

Scheme 15

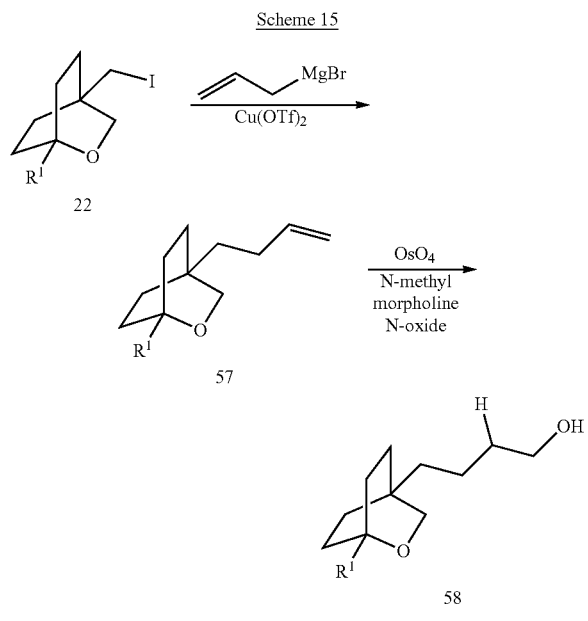

Scheme 16

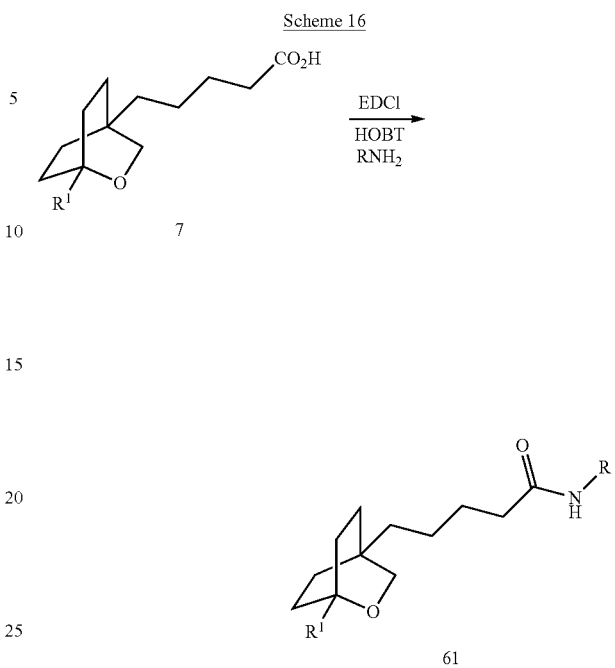

Scheme 16 shows the synthesis of amide analogs 61 from carboxylic acid analogs such as 7 by using standard coupling reaction conditions such as EDCI/HOBT.

Scheme 17 shows the synthesis of more highly functionalized aryl-substituted oxyacetic acid analogs 63 and 65. The phenol ester intermediate 17 is converted to the triflate 61, which in turn is treated with bis(pinacolato)boronate under palladium catalysis to give the pinacol boronate 62 (e.g., as described in US 2011/152246 A1). Aryl boronate 62 undergoes a palladium-mediated coupling reaction with thiophenols (e.g., as described in WO 2010/51030 A1) to give, after ester deprotection, the aryl thioether analogs 63. Alternatively, the pinacol boronate 62 is hydrolyzed under standard conditions (e.g., as described in WO 2009/63061 A2) to give boronic acid 64; this intermediate undergoes other functionalization reactions, such as Cu-mediated trifluoromethylation using sodium trifluoromethanesulfinate in the presence of t-BuOOH (e.g., as described in Ye, Y. et al., *Org. Lett.*, 14:4979 (2012)), followed by ester deprotection, to give the corresponding trifluoromethyl-aryl analogs 65.

Scheme 17

37

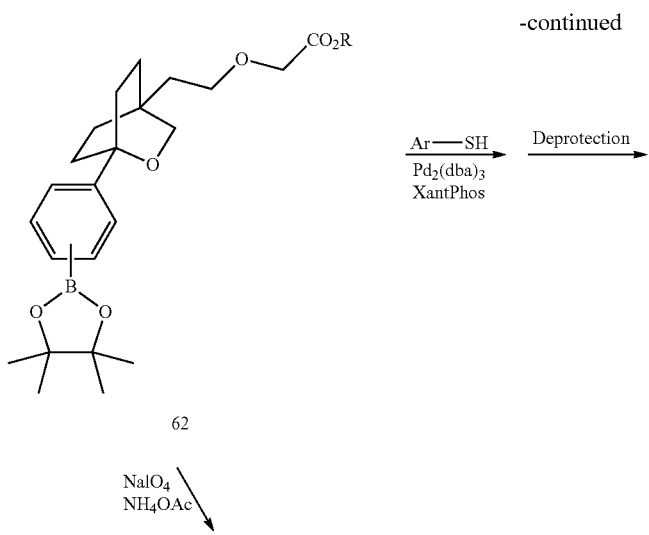

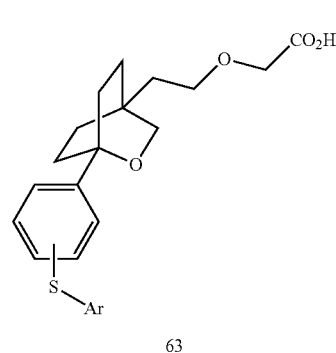

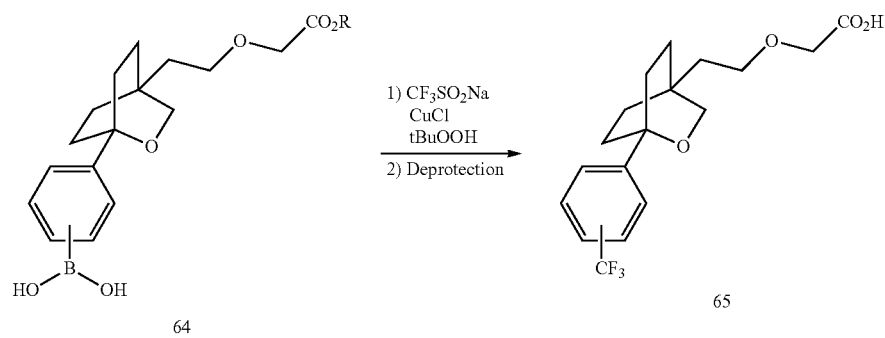

Scheme 18 shows the synthesis of hydroxamic acid analogs 66 and 67. Acids 13 and 30 are coupled under standard conditions with a protected hydroxylamine derivative (e.g. tetrahydropyranyl ether), and the protecting group is removed (e.g. mild acid) to provide the corresponding hydroxamic acid analogs 66 and 67.

Scheme 18

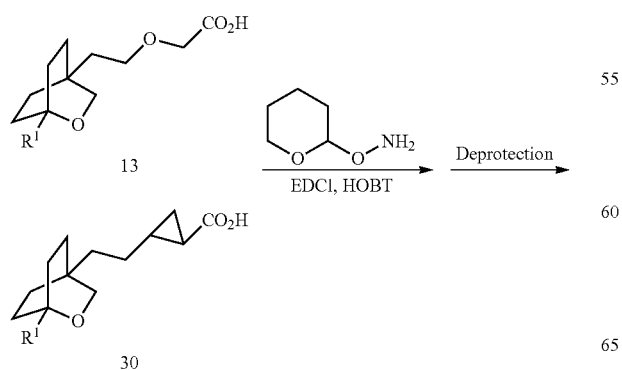

-continued

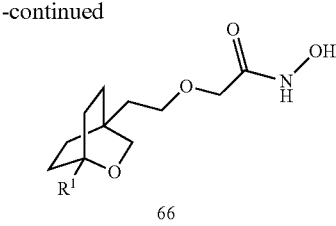

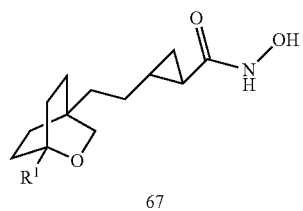

Scheme 19 shows the synthesis of δ-oxy-α,β-cyclopropyl acid analogs 72. Alcohol 8 is oxidized to aldehyde 68. Aldehyde 68 is then converted to the corresponding peroxide and undergoes a copper-mediated fragmentation in the presence of an N-oxy free radical (e.g. TEMPO) to provide alkoxyamine 69 (reference: *J. Org. Chem.*, 74:1567-1573

(2007)). Alkoxyamine 69 is then reduced (N—O bond reductive cleavage) to give the bridgehead alcohol intermediate 70, which then undergoes alkylation with a protected 4-bromobut-2-enoate ester to provide the α,β-unsaturated ester 71. Cyclopropanation using trimethylsulfoxonium ylide followed by deprotection furnished the δ-oxy-α,β-cyclopropyl acid analogs 72.

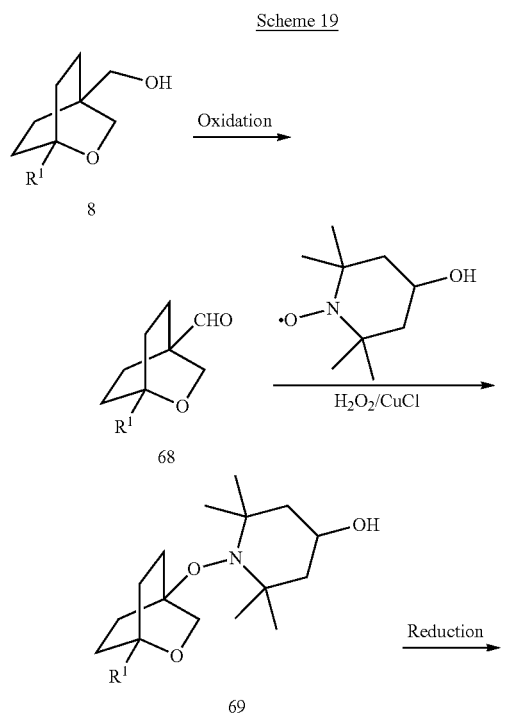

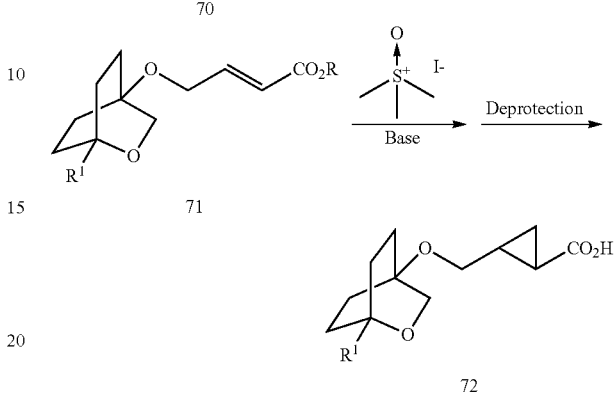

Scheme 20 shows an alternative synthesis of acid analogs 47 and 74. The alkenyl alcohol 40 is treated with a halogenating agent (e.g. N-bromosuccinimide) in the presence of water to give a mixture of the corresponding bromohydrin diastereomers 73, which is treated under basic conditions to give the corresponding epoxide diastereomers 41. Epoxides 41 are treated under acidic conditions to provide the intermediate alcohol 42. Alcohol 42 is then converted to oxyacetic acid analogs 47 according to the procedures previously described in Scheme 12. Alternatively, alcohol 42 is converted to the homologated alcohol 45 according to the procedures described in Scheme 12, then to the α,β-cyclopropyl acid analogs 74.

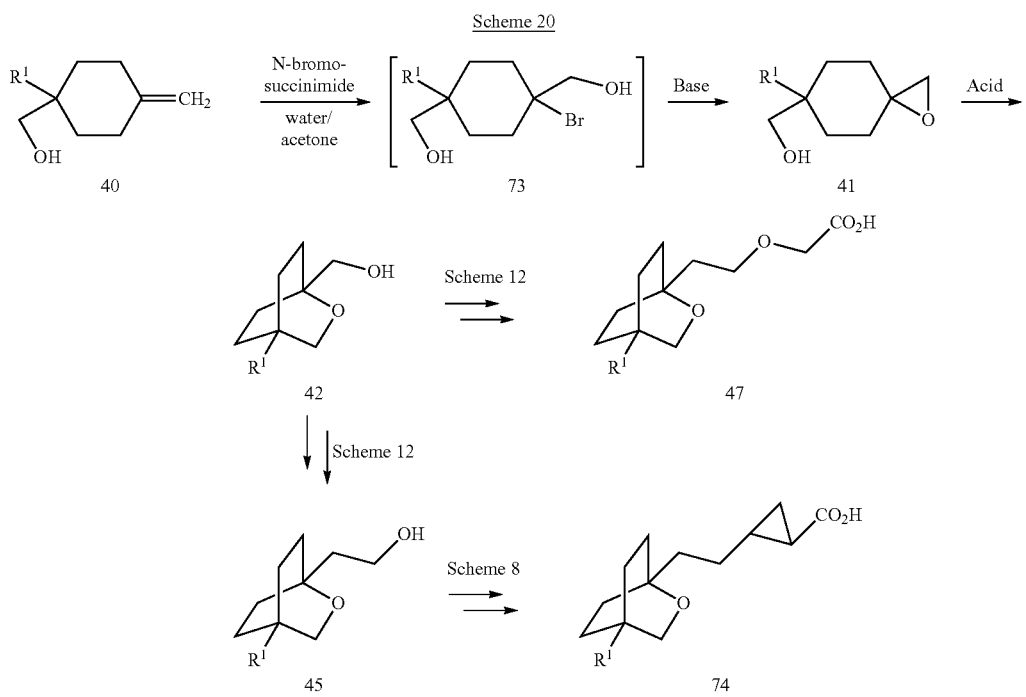

Scheme 21 shows the synthesis of acid analogs 76. Alcohol 45 is homologated using a sequence similar to that described in Scheme 4. Alcohol 45 is reacted with mesyl chloride to give the corresponding mesylate, which is then displaced with cyanide, followed by successive reductions to give first the corresponding aldehyde, then finally alcohol 75. Alcohol 75 is then reacted with an appropriate bromoacetate ester and then deprotected to furnish acid analogs 76.

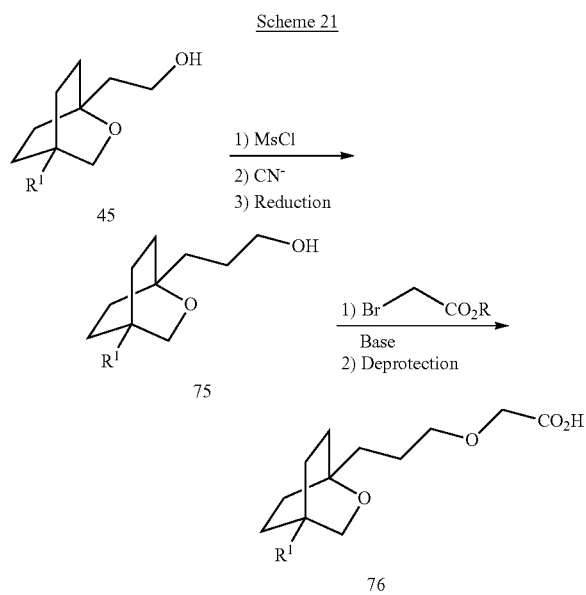

IV. BIOLOGY

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Recently, five GPCRs (FFAR1 (GPR40), FFAR2 (GPR43), FFAR3 (GPR41), GPR84, and GPR120) were reported to recognize free fatty acids FFAR1, recognizes medium-long chainfatty acids like palmitic acid and linoleic acid FFAR2 and FFAR3 recognize short-chain fatty acids like acetate and butyrate whereas GPR84 recognizes medium-chain fatty acid like lauric acid. GPR120 recognizes long-chain fatty acids, especially EPA and DHA (Im, D. S., Prog. Lipid Res., 51:232-237 (2012)). GPR120 has been detected in macrophages, dendritic cells, adipocytes, clara cells in bronchiole epithelium, and enteroendocrine L cells in colon (Miyauchi et al., Naunyn-Schmiedebergs Arch Pharmacol., 379:427-434 (2009)). The anti-inflammatory mechanism of omega-3 fatty acids using GPR120 knock-out mice was investigated (Oh et al., Cell, 142:687-698 (2010)). They suggested GPR120 activation by DHA interacts with TAB1 via b-arrestin-2, and that this interaction interrupts TAK1 activation by LPS or TNF-alpha, suppressing inflammatory responses via NF-κB and JNK in macrophages and dendritic cells (Oh et al., Cell, 142:687-698 (2010)). Furthermore, GPR120 activation was shown to enhance insulin-induced glucose uptake in adipose tissues through Gq/11 proteins and PI 3-kinase.

Similarly, GPR120-deficient mice fed a high-fat diet develop obesity, glucose intolerance and fatty liver with decreased adipocyte differentiation and lipogenesis and enhanced hepatic lipogenesis (Ichimura et al., Nature, 483 (7389):350-354 (2012). Insulin resistance in such mice was shown to be associated with reduced insulin signalling and enhanced inflammation in adipose tissue. In humans, GPR120 expression in adipose tissue was shown to be significantly higher in obese individuals than in lean controls. GPR120 gene sequencing in obese subjects revealed a deleterious non-synonymous mutation (p.R270H) that inhibits GPR120 signalling activity. Furthermore, the p.R270H variant was associated with increased risk of obesity in European populations.

Given the increase in the worldwide patient population afflicted by type 2 diabetes, there is a need for novel therapies which are effective with minimal adverse events. To decrease medical burden of type 2 diabetes through enhanced glycemic control, GPR120 modulator compounds of the present invention are being investigated here for their ability to increase glucose tolerance as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR120 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR120 and/or to prevent or treat the disorders listed herein. When applied to a combination, the term refers to combined amounts of the active ingredients that result in the preventive or therapeutic effect, whether administered in combination, serially, or simultaneously.

GPR120 activity was monitored by measuring phosphorylation of ERK (pERK), since G protein receptors are known to activate the ERK signaling cascade either directly and/or through recruitment of arrestin that serves as a scaffold for downstream signaling events. Molecules that activated GPR120 with sufficient potency and efficacy in the pERK assay that also possessed desirable pharmacokinetic properties were evaluated in mice for glucose lowering by monitoring disposition of an oral glucose load by an oral glucose tolerance test (oGTT).

GPR120 pERK AlphaScreen SureFire Assay

The human and mouse GPR120-mediated intracellular phosphorylated ERK assays were established using CHOA12 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029), 500 µg/mL GENETICIN® (Life Technologies Cat. #10131-027) and 250 µg/mL Zeocin (Invitrogen Cat. #R250-01). Cells were cryo preserved at a concentration of $2 \times 10^7$ cells/mL, in 90% Charcoal/Dextran FBS and 10% DMSO, and frozen in liquid nitrogen at a low passage number.

For the pERK assay, $2 \times 10^7$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.6 \times 10^6$ cells/mL. Cells were plated into 384-well clear bottom tissue culture plates (BD Cat. #353962) at 50 µL/well, for a density of 30,000 cells/well using a MULTIDROP® and incubated for 16-18 hours (overnight) at 37° C. with 5% $CO_2$. The next day, cells were serum starved in 30 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (LABCYTE® Cat. #LC-0200). Cells were then stimulated with 50 nL of compound dilutions using ECHO liquid handler for 7 minutes at 37° C. Compounds ranged from final assay concentrations of 33.33 µM to 0.56 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100× (average sample−average blank)/(average total−average blank) where sample is the luminescence activity in the presence of test compound, blank is equal to the luminescence activity in the presence of DMSO control and the total is signal induced by 50 µM linolenic acid as reference compound. Activation data for the test compound over a range of concentrations was plotted as percentage activation of the test compound (100%=maximum response). After correcting for background, $EC_{50}$ values were determined The $EC_{50}$ is defined as the concentration of test compound which produces 50% of the maximal response and was quantified using the 4 parameter logistic equation to fit the data.

The human and mouse GPR120-mediated intracellular phosphorylated ERK assays were also established using CHO-K1 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029) and 500 µg/mL GENETICIN® (Life Technologies Cat. #10131-027). Cells were cryo preserved at a concentration of $3 \times 10^6$ cells/mL, in 70% F-12, 20% Charcoal/Dextran FBS and 10% DMSO, and frozen in liquid nitrogen at a low passage number.

For the pERK assay, $3 \times 10^6$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.5 \times 10^6$ cells/mL. Cells were plated into 384-well clear bottom tissue culture plates (BD Cat. #353962) at 50 µL/well, for a density of 25,000 cells/well using a MULTIDROP® and incubated for 16-18 hours (overnight) at 37° C. with 5% CO$_2$. The next day, cells were washed once with 50 µL of PBS without Ca$^{++}$/Mg$^{++}$ (Gibco Cat. #14190-036) and serum starved in 25 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (LABCYTE® Cat. #LC-0200). Cells were then stimulated with 40 nL of compound dilutions using ECHO liquid handler for 7 minutes at 37° C. Compounds ranged from final assay concentrations of 32 µM to 0.54 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100× (average sample−average blank)/(average total−average blank) where sample is the luminescence activity in the presence of test compound, blank is equal to the luminescence activity in the presence of DMSO control and the total is signal induced by 50 µM linolenic acid as reference compound.

Activation data for the test compound over a range of concentrations was plotted as percentage activation of the test compound (100%=maximum response). After correcting for background, EC$_{50}$ values were determined. The EC$_{50}$ is defined as the concentration of test compound which produces 50% of the maximal response and was quantified using the 4 parameter logistic equation to fit the data.

The exemplified Examples disclosed below were tested in the GPR120 in vitro assays described above and were found having GPR120 agonist activity. Table 1 below lists the EC$_{50}$ values measured in the human GPR120 pERK assay for the following Examples.

| Example Number | EC$_{50}$ (µM) |
| --- | --- |
| 1 | 2.31 |
| 2 | 0.06 |
| 3 | 0.20 |
| 4 | 1.60 |
| 5 | 0.08 |
| 6 | 0.56 |
| 7 | 7.54 |
| 8 | 1.05 |
| 9 | 1.28 |
| 10 | 0.64 |
| 11 | 0.10 |
| 12 | 0.98 |
| 13 | 0.35 |
| 14 | 0.35 |
| 15 | 0.48 |
| 16 | 0.16 |
| 17 | 0.26 |
| 18 | 0.41 |
| 19 | 1.98 |
| 20 | 0.65 |
| 21 | 6.86 |
| 22 | 0.38 |
| 23 | 0.31 |
| 24 | 0.80 |
| 25 | 0.59 |
| 26 | 0.17 |
| 27 | 5.02 |
| 28 | 1.98 |
| 29 | 1.57 |
| 30 | 0.14 |
| 31 | 0.28 |
| 32 | 0.58 |
| 33 | 1.90 |
| 34 | 0.07 |
| 35 | 0.66 |
| 36 | 0.72 |
| 37 | 1.14 |
| 38 | 024 |
| 39 | 0.20 |
| 40 | 0.30 |
| 41 | 0.20 |
| 42 | 0.37 |
| 43 | 0.55 |
| 44 | 0.45 |
| 45 | 0.28 |
| 46 | 2.57 |
| 47 | 1.03 |
| 48 | 6.76 |
| 49 | 3.31 |
| 50 | 1.36 |
| 51 | 1.09 |
| 52 | 4.34 |
| 53 | 1.03 |
| 54 | 3.47 |
| 55 | 0.33 |
| 56 | 0.61 |
| 57 | 1.88 |
| 58 | 0.29 |
| 59 | 0.36 |
| 60 | 0.57 |
| 61 | 5.23 |
| 62 | 1.22 |
| 63 | 0.37 |
| 64 | 0.26 |
| 65 | 0.33 |
| 66 | 2.08 |
| 67 | 0.75 |
| 68 | 0.72 |
| 69 | 4.23 |
| 70 | 0.97 |
| 71 | 1.17 |
| 72 | 0.49 |
| 73 | 0.54 |
| 74 | 2.53 |
| 75 | 0.40 |
| 76 | 0.42 |
| 77 | 0.23 |
| 78 | 0.49 |
| 79 | 0.55 |
| 80 | 0.22 |
| 81 | 0.52 |
| 82 | 0.81 |
| 83 | 0.32 |
| 84 | 0.47 |
| 85 | 0.31 |
| 86 | 0.85 |
| 87 | 0.41 |
| 88 | 0.34 |
| 89 | 0.35 |
| 90 | 0.95 |
| 91 | 0.63 |
| 92 | 0.80 |
| 93 | 0.52 |
| 94 | 1.16 |
| 95 | 0.35 |
| 96 | 1.68 |

-continued

| Example Number | EC$_{50}$ (µM) |
|---|---|
| 97 | 0.39 |
| 98 | 1.02 |
| 99 | 0.34 |
| 100 | 0.55 |
| 101 | 0.32 |
| 102 | 0.66 |
| 103 | 0.54 |
| 104 | 7.78 |
| 105 | 3.44 |
| 106 | 0.58 |
| 107 | 1.87 |
| 108 | 0.73 |
| 109 | 5.55 |
| 110 | 0.49 |
| 111 | 0.64 |
| 112 | 0.27 |
| 113 | 0.86 |
| 114 | 2.73 |
| 115 | 5.56 |
| 116 | 1.15 |
| 117 | 5.21 |
| 118 | 1.89 |
| 119 | 1.60 |
| 120 | 2.21 |

In Vivo GPR120 Assays

1) Acute Oral Glucose Tolerance Test

C57BL/6 mice were housed individually and fed a standard rodent chow diet. At approximately 11 weeks age, after a 5 h fast, these mice were orally treated with vehicle or test compounds 60 min before a glucose challenge (2 g/kg). Blood glucose levels were determined from tail bleeds taken at −60, 0, 15, 30, 60 and 120 min after the glucose challenge. The blood glucose excursion profile from t=0-120 min was used to calculate an area under the curve (AUC) for compound treatment. This AUC for compound treatment is compared to vehicle treatment.

In an oral glucose tolerance test in mice at dose of 30 mg/kg, Examples 6, 14 and 80 reduced glucose AUC levels by 40%, 30% and 60% respectively.

2) Acute Intraperitoneal Insulin Tolerance Test

C57BL/6 mice were housed individually and fed a standard rodent chow diet. At approximately 11 weeks age, after 5 h fast, these mice were orally treated with vehicle or test compounds 30 min before an insulin challenge (0.1 U/kg). Blood glucose levels were determined from tail bleeds taken at −30, 0, 15, 30, 60, 90 and 120 min after insulin injection. The blood glucose excursion profile from t=0-120 min was used to calculate a negative area under the curve (AUC) for compound treatment. This AUC for compound treatment is compared to vehicle treatment.

The compounds of the present invention possess activity as modulators of GPR120, and, therefore, may be used in the treatment of diseases associated with GPR120 activity. Via modulation of GPR120, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, lipid disorders, lipodystrophy, liver diseases such as NASH (Non-Alcoholic SteatoHepatitis), NAFLD (Non-Alcoholic Fatty Liver Disease) and liver cirrhosis, and treatment of side-effects related to diabetes.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

V. PHARMACEUTICAL COMPOSITIONS, FORMULATIONS AND COMBINATIONS

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR120 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatitis agents, lipid lowering agents, anorectic agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin. alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, peliglitazar, tesaglitazar, aleglitazar), glucokinase activators (e.g., PF-04937319 and AMG-151, as well as other compounds described in Fyfe, M. C. T. et al., *Drugs of the Future*, 34(8):641-653 (2009) and incorporated herein by reference), GPR40 receptor modulators (e.g., TAK-875), GPR119 receptor modulators (e.g., MBX-2952, PSN821, APD597), other GPR120 receptor modulators (e.g., compound 43 from *J. Med. Chem.*, 55:4511-4515 (2012)), sodium-glucose transporter-2 (SGLT2) inhibitors (for example dapagliflozin, canagliflozin, remagliflozin), 11β-HSD-1 inhibitors (for example MK-0736, BI35585, BMS-823778, and LY2523199), amylin analogs such as pramlintide, and/or insulin. Reviews of current and emerging therapies for the treatment of diabetes can be found in: Mohler, M. L. et al., *Medicinal Research Reviews*, 29(1):125-195 (2009), and Mizuno, C. S. et al., *Current Medicinal Chemistry*, 15:61-74 (2008).

The GPR120 receptor modulator of the present invention may also be optionally employed in combination with agents for treating complication of diabetes. These agents include PKC inhibitors and/or AGE inhibitors.

The GPR120 receptor modulator of the present invention way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 (monoacylglycerol transferase 2) inhibitors (for example, compounds from WO 2012/124744, or compound (S)-10 from *Bioorg. Med. Chem. Lett.* (2013), doi: http://dx.doi.org/10.1016/j.bmcl.2013.02.084) and the like. The compound of structure I may also be employed in combination with an agonist of the glucagon-like peptide-1 receptor (GLP-1 R), such as exenatide, liraglutide, GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6): 2512-2517 (2009); and Elangbam, C. S., *Vet. Pathol.*, 46(1): 10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR120 receptor. Such compounds may be provided in a commercial kit, for example, for use in pharmaceutical research involving GPR120 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR120.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with GPR120 (as defined previously). In another embodiment, the package insert states that the pharmaceutical composition can be used in combination (as defined previously) with a second therapeutic agent for the treatment of multiple diseases or disorders associated with GPR120. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof

VI. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL® 400 MHz and 500 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography with one of following methods:

HPLC-1: SunFire C18 (4.6×150 mm) 3.5µ, gradient 10 to 100% B:A for 12 min, then 3 min hold at 100% B.
Mobile Phase A: 0.05% TFA in water:CH$_3$CN (95:5)
Mobile Phase B: 0.05% TFA in CH$_3$CN:water (95:5)
TFA Buffer pH=2.5; Flow rate: 1 mL/min; Wavelength: 254 nm, 220 nm.

HPLC-2: XBridge Phenyl (4.6×150 mm) 3.5µ, gradient 10 to 100% B:A for 12 min, then 3 min hold at 100% B.
Mobile Phase A: 0.05% TFA in water:CH$_3$CN (95:5)
Mobile Phase B: 0.05% TFA in CH$_3$CN:water (95:5)
TFA Buffer pH=2.5; Flow rate: 1 mL/min; Wavelength: 254 nm, 220 nm.

HPLC-3: CHIRALPAK® AD-H, 4.6×250 mm, 5µ.
Mobile Phase: 30% EtOH-heptane (1:1)/70% CO$_2$
Flow rate=40 mL/min, 100 Bar, 35° C.; Wavelength: 220 nm.

Example 1

3-(1-(3-Phenoxyphenyl)-2-oxabicyclo[2.2.2]octan-4-yl)propanoic acid

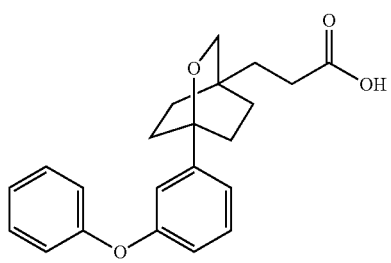 [SMILES: O=C(O)CCC12CCC(c3cccc(Oc4ccccc4)c3)(CC1)OC2]

1A. Ethyl 4,4-dimethoxycyclohexanecarboxylate

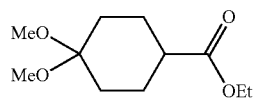

To a solution of ethyl-4-oxocyclohexane carboxylate (23.4 mL, 147 mmol) and p-TsOH (0.25 g, 1.31 mmol) in 25 mL MeOH was added HC(OMe)$_3$ (24.10 mL, 220 mmol) dropwise. The reaction was stirred at rt for 15 h and 1.5 g of anhydrous Na$_2$CO$_3$ was added. The reaction was stirred at rt for another 30 min and filtered. TEA (0.18 mL, 1.31 mmol) was added to the filtrate and the resulting mixture was concentrated in vacuo. The residue was diluted with EtOAc (30 mL), washed with water (4×30 mL), dried (MgSO$_4$), filtered, and concentrated in vacuo. The crude oil was purified by flash chromatography on SiO$_2$ (0 to 20% EtOAc:hexanes) to afford the title compound (32 g, 100% yield) as a clear oil. $^1$H NMR (500 MHz, CDCl$_3$) δ 4.15 (q, J=7.1 Hz, 2H), 3.21 (s, 3H), 3.18 (s, 3H), 2.41-2.28 (m, 1H), 2.08-1.96 (m, 2H), 1.91-1.79 (m, 2H), 1.77-1.61 (m, 2H), 1.43 (td, J=12.9, 4.1 Hz, 2H), 1.27 (t, J=7.1 Hz, 3H).

1B. 1-Ethyl 1-methyl 4,4-dimethoxycyclohexane-1,1-dicarboxylate

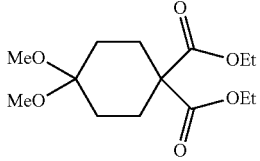 [SMILES: CCOC(=O)C1(C(=O)OCC)CCC(OC)(OC)CC1]

To a −78° C. solution of iPr$_2$NEt (3.95 mL, 27.7 mmol) in THF (50 mL) was added n-BuLi (17.3 mL of a 1.6 M solution in hexanes; 27.7 mmol) was added. After 15 min, ethyl 4,4-dimethoxycyclohexane-carboxylate (4.0 g, 18.50 mmol) was added and the reaction mixture was stirred at −78° C. for 1 h. Methyl chloroformate (2.87 mL, 37.0 mmol) was added and the reaction mixture was warmed to rt. The reaction was quenched with saturated aqueous NH$_4$Cl and extracted with EtOAc (100 mL). The organic layer was dried (Na$_2$SO$_4$) and concentrated in vacuo. The crude oil was chromatographed (SiO$_2$; continuous gradient from 0 to 20% EtOAc:hexanes) to afford the title compound (4.7 g, 93% yield) as a clear oil. $^1$H NMR (500 MHz, CDCl$_3$) δ 4.21 (q, J=7.1 Hz, 2H), 3.75 (s, 3H), 3.19 (s, 6H), 2.16-2.05 (m, 4H), 1.79-1.69 (m, 4H), 1.27 (t, J=7.1 Hz, 3H).

1C. (4,4-Dimethoxycyclohexane-1,1-diyl)dimethanol

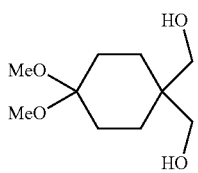

To a solution of 1-ethyl 1-methyl 4,4-dimethoxycyclohexane-1,1-dicarboxylate (4.7 g, 17.13 mmol) in dry Et$_2$O (250 mL) at 0° C. was added LiAlH₄ (17.1 mL of a 2 M solution in THF; 34.3 mmol) dropwise over 15 min. The reaction mixture was stirred at 0° C. for 15 min, then warmed to rt and stirred for 1 h. It was then cooled to 0° C. and carefully quenched with aqueous NaOH (7.3 mL of a 1N solution; 7.3 mmol). The mixture was filtered and the filtrate was concentrated in vacuo to afford the title compound (3.6 g, 100% yield) as a semisolid. ¹H NMR (500 MHz, CDCl₃) δ 3.65 (d, J=4.4 Hz, 4H), 3.20 (s, 6H), 2.42 (t, J=4.6 Hz, 2H), 1.67 (dd, J=7.3, 4.9 Hz, 4H), 1.53-1.41 (m, 4H).

1D. (4,4-Dimethoxycyclohexane-1,1-diyl)bis(methylene) bis(4-methylbenzenesulfonate)

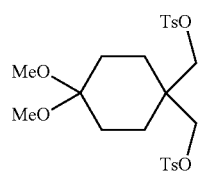 [SMILES: COC1(OC)CCC(COS(=O)(=O)c2ccc(C)cc2)(COS(=O)(=O)c2ccc(C)cc2)CC1]

To a solution of (4,4-dimethoxycyclohexane-1,1-diyl) dimethanol (3.6 g, 17.62 mmol) in pyridine (20 mL) was added tosyl chloride (7.39 mL, 38.8 mmol). The reaction mixture was stirred at rt for 18 h and then diluted with EtOAc (50 mL). The organic mixture and washed with 10% aq. citric acid, dried (Na₂SO₄) and concentrated in vacuo to afford the title compound (5.4 g, 60% yield) as a white solid. ¹H NMR (500 MHz, CDCl₃) δ 7.73 (d, J=8.3 Hz, 4H), 7.35 (d, J=8.2 Hz, 4H), 3.84 (s, 4H), 3.09 (s, 6H), 2.45 (s, 6H), 1.54-1.45 (m, 4H), 1.42-1.34 (m, 4H).

1E. (4-Oxocyclohexane-1,1-diyl)bis(methylene) bis(4-methylbenzenesulfonate)

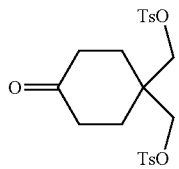

To a solution of (4,4-dimethoxycyclohexane-1,1-diyl)bis (methylene) bis(4-methylbenzenesulfonate) (5.4 g, 10.53 mmol) in THF (20 mL) was added 1 N aq HCl (60 mL, 60.0 mmol) and the reaction mixture was refluxed for 3 h. Volatiles were removed in vacuo, and the aqueous layer was extracted with EtOAc (5×10 mL). The combined organic extracts were dried (MgSO₄), filtered, and concentrated in vacuo. The crude oil was purified by flash chromatography on SiO₂ (0 to 50% EtOAc:hexanes) to afford the title compound (4.3 g, 87% yield) as a clear oil. ¹H NMR (500 MHz, CDCl₃) δ 7.78 (d, J=8.3 Hz, 4H), 7.39 (d, J=8.0 Hz, 4H), 3.97 (s, 4H), 2.50 (s, 6H), 2.25 (t, J=7.0 Hz, 4H), 1.75 (t, J=7.0 Hz, 4H).

1F. (4-Hydroxy-4-(3-phenoxyphenyl)cyclohexane-1,1-diyl)bis(methylene) bis(4-methylbenzenesulfonate)

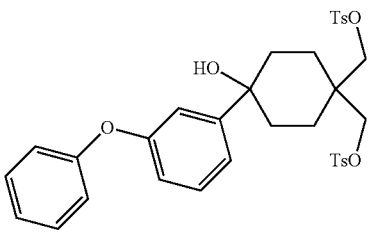 [SMILES: Cc1ccc(S(=O)(=O)OCC2(COS(=O)(=O)c3ccc(C)cc3)CCC(O)(c3cccc(Oc4ccccc4)c3)CC2)cc1]

To a solution of 1-bromo-3-phenoxybenzene (0.320 g, 1.29 mmol) in anhydrous THF (10 mL) at −78° C. was added n-BuLi (0.804 mL of a 1.6 M solution in hexanes; 1.286 mmol). The reaction was stirred at −78° C. for 0.5 h and a solution of (4-oxocyclohexane-1,1-diyl)bis(methylene) bis (4-methylbenzenesulfonate) (0.5 g, 1.07 mmol) in THF (5 mL) was then added dropwise. The reaction mixture was slowly warmed to rt and stirred overnight. The reaction was quenched with sat'd aq NH₄Cl and diluted with water. The mixture was extracted with EtOAc. The organic layer was dried (Na₂SO₄) and concentrated in vacuo. The crude oil was purified by flash chromatography on SiO₂ (0 to 50% EtOAc: hexanes) to afford the title compound (0.39 g, 57% yield) as a white foam. ¹H NMR (500 MHz, CDCl₃) δ 7.78 (t, J=8.6 Hz, 4H), 7.41-7.33 (m, 6H), 7.29 (dd, J=11.4, 5.0 Hz, 1H), 7.16-7.10 (m, 1H), 7.08-6.99 (m, 4H), 6.89-6.84 (m, 1H), 4.01 (s, 2H), 3.81 (s, 2H), 2.49 (s, 3H), 2.45 (s, 3H), 1.75-1.47 (m, 8H).

1G. (1-(3-Phenoxyphenyl)-2-oxabicyclo[2.2.2]octan-4-yl)methyl 4-methylbenzenesulfonate

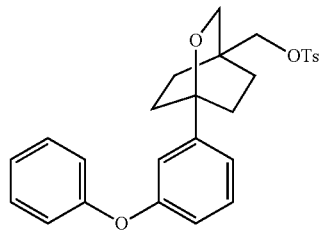 [SMILES: Cc1ccc(S(=O)(=O)OCC23CCC(c4cccc(Oc5ccccc5)c4)(CC2)OC3)cc1]

A mixture of (4-hydroxy-4-(3-phenoxyphenyl)cyclohexane-1,1-diyl)bis(methylene) bis(4-methylbenzenesulfonate) (390 mg, 0.612 mmol) and powdered NaOH (320 mg, 8.00 mmol) in THF (5 mL) was refluxed for 24 h. The reaction was cooled to rt, diluted with water, and extracted with EtOAc. The organic layer was dried (MgSO₄) and concentrated in vacuo. The crude oil was purified by flash chromatography on SiO₂ (0 to 30% EtOAc:hexanes) to afford the title compound (244 mg, 86% yield) as a white solid. LCMS, [M+H]⁺=465.2. ¹H NMR (500 MHz, CDCl₃) δ 7.81 (d, J=8.3 Hz, 2H), 7.42-7.36 (m, 2H), 7.37-7.31 (m, 2H), 7.28 (dd, J=9.6, 6.3 Hz, 1H), 7.15-7.08 (m, 3H), 7.03-6.98 (m, 2H), 6.87 (ddd, J=8.1, 2.4, 0.9 Hz, 1H), 3.83 (d, J=1.3 Hz, 2H), 3.77 (s, 2H), 2.49 (s, 3H), 2.09-1.97 (m, 4H), 1.75 (tt, J=9.6, 2.8 Hz, 2H), 1.69-1.60 (m, 2H).

1H. Diethyl 2-((1-(3-phenoxyphenyl)-2-oxabicyclo[2.2.2]octan-4-yl)methyl)malonate

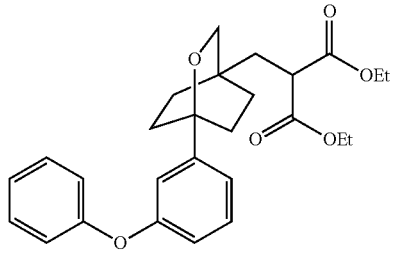 [SMILES: CCOC(=O)C(CC12CCC(c3cccc(Oc4ccccc4)c3)(CC1)OC2)C(=O)OCC]

Sodium (5 mg, 0.215 mmol) was dissolved in EtOH (2 mL) to form a solution of NaOEt and then diethyl malonate (0.033 mL, 0.215 mmol) was added. The reaction mixture was stirred at rt for 30 min and (1-(3-phenoxyphenyl)-2-oxabicyclo[2.2.2]octan-4-yl)methyl 4-methylbenzenesulfonate (10 mg, 0.022 mmol) was then added. The reaction was stirred at 120° C. under microwave conditions for 30 min. Catalytic amount of n-Bu$_4$NI was added and the reaction was stirred at 120° C. under microwave conditions for 18 h. The reaction was added sat'd aq NH$_4$Cl and extracted with ethyl acetate. The organic layer was washed with brine, dried over anhydrous MgSO$_4$, filtered, and concentrated in vacuo. The crude oil was purified by flash chromatography on SiO$_2$ (0 to 50% EtOAc:hexanes) to afford the title compound (8 mg, 82% yield) as a clear oil. LCMS, [M-Et+H]$^+$=425.4.

Example 1

A mixture of diethyl 2-((1-(3-phenoxyphenyl)-2-oxabicyclo[2.2.2]octan-4-yl)methyl)malonate (50 mg, 0.110 mmol), LiCl (9.4 mg, 0.221 mmol), and water (8 μL, 0.442 mmol) in DMSO (1 mL) was stirred at 190° C. under microwave conditions for 1 h. The reaction mixture was cooled to room temperature and partitioned between ethyl acetate and brine. The organic layer was washed with brine, dried over anhydrous MgSO$_4$, filtered, and concentrated in vacuo. The residue was dissolved in MeOH (1 mL), added 1 N aqueous NaOH (0.5 mL) and stirred at rt for 18 h. The mixture was acidified to pH 2 with conc. HCl and concentrated in vacuo. The residue was purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H$_2$O:MeOH:TFA and B=90:10:0.1 MeOH:H$_2$O:TFA) to afford the title compound (12 mg, 29% yield) as a white solid. LCMS, [M-H]$^+$=351.3. $^1$H NMR (500 MHz, CDCl$_3$) δ 7.38-7.31 (m, 2H), 7.29 (t, J=7.9 Hz, 1H), 7.19-7.07 (m, 3H), 7.04-6.98 (m, 2H), 6.87 (ddd, J=8.1, 2.4, 0.9 Hz, 1H), 3.84 (s, 2H), 2.43-2.29 (m, 2H), 2.12-1.98 (m, 4H), 1.77-1.61 (m, 4H), 1.62-1.52 (m, 2H). HPLC-1: RT=11.2 min, purity=100%; HPLC-2: RT=9.7 min, purity=94.2%.

Example 2

3-(1-(3-Phenoxyphenyl)-2-oxabicyclo[2.2.2]octan-4-yl)propanoic acid

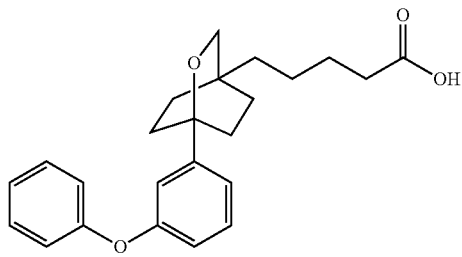

2A. 1-Diazo-4-(1-(3-phenoxyphenyl)-2-oxabicyclo[2.2.2]octan-4-yl)butan-2-one

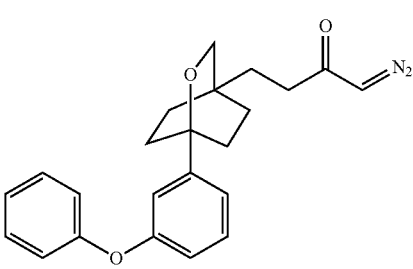

To a solution of Example 1 (75 mg, 0.213 mmol) in DCM (1 mL) at 0° C. was added (COCl)$_2$ (0.32 mL of a 2 M solution in DCM; 0.638 mmol), and a catalytic amount of DMF. The reaction was stirred at rt for 1 h and concentrated in vacuo. The residue was dissolved in THF/MeCN (1:1) (1 mL) and TMSCHN$_2$ (0.532 mL, 1.064 mmol) was added at 0° C. The reaction was then stirred at rt for 18 h. The solvent was removed under reduced pressure and the residue was re-dissolved in EtOAc (5 mL), washed with water (5 mL), sat'd aqueous NaHCO$_3$ (5 mL) and brine (5 mL). The organic phase was dried (MgSO$_4$) and concentrated in vacuo. The crude oil was purified by flash chromatography on SiO$_2$ (50% EtOAc:hexanes) to afford the title compound (70 mg, 87% yield) as a yellowish oil. LCMS, [M+H]$^+$=377.1.

2B. 4-(1-(3-Phenoxyphenyl)-2-oxabicyclo[2.2.2]octan-4-yl)butanoic acid

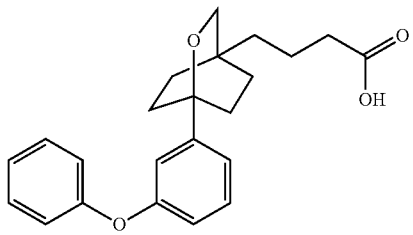 [SMILES: O=C(O)CCCC12CCC(c3cccc(Oc4ccccc4)c3)(CC1)OC2]

A mixture of 1-diazo-4-(1-(3-phenoxyphenyl)-2-oxabicyclo[2.2.2]octan-4-yl)butan-2-one (70 mg, 0.186 mmol) and silver nitrate (95 mg, 0.558 mmol) in THF (1 mL) and water (0.3 mL) was stirred at rt in dark for 3 h. The reaction mixture was concentrated in vacuo to remove THF, and the resulting slurry was partitioned between H$_2$O and EtOAc. The aqueous layer was extracted with EtOAc (2×2 mL). The combined organic layers were concentrated in vacuo and the residue was purified by preparative HPLC (PHENOMENEX® Axia 5µ C18 30×100 mm column; detection at 220 nm; flow rate=40 mL/min; continuous gradient from 50% B to 100% B over 10 min+5 min hold time at 100% B, where A=90:10:0.1 H$_2$O: MeOH:TFA and B=90:10:0.1 MeOH:H$_2$O:TFA) to afford the title compound (61 mg, 85% yield) as a white solid. LCMS, [M−H]$^+$=365.4. $^1$H NMR (500 MHz, CDCl$_3$) δ 7.37-7.26 (m, 3H), 7.19-7.07 (m, 3H), 7.04-6.99 (m, 2H), 6.89-6.84 (m, 1H), 3.83 (s, 2H), 2.37 (t, J=7.4 Hz, 2H), 2.12-1.95 (m, 4H), 1.79-1.54 (m, 6H), 1.26-1.16 (m, 2H).

Example 2

Example 2 was prepared from Intermediate 2B using the same 3-step sequence as described for the synthesis of 2B from 2A (i.e., acid chloride synthesis, followed by conversion to the corresponding diazoketone, then Wolff rearrangement with aqueous AgNO$_3$). The title compound was obtained (19 mg, 0.047 mmol, 57.9% yield) as a white solid. LCMS, [M−H]$^+$=379.4. $^1$H NMR (500 MHz, CDCl$_3$) δ 7.34 (t, J=8.0 Hz, 2H), 7.28 (t, J=7.9 Hz, 2H), 7.20-7.06 (m, 3H), 7.01 (d, J=7.8 Hz, 2H), 6.86 (dd, J=8.0, 1.6 Hz, 1H), 3.81 (s, 2H), 2.39 (t, J=7.4 Hz, 2H), 2.16-1.91 (m, 4H), 1.80-1.51 (m, 6H), 1.40-1.25 (m, 2H), 1.25-1.10 (m, 2H). HPLC-1: RT=12.3 min, purity=93.7%; HPLC-2: RT=10.5 min, purity=94.0%.

Example 3

5-(1-(3-Methoxyphenyl)-2-oxabicyclo[2.2.2]octan-4-yl)pentanoic acid

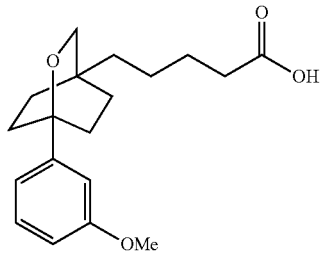 [SMILES: COc1cccc(C23CCC(CCCCC(=O)O)(CC2)CO3)c1]

3A. (4-Hydroxy-4-(3-methoxyphenyl)cyclohexane-1,1-diyl)bis(methylene) bis(4-methylbenzenesulfonate)

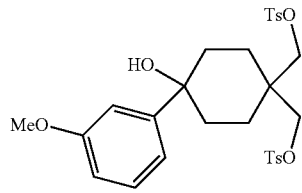 [SMILES: COc1cccc(C2(O)CCC(COS(=O)(=O)c3ccc(C)cc3)(COS(=O)(=O)c3ccc(C)cc3)CC2)c1]

To a solution of (4-oxocyclohexane-1,1-diyl)bis(methylene) bis(4-methylbenzenesulfonate) (417 mg, 0.894 mmol) in THF (5 mL) at 0° C. was added 3-methoxyphenylmagnesium bromide (1.073 mL, 1.073 mmol) dropwise over a period of 5 min. The reaction was stirred at 0° C. for 2 h and quenched with sat'd aqueous NH$_4$Cl (1 mL). The mixture was diluted with EtOAc (10 mL) and washed with water. The organic layer was dried over MgSO$_4$, filtered, and concentrated in vacuo. The residual crude oil was purified by flash chromatography on SiO$_2$ (0-50% EtOAc:hexanes) to afford the title compound (372 mg, 72% yield) as a white solid. $^1$H NMR (500 MHz, CDCl$_3$) δ 7.76 (dd, J=10.9, 8.3 Hz, 4H), 7.37 (d, J=7.7 Hz, 4H), 7.23 (t, J=8.0 Hz, 1H), 6.93-6.88 (m, 1H), 6.88-6.82 (m, 1H), 6.78 (dd, J=8.1, 2.3 Hz, 1H), 4.00 (s, 2H), 3.81-3.78 (m, 5H), 2.47 (s, 3H), 2.43 (s, 3H), 1.79 (s, 1H), 1.73-1.60 (m, 2H), 1.61-1.53 (m, 4H), 1.53-1.45 (m, 2H).

Example 3

Example 3 was prepared using a sequence analogous to that of Examples 1 and 2 except that (4-hydroxy-4-(3-phenoxyphenyl)cyclohexane-1,1-diyl)bis(methylene) bis(4-methylbenzenesulfonate) was replaced with (4-hydroxy-4-(3-methoxyphenyl)cyclohexane-1,1-diyl)bis(methylene) bis(4-methylbenzenesulfonate). The title compound was obtained (12 mg, 0.036 mmol, 49.5% yield) as a white solid. LCMS, [M−H]$^+$=317.2. $^1$H NMR (500 MHz, CDCl$_3$) δ 7.24 (t, J=8.0 Hz, 1H), 7.04-7.00 (m, 1H), 7.00-6.95 (m, 1H), 6.80-6.76 (m, 1H), 3.85-3.82 (m, 5H), 2.40 (t, J=7.4 Hz, 2H), 2.04 (t, J=7.9 Hz, 4H), 1.74-1.60 (m, 6H), 1.38-1.27 (m, 2H), 1.24-1.16 (m, 2H). HPLC-1: RT=9.8 min, purity=100%; HPLC-2: RT=8.5 min, purity=95%.

Example 4

5-(1-(2-Methyl-4-phenylthiazol-5-yl)-2-oxabicyclo[2.2.2]octan-4-yl)pentanoic acid

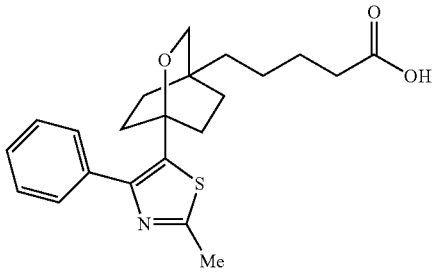 [SMILES: Cc1nc(-c2ccccc2)c(C23CCC(CCCCC(=O)O)(CC2)CO3)s1]

4A. (1-(2-Methyl-4-phenylthiazol-5-yl)-2-oxabicyclo[2.2.2]octan-4-yl)methyl 4-methylbenzenesulfonate

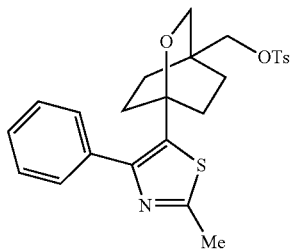 [SMILES: Cc1ccc(S(=O)(=O)OCC23CCC(c4sc(C)nc4-c4ccccc4)(CC2)OC3)cc1]

(1-(2-Methyl-4-phenylthiazol-5-yl)-2-oxabicyclo[2.2.2]octan-4-yl)methyl 4-methylbenzenesulfonate was prepared using a procedure analogous to (1-(3-phenoxyphenyl)-2-oxabicyclo[2.2.2]octan-4-yl)methyl 4-methylbenzenesulfonate except that 1-bromo-3-phenoxybenzene was replaced with 2-methyl-4-phenylthiazole. The title compound was obtained (0.125 g, 0.266 mmol, 62.1% yield) as a light yellowish oil. LCMS, [M+H]$^+$=470.1. $^1$H NMR (500 MHz, CDCl$_3$) δ 7.77-7.72 (m, 2H), 7.43-7.32 (m, 7H), 3.75 (s, 2H), 3.66 (s, 2H), 2.64 (s, 3H), 2.45 (s, 3H), 2.08-1.99 (m, 2H), 1.82 (ddd, J=13.3, 11.6, 4.3 Hz, 2H), 1.61 (qd, J=7.2, 3.0 Hz, 2H), 1.43 (td, J=12.4, 4.8 Hz, 2H).

4B. 5-(4-(Iodomethyl)-2-oxabicyclo[2.2.2]octan-1-yl)-2-methyl-4-phenylthiazole

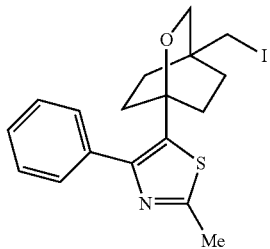 [SMILES: Cc1nc(-c2ccccc2)c(C23CCC(CI)(CC2)CO3)s1]

A mixture of (1-(2-Methyl-4-phenylthiazol-5-yl)-2-oxabicyclo[2.2.2]octan-4-yl)methyl 4-methylbenzenesulfonate (125 mg, 0.266 mmol) and NaI (120 mg, 0.799 mmol) in acetone (5 mL) was stirred in a seal tube at 85° C. for 18 h. The reaction was cooled to rt, diluted with DCM (5 mL), and filtered. The filtrate was concentrated in vacuo and the residue was purified by flash chromatography on SiO$_2$ (0-30% EtOAc:hexanes) to afford the title compound (100 mg, 88% yield) as a light yellow oil. $^1$H NMR (500 MHz, CDCl$_3$) δ 7.45-7.34 (m, 5H), 3.79 (s, 2H), 2.96 (s, 2H), 2.66 (s, 3H), 2.12-2.00 (m, 2H), 1.90-1.78 (m, 2H), 1.71-1.51 (m, 4H).

4C. Methyl 4-(1-(2-methyl-4-phenylthiazol-5-yl)-2-oxabicyclo[2.2.2]octan-4-yl)butanoate

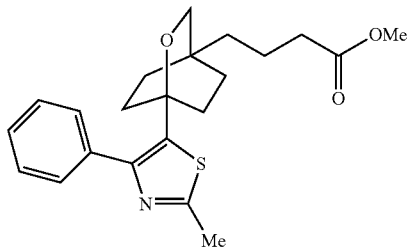 [SMILES: COC(=O)CCCC12CCC(c3sc(C)nc3-c3ccccc3)(CC1)OC2]

To a mixture of zinc powder (154 mg, 2.351 mmol), anhydrous pyridine (5 mL) and methyl acrylate (0.212 ml, 2.351 mmol) at 50° C. was added NiCl$_2$.6H$_2$O (56 mg, 0.235 mmol). The resulting mixture was warmed to 75° C. and stirred for 2 h until its green color turned to reddish brown. After cooling to 0° C., a solution of 5-(4-(iodomethyl)-2-oxabicyclo[2.2.2]octan-1-yl)-2-methyl-4-phenylthiazole (100 mg, 0.235 mmol) in anhydrous pyridine (3 mL) was added and the reaction mixture was stirred for 2 h at room temperature. The mixture was diluted with EtOAc (10 mL) and the resulting precipitate was filtered off through a pad of CELITE®. The filtrate was washed with 1 N aqueous HCl and brine, dried (Na$_2$SO$_4$), and concentrated in vacuo to afford the title compound (77 mg, 85% yield) as a clear oil. LCMS, [M+H]$^+$=386.0. $^1$H NMR (500 MHz, CDCl$_3$) δ 7.46-7.40 (m, 2H), 7.40-7.32 (m, 3H), 3.72 (s, 2H), 3.65 (s, 3H), 2.64 (s, 3H), 2.24 (t, J=7.4 Hz, 2H), 2.07-1.97 (m, 2H), 1.87-1.77 (m, 2H), 1.57-1.45 (m, 6H), 1.12-1.02 (m, 2H).

4D. 4-(1-(2-Methyl-4-phenylthiazol-5-yl)-2-oxabicyclo[2.2.2]octan-4-yl)butanoic acid

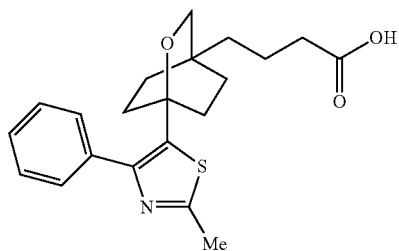 [SMILES: Cc1nc(-c2ccccc2)c(C23CCC(CCCC(=O)O)(CC2)CO3)s1]

A mixture of methyl 4-(1-(2-methyl-4-phenylthiazol-5-yl)-2-oxabicyclo[2.2.2]octan-4-yl)butanoate (77 mg, 0.200 mmol) and 1 N aqueous NaOH (0.200 mL, 0.200 mmol) in MeOH (1 mL) was stirred at rt for 18 h and then concentrated in vacuo. The residue was acidified to pH 2 with 1 N aqueous HCl and extracted with EtOAc. The organic layer was washed with water and concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (51 mg, 65% yield) as a clear oil. LCMS, [M+H]$^+$=372.2. $^1$H NMR (500 MHz, CDCl$_3$) δ 9.86 (s, 1H), 7.56-7.39 (m, 3H), 7.39-7.31 (m, 2H), 3.76 (s, 2H), 2.89 (s, 3H), 2.27 (t, J=7.3 Hz, 2H), 1.99-1.86 (m, 2H), 1.85-1.71 (m, 2H), 1.61-1.41 (m, 6H), 1.17-1.04 (m, 2H).

Example 4

Example 4 was prepared using a procedure analogous to 2B except that Example 1 was replaced with 4-(1-(2-methyl-4-phenylthiazol-5-yl)-2-oxabicyclo[2.2.2]octan-4-yl)butanoic acid. The title compound was obtained (14 mg, 0.034 mmol, 26.7% yield) as a white solid. LCMS, [M+H]$^+$=386.2. $^1$H NMR (500 MHz, CDCl$_3$) δ 9.81 (br, 1H), 7.57-7.51 (m, 1H), 7.48 (t, J=7.5 Hz, 2H), 7.41-7.34 (m, 2H), 3.77 (s, 2H), 2.93 (s, 3H), 2.35 (t, J=7.4 Hz, 2H), 2.00-1.88 (m, 2H), 1.86-1.75 (m, 2H), 1.63-1.47 (m, 6H), 1.22 (dt, J=10.6, 8.0 Hz, 2H), 1.15-1.06 (m, 2H). HPLC-1: RT=11.5 min, purity=100%; HPLC-2: RT=9.9 min, purity=99.0%.

Example 5

3-((1-(3-Phenoxyphenyl)-2-oxabicyclo[2.2.2]octan-4-yl)methoxy)propanoic acid

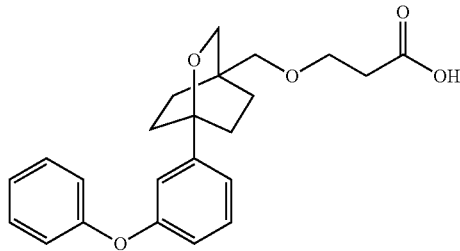

5A. (1-(3-Phenoxyphenyl)-2-oxabicyclo[2.2.2]octan-4-yl)methanol

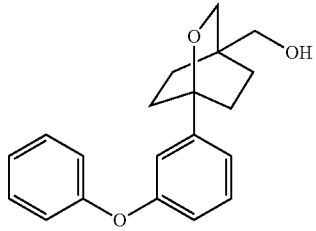 [SMILES: OCC12CCC(c3cccc(Oc4ccccc4)c3)(CC1)OC2]

A mixture of (1-(3-phenoxyphenyl)-2-oxabicyclo[2.2.2]octan-4-yl)methyl 4-methylbenzenesulfonate (0.1 g, 0.215 mmol) and sodium acetate (0.212 g, 2.58 mmol) in DMSO (5 mL) was stirred at 70° C. in a seal tube for 3 days. The reaction was diluted with EtOAc (5 mL) and washed with water (3×5 mL). The organic layer was dried over MgSO$_4$, filtered, and concentrated in vacuo to give (1-(3-phenoxyphenyl)-2-oxabicyclo[2.2.2]octan-4-yl)methyl acetate. The mixture of the above acetate (0.076 g, 0.216 mmol) and 1 M NaOH (0.65 mL, 0.647 mmol) in THF/MeOH (1:1 of a 2 mL solution) was stirred at rt for 18 h. The reaction was diluted with EtOAc (5 mL) and washed with water (3×5 mL). The organic layer was dried over MgSO$_4$, filtered, and concentrated in vacuo. The crude oil was purified by flash chromatography on SiO$_2$ (0 to 50% EtOAc:hexanes) to afford the title compound (0.05 g, 75% yield) as a clear oil. $^1$H NMR (500 MHz, CDCl$_3$) δ 7.39-7.26 (m, 3H), 7.21-7.14 (m, 2H), 7.14-7.08 (m, 1H), 7.05-7.00 (m, 2H), 6.88 (ddd, J=8.1, 2.5, 1.0 Hz, 1H), 3.99-3.89 (m, 2H), 3.38 (s, 2H), 2.16-2.00 (m, 4H), 1.84-1.71 (m, 3H), 1.71-1.57 (m, 2H).

5B. tert-Butyl 3-((1-(3-phenoxyphenyl)-2-oxabicyclo[2.2.2]octan-4-yl)methoxy)propanoate

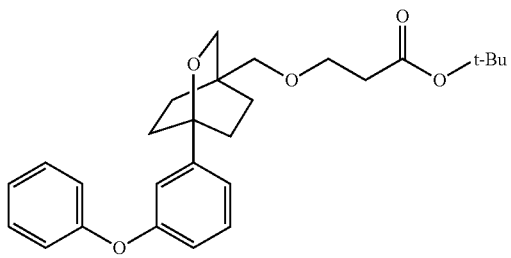 [SMILES: CC(C)(C)OC(=O)CCOCC12CCC(c3cccc(Oc4ccccc4)c3)(CC1)OC2]

A mixture of (1-(3-phenoxyphenyl)-2-oxabicyclo[2.2.2]octan-4-yl)methanol (50 mg, 0.161 mmol), tert-butyl acrylate (0.059 mL, 0.403 mmol), and Triton B (40% in MeOH) (7 μL, 0.016 mmol) in toluene (1 mL) was stirred at rt for 5 h. The mixture was concentrated in vacuo and the residue was purified by flash chromatography on SiO$_2$ (0-30% EtOAc:hexanes) to afford the title compound (61 mg, 85% yield) as a clear oil. $^1$H NMR (500 MHz, CDCl$_3$) δ 7.37-7.31 (m, 2H), 7.28 (dd, J=9.1, 6.7 Hz, 1H), 7.19-7.13 (m, 2H), 7.12-7.07 (m, 1H), 7.01 (ddd, J=4.4, 3.3, 1.8 Hz, 2H), 6.86 (ddd, J=8.0, 2.4, 1.0 Hz, 1H), 3.92 (s, 2H), 3.65 (t, J=6.3 Hz, 2H), 3.17 (s, 2H), 2.48 (t, J=6.3 Hz, 2H), 2.10-1.95 (m, 4H), 1.86-1.73 (m, 2H), 1.70-1.58 (m, 2H), 1.49 (s, 9H).

Example 5

A mixture of tert-butyl 3-((1-(3-phenoxyphenyl)-2-oxabicyclo[2.2.2]octan-4-yl)methoxy)propanoate (61 mg, 0.139 mmol) and 1 M NaOH (1.39 mL, 1.391 mmol) in MeOH (1 mL) was stirred at 70° C. in a sealed tube for 5 h. The reaction was then cooled to rt and concentrated in vacuo. The residue was acidified with TFA and then purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H$_2$O:MeOH:TFA and B=90:10:0.1 MeOH:H$_2$O:TFA) to afford the title compound (43 mg, 79% yield) as a white solid. LCMS, [M−H]$^+$=381.0. $^1$H NMR (500 MHz, CDCl$_3$) δ 10.54 (bs, 1H), 7.39-7.31 (m, 2H), 7.29 (t, J=7.9 Hz, 1H), 7.16 (ddd, J=9.8, 3.1, 1.4 Hz, 2H), 7.13-7.07 (m, 1H), 7.01 (dd, J=8.6, 0.9 Hz, 2H), 6.87 (ddd, J=8.0, 2.4, 0.8 Hz, 1H), 3.93 (s, 2H), 3.70 (t, J=6.2 Hz, 2H), 3.20 (s, 2H), 2.63 (t, J=6.2 Hz, 2H), 2.14-1.97 (m, 4H), 1.86-1.74 (m, 2H), 1.70-1.58 (m, 2H). HPLC-1: RT=11.5 min, purity=100%; HPLC-2: RT=9.9 min, purity=99.0%.

Example 6

2-(2-(1-(3-Phenoxyphenyl)-2-oxabicyclo[2.2.2]octan-4-yl)ethoxy)acetic acid

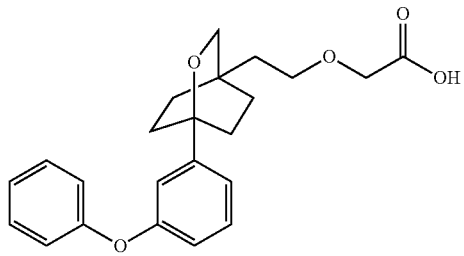 [SMILES: O=C(O)COCCC12CCC(c3cccc(Oc4ccccc4)c3)(CC1)OC2]

6A. 2-(1-(3-Phenoxyphenyl)-2-oxabicyclo[2.2.2]octan-4-yl)acetic acid

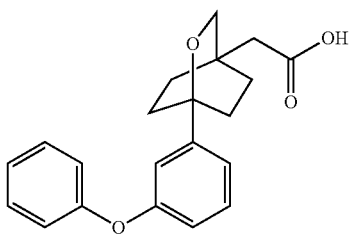 [SMILES: O=C(O)CC12CCC(c3cccc(Oc4ccccc4)c3)(CC1)OC2]

A mixture of (1-(3-phenoxyphenyl)-2-oxabicyclo[2.2.2]octan-4-yl)methyl 4-methylbenzenesulfonate (400 mg, 0.861 mmol), NaCN (127 mg, 2.58 mmol), and tetrabutylammoniumiodide (31.8 mg, 0.086 mmol) was stirred at 165° C. overnight. The reaction mixture was then cooled to rt and extracted with EtOAc (10 mL). The organic extract was washed with water and concentrated in vacuo. The residue was taken up with ethylene glycol (5 mL) and water (1 mL), and 40% aqueous KOH (1208 mg, 8.61 mmol) was added. The reaction was heated at 165° C. for 18 h. The mixture was concentrated in vacuo and the remaining solution was diluted with water and adjusted to pH 3 with conc. HCl. The mixture was extracted with EtOAc (2×5 mL). The combined organic layers were washed with water, dried (MgSO$_4$), filtered, and concentrated in vacuo to afford the title compound (280 mg, 91% yield) as a white solid. LCMS, [M−H]$^+$=337.0. $^1$H NMR (500 MHz, CDCl$_3$) δ 7.38-7.27 (m, 3H), 7.19-7.08 (m, 3H), 7.03-6.99 (m, 2H), 6.87 (ddd, J=8.1, 2.4, 0.9 Hz, 1H), 3.97 (s, 2H), 2.23 (s, 2H), 2.17-2.00 (m, 4H), 1.95-1.79 (m, 4H).

6B. 2-(1-(3-Phenoxyphenyl)-2-oxabicyclo[2.2.2]octan-4-yl)ethanol

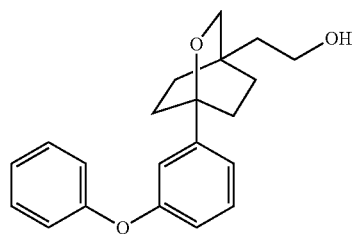 [SMILES: OCCC12CCC(c3cccc(Oc4ccccc4)c3)(CC1)OC2]

A mixture of 2-(1-(3-phenoxyphenyl)-2-oxabicyclo[2.2.2]octan-4-yl)acetic acid (140 mg, 0.414 mmol) and LAH (0.414 mL, 0.414 mmol) in THF (5 mL) was stirred at 0° C. for 2 h. The reaction was quenched with water (1 mL) dropwise and then stirred at rt for 10 min. The mixture was diluted with EtOAc (5 mL) and filtered. The filtrate was washed with water, dried with MgSO$_4$, filtered, and concentrated in vacuo to afford the title compound (64 mg, 48% yield) as a clear oil. LCMS, [M+Na]$^+$=347.1. $^1$H NMR (500 MHz, CDCl$_3$) δ 7.29-7.16 (m, 3H), 7.10-6.96 (m, 3H), 6.96-6.87 (m, 2H), 6.76 (ddd, J=8.1, 2.5, 1.0 Hz, 1H), 3.77 (s, 2H), 3.62 (t, J=7.3 Hz, 2H), 2.07-1.88 (m, 4H), 1.73-1.57 (m, 4H), 1.38 (t, J=7.3 Hz, 2H).

Example 6

To a solution of 2-(1-(3-phenoxyphenyl)-2-oxabicyclo[2.2.2]octan-4-yl)ethanol (60 mg, 0.185 mmol) in toluene (5 mL) was added tetrabutylammonium chloride hydrate (16.4 mg, 0.055 mmol). The reaction mixture was cooled to 0° C. and added 35% NaOH (5 mL), followed by tert-butyl bromoacetate (0.041 mL, 0.277 mmol). The reaction was stirred at rt for 4 h. The organic layer was separated, washed with 1 N aqueous HCl (3×5 mL) and brine (5 mL), dried, and concentrated in vacuo to afford tert-butyl 2-(2-(1-(3-phenoxyphenyl)-2-oxabicyclo[2.2.2]octan-4-yl)ethoxy)acetate. The above ester was stirred with 1 N aqueous NaOH (3 mL) and MeOH (5 mL) under reflux for 2 h. The mixture was concentrated in vacuo. The residue was dissolved in EtOAc (5 mL), washed with 1 N aqueous HCl (5 mL) and H$_2$O (3×5 mL), and concentrated in vacuo. The crude product was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (50 mg, 67% yield) as a clear oil. LCMS, [M+H]$^+$=383.2. $^1$H NMR (500 MHz, CDCl$_3$) δ 9.59 (s, 1H), 7.35-7.21 (m, 3H), 7.17-7.02 (m, 3H), 7.02-6.92 (m, 2H), 6.85 (ddd, J=8.1, 2.4, 1.0 Hz, 1H), 4.10 (s, 2H), 3.87 (s, 2H), 3.59 (t, J=6.9 Hz, 2H), 2.16-1.92 (m, 4H), 1.72 (q, J=7.6 Hz, 4H), 1.53 (t, J=6.9 Hz, 2H). HPLC-1: RT=11.0 min, purity=92.1%; HPLC-2: RT=9.7 min, purity=91.1%.

Example 7

2-(2-(1-(3-Isopropoxyphenyl)-2-oxabicyclo[2.2.2]octan-4-yl)ethoxy)acetic acid

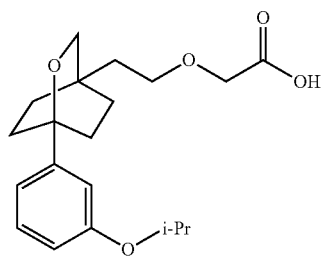 [SMILES: CC(C)Oc1cccc(C23CCC(CCOCC(=O)O)(CC2)CO3)c1]

7A. 4-(Iodomethyl)-1-(3-(tetrahydro-2H-pyran-2-yloxy)phenyl)-2-oxabicyclo[2.2.2]octane

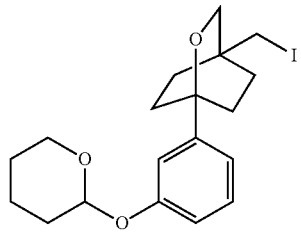 [SMILES: ICC12CCC(c3cccc(OC4CCCCO4)c3)(CC1)OC2]

4-(Iodomethyl)-1-(3-(tetrahydro-2H-pyran-2-yloxy)phenyl)-2-oxabicyclo[2.2.2]octane was prepared using a procedure analogous to 5-(4-(iodomethyl)-2-oxabicyclo[2.2.2]octan-1-yl)-2-methyl-4-phenylthiazole except that 2-methyl-4-phenylthiazole was replaced with 2-(3-bromophenoxy)tetrahydro-2H-pyran. The title compound was obtained (1.2 g, 2.80 mmol, 100% yield) as a white solid. $^1$H NMR (500 MHz, CDCl$_3$) δ 7.24 (t, J=8.0 Hz, 1H), 7.14-7.11 (m, 1H), 7.02 (ddd, J=7.8, 1.6, 1.0 Hz, 1H), 6.96 (ddd, J=8.2, 2.5, 0.9 Hz, 1H), 5.45 (t, J=3.2 Hz, 1H), 4.00-3.87 (m, 3H), 3.62 (dtd, J=11.3, 4.1, 1.2 Hz, 1H), 3.08 (s, 2H), 2.16-1.98 (m, 5H), 1.93-1.58 (m, 9H).

7B. 2-(1-(3-Hydroxyphenyl)-2-oxabicyclo[2.2.2]octan-4-yl)acetic acid

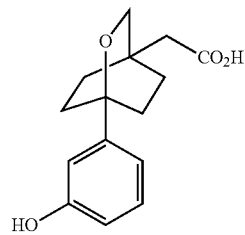 [SMILES: O=C(O)CC12CCC(c3cccc(O)c3)(CC1)OC2]

A mixture of 4-(iodomethyl)-1-(3-(tetrahydro-2H-pyran-2-yloxy)phenyl)-2-oxabicyclo[2.2.2]octane (1.5 g, 3.50 mmol) and NaCN (0.687 g, 14.01 mmol) in DMF (8 mL) was stirred at 80° C. for 18 h. The reaction was diluted with EtOAc (10 mL), washed with water (3×10 mL). The organic layer was dried over MgSO₄, filtered, and concentrated in vacuo to give 2-(1-(3-(tetrahydro-2H-pyran-2-yloxy)phenyl)-2-oxabicyclo[2.2.2]octan-4-yl)acetonitrile (1.15 g, 3.50 mmol, 100% yield) as light brown oil. The above nitrile (1.15 g, 3.50 mmol) was taken up in ethylene glycol (20 mL) and treated with 40% KOH (5.00 mL, 35.0 mmol). The reaction was stirred at 165° C. for 18 h and concentrated in vacuo. The residue was dissolved in water (15 mL), acidified to pH 2 with 1 N aqueous HCl, and extracted with EtOAc (5×5 mL). The combined extracts were washed with brine, dried with MgSO₄, filtered, and concentrated in vacuo to afford the title compound (0.91 g, 99% yield) as a light brown solid. LCMS, [M−H]⁺=261.3.

7C. Methyl 2-(1-(3-hydroxyphenyl)-2-oxabicyclo[2.2.2]octan-4-yl)acetate

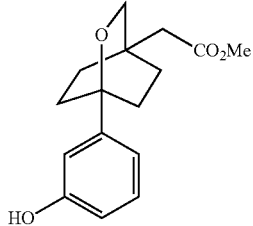 [SMILES: COC(=O)CC12CCC(c3cccc(O)c3)(CC1)OC2]

A mixture of 2-(1-(3-hydroxyphenyl)-2-oxabicyclo[2.2.2]octan-4-yl)acetic acid (910 mg, 3.47 mmol) and p-TsOH (66 mg, 0.347 mmol) in MeOH (10 mL) was stirred at 60° C. for 18 h. The reaction was concentrated in vacuo. The crude oil was purified by flash chromatography on SiO₂ (0 to 50% EtOAc:hexanes) to afford the title compound (887 mg, 93% yield) as a clear oil. LCMS, [M+H]⁺=277.3. ¹H NMR (500 MHz, CDCl₃) δ 7.13 (t, J=7.9 Hz, 1H), 6.93-6.84 (m, 2H), 6.69-6.63 (m, 1H), 6.13 (s, 1H), 3.94 (s, 2H), 3.67 (s, 3H), 2.18 (s, 2H), 2.06-1.94 (m, 4H), 1.86-1.72 (m, 4H).

7D. Methyl 2-(1-(3-(tetrahydro-2H-pyran-2-yloxy)phenyl)-2-oxabicyclo[2.2.2]octan-4-yl)acetate

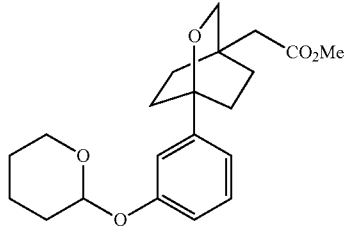 [SMILES: COC(=O)CC12CCC(c3cccc(OC4CCCCO4)c3)(CC1)OC2]

A mixture of methyl 2-(1-(3-hydroxyphenyl)-2-oxabicyclo[2.2.2]octan-4-yl)acetate (887 mg, 3.21 mmol), 3,4-dihydro-2H-pyran (0.5 ml, 5.47 mmol), and PPTS (81 mg, 0.321 mmol) in DCM (10 ml) was stirred at rt for 4 days. The reaction was concentrated in vacuo. The crude oil was purified by flash chromatography on SiO₂ (0 to 30% EtOAc:hexanes) to afford the title compound (887 mg, 77% yield) as a white solid. LCMS, [M+NH₄]⁺=378.4. ¹H NMR (500 MHz, CDCl₃) δ 7.21 (t, J=8.0 Hz, 1H), 7.13-7.08 (m, 1H), 6.99 (ddd, J=7.8, 1.5, 1.0 Hz, 1H), 6.93 (ddd, J=8.2, 2.5, 0.9 Hz, 1H), 5.43 (t, J=3.2 Hz, 1H), 3.97-3.86 (m, 3H), 3.67 (s, 3H), 3.64-3.54 (m, 1H), 2.17 (s, 2H), 2.11-1.96 (m, 5H), 1.90-1.74 (m, 6H), 1.72-1.49 (m, 3H).

7E. tert-Butyl 2-(2-(1-(3-(tetrahydro-2H-pyran-2-yloxy)phenyl)-2-oxabicyclo[2.2.2]octan-4-yl)ethoxy)acetate

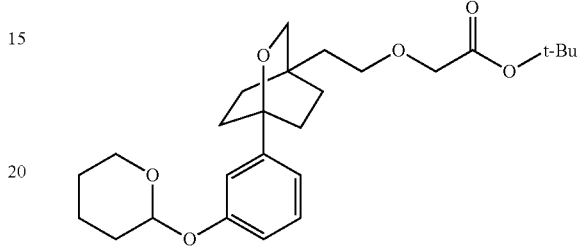

tert-Butyl 2-(2-(1-(3-(tetrahydro-2H-pyran-2-yloxy)phenyl)-2-oxabicyclo[2.2.2]octan-4-yl)ethoxy)acetate was prepared using a procedure analogous to tert-butyl 2-(2-(1-(3-phenoxyphenyl)-2-oxabicyclo[2.2.2]octan-4-yl)ethoxy)acetate except that 2-(1-(3-phenoxyphenyl)-2-oxabicyclo[2.2.2]octan-4-yl)acetic acid was replace with methyl 2-(1-(3-(tetrahydro-2H-pyran-2-yloxy)phenyl)-2-oxabicyclo[2.2.2]octan-4-yl)acetate. The title compound was obtained (1 g, 2.24 mmol, 91% yield) as a clear oil. ¹H NMR (500 MHz, CDCl₃) δ 7.23-7.19 (m, 1H), 7.12-7.09 (m, 1H), 7.02-6.98 (m, 1H), 6.93 (ddd, J=8.3, 2.5, 0.8 Hz, 1H), 5.43 (t, J=3.3 Hz, 1H), 5.31 (s, 1H), 3.94 (s, 2H), 3.88-3.86 (m, 2H), 3.63-3.54 (m, 3H), 2.05-1.99 (m, 5H), 1.88-1.82 (m, 2H), 1.75-1.69 (m, 5H), 1.69-1.56 (m, 4H), 1.55-1.51 (m, 2H), 1.50 (s, 9H).

7F. tert-Butyl 2-(2-(1-(3-hydroxyphenyl)-2-oxabicyclo[2.2.2]octan-4-yl)ethoxy)acetate

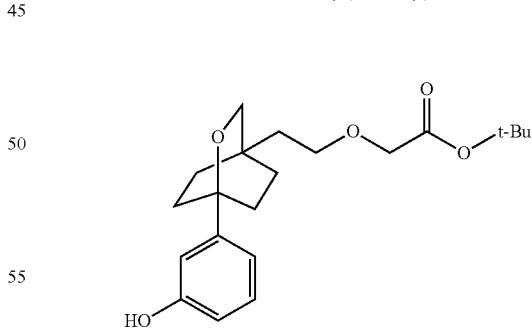

A mixture of tert-butyl 2-(2-(1-(3-(tetrahydro-2H-pyran-2-yloxy)phenyl)-2-oxabicyclo[2.2.2]octan-4-yl)ethoxy)acetate (1000 mg, 2.24 mmol) and PPTS (169 mg, 0.672 mmol) in MeOH (10 ml) was stirred at 50° C. for 3 h. The reaction was concentrated in vacuo. The crude oil was purified by flash chromatography on SiO₂ (0 to 30% EtOAc:hexanes) to afford the title compound (723 mg, 89% yield) as a white solid. LCMS, [M−H]⁺=361.4. ¹H NMR (500 MHz, CDCl₃) δ 7.19 (t, J=8.1 Hz, 1H), 6.96-6.91 (m, 2H), 6.71 (ddd, J=8.0, 2.5, 1.0

Hz, 1H), 4.83 (s, 1H), 3.96 (s, 2H), 3.89 (s, 2H), 3.59 (t, J=6.9 Hz, 2H), 2.06-2.00 (m, 4H), 1.78-1.71 (m, 4H), 1.54 (t, J=7.0 Hz, 2H), 1.51 (s, 9H).

Example 7

A mixture of tert-butyl 2-(2-(1-(3-hydroxyphenyl)-2-oxabicyclo[2.2.2]octan-4-yl)ethoxy)acetate (25 mg, 0.069 mmol), K$_2$CO$_3$ (47.7 mg, 0.345 mmol) and 2-iodopropane (0.014 ml, 0.140 mmol) in DMF (0.5 mL) was stirred at 70° C. for 3 h. The reaction was diluted with EtOAc (5 mL) and washed with water. The organic layer was concentrated in vacuo to give the crude tert-butyl ester. This ester was stirred with 1 M NaOH (0.690 mL, 0.690 mmol) in THF (2 mL) at rt for 18 h. The reaction was concentrated in vacuo. The residue was dissolved in EtOAc (3 mL) and washed with 1 N aqueous HCl, water, and concentrated in vacuo. The crude product was purified by preparative HPLC (PHENOMENEX® Axia 5μ C18 30×100 mm column; detection at 220 nm; flow rate=40 mL/min; continuous gradient from 40% B to 100% B over 10 min+2 min hold time at 100% B, where A=90:10:0.1 H$_2$O:MeOH:TFA and B=90:10:0.1 MeOH:H$_2$O:TFA) to afford the title compound (14 mg, 55% yield) as a clear oil. LCMS, [M−H]$^+$=347.4. $^1$H NMR (500 MHz, CDCl$_3$) δ 8.45 (s, 1H), 7.22 (t, J=8.0 Hz, 1H), 7.02-6.89 (m, 2H), 6.77 (ddd, J=8.2, 2.4, 0.6 Hz, 1H), 4.58 (dt, J=12.1, 6.1 Hz, 1H), 4.13 (s, 2H), 3.90 (s, 2H), 3.64 (t, J=7.0 Hz, 2H), 2.14-1.97 (m, 4H), 1.73 (t, J=7.9 Hz, 4H), 1.56 (t, J=7.0 Hz, 2H), 1.34 (d, J=6.1 Hz, 6H). HPLC-1: RT=10.0 min, purity=100%; HPLC-2: RT=8.4 min, purity=100%.

Example 8

2-(2-(1-(3-(Cyclohexyloxy)phenyl)-2-oxabicyclo[2.2.2]octan-4-yl)ethoxy)acetic acid

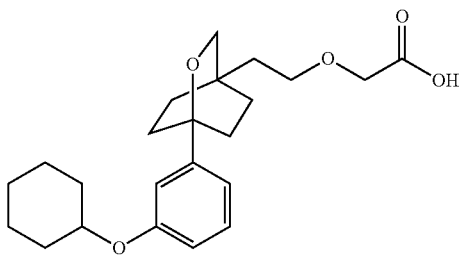 [SMILES: O=C(O)COCCC12CCC(c3cccc(OC4CCCCC4)c3)(CC1)OC2]

Example 8 was prepared using a procedure analogous to that used for the synthesis of Example 7 except that 2-iodopropane was replaced with iodocyclohexane. The title compound was obtained (4 mg, 9.8 μmol, 18% yield) as a clear oil. LCMS, [M−H]$^+$=387.2. $^1$H NMR (500 MHz, CDCl$_3$) δ 7.21 (t, J=7.8 Hz, 1H), 7.01-6.97 (m, 1H), 6.94 (dt, J=7.8, 1.3 Hz, 1H), 6.78 (ddd, J=8.3, 2.5, 0.8 Hz, 1H), 4.30-4.23 (m, 1H), 4.13 (s, 2H), 3.89 (s, 2H), 3.65 (t, J=7.0 Hz, 2H), 2.11-1.95 (m, 6H), 1.82 (dd, J=9.5, 3.7 Hz, 2H), 1.78-1.70 (m, 4H), 1.63-1.48 (m, 5H), 1.44-1.27 (m, 3H). HPLC-1: RT=12.0 min, purity=100%; HPLC-2: RT=9.8 min, purity=95.0%.

Example 9

2-(2-(1-(3-Isobutoxyphenyl)-2-oxabicyclo[2.2.2]octan-4-yl)ethoxy)acetic acid

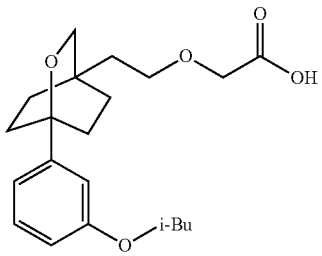

Example 9 was prepared using a procedure analogous to Example 7 except that 2-iodopropane was replaced with 1-iodo-2-methylpropane. The title compound was obtained (14 mg, 0.037 mmol, 83% yield) as clear oil. LCMS, [M−H]$^+$=361.1. $^1$H NMR (500 MHz, CDCl$_3$) δ 7.23 (t, J=8.0 Hz, 1H), 7.01-6.98 (m, 1H), 6.96-6.92 (m, 1H), 6.78 (ddd, J=8.1, 2.6, 1.1 Hz, 1H), 4.13 (s, 2H), 3.91 (s, 2H), 3.74 (d, J=6.6 Hz, 2H), 3.63 (t, J=7.0 Hz, 2H), 2.14-2.01 (m, 5H), 1.74 (t, J=7.8 Hz, 4H), 1.56 (t, J=7.0 Hz, 2H), 1.04 (d, J=6.6 Hz, 6H). HPLC-1: RT=6.6 min, purity=95.0%; HPLC-2: RT=5.5 min, purity=95.0%.

Example 10

5-(1-(3-(Tetrahydro-2H-pyran-2-yloxy)phenyl)-2-oxabicyclo[2.2.2]octan-4-yl)pentanoic acid

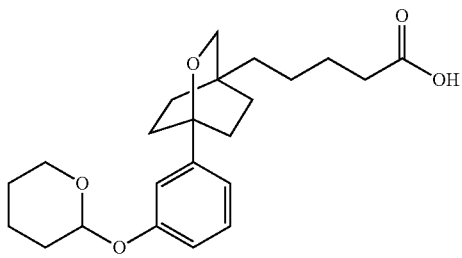 [SMILES: O=C(O)CCCCC12CCC(c3cccc(OC4CCCCO4)c3)(CC1)OC2]

10A. 4-(1-(3-(Tetrahydro-2H-pyran-2-yloxy)phenyl)-2-oxabicyclo[2.2.2]octan-4-yl)butanoic acid

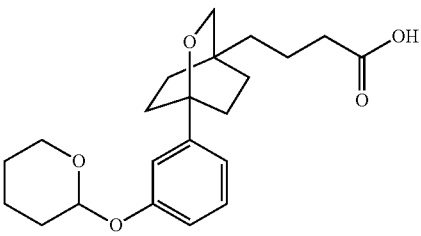 [SMILES: O=C(O)CCCC12CCC(c3cccc(OC4CCCCO4)c3)(CC1)OC2]

4-(1-(3-(Tetrahydro-2H-pyran-2-yloxy)phenyl)-2-oxabicyclo[2.2.2]octan-4-yl)butanoic acid was prepared using a procedure analogous to 5-(1-(2-methyl-4-phenylthiazol-5- yl)-2-oxabicyclo[2.2.2]octan-4-yl)pentanoic acid except that 5-(4-(iodomethyl)-2-oxabicyclo[2.2.2]octan-1-yl)-2-methyl-4-phenylthiazole was replaced with 4-(iodomethyl)-1-(3-(tetrahydro-2H-pyran-2-yloxy)phenyl)-2-oxabicyclo[2.2.2]octane. The title compound was obtained (0.88 g, 2.2 mmol, 95% yield) as a clear oil. LCMS, [M−H]⁺=373.1. ¹H NMR (500 MHz, CDCl₃) δ 7.23 (t, J=8.0 Hz, 1H), 7.17-7.10 (m, 1H), 7.05-6.99 (m, 1H), 6.95 (ddd, J=8.2, 2.5, 0.9 Hz, 1H), 5.45 (t, J=3.2 Hz, 1H), 3.94 (ddd, J=11.3, 9.9, 3.0 Hz, 1H), 3.84 (s, 2H), 3.67-3.58 (m, 1H), 2.36 (t, J=7.4 Hz, 2H), 2.11-1.99 (m, 5H), 1.91-1.82 (m, 2H), 1.77-1.54 (m, 9H), 1.26-1.16 (m, 2H).

10B. 4-(1-(3-(Tetrahydro-2H-pyran-2-yloxy)phenyl)-2-oxabicyclo[2.2.2]octan-4-yl)butan-1-ol

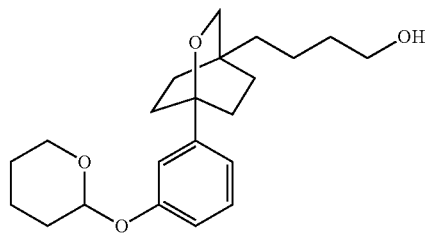 [SMILES: OCCCCC12CCC(c3cccc(OC4CCCCO4)c3)(CC1)OC2]

To a solution of 4-(1-(3-(tetrahydro-2H-pyran-2-yloxy)phenyl)-2-oxabicyclo[2.2.2]octan-4-yl)butanoic acid (115 mg, 0.307 mmol) in dry THF (1 mL) at 0° C. under N₂ was added BH₃.THF (0.461 ml, 0.461 mmol) over a period of 3 min. The resulting mixture was stirred at 0° C. for 30 min and at room temperature 3 h. The reaction was cooled to 0° C. and quenched with water carefully. The mixture was extracted with ethyl acetate. The organic layer was washed with sat'd aqueous NaHCO₃, water, dried, and the concentrated in vacuo to afford the title compound (111 mg, 100% yield) as a clear oil. ¹H NMR (500 MHz, CDCl₃) δ 7.23 (t, J=8.0 Hz, 1H), 7.14-7.11 (m, 1H), 7.04-7.00 (m, 1H), 6.94 (ddd, J=8.2, 2.5, 0.8 Hz, 1H), 5.45 (t, J=3.2 Hz, 1H), 3.98-3.91 (m, 1H), 3.83 (s, 2H), 3.67 (t, J=6.5 Hz, 2H), 3.64-3.58 (m, 1H), 2.04 (t, J=7.8 Hz, 5H), 1.90-1.83 (m, 2H), 1.75-1.50 (m, 10H), 1.38-1.26 (m, 2H), 1.22-1.15 (m, 2H).

10C. 4-(1-(3-(Tetrahydro-2H-pyran-2-yloxy)phenyl)-2-oxabicyclo[2.2.2]octan-4-yl)butyl methanesulfonate

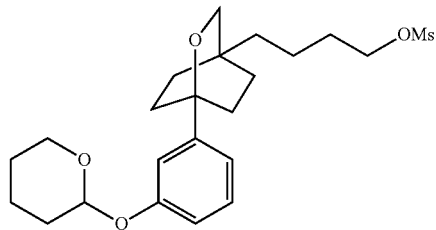 [SMILES: CS(=O)(=O)OCCCCC12CCC(c3cccc(OC4CCCCO4)c3)(CC1)OC2]

MsCl (0.036 ml, 0.462 mmol) was added to a solution of 4-(1-(3-(tetrahydro-2H-pyran-2-yloxy)phenyl)-2-oxabicyclo[2.2.2] octan-4-yl)butan-1-ol (111 mg, 0.31 mmol) and TEA (0.129 ml, 0.92 mmol) in DCM (2 mL) at 0° C. The reaction was then stirred at rt for 2 h and concentrated in vacuo. The residue was dissolved in EtOAc (5 mL), washed with water (4×5 mL), dried over MgSO₄, filtered, and concentrated in vacuo. The residue was purified by flash chromatography on SiO₂ (gradient from 0 to 50% EtOAc: hexanes) to afford the title compound (133 mg, 98% yield) as a clear oil. ¹H NMR (500 MHz, CDCl₃) δ 7.23 (t, J=8.0 Hz, 1H), 7.13-7.10 (m, 1H), 7.03-6.99 (m, 1H), 6.94 (ddd, J=8.2, 2.5, 0.8 Hz, 1H), 5.44 (t, J=3.2 Hz, 1H), 4.25 (t, J=6.5 Hz, 2H), 4.04-3.88 (m, 1H), 3.82 (s, 2H), 3.67-3.55 (m, 1H), 3.03 (s, 3H), 2.06-1.99 (m, 5H), 1.90-1.83 (m, 2H), 1.79-1.57 (m, 9H), 1.43-1.34 (m, 2H), 1.23-1.16 (m, 2H).

10D. 5-(1-(3-(Tetrahydro-2H-pyran-2-yloxy)phenyl)-2-oxabicyclo[2.2.2]octan-4-yl)pentanenitrile

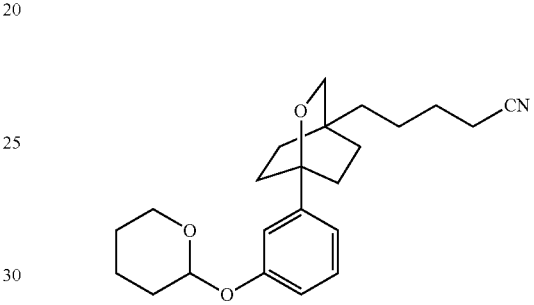

A mixture of 4-(1-(3-(tetrahydro-2H-pyran-2-yloxy)phenyl)-2-oxabicyclo [2.2.2]octan-4-yl)butyl methanesulfonate (133 mg, 0.303 mmol) and NaCN (60 mg, 1.224 mmol) in DMF (2 mL) was stirred at 60° C. for 18 h. The reaction was cooled to rt and diluted with EtOAc (6 mL). The organic phase was washed with water (5×5 mL), dried (MgSO₄), and concentrated in vacuo to afford the title compound (102 mg, 91% yield) as a light yellow oil. LCMS, [M+H]⁺=370.5. ¹H NMR (500 MHz, CDCl₃) δ 7.23 (t, J=8.0 Hz, 1H), 7.13-7.10 (m, 1H), 7.01 (ddd, J=7.8, 1.6, 1.0 Hz, 1H), 6.94 (ddd, J=8.2, 2.5, 0.9 Hz, 1H), 5.45 (t, J=3.2 Hz, 1H), 3.98-3.89 (m, 1H), 3.83 (s, 2H), 3.66-3.57 (m, 1H), 2.38 (t, J=7.1 Hz, 2H), 2.10-1.96 (m, 5H), 1.90-1.81 (m, 2H), 1.75-1.55 (m, 10H), 1.49-1.37 (m, 2H), 1.22-1.14 (m, 2H).

Example 10

A mixture of 5-(1-(3-(tetrahydro-2H-pyran-2-yloxy)phenyl)-2-oxabicyclo [2.2.2]octan-4-yl)pentanenitrile (102 mg, 0.276 mmol) and 4 N aq. NaOH (0.690 mL, 2.76 mmol) in EtOH (5 mL) was stirred under reflux for 3 days. The reaction was cooled to 0° C. and carefully acidified to pH 3 with 1 N aq. HCl. The mixture was extracted with EtOAc (3×5 mL). The combined organic extracts were washed with water (3×5 mL), dried (MgSO₄) and concentrated in vacuo to afford the title compound (98 mg, 87% yield) as a light yellow solid. LCMS, [M−H]⁺=387.4. ¹H NMR (500 MHz, CDCl₃) δ 7.23 (t, J=8.0 Hz, 1H), 7.15-7.11 (m, 1H), 7.02 (d, J=7.9 Hz, 1H), 6.94 (dd, J=8.1, 2.4 Hz, 1H), 5.45 (t, J=3.2 Hz, 1H), 3.98-3.90 (m, 1H), 3.83 (s, 2H), 3.67-3.58 (m, 1H), 2.39 (t, J=7.4 Hz, 2H), 2.11-1.97 (m, 5H), 1.91-1.83 (m, 2H), 1.77-1.55 (m, 9H), 1.38-1.26 (m, 2H), 1.23-1.15 (m, 2H).

Example 11

(E)-5-(1-(3-Phenoxyphenyl)-2-oxabicyclo[2.2.2]octan-4-yl)pent-2-enoic acid

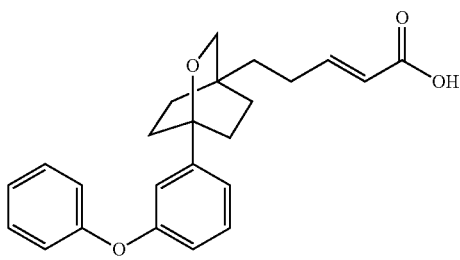 [SMILES: O=C(O)/C=C/CCC12CCC(c3cccc(Oc4ccccc4)c3)(CC1)OC2]

11A. 3-(1-(3-(Tetrahydro-2H-pyran-2-yloxy)phenyl)-2-oxabicyclo[2.2.2]octan-4-yl)propanenitrile

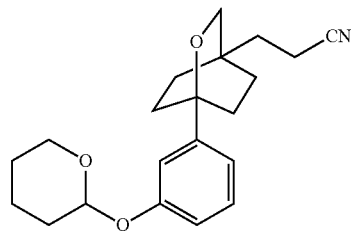 [SMILES: N#CCCC12CCC(c3cccc(OC4CCCCO4)c3)(CC1)OC2]

3-(1-(3-(Tetrahydro-2H-pyran-2-yloxy)phenyl)-2-oxabicyclo[2.2.2]octan-4-yl)propanenitrile was prepared using a procedure analogous to 5-(1-(3-(tetrahydro-2H-pyran-2-yloxy)phenyl)-2-oxabicyclo[2.2.2]octan-4-yl)pentanenitrile except that 4-(1-(3-(tetrahydro-2H-pyran-2-yloxy)phenyl)-2-oxabicyclo[2.2.2]octan-4-yl)butan-1-ol was replaced with 2-(1-(3-(tetrahydro-2H-pyran-2-yloxy)phenyl)-2-oxabicyclo[2.2.2]octan-4-yl)ethanol. The title compound was obtained (490 mg, 1.435 mmol, 87% yield) as a white solid. LCMS, $[M+NH_4]^+$=359.2. $^1$H NMR (500 MHz, CDCl$_3$) δ 7.24 (t, J=8.0 Hz, 1H), 7.14-7.10 (m, 1H), 7.03-6.99 (m, 1H), 6.96 (ddd, J=8.2, 2.5, 0.8 Hz, 1H), 5.45 (t, J=3.2 Hz, 1H), 3.94 (ddd, J=11.3, 9.7, 3.2 Hz, 1H), 3.85 (s, 2H), 3.62 (m, 1H), 2.36-2.30 (m, 2H), 2.11-1.98 (m, 5H), 1.90-1.84 (m, 2H), 1.77-1.59 (m, 9H).

11B. 3-(1-(3-(Tetrahydro-2H-pyran-2-yloxy)phenyl)-2-oxabicyclo[2.2.2]octan-4-yl)propanal

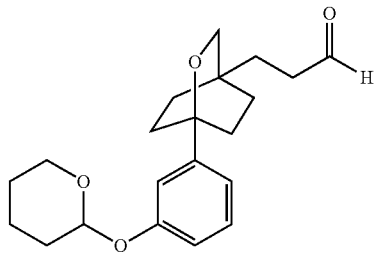 [SMILES: O=CCCC12CCC(c3cccc(OC4CCCCO4)c3)(CC1)OC2]

1.0 M DIBAL-H in DCM (2.153 ml, 2.153 mmol) was added dropwise to a solution of 3-(1-(3-(tetrahydro-2H-pyran-2-yloxy)phenyl)-2-oxabicyclo[2.2.2]octan-4-yl)propanenitrile (490 mg, 1.435 mmol) in DCM (10 mL) at −78° C. under N$_2$. The reaction mixture was stirred at −78° C. for 2 h, added CELITE® (750 mg), and quenched with sat'd aqueous NH$_4$Cl (1 mL) at −78° C. The reaction was stirred at rt for 30 min and then added MgSO$_4$ (500 mg). The mixture was stirred at rt for another 1 h and then filtered. The solid was washed with DCM. The filtrate was concentrated in vacuo and purified by flash chromatography on SiO$_2$ (0 to 30% EtOAc:hexanes) to afford the title compound (493 mg, 100% yield) as a white solid. LCMS, $[M-H]^+$=343.2. $^1$H NMR (500 MHz, CDCl$_3$) δ 9.82 (t, J=1.5 Hz, 1H), 7.24 (t, J=8.0 Hz, 1H), 7.15-7.10 (m, 1H), 7.04-6.98 (m, 1H), 6.95 (ddd, J=8.2, 2.5, 0.8 Hz, 1H), 5.45 (t, J=3.3 Hz, 1H), 3.94 (ddd, J=11.4, 9.9, 3.2 Hz, 1H), 3.84 (s, 2H), 3.65-3.59 (m, 1H), 2.47-2.42 (m, 2H), 2.10-1.98 (m, 5H), 1.89-1.84 (m, 2H), 1.75-1.60 (m, 7H), 1.56-1.51 (m, 2H).

11C. (E)-Methyl 5-(1-(3-(tetrahydro-2H-pyran-2-yloxy)phenyl)-2-oxabicyclo[2.2.2]octan-4-yl)pent-2-enoate

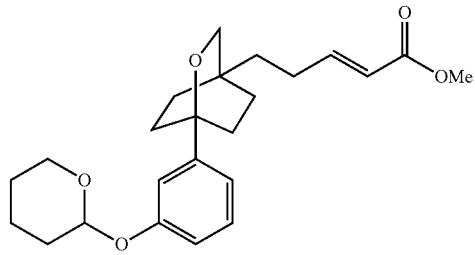 [SMILES: COC(=O)/C=C/CCC12CCC(c3cccc(OC4CCCCO4)c3)(CC1)OC2]

To a 0° C. suspension of LiCl (55.4 mg, 1.306 mmol) in MeCN (2 mL) under N$_2$ was added trimethyl phosphonoacetate (0.188 mL, 1.306 mmol) and DBU (0.197 mL, 1.31 mmol). The reaction was stirred at 0° C. for 30 minutes, and then 3-(1-(3-(tetrahydro-2H-pyran-2-yloxy)phenyl)-2-oxabicyclo[2.2.2]octan-4-yl)propanal (300 mg, 0.871 mmol) was added. The reaction was stirred at rt for 2 h and concentrated in vacuo. The residue was diluted with Et$_2$O, washed with 1 N aq. HCl, satd aq. NaHCO$_3$, brine, dried (MgSO$_4$), filtered, and concentrated in vacuo. The crude oil was purified by flash chromatography on SiO$_2$ (0 to 30% EtOAc:hexanes) to afford the title compound (300 mg, 86% yield) as a white solid. LCMS, $[M+NH_4]^+$=418.2. $^1$H NMR (500 MHz, CDCl$_3$) δ 7.23 (t, J=8.0 Hz, 1H), 7.14-7.11 (m, 1H), 7.03-6.93 (m, 3H), 5.86 (dt, J=15.7, 1.5 Hz, 1H), 5.45 (t, J=3.2 Hz, 1H), 3.94 (ddd, J=11.3, 9.9, 3.0 Hz, 1H), 3.84 (s, 2H), 3.75 (s, 3H), 3.65-3.59 (m, 1H), 2.23-2.15 (m, 2H), 2.09-1.98 (m, 5H), 1.89-1.84 (m, 2H), 1.75-1.58 (m, 8H), 1.37-1.31 (m, 2H).

11D. (E)-Methyl 5-(1-(3-hydroxyphenyl)-2-oxabicyclo[2.2.2]octan-4-yl)pent-2-enoate

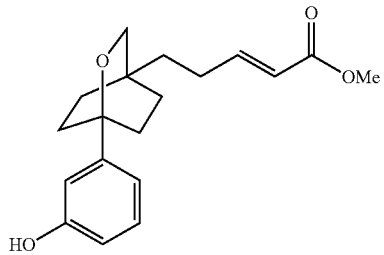 [SMILES: COC(=O)/C=C/CCC12CCC(c3cccc(O)c3)(CC1)OC2]

(E)-Methyl 5-(1-(3-hydroxyphenyl)-2-oxabicyclo[2.2.2]octan-4-yl)pent-2-enoate was prepared using a procedure analogous to tert-butyl 2-(2-(1-(3-hydroxyphenyl)-2-oxabicyclo[2.2.2]octan-4-yl)ethoxy)acetate except that tert-butyl 2-(2-(1-(3-(tetrahydro-2H-pyran-2-yloxy)phenyl)-2-oxabicyclo[2.2.2]octan-4-yl)ethoxy)acetate was replaced with (E)-methyl 5-(1-(3-(tetrahydro-2H-pyran-2-yloxy)phenyl)-2-oxabicyclo[2.2.2]octan-4-yl)pent-2-enoate. The title compound was obtained (210 mg, 0.66 mmol, 89% yield) as a white solid. LCMS, [M−H]+=315.2. 1H NMR (500 MHz, CDCl3) δ 7.17 (t, J=8.0 Hz, 1H), 7.03-6.89 (m, 3H), 6.70 (ddd, J=8.0, 2.5, 1.0 Hz, 1H), 5.87 (dt, J=15.7, 1.5 Hz, 1H), 5.71 (s, 1H), 3.85 (s, 2H), 3.76 (s, 3H), 2.23-2.15 (m, 2H), 2.03 (dd, J=9.1, 4.7 Hz, 4H), 1.74-1.62 (m, 4H), 1.37-1.30 (m, 2H).

Example 11

Example 11 was prepared using a procedure analogous to Example 22 except that tert-butyl 2-(2-(1-(3-hydroxyphenyl)-2-oxabicyclo[2.2.2]octan-4-yl)ethoxy)acetate was replaced with (E)-methyl 5-(1-(3-hydroxyphenyl)-2-oxabicyclo[2.2.2]octan-4-yl)pent-2-enoate and pyridine-3-boronic acid was replaced with phenylboronic acid. The title compound was obtained (73 mg, 0.183 mmol, 71.9% yield) as white solid. LCMS, [M−H]+=377.1. 1H NMR (500 MHz, CDCl3) δ 7.38-7.27 (m, 3H), 7.20-7.07 (m, 4H), 7.02 (dd, J=8.7, 1.0 Hz, 2H), 6.88 (ddd, J=8.0, 2.5, 0.8 Hz, 1H), 5.90-5.84 (m, 1H), 3.85 (s, 2H), 2.27-2.18 (m, 2H), 2.12-2.00 (m, 4H), 1.76-1.64 (m, 4H), 1.40-1.32 (m, 2H). HPLC-1: RT=11.9 min, purity=100%; HPLC-2: RT=9.9 min, purity=96.9%.

Example 12

2-(3-(1-(3-Phenoxyphenyl)-2-oxabicyclo[2.2.2]octan-4-yl)propoxy)acetic acid

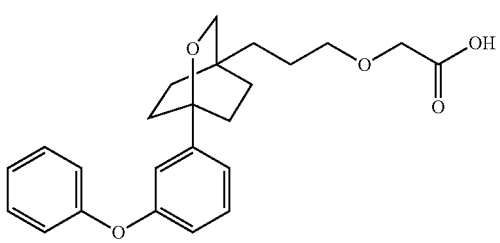 [SMILES: O=C(O)COCCCC12CCC(c3cccc(Oc4ccccc4)c3)(CC1)OC2]

12A. 3-(1-(3-Phenoxyphenyl)-2-oxabicyclo[2.2.2]octan-4-yl)propanal

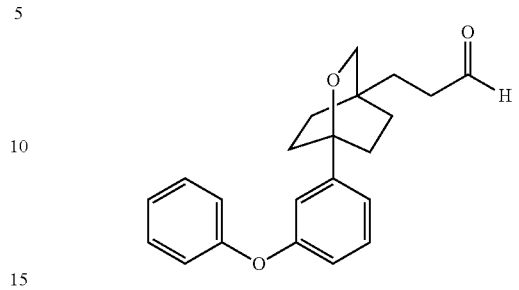

3-(1-(3-Phenoxyphenyl)-2-oxabicyclo[2.2.2]octan-4-yl)propanal (clear oil) was prepared using a procedure analogous to 3-(1-(3-(tetrahydro-2H-pyran-2-yloxy)phenyl)-2-oxabicyclo[2.2.2]octan-4-yl)propanal except that 2-(1-(3-(tetrahydro-2H-pyran-2-yloxy)phenyl)-2-oxabicyclo[2.2.2]octan-4-yl)ethanol was replaced with 2-(1-(3-phenoxyphenyl)-2-oxabicyclo[2.2.2]octan-4-yl)ethanol. LCMS, [M−H]+=335.2. 1H NMR (500 MHz, CDCl3) δ 9.78 (t, J=1.5 Hz, 1H), 7.34-7.23 (m, 3H), 7.14-7.03 (m, 3H), 7.01-6.95 (m, 2H), 6.87-6.81 (m, 1H), 3.81-3.78 (m, 2H), 2.43-2.36 (m, 2H), 2.09-1.94 (m, 4H), 1.69-1.58 (m, 4H), 1.54-1.47 (m, 2H).

12B. 3-(1-(3-Phenoxyphenyl)-2-oxabicyclo[2.2.2]octan-4-yl)propan-1-ol

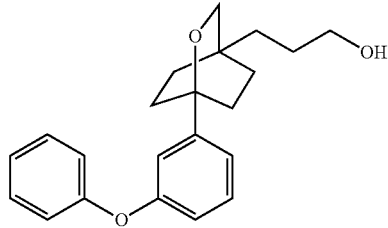 [SMILES: OCCCC12CCC(c3cccc(Oc4ccccc4)c3)(CC1)OC2]

To a solution of 3-(1-(3-phenoxyphenyl)-2-oxabicyclo[2.2.2]octan-4-yl)propanal (40 mg, 0.119 mmol) in DCM (1 mL) at −78° C. under N2 was added 1M DIBAL-H in DCM (0.178 ml, 0.178 mmol). The reaction mixture was stirred at −78° C. for 2 h and then added CELITE® (250 mg). The reaction was quenched with sat'd aqueous NH4Cl (0.5 mL) at −78° C. and then stirred at rt for 30 min. MgSO4 (200 mg) was added and the mixture was stirred at rt for 1 h. The mixture was filtered. The solid was washed with DCM. The combined filtrates were concentrated in vacuo to afford the title compound (40 mg, 99% yield) as an oil. LCMS, [M+NH4]+=356.2.

Example 12

Example 12 (a white solid) was prepared using a procedure analogous to Example 6 except that 2-(1-(3-phenoxyphenyl)-2-oxabicyclo[2.2.2]octan-4-yl)ethanol was replaced with 3-(1-(3-phenoxyphenyl)-2-oxabicyclo[2.2.2]octan-4-yl)propan-1-ol. LCMS, [M−H]+=395.1. 1H NMR (500 MHz, CDCl3) δ 7.36-7.27 (m, 3H), 7.19-7.07 (m, 3H), 7.04-6.98 (m, 2H), 6.90-6.85 (m, 1H), 4.14 (s, 2H), 3.84 (s, 2H), 3.56 (t, J=6.6 Hz, 2H), 2.12-1.99 (m, 4H), 1.74-1.57 (m, 6H), 1.29-1.20 (m, 2H). HPLC-1: RT=11.5 min, purity=96.7%; HPLC-2: RT=9.6 min, purity=93.6%.

Example 13 trans-2-(2-(1-(3-Phenoxyphenyl)-2-oxabicyclo[2.2.2]octan-4-yl)ethyl)cyclopropanecarboxylic acid

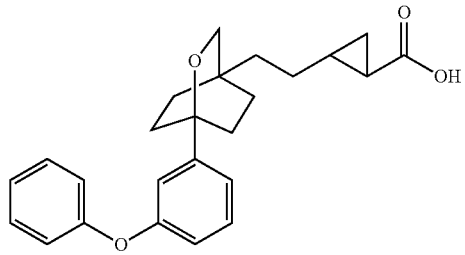 [SMILES: O=C(O)C1CC1CCC12CCC(c3cccc(Oc4ccccc4)c3)(CC1)OC2]

To a vigorously stirred mixed of Et₂O (5 mL) and 40% KOH (1 mL) was added N-methyl-N'-nitro-N-nitrosoguanidine (1.00 g, 6.80 mmol) portionwise over 15 min at 0° C. Upon complete addition, stirring was stopped. The organic layer was separated and was dried with KOH pellets. The solution was poured onto a solution of (E)-methyl 5-(1-(3-phenoxyphenyl)-2-oxabicyclo[2.2.2]octan-4-yl)pent-2-enoate (230 mg, 0.586 mmol) in THF (2 mL/mL). Pd(OAc)₂ (13.16 mg, 0.059 mmol) was then added and the reaction was allowed to warm to rt and stirred for 1 h. The reaction was concentrated in vacuo and purified by flash chromatography on SiO₂ (0 to 30% EtOAc:hexanes) to afford methyl 2-(2-(1-(3-phenoxyphenyl)-2-oxabicyclo[2.2.2]octan-4-yl)ethyl)cyclopropanecarboxylate (149 mg, 63%) as clear oil. A mixture of the above ester (149 mg, 0.367 mmol) and 1 N aqueous NaOH (1.1 mL, 1.10 mmol) in THF (1 mL) was stirred at rt for 18 h and then concentrated in vacuo. The residue was acidified to pH 5 with 1 N aqueous HCl and extracted with EtOAc. The organic layer was washed with brine and concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to afford the title compound (110 mg, 73% yield) as a white solid. LCMS, [M–H]⁺=391.2. ¹H NMR (500 MHz, CDCl₃) δ 7.36-7.23 (m, 3H), 7.17-7.05 (m, 3H), 6.98 (d, J=7.7 Hz, 2H), 6.83 (dd, J=8.0, 1.7 Hz, 1H), 3.77 (s, 2H), 2.07-1.92 (m, 4H), 1.69-1.55 (m, 4H), 1.44-1.18 (m, 7H), 0.82-0.73 (m, 1H). HPLC-1: RT=12.3 min, purity=100%; HPLC-2: RT=10.2 min, purity=96.3%.

Example 14 and Example 15

(1S,2S)-2-(2-(1-(3-Phenoxyphenyl)-2-oxabicyclo[2.2.2]octan-4-yl)ethyl)cyclopropanecarboxylic acid, and (1R,2R)-2-(2-(1-(3-Phenoxyphenyl)-2-oxabicyclo[2.2.2]octan-4-yl)ethyl)cyclopropanecarboxylic acid

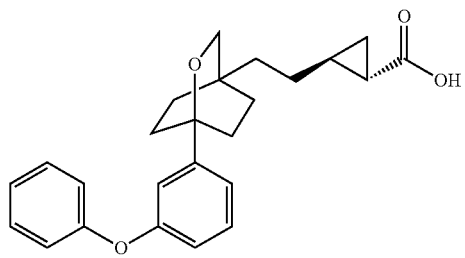

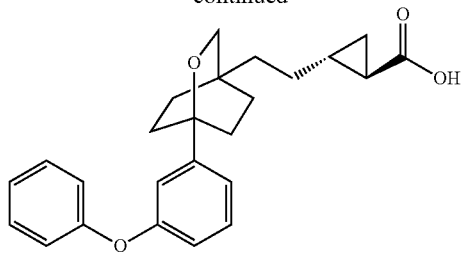

Example 13 was separated by chiral preparative HPLC (CHIRALPAK® AD-H, 21×250 mm, 5 μm column; detection at 220 nm; flow rate=40 mL/min, 100 Bar, 35° C.; Mobile Phase: 25% heptane:EtOH (1:1)/75% CO₂; Injection: 0.5 mL of 3 mg/mL EtOH:iPrOH:MeOH:CHCl₃ (5:1:1:0.4)) to afford Example 14 as the faster eluting isomer on HPLC and Example 15 as the slower eluting isomer on HPLC. Analysis for Example 14 (white solid): LCMS, [M–H]⁺=391.2. ¹H NMR (400 MHz, CDCl₃) δ 7.38-7.20 (m, 3H), 7.18-6.94 (m, 5H), 6.83 (dt, J=8.0, 1.2 Hz, 1H), 3.77 (s, 2H), 2.07-1.92 (m, 4H), 1.69-1.55 (m, 4H), 1.48-1.17 (m, 7H), 0.98-0.72 (m, 1H). HPLC-3: purity=98.1%, 96.2% ee. [α]=+56.1° (1.1% in DCM) @589 nm Analysis for Example 15 (white solid): LCMS, [M–H]⁺=391.2. ¹H NMR (400 MHz, CDCl₃) δ 7.38-7.20 (m, 3H), 7.18-6.94 (m, 5H), 6.83 (dt, J=8.0, 1.2 Hz, 1H), 3.77 (s, 2H), 2.07-1.92 (m, 4H), 1.69-1.55 (m, 4H), 1.48-1.17 (m, 7H), 0.98-0.72 (m, 1H). HPLC-3: purity=96.0%, 92.0% ee. [α]=−52.2° (1.1% in DCM) @589 nm

Example 16

2-(2-((1-(3-Phenoxyphenyl)-2-oxabicyclo[2.2.2]octan-4-yl)methyl)cyclopropyl)acetic acid (trans)

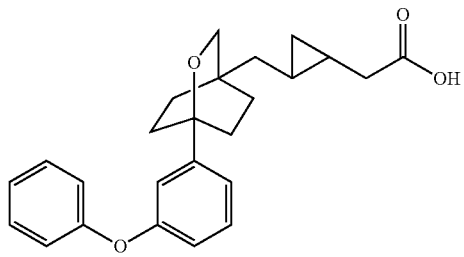 [SMILES: O=C(O)CC1CC1CC12CCC(c3cccc(Oc4ccccc4)c3)(CC1)OC2]

16A. Methyl 2-((1-(3-phenoxyphenyl)-2-oxabicyclo[2.2.2]octan-4-yl)methyl)cyclopropanecarboxylate

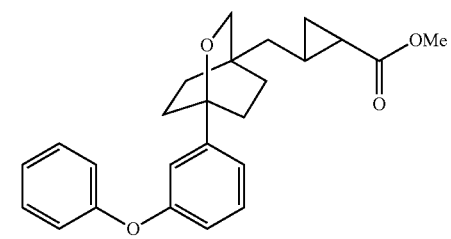 [SMILES: COC(=O)C1CC1CC12CCC(c3cccc(Oc4ccccc4)c3)(CC1)OC2]

Methyl 2-((1-(3-phenoxyphenyl)-2-oxabicyclo[2.2.2]octan-4-yl)methyl) cyclopropanecarboxylate (clear oil) was prepared using a procedure analogous to methyl 2-(2-(1-(3-phenoxyphenyl)-2-oxabicyclo[2.2.2]octan-4-yl)ethyl)cyclopropanecarboxylate except that 3-(1-(3-(tetrahydro-2H-pyran-2-yloxy)phenyl)-2-oxabicyclo[2.2.2]octan-4-yl)propanenitrile was replaced with 2-(1-(3-(tetrahydro-2H-pyran-2-yloxy)phenyl)-2-oxabicyclo[2.2.2]octan-4-yl)acetonitrile. LCMS, [M+H]⁺=393.1. ¹H NMR (500 MHz, CDCl₃) δ 7.37-7.26 (m, 3H), 7.19-7.08 (m, 3H), 7.04-6.99 (m, 2H), 6.87 (ddd, J=8.1, 2.5, 1.0 Hz, 1H), 3.89-3.86 (m, 2H), 3.71 (s, 3H), 2.09-2.01 (m, 4H), 1.80-1.71 (m, 4H), 1.39-1.33 (m, 2H), 1.30-1.21 (m, 2H), 1.18-1.11 (m, 1H).

16B. (2-((1-(3-Phenoxyphenyl)-2-oxabicyclo[2.2.2]octan-4-yl)methyl)cyclopropyl)methanol

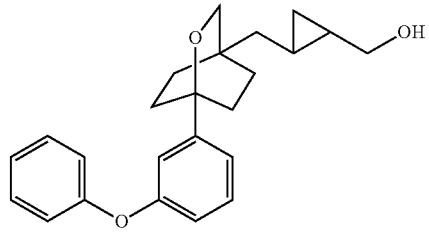 [SMILES: OCC1CC1CC12CCC(c3cccc(Oc4ccccc4)c3)(CC1)OC2]

To a solution of methyl 2-((1-(3-phenoxyphenyl)-2-oxabicyclo[2.2.2]octan-4-yl)methyl)cyclopropanecarboxylate (110 mg, 0.280 mmol) in THF (1 mL) at 0° C. was added LAH (0.280 ml, 0.280 mmol) dropwise. The reaction was stirred at rt for 3 h, added CELITE® (200 mg), cooled to −78° C., and then quenched with sat'd aqueous NH₄Cl (0.5 mL). The mixture was stirred at rt for 30 min, added MgSO₄ (200 mg), and stirred at rt for another 1 h. The mixture was filtered. The solid was washed with DCM. The combined filtrates were concentrated in vacuo and the residue was purified by flash chromatography on SiO₂ (0 to 30% EtOAc:hexanes) to afford the title compound (101 mg, 99% yield) as a clear oil. LCMS, [M+NH₄]⁺=382.2. ¹H NMR (500 MHz, CDCl₃) δ 7.34-7.24 (m, 3H), 7.16-7.10 (m, 2H), 7.09-7.05 (m, 1H), 7.00-6.96 (m, 2H), 6.85-6.81 (m, 1H), 3.87 (s, 2H), 3.55 (dd, J=11.0, 6.6 Hz, 1H), 3.41 (dd, J=11.0, 7.2 Hz, 1H), 2.05-1.99 (m, 4H), 1.76-1.69 (m, 4H), 1.14 (dd, J=6.9, 4.7 Hz, 2H), 0.84-0.76 (m, 1H), 0.62-0.54 (m, 1H), 0.45-0.39 (m, 1H), 0.28 (dt, J=8.3, 4.8 Hz, 1H).

Example 16

Example 16 (clear oil) was prepared using a procedure analogous to Example 10 except that 4-(1-(3-(tetrahydro-2H-pyran-2-yloxy)phenyl)-2-oxabicyclo[2.2.2]octan-4-yl)butan-1-ol was replaced with (2-((1-(3-phenoxyphenyl)-2-oxabicyclo[2.2.2]octan-4-yl)methyl)cyclopropyl)methanol. LCMS, [M−H]⁺=391.2. ¹H NMR (500 MHz, CDCl₃) δ 9.35 (br. s., 1H), 7.33-7.23 (m, 3H), 7.16-7.09 (m, 2H), 7.09-7.03 (m, 1H), 7.01-6.95 (m, 2H), 6.83 (ddd, J=8.0, 2.4, 0.8 Hz, 1H), 3.90-3.81 (m, 2H), 2.37-2.16 (m, 2H), 2.08-1.94 (m, 4H), 1.70 (t, J=7.8 Hz, 4H), 1.18-1.07 (m, 2H), 0.79-0.70 (m, 1H), 0.56-0.47 (m, 1H), 0.38 (dt, J=8.4, 4.9 Hz, 1H), 0.31 (dt, J=8.1, 5.2 Hz, 1H). HPLC-1: RT=12.3 min, purity=93.4%; HPLC-2: RT=10.2 min, purity=95.9%.

Example 17 and Example 18

2-((1R,2R)-2-((1-(3-Phenoxyphenyl)-2-oxabicyclo[2.2.2]octan-4-yl)methyl)cyclopropyl)acetic acid, and 2-((1S,2S)-2-((1-(3-Phenoxyphenyl)-2-oxabicyclo[2.2.2]octan-4-yl)methyl)cyclopropyl)acetic acid

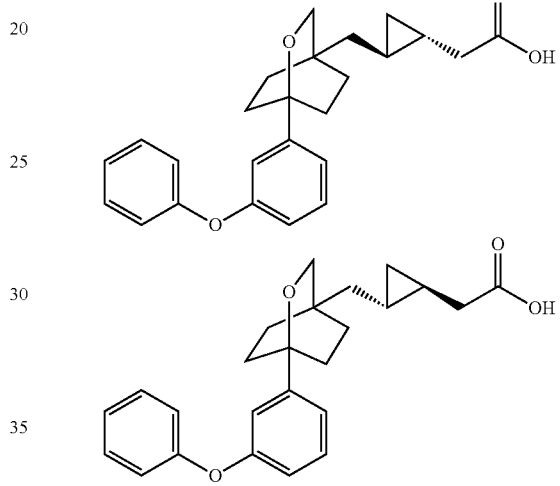

Example 16 was separated by chiral preparative HPLC (CHIRALPAK® AD-H, 21×250 mm, 5μ column; detection at 220 nm; Flow rate=50 mL/min, 100 Bar, 35° C.; Mobile Phase: 10% methanol/90% CO₂; Injection: 0.5 mL of 3 mg/mL methanol) to afford Example 17 as the faster eluting isomer on HPLC and Example 18 as the slower eluting isomer on HPLC. Analysis for Example 17 (clear oil): LCMS, [M−H]⁺=391.2. ¹H NMR (500 MHz, CDCl₃) δ 7.35-7.23 (m, 3H), 7.16-7.03 (m, 3H), 7.01-6.95 (m, 2H), 6.84 (ddd, J=8.0, 2.5, 0.8 Hz, 1H), 3.90-3.81 (m, 2H), 2.37-2.16 (m, 2H), 2.08-1.94 (m, 4H), 1.70 (t, J=7.8 Hz, 4H), 1.18-1.07 (m, 2H), 0.79-0.70 (m, 1H), 0.56-0.47 (m, 1H), 0.38 (dt, J=8.4, 4.9 Hz, 1H), 0.31 (dt, J=8.1, 5.2 Hz, 1H). HPLC-3: purity=99.5%, 99.0% ee. Analysis for Example 18 (clear oil): LCMS, [M−H]⁺=391.2. ¹H NMR (500 MHz, CDCl₃) δ 7.35-7.23 (m, 3H), 7.16-7.03 (m, 3H), 7.01-6.95 (m, 2H), 6.84 (ddd, J=8.0, 2.5, 0.8 Hz, 1H), 3.90-3.81 (m, 2H), 2.37-2.16 (m, 2H), 2.08-1.94 (m, 4H), 1.70 (t, J=7.8 Hz, 4H), 1.18-1.07 (m, 2H), 0.79-0.70 (m, 1H), 0.56-0.47 (m, 1H), 0.38 (dt, J=8.4, 4.9 Hz, 1H), 0.31 (dt, J=8.1, 5.2 Hz, 1H). HPLC-3: purity=99.5%, 99.0% ee.

Example 19

2-(2-(1-(3-(2-Methylallyloxy)phenyl)-2-oxabicyclo[2.2.2]octan-4-yl)ethoxy)acetic acid

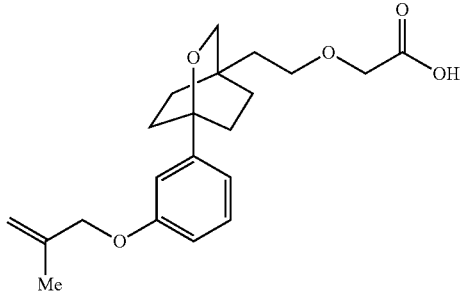 [SMILES: C=C(C)COc1cccc(C23CCC(CCOCC(=O)O)(CC2)CO3)c1]

Example 19 (clear oil) was prepared using a procedure analogous to Example 7 except that 2-iodopropane was replaced with 3-chloro-2-methylprop-1-ene. LCMS, [M−H]$^+$=359.2. $^1$H NMR (500 MHz, CDCl$_3$) δ 7.23 (t, J=8.0 Hz, 1H), 7.03 (dd, J=2.5, 1.7 Hz, 1H), 6.99-6.94 (m, 1H), 6.80 (ddd, J=8.1, 2.6, 0.8 Hz, 1H), 5.14-4.96 (m, 2H), 4.45 (s, 2H), 4.13 (s, 2H), 3.90 (s, 2H), 3.64 (t, J=7.0 Hz, 2H), 2.10-2.02 (m, 4H), 1.85 (s, 3H), 1.79-1.70 (m, 4H), 1.56 (t, J=7.0 Hz, 2H). HPLC-1: RT=10.6 min, purity=100%; HPLC-2: RT=8.9 min, purity=91.2%.

Example 20

2-(2-(1-(3-(2-Methylprop-1-enyloxy)phenyl)-2-oxabicyclo[2.2.2]octan-4-yl)ethoxy)acetic acid

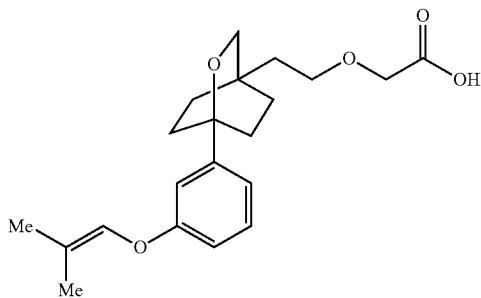 [SMILES: CC(C)=COc1cccc(C23CCC(CCOCC(=O)O)(CC2)CO3)c1]

A mixture of tert-butyl 2-(2-(1-(3-(2-methylallyloxy)phenyl)-2-oxabicyclo[2.2.2]octan-4-yl)ethoxy)acetate (39 mg, 0.094 mmol) and KO-t-Bu (10.51 mg, 0.094 mmol) in DMSO (1 mL) was stirred at 100° C. for 18 h. The reaction was acidified to pH 5 with 1 N aqueous HCl and extracted with EtOAc. The organic layer was washed with brine and concentrated in vacuo. The residue was purified by preparative HPLC (PHENOMENEX® Axia 5µ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to afford the title compound (32 mg, 90% yield) as a light brown solid. LCMS, [M−H]$^+$=359.2. $^1$H NMR (500 MHz, CDCl$_3$) δ 8.57-8.02 (sb, 1H), 7.24 (t, J=8.0 Hz, 1H), 7.08-7.00 (m, 2H), 6.85 (ddd, J=8.0, 2.5, 1.0 Hz, 1H), 6.23 (dt, J=2.8, 1.4 Hz, 1H), 4.13 (s, 2H), 3.90 (s, 2H), 3.63 (t, J=6.9 Hz, 2H), 2.10-1.99 (m, 4H), 1.79-1.66 (m, 10H), 1.56 (t, J=6.9 Hz, 2H). HPLC-1: RT=11.4 min, purity=100%; HPLC-2: RT=9.3 min, purity=96.5%.

Example 21

2-(2-(1-(3-(Pyridin-3-yloxy)phenyl)-2-oxabicyclo[2.2.2]octan-4-yl)ethoxy)acetic acid, TFA salt

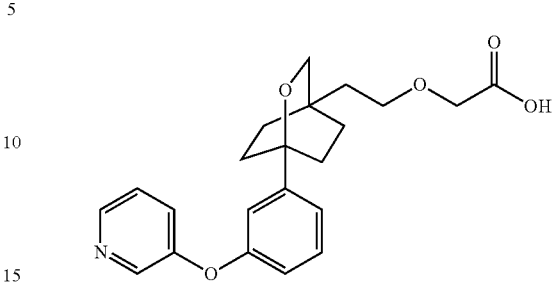

A mixture of tert-butyl 2-(2-(1-(3-hydroxyphenyl)-2-oxabicyclo[2.2.2]octan-4-yl)ethoxy)acetate (46 mg, 0.127 mmol), pyridine-3-boronic acid (93.6 mg, 0.762 mmol), TEA (0.1 ml, 0.717 mmol), pyridine (0.1 ml, 1.236 mmol), and copper (II) acetate (25.4 mg, 0.140 mmol) in DCM (2 mL) was stirred under air at rt for 3 days. The reaction was filtered and the filtrate was concentrated in vacuo. The residue was dissolved in EtOAc (5 mL) and washed with water (5×5 mL). The organic layer was dried over MgSO$_4$, filtered, and concentrated in vacuo. The residue was stirred with 1 N aqueous NaOH in MeOH (1 mL) at rt for 18 h. The reaction was concentrated in vacuo. The residue was acidified to pH 5 with 1 N aqueous HCl and extracted with EtOAc. The organic layer was washed with brine and concentrated in vacuo. The residue was purified by preparative HPLC (PHENOMENEX® Axia 5µ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (19 mg, 28% yield) as a clear oil. LCMS, [M−H]$^+$=382.1. $^1$H NMR (500 MHz, CDCl$_3$) δ 8.60 (d, J=5.2 Hz, 1H), 8.50 (d, J=2.5 Hz, 2H), 7.86 (dd, J=8.6, 2.2 Hz, 1H), 7.78 (dd, J=8.7, 5.3 Hz, 1H), 7.42 (t, J=8.0 Hz, 1H), 7.32-7.28 (m, 1H), 7.27-7.21 (m, 1H), 6.98 (dd, J=7.9, 2.2 Hz, 1H), 4.10 (s, 2H), 3.88 (s, 2H), 3.61 (t, J=6.8 Hz, 2H), 2.04 (dd, J=10.2, 5.9 Hz, 4H), 1.78-1.70 (m, 4H), 1.55 (t, J=6.8 Hz, 2H). HPLC-1: RT=5.4 min, purity=100%; HPLC-2: RT=5.3 min, purity=98.8%.

Example 22

2-(2-(1-(3-(3-Methoxyphenoxy)phenyl)-2-oxabicyclo[2.2.2]octan-4-yl)ethoxy)acetic acid

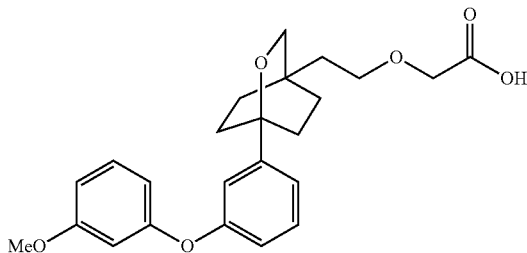 [SMILES: COc1cccc(Oc2cccc(C34CCC(CCOCC(=O)O)(CC3)CO4)c2)c1]

Example 22 (light brownish oil) was prepared using a procedure analogous to Example 21 except that pyridine-3-boronic acid was replaced with (3-methoxyphenyl) boronic acid. LCMS [M−H]$^+$=411.1. $^1$H NMR (500 MHz, CDCl$_3$) δ 7.25-7.09 (m, 4H), 6.85 (ddd, J=8.1, 2.5, 1.0 Hz, 1H), 6.63

(ddd, J=8.2, 2.4, 0.8 Hz, 1H), 6.57-6.53 (m, 2H), 4.10 (s, 2H), 3.86 (s, 2H), 3.76 (s, 3H), 3.60 (t, J=6.9 Hz, 2H), 2.09-1.95 (m, 4H), 1.77-1.65 (m, 4H), 1.53 (t, J=6.9 Hz, 2H). HPLC-1: RT=10.9 min, purity=95.3%; HPLC-2: RT=9.3 min, purity=90.7%.

Example 23

2-(2-(1-(3-Fluoro-5-phenoxyphenyl)-2-oxabicyclo[2.2.2]octan-4-yl)ethoxy)acetic acid

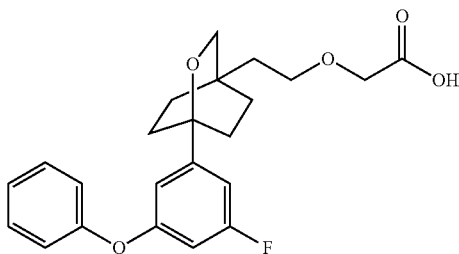 [SMILES: O=C(O)COCCC12CCC(c3cc(F)cc(Oc4ccccc4)c3)(CC1)OC2]

Example 23 (light brownish solid) was prepared using a procedure analogous to Example 21 except that pyridine-3-boronic acid was replaced with phenylboronic acid and 2-(3-bromophenoxy)tetrahydro-2H-pyran was replaced with 2-(3-bromo-5-fluoro-phenoxy)tetrahydro-2H-pyran. LCMS, [M–H]+=399.1. $^1$H NMR (500 MHz, CDCl$_3$) δ 8.97-8.40 (bs, 1H), 7.41-7.34 (m, 2H), 7.18-7.12 (m, 1H), 7.07-7.00 (m, 2H), 6.91-6.86 (m, 2H), 6.54 (dt, J=9.8, 2.2 Hz, 1H), 4.13 (s, 2H), 3.88 (s, 2H), 3.62 (t, J=6.9 Hz, 2H), 2.08-1.94 (m, 4H), 1.77-1.69 (m, 4H), 1.55 (t, J=6.9 Hz, 2H). HPLC-1: RT=6.4 min, purity=95.0%; HPLC-2: RT=5.5 min, purity=94.4%.

Example 24

2-(2-(1-(3-Cyclopentenylphenyl)-2-oxabicyclo[2.2.2]octan-4-yl)ethoxy)acetic acid

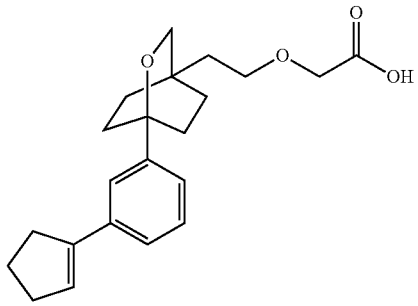 [SMILES: O=C(O)COCCC12CCC(c3cccc(C4=CCCC4)c3)(CC1)OC2]

24A. Methyl 2-(2-(1-(3-(trifluoromethylsulfonyloxy)phenyl)-2-oxabicyclo[2.2.2]octan-4-yl)ethoxy)acetate

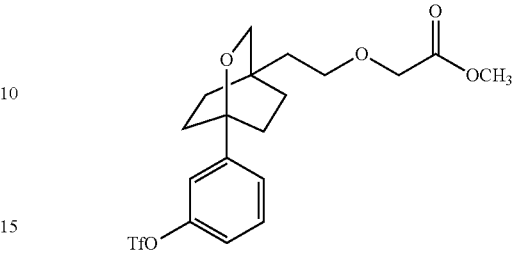

A mixture of tert-butyl 2-(2-(1-(3-hydroxyphenyl)-2-oxabicyclo[2.2.2]octan-4-yl)ethoxy)acetate (Intermediate 7F; 230 mg, 0.635 mmol) and TEA (0.177 mL, 1.269 mmol) in CH$_2$Cl$_2$ (1 mL) at −78° C. under N$_2$ was added triflic anhydride (0.107 mL, 0.635 mmol) dropwise. The reaction was warmed up to rt and stirred for 30 min. The reaction was concentrated in vacuo. The residue was dissolved in EtOAc (5 mL), washed with water, dried over MgSO$_4$, filtered, and concentrated in vacuo. The crude acid was dissolved in THF/MeOH (1:1, 2 mL) and treated with TMSCHN$_2$ (1 M in hexanes, 0.635 mL, 0.635 mmol). The reaction was stirred at rt for 1 h and then concentrated in vacuo. The crude oil was purified by flash chromatography on SiO$_2$ (0 to 30% EtOAc:hexanes) to afford the title compound (179 mg, 62% yield) as a clear oil. LCMS, [M+H]+=453.1. $^1$H NMR (500 MHz, CDCl$_3$) δ 7.40-7.35 (m, 3H), 7.14-7.11 (m, 1H), 4.08 (s, 2H), 3.89 (s, 2H), 3.78 (s, 3H), 3.60 (t, J=6.9 Hz, 2H), 2.06-1.98 (m, 4H), 1.76 (t, J=7.8 Hz, 4H), 1.55 (t, J=6.9 Hz, 2H).

Example 24

Pd(Ph$_3$P)$_4$ (10 mg, 8.65 μmol) was added in one portion to a degassed mixture of 2-(2-(1-(3-(trifluoromethylsulfonyloxy)phenyl)-2-oxabicyclo[2.2.2]octan-4-yl)ethoxy)acetic acid (34 mg, 0.075 mmol), cyclopent-1-en-1-ylboronic acid (17 mg, 0.150 mmol), and K$_2$CO$_3$ (31 mg, 0.225 mmol) in 1,4-dioxane (1 mL) and water (0.1 mL) under N$_2$. The reaction was stirred at 130° C. for 1 h. 1 N aqueous NaOH (0.5 mL) was added and the reaction was stirred at rt for 3 days. The reaction was concentrated in vacuo. The residue was acidified to pH 5 with 1 N aqueous HCl and extracted with EtOAc. The organic layer was washed with brine and concentrated in vacuo. The residue was purified by preparative HPLC (PHENOMENEX® Axia 5μ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to afford the title compound (10 mg, 36% yield) as a clear oil. LCMS, [M–H]+=355.1. $^1$H NMR (500 MHz, CDCl$_3$) δ 7.50 (s, 1H), 7.35-7.22 (m, 3H), 6.20 (quin, J=2.2 Hz, 1H), 4.17-4.10 (m, 2H), 3.91 (s, 2H), 3.68-3.60 (m, 2H), 2.77-2.69 (m, 2H), 2.54 (tq, J=7.4, 2.4 Hz, 2H), 2.12-1.98 (m, 6H), 1.79-1.71 (m, 4H), 1.57 (t, J=6.9 Hz, 2H). HPLC-1: RT=12.0 min, purity=98.5%; HPLC-2: RT=9.5 min, purity=93.4%.

Example 25

5-(1-(3-Phenoxyphenyl)-2-oxabicyclo[2.2.2]octan-4-yl)-N-(phenylsulfonyl)pentanamide

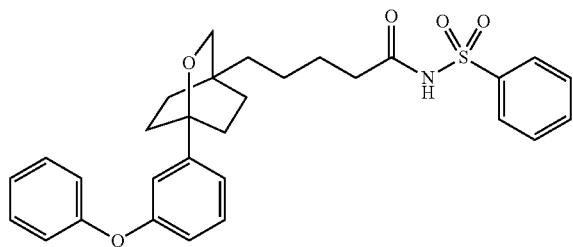 [SMILES: O=C(CCCCC12CCC(c3cccc(Oc4ccccc4)c3)(CC1)OC2)NS(=O)(=O)c1ccccc1]

A mixture of 3-(1-(3-phenoxyphenyl)-2-oxabicyclo[2.2.2]octan-4-yl)propanoic acid (Example 2; 14 mg, 0.037 mmol), benzenesulfonamide (6.94 mg, 0.044 mmol), DMAP (7.64 mg, 0.063 mmol), and EDC (10.58 mg, 0.055 mmol) in DCM (0.5 mL) was stirred at rt for 18 h. The reaction was concentrated in vacuo. The residue was purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H$_2$O:MeOH:TFA and B=90:10:0.1 MeOH:H$_2$O:TFA) to afford the title compound (10 mg, 50% yield) as a clear oil. LCMS, [M−H]$^+$=518.1. $^1$H NMR (500 MHz, CDCl$_3$) δ 8.47 (s, 1H), 8.12-8.06 (m, 2H), 7.74-7.64 (m, 1H), 7.63-7.55 (m, 2H), 7.38-7.25 (m, 4H), 7.18-7.06 (m, 3H), 7.05-6.97 (m, 2H), 6.86 (ddd, J=8.1, 2.5, 0.9 Hz, 1H), 3.74 (s, 2H), 2.28 (t, J=7.3 Hz, 2H), 2.09-1.92 (m, 4H), 1.66-1.49 (m, 6H), 1.24-1.04 (m, 4H). HPLC-1: RT=13.1 min, purity=94.1%; HPLC-2: RT=11.5 min, purity=95.6%.

Example 26

N-(Methylsulfonyl)-5-(1-(3-phenoxyphenyl)-2-oxabicyclo[2.2.2]octan-4-yl)pentanamide

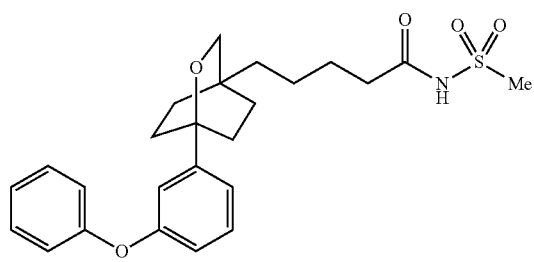 [SMILES: CS(=O)(=O)NC(=O)CCCCC12CCC(c3cccc(Oc4ccccc4)c3)(CC1)OC2]

Example 26 (clear oil) was prepared using a procedure analogous to Example 25 except that methanesulfonamide was used instead of benzenesulfonamide in the reaction. LCMS, [M−H]$^+$=456.1. $^1$H NMR (500 MHz, CDCl$_3$) δ 8.53 (s, 1H), 7.38-7.25 (m, 3H), 7.19-7.06 (m, 3H), 7.04-6.97 (m, 2H), 6.86 (ddd, J=8.1, 2.5, 0.9 Hz, 1H), 3.81 (s, 2H), 3.32 (s, 3H), 2.34 (t, J=7.4 Hz, 2H), 2.10-1.96 (m, 4H), 1.72-1.58 (m, 6H), 1.36-1.24 (m, 2H), 1.22-1.13 (m, 2H). HPLC-1: RT=12.1 min, purity=94.0%; HPLC-2: RT=10.6 min, purity=96.5%.

Example 27

2-(2-(1-(3-Phenoxyphenyl)-2-oxabicyclo[2.2.2]octan-4-yl)acetamido)acetic acid

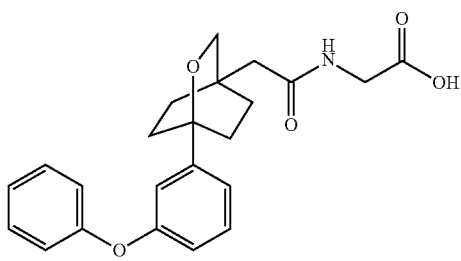 [SMILES: O=C(O)CNC(=O)CC12CCC(c3cccc(Oc4ccccc4)c3)(CC1)OC2]

A mixture of 2-(1-(3-phenoxyphenyl)-2-oxabicyclo[2.2.2]octan-4-yl)acetic acid (6A; 31 mg, 0.092 mmol), glycine methyl ester hydrochloride (11.50 mg, 0.092 mmol), HOBT (14.03 mg, 0.092 mmol), Hunig's base (0.016 mL, 0.092 mmol), and EDC (17.56 mg, 0.092 mmol) in DCM (0.5 mL) and DMF (0.5 mL) was stirred at rt for 2 h. The reaction was concentrated in vacuo. The residue was dissolved in EtOAc (2 mL), washed successively with 1 N aqueous HCl, water, and concentrated in vacuo. The residue was dissolved in THF (1 mL) and 1 N aqueous NaOH (0.5 mL) was added. The reaction was stirred at rt for 18 h and concentrated in vacuo. The residue was diluted with EtOAc (4 mL) and washed successively with 1 N aqueous HCl and water. The organic layer was concentrated in vacuo and the residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (27 mg, 71% yield) as a clear oil. LCMS, [M−H]$^+$=394.0. $^1$H NMR (500 MHz, CDCl$_3$) δ 7.40-7.23 (m, 3H), 7.16-7.06 (m, 3H), 7.05-6.96 (m, 2H), 6.86 (ddd, J=8.2, 2.4, 0.9 Hz, 1H), 6.58 (t, J=5.3 Hz, 1H), 4.03 (d, J=5.4 Hz, 2H), 3.96 (s, 2H), 2.13 (s, 2H), 2.12-1.97 (m, 4H), 1.81 (t, J=7.9 Hz, 4H). HPLC-1: RT=9.1 min, purity=98.5%; HPLC-2: RT=8.3 min, purity=99.2%.

Example 28

2-((1-(3-Phenoxyphenyl)-2-oxabicyclo[2.2.2]octan-4-yl)methylcarbamoyloxy)acetic acid

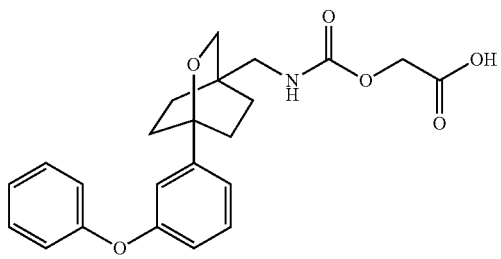 [SMILES: O=C(O)COC(=O)NCC12CCC(c3cccc(Oc4ccccc4)c3)(CC1)OC2]

28A. 2-(1-(3-Phenoxyphenyl)-2-oxabicyclo[2.2.2]octan-4-yl)acetyl azide

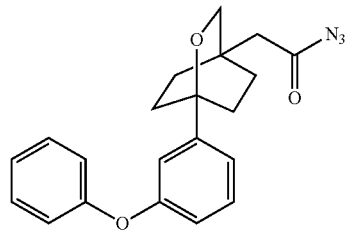 [SMILES: [N-]=[N+]=NC(=O)CC12CCC(c3cccc(Oc4ccccc4)c3)(CC1)OC2]

To a solution of 2-(1-(3-phenoxyphenyl)-2-oxabicyclo[2.2.2]octan-4-yl)acetic acid (6A: 97 mg, 0.287 mmol) in acetone (1 mL) at 0° C. was added TEA (0.064 mL, 0.459 mmol), followed by ethyl chloroformate (0.044 mL, 0.459 mmol) dropwise. The mixture was stirred at 0° C. for 30 min. A solution of $NaN_3$ (37.3 mg, 0.573 mmol) in 0.5 mL water was added slowly and the mixture was stirred at 0° C. for another 1 h. The reaction mixture was then poured into ice-water (5 mL) and extracted with diethyl ether (3×2 mL). The combined extracts were washed successively with water (5 mL), saturated aqueous $NaHCO_3$ (5 mL) and water (5 mL), dried over $Na_2SO_4$, filtered, and concentrated in vacuo to afford the title compound (104 mg, 100% yield). LCMS, $[M+Na]^+$=386.1.

Example 28

A mixture of 2-(1-(3-phenoxyphenyl)-2-oxabicyclo[2.2.2]octan-4-yl)acetyl azide (104 mg, 0.286 mmol) and ethyl glycolate (0.1 mL, 1.057 mmol) in toluene (1 mL) was stirred at 80° C. for 18 h and then concentrated in vacuo. The residue was purified by flash chromatography on $SiO_2$ (0 to 50% EtOAc:hexanes) to afford ethyl 2-((1-(3-phenoxy-phenyl)-2-oxabicyclo[2.2.2]octan-4-yl)methylcarbamoyloxy)acetate as a clear oil. The above ester was stirred with 1 N aqueous NaOH (0.572 mL, 0.572 mmol) in THF (1 mL) at rt for 2 h. The reaction was diluted with EtOAc (2 mL), washed with 1 N aqueous HCl, water, and then concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 $H_2O$:MeOH:TFA and B=90:10:0.1 MeOH:$H_2O$:TFA) to afford the title compound (58 mg, 47% yield) as a white foam. LCMS, $[M+H]^+$=412.3. $^1H$ NMR (500 MHz, $CDCl_3$) δ 10.90 (s, 1H), 7.37-7.31 (m, 2H), 7.31-7.26 (m, 1H), 7.16-7.07 (m, 3H), 7.01 (dd, J=8.6, 0.9 Hz, 2H), 6.88 (ddd, J=8.2, 2.3, 0.7 Hz, 1H), 5.23 (t, J=6.5 Hz, 1H), 4.67 (d, J=15.8 Hz, 2H), 3.91 (d, J=11.1 Hz, 2H), 3.08 (dd, J=14.4, 6.5 Hz, 2H), 2.18-1.96 (m, 4H), 1.81-1.59 (m, 4H). HPLC-1: RT=10.0 min, purity=100%; HPLC-2: RT=9.0 min, purity=100%.

Example 29

3-((1-(3-Phenoxyphenyl)-2-oxabicyclo[2.2.2]octan-4-yl)methylsulfonyl)propanoic acid

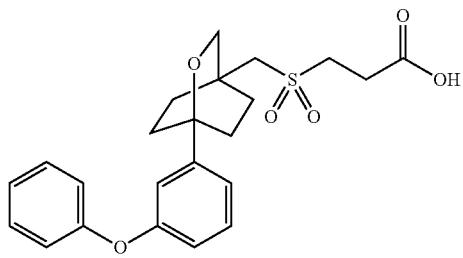 [SMILES: O=C(O)CCS(=O)(=O)CC12CCC(c3cccc(Oc4ccccc4)c3)(CC1)OC2]

29A. Methyl 3-((1-(3-phenoxyphenyl)-2-oxabicyclo[2.2.2]octan-4-yl)methylthio)propanoate

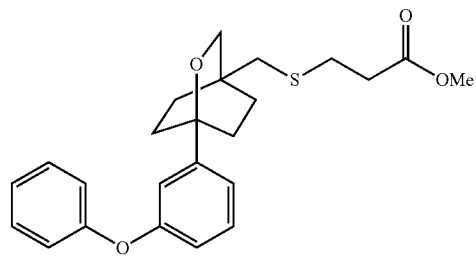 [SMILES: COC(=O)CCSCC12CCC(c3cccc(Oc4ccccc4)c3)(CC1)OC2]

A mixture of 4-(iodomethyl)-1-(3-phenoxyphenyl)-2-oxabicyclo[2.2.2]octane (7A; 41 mg, 0.098 mmol), methyl 3-mercaptopropanoate (21.14 μl, 0.195 mmol), and $K_2CO_3$ (135 mg, 0.976 mmol) in acetonitrile was stirred at rt for 2 days. The reaction was diluted with DCM (5 mL) and then filtered. The filtrate was concentrated in vacuo. The crude oil was purified by flash chromatography on $SiO_2$ (0 to 30% EtOAc:hexanes) to afford the title compound (35 mg, 87% yield) as a clear oil. LCMS, $[M+H]^+$=413.1.

Example 29

A mixture of methyl 3-((1-(3-phenoxyphenyl)-2-oxabicyclo[2.2.2]octan-4-yl)methylthio)propanoate (35 mg, 0.085 mmol) and mCPBA (43.9 mg, 0.255 mmol) in DCM (3 mL) was stirred at rt for 18 h. The reaction was diluted with EtOAc (5 mL) and washed with sat'd aqueous $NaHCO_3$. The organic layer was concentrated in vacuo. The residue was dissolved in THF (2 mL) and added 1 N aqueous NaOH (0.848 mL, 0.848 mmol). The reaction was stirred at rt for 5 h and diluted with EtOAc (5 mL). The mixture was washed with 1 N aqueous HCl. The organic layer was concentrated in vacuo and the residue was purified on preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 $H_2O$:MeOH:TFA and B=90:10:0.1 MeOH:$H_2O$:TFA) to afford the title compound (11 mg, 29% yield) as a white solid. LCMS, $[M+H]^+$=431.0. $^1H$ NMR (500 MHz, $CDCl_3$) δ 7.36-7.22 (m, 3H), 7.09 (dt, J=8.7, 7.5 Hz, 3H), 7.02-6.95 (m, 2H), 6.88-6.82 (m, 1H), 4.06 (s, 2H), 3.30 (t, J=7.3 Hz, 2H), 2.97-2.86 (m, 4H), 2.17-1.97 (m, 8H). HPLC-1: RT=11.6 min, purity=97.9%; HPLC-2: RT=10.5 min, purity=98.0%.

Example 30

3-((4-(3-Phenoxyphenyl)-2-oxabicyclo[2.2.2]octan-1-yl)methoxy)propanoic acid

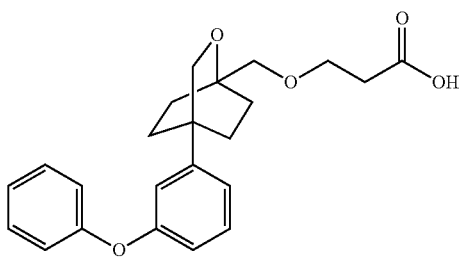 [SMILES: O=C(O)CCOCC12CCC(c3cccc(Oc4ccccc4)c3)(CC1)CO2]

30A. Ethyl 4-methylenecyclohexanecarboxylate

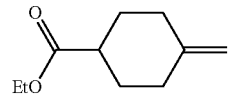

To a solution of (methyl)triphenylphosphonium bromide (5.18 g, 14.51 mmol) in THF (50 mL) at 0° C. was added n-butyllithium (9.07 mL, 14.51 mmol). The reaction mixture was stirred at 0° C. for 30 min. Ethyl 4-oxocyclohexanecarboxylate (1.9 g, 11.16 mmol) in THF (8 mL) was then added at 0° C. and the reaction was warmed to rt and stirred for 2 h. The reaction was quenched with sat'd aq. NH$_4$Cl and diluted with EtOAc. The organic layer was washed with water and brine, dried over MgSO$_4$, filtered, and concentrated in vacuo. The residue was purified by flash chromatography on SiO$_2$ (0 to 50% EtOAc:hexanes) to afford the title compound (1.58 g, 84% yield) as a colorless oil. $^1$H NMR (500 MHz, CDCl$_3$) δ 4.65 (s, 2H), 4.17-4.11 (m, 2H), 2.44 (tt, J=11.1, 3.8 Hz, 1H), 2.35 (dt, J=13.7, 4.0 Hz, 2H), 2.11-1.96 (m, 4H), 1.64-1.54 (m, 2H), 1.28-1.23 (m, 3H).

30B. Ethyl 4-methylene-1-(3-phenoxyphenyl)cyclohexanecarboxylate

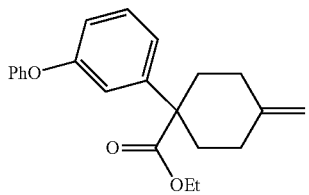 [SMILES: C=C1CCC(C(=O)OCC)(c2cccc(Oc3ccccc3)c2)CC1]

To a solution of dry dicyclohexylamine (0.777 mL, 3.90 mmol) in toluene (20 mL) in a round-bottom flask at 0° C. under Ar was added n-butyllithium (2.44 mL, 3.90 mmol) slowly. The reaction was stirred at 0° C. for 30 min. To this prepared lithium dicyclohexylamide solution was added ethyl 4-methylenecyclohexanecarboxylate (555 mg, 3.30 mmol) in toluene (1 mL) slowly over a period of 5 min. The reaction mixture was stirred at 0° C. for additional 30 min to generate the lithium enolate. In a 5 mL pear-shaped flask was placed di-p-bromobis(tri-tert-butylphosphino)dipalladium (I) (1.2 mg, 1.5 μmol) and the flask was capped with a rubber septum. Argon gas was flushed through the flask for 10 min. 1-Bromo-3-phenoxybenzene (747 mg, 3 mmol) in toluene (1 mL) was then added. The resulting solution was transferred via cannula into the round-bottom flask containing the 0° C. THF solution of the lithium enolate of the ethyl ester. Additional toluene (2×0.5 mL) was added to the pear-shaped flask, and this solution was also transferred into the round-bottom flask by cannula. The reaction mixture was allowed to warm to rt and stirred at rt for 3 days. The reaction was quenched with saturated aq. NH$_4$Cl and diluted with EtOAc. The organic layer was washed with water and brine, dried over MgSO$_4$, filtered, and concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (221 mg, 22% yield) as a colorless oil. LCMS, [M+H]$^+$=337.1. $^1$H NMR (500 MHz, CDCl$_3$) δ 7.38-7.33 (m, 2H), 7.33-7.27 (m, 1H), 7.19-7.10 (m, 3H), 7.04-6.99 (m, 2H), 6.89 (ddd, J=8.0, 2.4, 0.8 Hz, 1H), 4.68 (s, 2H), 4.17 (q, J=7.2 Hz, 2H), 2.61-2.53 (m, 2H), 2.36-2.21 (m, 4H), 1.88-1.79 (m, 2H), 1.22 (t, J=7.0 Hz, 3H).

30C. (4-Methylene-1-(3-phenoxyphenyl)cyclohexyl)methanol

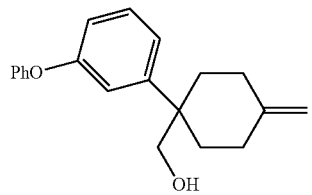 [SMILES: C=C1CCC(CO)(c2cccc(Oc3ccccc3)c2)CC1]

To a solution of ethyl 4-methylene-1-(3-phenoxyphenyl) cyclohexanecarboxylate (96 mg, 0.285 mmol) in THF (5 mL) at 0° C. was added lithium aluminum hydride (0.314 mL of a 1.0 M in Et$_2$O; 0.314 mmol). The solution was warmed to rt and stirred for 1 h. The reaction was then quenched at 0° C. by adding EtOAc followed by a saturated aq sodium sulfate. The mixture was diluted with EtOAc and filtered through a pad of CELITE®. The filtrate was dried (Na$_2$SO$_4$) and concentrated in vacuo to afford the title compound (84 mg, 100% yield) as a colorless oil. LCMS, [M+Na]$^+$=317.1. $^1$H NMR (500 MHz, CDCl$_3$) δ 7.38-7.32 (m, 3H), 7.20-7.16 (m, 1H), 7.15-7.09 (m, 2H), 7.04-7.00 (m, 2H), 6.88 (ddd, J=8.1, 2.3, 0.8 Hz, 1H), 4.63 (s, 2H), 3.53 (s, 2H), 2.28-2.19 (m, 4H), 2.16-2.07 (m, 2H), 1.72-1.64 (m, 2H).

30D. (6-(3-Phenoxyphenyl)-1-oxaspiro[2.5]octan-6-yl)methanol

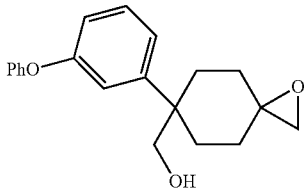 [SMILES: OCC1(c2cccc(Oc3ccccc3)c2)CCC2(CC1)CO2]

To a solution of (4-methylene-1-(3-phenoxyphenyl)cyclohexyl)methanol (53 mg, 0.180 mmol) in CH$_2$Cl$_2$ (0.9 mL) at 0° C. was added m-chloroperbenzoic acid (43.5 mg, 0.252 mmol). The solution was warmed to rt and stirred for 1 h. The reaction mixture was diluted with EtOAc, washed successively with 1 N aqueous NaOH, water, and brine, dried (MgSO$_4$), filtered, and concentrated in vacuo to afford the title compound (56 mg, 100% yield) as a colorless oil. LCMS, [M+H]$^+$=311.1.

30E. (4-(3-Phenoxyphenyl)-2-oxabicyclo[2.2.2]octan-1-yl)methanol

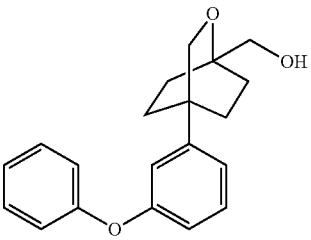 [SMILES: OCC12CCC(c3cccc(Oc4ccccc4)c3)(CC1)CO2]

To a solution of (6-(3-phenoxyphenyl)-1-oxaspiro[2.5]octan-6-yl)methanol (55.9 mg, 0.180 mmol) in CH$_2$Cl$_2$ (2 mL) at 0° C. was added p-toluenesulfonic acid monohydrate (3.43 mg, 0.018 mmol). The solution was warmed to rt and stirred for 1 h. The reaction was then diluted with EtOAc, washed successively with sat'd aq NaHCO$_3$, water, and brine, dried (MgSO$_4$), filtered, and concentrated in vacuo. The residue was purified by flash chromatography on SiO$_2$ (0 to 100% EtOAc:hexanes) to afford the title compound (15 mg, 27% yield) as an oil. LCMS, [M+Na]$^+$=333.0.

30F. Methyl 3-((4-(3-phenoxyphenyl)-2-oxabicyclo[2.2.2]octan-1-yl)methoxy)propanoate

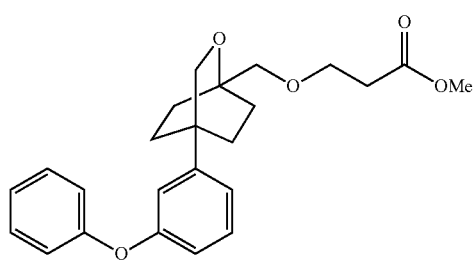 [SMILES: COC(=O)CCOCC12CCC(c3cccc(Oc4ccccc4)c3)(CC1)CO2]

To a solution of (4-(3-phenoxyphenyl)-2-oxabicyclo[2.2.2]octan-1-yl)methanol (15 mg, 0.048 mmol) in 1.5 mL of toluene was added methyl acrylate (10.88 µL, 0.121 mmol) and a 40% solution of N,N,N-trimethyl-1-phenylmethanaminium hydroxide (20.21 mg, 0.048 mmol) in methanol. The reaction was stirred at rt for 40 h and then diluted with EtOAc. The organic solution was washed with water and brine, dried (MgSO$_4$), filtered, and concentrated in vacuo. The residue was purified by preparative HPLC (PHENOMENEX® Axia 5µ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to afford the title compound (2.2 mg, 11% yield) as a colorless oil. LCMS, [M+Na]$^+$=419.1. $^1$H NMR (500 MHz, CDCl$_3$) δ 7.38-7.31 (m, 2H), 7.29-7.24 (m, 1H), 7.11 (t, J=7.4 Hz, 1H), 7.03-6.95 (m, 4H), 6.83 (dd, J=7.7, 1.9 Hz, 1H), 4.00 (s, 2H), 3.78 (s, 2H), 3.70 (s, 3H), 3.34 (s, 2H), 2.63 (t, J=6.5 Hz, 2H), 2.10-1.96 (m, 4H), 1.95-1.86 (m, 2H), 1.72-1.63 (m, 2H).

Example 30

To a solution of methyl 3-((4-(3-phenoxyphenyl)-2-oxabicyclo[2.2.2]octan-1-yl)methoxy)propanoate (2.2 mg, 5.55 µmol) in THF (0.8 mL) and water (0.400 mL) was added LiOH.H$_2$O (0.664 mg, 0.028 mmol). The reaction was stirred at rt for 15 h. The mixture was acidified to pH ~5 with 1 N aqueous HCl and extracted with EtOAc. The organic layer was washed with water and brine, dried (MgSO$_4$), filtered, and concentrated in vacuo. The residue was purified by preparative HPLC (PHENOMENEX® Axia 5µ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to afford the title compound (1.4 mg, 63% yield) as a colorless oil. LCMS, [M+H]$^+$=383.0. $^1$H NMR (500 MHz, CDCl$_3$) δ 7.37-7.32 (m, 2H), 7.29-7.25 (m, 1H), 7.13-7.09 (m, 1H), 7.03-6.98 (m, 3H), 6.97 (t, J=2.1 Hz, 1H), 6.84 (ddd, J=8.0, 2.4, 0.8 Hz, 1H), 4.01 (s, 2H), 3.79 (t, J=5.9 Hz, 2H), 3.40 (s, 2H), 2.68 (t, J=5.9 Hz, 2H), 2.11-2.00 (m, 4H), 1.98-1.89 (m, 2H), 1.72-1.63 (m, 2H). HPLC-1: RT=10.7 min, purity=100%; HPLC-2: RT=9.1 min, purity=90.7%.

Example 31

2-(2-(4-(3-Phenoxyphenyl)-2-oxabicyclo[2.2.2]octan-1-yl)ethoxy)acetic acid

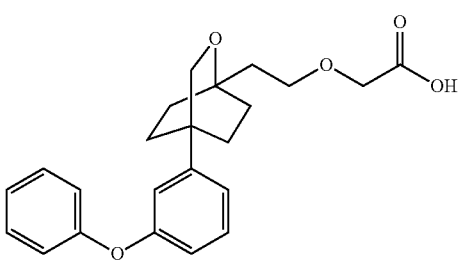 [SMILES: O=C(O)COCCC12CCC(c3cccc(Oc4ccccc4)c3)(CC1)CO2]

31A. 4-(3-Phenoxyphenyl)-2-oxabicyclo[2.2.2]octane-1-carbaldehyde

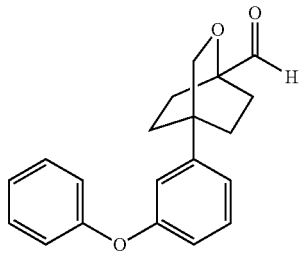 [SMILES: O=CC12CCC(c3cccc(Oc4ccccc4)c3)(CC1)CO2]

To a mixture of (4-(3-phenoxyphenyl)-2-oxabicyclo[2.2.2]octan-1-yl)methanol (5A; 182 mg, 0.586 mmol) and NaHCO$_3$ (59 mg, 0.704 mmol) in CH$_2$Cl$_2$ (5 mL) at 0° C. was added Dess-Martin periodinane (298 mg, 0.70 mmol). The solution was warmed to rt and stirred for 1 h. The reaction was diluted with EtOAc, washed successively with sat'd aq NaHCO$_3$, water, and brine, dried (MgSO$_4$), filtered, and concentrated in vacuo. The residue was purified by flash chromatography on SiO$_2$ (0 to 100% EtOAc:hexanes) to afford the title compound (123 mg, 68% yield) as a colorless oil. $^1$H NMR (500 MHz, CDCl$_3$) δ 9.65 (s, 1H), 7.41-7.28 (m, 3H), 7.12-7.16 (m, 1H), 7.06-6.89 (m, 4H), 6.88 (ddd, J=8.3, 2.5, 0.8 Hz, 1H), 4.12-4.09 (m, 2H), 2.17-1.90 (m, 8H).

31B. 4-(3-Phenoxyphenyl)-1-vinyl-2-oxabicyclo[2.2.2]octane

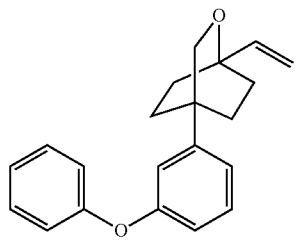 [SMILES: C=CC12CCC(c3cccc(Oc4ccccc4)c3)(CC1)CO2]

To a solution of (methyl)triphenylphosphonium bromide (80 mg, 0.224 mmol) in THF (1 mL) at 0° C. was added n-butyllithium (0.140 ml, 0.224 mmol). The reaction mixture was stirred at 0° C. for 30 min. A solution of 4-(3-Phenoxyphenyl)-2-oxabicyclo[2.2.2]octane-1-carbaldehyde (23 mg, 0.075 mmol) in THF (0.5 mL) was then added at 0° C. The reaction was warmed to rt and stirred for 4 h. The reaction was then quenched with saturated aq. NH$_4$Cl, diluted with EtOAc, washed with water and brine, dried (MgSO$_4$), filtered, and concentrated in vacuo. The residue was purified by flash chromatography on SiO$_2$ (0 to 50% EtOAc:hexanes) to afford the title compound (14 mg, 61% yield) as a colorless oil. $^1$H NMR (500 MHz, CDCl$_3$) δ 7.37-7.29 (m, 3H), 7.14-7.10 (m, 1H), 7.01 (d, J=7.7 Hz, 4H), 6.84 (ddd, J=8.0, 2.4, 0.8 Hz, 1H), 5.89 (dd, J=17.5, 10.9 Hz, 1H), 5.20 (d, J=17.3 Hz, 1H), 5.07 (d, J=10.7 Hz, 1H), 4.08-4.03 (m, 2H), 2.13-1.91 (m, 6H), 1.87-1.80 (m, 2H).

31C. 2-(4-(3-Phenoxyphenyl)-2-oxabicyclo[2.2.2]octan-1-yl)ethanol

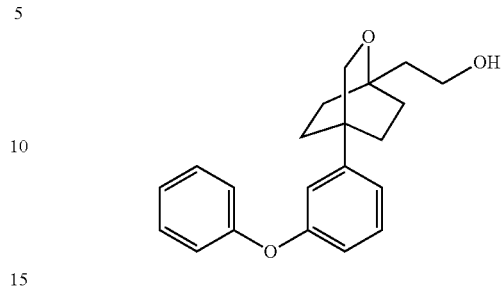

To a solution of 4-(3-phenoxyphenyl)-1-vinyl-2-oxabicyclo[2.2.2]octane (14 mg, 0.046 mmol) in THF (1 mL) at 0° C. was added BH$_3$.SMe$_2$ complex (0.046 mL of a 2.0 M solution in Et$_2$O; 0.091 mmol). The reaction mixture was stirred at 0° C. for 10 min and then warmed to rt. After stirring for 1 h at rt, the reaction mixture was cooled to 0° C. and a few drops of 1 N aqueous NaOH and 30% aqueous H$_2$O$_2$ solution were added. The resulting mixture was warmed to rt and stirred for 2 h. The reaction was diluted with EtOAc, washed with water and brine, dried (MgSO$_4$), filtered, and concentrated in vacuo. The residue was purified by flash chromatography on SiO$_2$ (0 to 70% gradient EtOAc:hexanes) to afford the title compound (9 mg, 57% yield) as a colorless oil. LCMS, [M+H]$^+$=325.1. $^1$H NMR (400 MHz, CDCl$_3$) δ 7.37-7.27 (m, 3H), 7.14-7.08 (m, 2H), 7.04-6.95 (m, 4H), 6.84 (ddd, J=8.1, 2.3, 0.8 Hz, 1H), 4.01-3.94 (m, 2H), 3.85-3.78 (m, 2H), 2.17-1.89 (m, 6H), 1.74-1.69 (m, 2H), 1.68-1.62 (m, 2H).

Example 31

Example 31 was prepared using a procedure analogous to that used to synthesize Example 6 except that 2-(1-(3-phenoxyphenyl)-2-oxabicyclo[2.2.2]octan-4-yl)ethanol was replaced with 2-(4-(3-phenoxyphenyl)-2-oxabicyclo[2.2.2]octan-1-yl)ethanol. LCMS, [M+Na]$^+$=405.2. $^1$H NMR (500 MHz, CDCl$_3$) δ 7.37-7.26 (m, 3H), 7.11 (t, J=7.4 Hz, 1H), 7.03-6.95 (m, 4H), 6.85 (dd, J=8.1, 2.3 Hz, 1H), 4.09 (s, 2H), 4.04 (s, 2H), 3.74 (t, J=5.4 Hz, 2H), 2.16-2.04 (m, 4H), 2.01-1.92 (m, 2H), 1.80 (t, J=5.4 Hz, 2H), 1.72-1.64 (m, 2H). HPLC-1: RT=10.8 min, purity=95.0%; HPLC-2: RT=9.2 min, purity=100%.

Example 32

Cis-2-(2-(1-(3-phenoxyphenyl)-2-oxabicyclo[2.2.2]octan-4-yl)ethyl)cyclopropanecarboxylic acid (racemic)

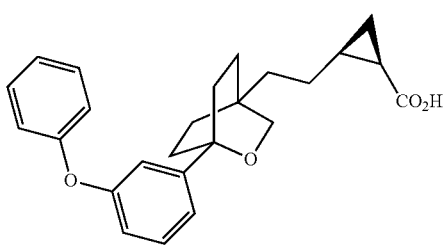 [SMILES: O=C(O)[C@@H]1C[C@@H]1CCC12CCC(c3cccc(Oc4ccccc4)c3)(CC1)OC2]

32A. (Z)-Methyl 5-(1-(3-phenoxyphenyl)-2-oxabicyclo[2.2.2]octan-4-yl)pent-2-enoate

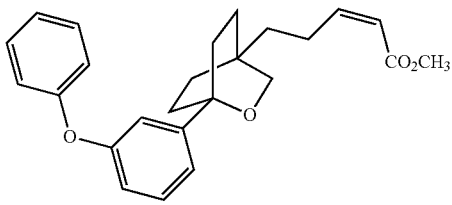 [SMILES: COC(=O)/C=C\CCC12CCC(c3cccc(Oc4ccccc4)c3)(CC1)OC2]

To a solution of bis (2,2,2-trifluoroethyl)(methoxycarbonylmethyl) phosphonate (0.113 mL, 0.535 mmol) and 18-crown-6 (471 mg, 1.78 mmol) in THF (10 mL) at −78° C. was added KHMDS (1.07 mL of a 0.5 M solution in toluene; 0.535 mmol) dropwise. The reaction mixture was stirred at −78° C. for 15 min, and then a solution of 2-(1-(3-phenoxyphenyl)-2-oxabicyclo[2.2.2]octan-4-yl)acetaldehyde (11B compound; 120 mg, 0.357 mmol) in THF (4 mL) was added slowly over 15 min. The reaction mixture was stirred at −78° C. for 30 min and then was quenched with sat. aq. NH$_4$Cl (1 mL), warmed to rt and extracted with EtOAc (3×5 mL). The combined organic extracts were dried (MgSO$_4$) and concentrated in vacuo. The crude oil was purified by flash chromatography on SiO$_2$ (0 to 20% gradient EtOAc:hexanes) to give the title compound (130 mg, 0.331 mmol, 93% yield) as a clear, light yellowish oil. LCMS, [M+H]$^+$=393.2. $^1$H NMR (CDCl$_3$) δ: 7.38-7.31 (m, 2H), 7.31-7.26 (m, 1H), 7.19-7.13 (m, 2H), 7.12-7.07 (tt, J=7.4, 1.1 Hz, 1H), 7.04-6.98 (m, 2H), 6.89-6.84 (ddd, J=8.0, 2.5, 1.0 Hz, 1H), 6.28-6.20 (dt, J=11.4, 7.5 Hz, 1H), 5.82-5.77 (dt, J=11.3, 1.6 Hz, 1H), 3.85 (s, 2H), 3.74 (s, 3H), 2.69-2.60 (m, 2H), 2.12-1.97 (m, 4H), 1.79-1.65 (m, 4H), 1.35-1.27 (m, 2H);

32B. Cis-methyl 2-(2-(1-(3-phenoxyphenyl)-2-oxabicyclo[2.2.2]octan-4-yl)ethyl) cyclopropanecarboxylate

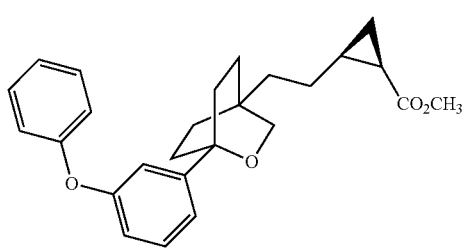 [SMILES: COC(=O)[C@@H]1C[C@@H]1CCC12CCC(c3cccc(Oc4ccccc4)c3)(CC1)OC2]

To a vigorously stirred mixture of Et$_2$O (5 mL) and aq. 40% KOH (1 mL) was added N-methyl-N'-nitro-N-nitrosoguanidine (750 mg, 2.55 mmol) portionwise over 10 min at 0° C. Upon completion of addition, the ether layer was separated and dried (KOH pellets) for 5 min. The ethereal solution was dried again (KOH pellets) and then added slowly into a THF solution (1 mL/mL of ethereal diazomethane solution) containing (Z)-methyl 5-(1-(3-phenoxyphenyl)-2-oxabicyclo[2.2.2]octan-4-yl)pent-2-enoate (100 mg, 0.255 mmol). Pd(OAc)$_2$ (5.7 mg, 0.025 mmol) was then added and the reaction was allowed to warm to rt and stirred for 1 h. The reaction was concentrated in vacuo and the crude oil was purified by flash chromatography (SiO$_2$) using a 0% to 30% gradient of EtOAc/hexane to give the title compound (100 mg, 0.246 mmol, 97% yield) as a yellowish oil. LCMS [M+H]$^+$=407.2. $^1$H NMR (CDCl$_3$) δ: 7.36-7.31 (m, 2H), 7.30-7.25 (t, J=7.9 Hz, 1H), 7.19-7.12 (m, 2H), 7.12-7.07 (m, 1H), 7.04-6.98 (m, 2H), 6.88-6.84 (ddd, J=8.0, 2.5, 1.0 Hz, 1H), 3.83-3.76 (d, J=1.7 Hz, 2H), 3.73-3.68 (s, 3H), 2.07-1.96 (m, 4H), 1.77-1.52 (m, 6H), 1.49-1.37 (m, 1H), 1.34-1.16 (m, 2H), 1.15-1.01 (m, 2H), 1.00-0.93 (dt, J=7.0, 4.9 Hz, 1H).

Example 32

A solution of cis-methyl 2-(2-(1-(3-phenoxyphenyl)-2-oxabicyclo[2.2.2]octan-4-yl)ethyl) cyclopropanecarboxylate (100 mg, 0.246 mmol) and aqueous NaOH (0.8 mL of a 1 M solution, 0.80 mmol) in MeOH (2 mL) was stirred at rt for 18 h. The reaction was acidified to pH=2 with 1N aq. HCl and the mixture was extracted with EtOAc (5 mL). The organic layer was washed with water and concentrated in vacuo. The crude oil was purified by preparative HPLC (PHENOMENEX® Axia 5µ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (92 mg, 0.223 mmol, 91% yield) as a white solid. LCMS [M−H]$^+$=391.2. $^1$H NMR (CDCl$_3$) δ: 7.34-7.21 (m, 3H), 7.15-7.03 (m, 3H), 7.01-6.94 (m, 2H), 6.86-6.80 (ddd, J=8.1, 2.5, 1.0 Hz, 1H), 3.77 (s, 2H), 2.08-1.91 (m, 4H), 1.74-1.40 (m, 7H), 1.34-1.20 (m, 2H), 1.20-1.05 (m, 2H), 1.00-0.93 (dt, J=7.1, 4.9 Hz, 1H).

Example 33

3-Methoxy-5-(1-(3-phenoxyphenyl)-2-oxabicyclo[2.2.2]octan-4-yl)pentanoic acid

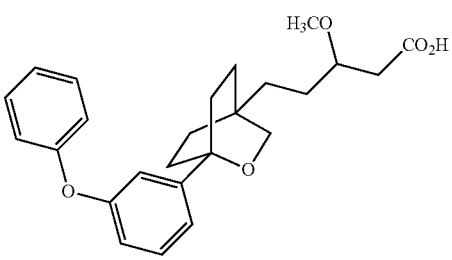 [SMILES: COC(CCC12CCC(c3cccc(Oc4ccccc4)c3)(CC1)OC2)CC(=O)O]

Example 34

(E)-5-(1-(3-Phenoxyphenyl)-2-oxabicyclo[2.2.2]octan-4-yl)pent-3-enoic acid

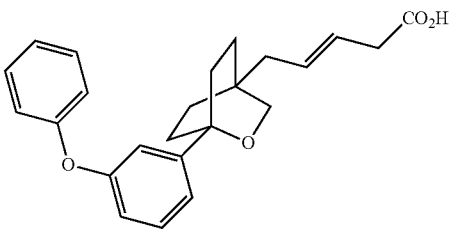 [SMILES: O=C(O)C/C=C/CC12CCC(c3cccc(Oc4ccccc4)c3)(CC1)OC2]

Example 35

(Z)-5-(1-(3-Phenoxyphenyl)-2-oxabicyclo[2.2.2]octan-4-yl)pent-2-enoic acid

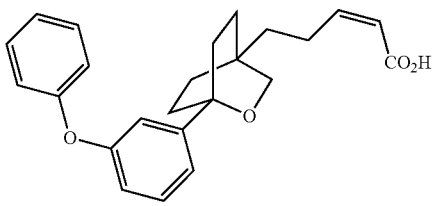 [SMILES: O=C(O)/C=C\CCC12CCC(c3cccc(Oc4ccccc4)c3)(CC1)OC2]

A mixture of (Z)-methyl 5-(1-(3-phenoxyphenyl)-2-oxabicyclo[2.2.2]octan-4-yl)pent-2-enoate (30 mg, 0.076 mmol) and 1N aq. NaOH (0.5 mL, 0.500 mmol) in MeOH (1 mL) was stirred at rt for 3 h, after which LC-MS showed that starting material had been consumed. The reaction was acidified to pH=2 with 1N aq. HCl, and the mixture was extracted with EtOAc (5 mL). The organic layer was washed with water and concentrated in vacuo. The residual crude oil was purified by preparative HPLC (Waters XBridge C18, 19×100 mm, 5-μm particles; Mobile Phase A: 5:95 MeCN/water with 10 mM NH$_4$OAc buffer; Mobile Phase B: 95:5 MeCN/water with 10 mM NH$_4$OAc buffer; Gradient: 15-65% B over 25 minutes, then a 10-minute hold at 65% B; Flow: 20 mL/min) to give Example 33 (7.2 mg, 0.017 mmol, 22% yield) as an oil, Example 34 (4 mg, 10.0 μmol, 13% yield) as an oil, and Example 35 (3.8 mg, 9.5 μmol, 12% yield) as an oil.

Example 33

LCMS [M−H]$^+$=409.1. $^1$H NMR (DMSO-d$_6$) δ: 7.43-7.36 (m, 2H), 7.33-7.28 (t, J=7.9 Hz, 1H), 7.16-7.10 (m, 2H), 7.05-7.02 (m, 1H), 7.01-6.96 (m, 2H), 6.86-6.82 (ddd, J=8.1, 2.5, 0.9 Hz, 1H), 3.72-3.64 (m, 2H), 3.55-3.45 (m, 1H), 3.21 (s, 3H), 2.42-2.35 (dd, J=15.1, 6.8 Hz, 1H), 2.32-2.23 (dd, J=15.1, 5.8 Hz, 1H), 2.08-1.97 (ddd, J=13.3, 11.3, 4.2 Hz, 2H), 1.87-1.73 (m, 2H), 1.68-1.47 (m, 4H), 1.49-1.32 (m, 2H), 1.25-1.13 (td, J=12.9, 12.4, 4.7 Hz, 1H), 1.13-1.03 (td, J=13.4, 12.9, 4.9 Hz, 1H).

Example 34

LCMS [M−H]$^+$=377.1; $^1$H NMR (DMSO-d$_6$) δ: 7.42-7.36 (m, 2H), 7.33-7.27 (t, J=7.9 Hz, 1H), 7.16-7.09 (m, 2H), 7.05-7.01 (m, 1H), 7.01-6.96 (dd, J=7.5, 1.5 Hz, 2H), 6.85-6.80 (dd, J=8.0, 2.6 Hz, 1H), 5.50-5.44 (m, 2H), 3.72-3.65 (s, 2H), 2.97-2.91 (d, J=4.6 Hz, 2H), 2.10-1.98 (ddd, J=13.0, 10.8, 4.9 Hz, 2H), 1.88-1.83 (d, J=5.5 Hz, 2H), 1.83-1.74 (m, 2H), 1.67-1.51 (m, 4H).

Example 35

LCMS [M−H]$^+$=377.1; $^1$H NMR (DMSO-d$_6$) δ: 7.42-7.36 (m, 2H), 7.33-7.28 (t, J=7.9 Hz, 1H), 7.17-7.10 (m, 2H), 7.05-7.02 (m, 1H), 7.01-6.96 (dd, J=7.7, 1.4 Hz, 2H), 6.86-6.81 (dd, J=8.0, 2.3 Hz, 1H), 6.21-6.12 (dt, J=11.4, 7.7 Hz, 1H), 5.72-5.66 (dt, J=11.4, 1.5 Hz, 1H), 3.74-3.66 (d, J=1.4 Hz, 2H), 2.09-1.99 (ddd, J=13.2, 11.2, 4.3 Hz, 2H), 1.85-1.76 (td, J=11.3, 4.7 Hz, 2H), 1.71-1.51 (m, 4H), 1.26-1.16 (m, 2H).

Example 36

2-(2-(1-(3-Fluoro-5-isobutoxyphenyl)-2-oxabicyclo[2.2.2]octan-4-yl)ethoxy)acetic acid

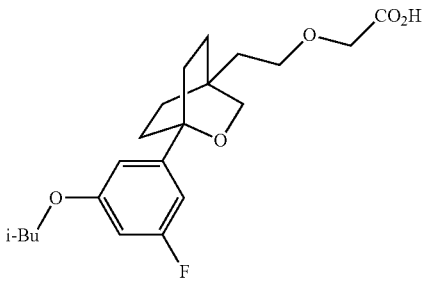

36A.
2-(3-Bromo-5-fluorophenoxy)tetrahydro-2H-pyran

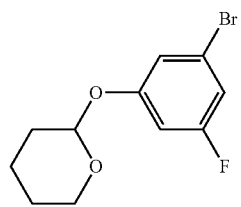 [SMILES: Fc1cc(Br)cc(OC2CCCCO2)c1]

A solution of 3-bromo-5-fluorophenol (1.64 g, 8.59 mmol), 3,4-dihydro-2H-pyran (1.56 mL, 17.2 mmol) and PPTS (0.216 g, 0.859 mmol) in DCM (10 mL) was stirred for 16 h at rt. The reaction was concentrated in vacuo. The residual crude oil was purified by chromatography (SiO$_2$) using a 0% to 20% EtOAc/hexane over 15 min to give the title compound (2.24 g, 8.14 mmol, 95% yield) as a clear oil. $^1$H NMR (CDCl$_3$) δ: 7.05 (dd, J=2.8, 2.1 Hz, 1H), 6.90 (ddd, J=8.0, 2.2, 1.8 Hz, 1H), 6.77 (dt, J=10.6, 2.2 Hz, 1H), 5.41 (t, J=3.1 Hz, 1H), 3.91-3.81 (m, 1H), 3.72-3.58 (m, 1H), 2.05-1.92 (m, 1H), 1.92-1.82 (m, 2H), 1.81-1.58 (m, 3H); $^{19}$F NMR (CDCl$_3$) δ: −110.28 (s); $^{13}$C NMR (CDCl$_3$) δ: 164.22 (s), 162.24 (s), 158.78 (d, J=11.8 Hz), 122.41 (d, J=12.5 Hz), 115.88 (d, J=3.3 Hz), 112.33 (s), 112.13 (s), 103.42 (s), 103.22 (s), 96.67 (s), 61.97 (s), 30.05 (s), 25.01 (s), 18.39 (s).

36B. (4-(3-Fluoro-5-(tetrahydro-2H-pyran-2-yloxy)phenyl)-4-hydroxycyclohexane-1,1-diyl)bis(methylene)bis(4-methylbenzenesulfonate)

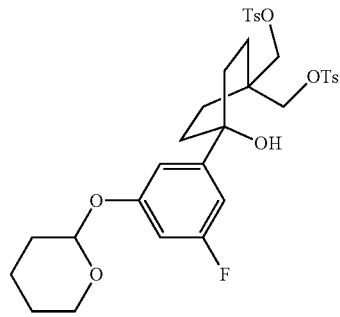 [SMILES: Cc1ccc(S(=O)(=O)OCC2(COS(=O)(=O)c3ccc(C)cc3)CCC(O)(c3cc(F)cc(OC4CCCCO4)c3)CC2)cc1]

To a −78° C. solution of 2-(3-bromo-5-fluorophenoxy)tetrahydro-2H-pyran (2.24 g, 8.14 mmol) in THF (30 mL) was added dropwise n-BuLi (6 mL of a 1.6 M solution in hexane; 9.60 mmol). After stirring at −78° C. for 1 h, a solution of 4-oxocyclohexane-1,1-diyl)bis(methylene)bis(4-methylbenzenesulfonate (1E; 3.44 g, 7.37 mmol) in THF (10 mL) was added dropwise. The reaction mixture was slowly warmed up to rt over 1 h and stirred at rt for 2 h. The reaction was quenched with sat. aq. NH$_4$Cl, then concentrated in vacuo. The residue was dissolved into EtOAc (10 mL), washed with water, dried (MgSO$_4$) and concentrated in vacuo. The crude oil was purified by flash chromatography (SiO$_2$) with a gradient of 0% to 50% EtOAc/hexane (over 15 min) to give the title compound (2.39 g, 3.61 mmol, 49% yield) as a clear oil.

36C. (1-(3-Fluoro-5-(tetrahydro-2H-pyran-2-yloxy)phenyl)-2-oxabicyclo[2.2.2]octan-4-yl)methyl 4-methylbenzenesulfonate

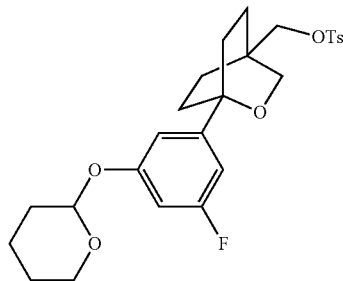 [SMILES: Cc1ccc(S(=O)(=O)OCC23CCC(c4cc(F)cc(OC5CCCCO5)c4)(CC2)OC3)cc1]

A mixture of (4-(3-fluoro-5-(tetrahydro-2H-pyran-2-yloxy)phenyl)-4-hydroxycyclohexane-1,1-diyl)bis(methylene)bis(4-methylbenzenesulfonate) (2.39 g, 3.61 mmol) and powdered NaOH (1.442 g, 36.1 mmol) in THF (50 mL) was stirred at 60° C. for 2 days. The reaction was filtered and the filtrate was concentrated in vacuo. The residue was dissolved in EtOAc (20 mL), washed with water (20 mL×3). The organic layer was dried (MgSO$_4$), filtered, and concentrated in vacuo. The crude oil was purified by flash chromatography (SiO$_2$) using a 0% to 50% gradient of EtOAc/hexane (over 15 min) to give the title compound (0.9 g, 1.84 mmol, 51% yield) as a clear oil. $^1$H NMR (CDCl$_3$) δ: 7.80 (d, J=8.3 Hz, 2H), 7.42-7.35 (m, 2H), 6.84 (t, J=1.7 Hz, 1H), 6.75-6.65 (m, 2H), 5.39 (t, J=3.1 Hz, 1H), 3.93-3.84 (m, 1H), 3.82 (s, 2H), 3.77 (s, 2H), 3.66-3.58 (m, 1H), 2.48 (s, 3H), 2.00 (t, J=8.0 Hz, 5H), 1.88-1.81 (m, 2H), 1.80-1.58 (m, 7H); $^{19}$F NMR (CDCl$_3$) δ: −111.87 (s).

36D. 1-(3-Fluoro-5-(tetrahydro-2H-pyran-2-yloxy)phenyl)-4-(iodomethyl)-2-oxabicyclo[2.2.2]octane

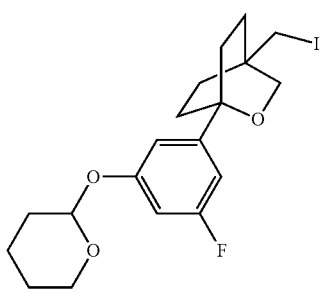 [SMILES: Fc1cc(OC2CCCCO2)cc(C23CCC(CI)(CC2)CO3)c1]

A mixture of 36C (0.9 g, 1.84 mmol) and sodium iodide (3.8 g, 25.4 mmol) in acetone (15 mL) was stirred at 78° C. for 18 h. The reaction cooled to rt and filtered. The filtrate was concentrated in vacuo, taken up in DCM (10 mL) and filtered. The residual solid was washed with DCM (5 mL×2). The combined organic filtrates were concentrated in vacuo. The residual crude oil was purified by flash chromatography using a 0% to 30% gradient of EtOAc/hexane (15 min) to give the title compound (0.730 g, 1.64 mmol, 89% yield) as a white solid. $^1$H NMR (CDCl$_3$) δ: 6.88 (t, J=1.7 Hz, 1H), 6.76 (ddd, J=10.1, 2.3, 1.6 Hz, 1H), 6.70 (dt, J=10.5, 2.3 Hz, 1H), 5.41 (t, J=3.1 Hz, 1H), 3.96-3.85 (m, 3H), 3.68-3.60 (m, 1H), 3.07 (s, 2H), 2.10-1.95 (m, 5H), 1.89-1.58 (m, 9H); $^{19}$F NMR (CDCl$_3$) δ: −111.9 (s).

36E. 2-(1-(3-Fluoro-5-(tetrahydro-2H-pyran-2-yloxy)phenyl)-2-oxabicyclo[2.2.2]octan-4-yl)acetonitrile

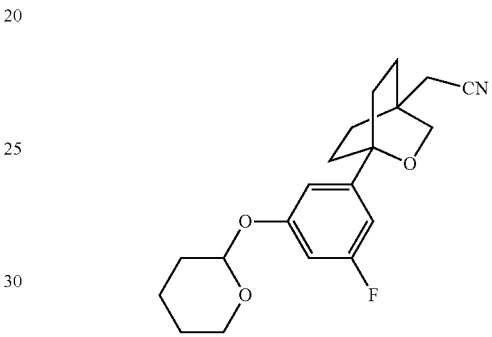

A mixture of 1-(3-fluoro-5-(tetrahydro-2H-pyran-2-yloxy)phenyl)-4-(iodomethyl)-2-oxabicyclo[2.2.2]octane (732 mg, 1.640 mmol), 18-crown-6 (43 mg, 0.164 mmol), and NaCN (88 mg, 1.80 mmol) in DMF (1 mL) was stirred at 40° C. under N$_2$ for 18 h. The reaction was cooled to rt and filtered. The filtrate was concentrated in vacuo. The residue was taken up in DCM (50 mL) and filtered. The residual solid was washed with DCM (10 mL×2). The combined organic filtrates were concentrated in vacuo. The crude oil was purified by flash chromatography (SiO$_2$) using a 0% to 30% EtOAc/hexane gradient (15 min) to give the title compound (560 mg, 1.62 mmol, 99% yield) as a white solid.

36F. 2-(1-(3-Fluoro-5-(tetrahydro-2H-pyran-2-yloxy)phenyl)-2-oxabicyclo[2.2.2]octan-4-yl) acetaldehyde

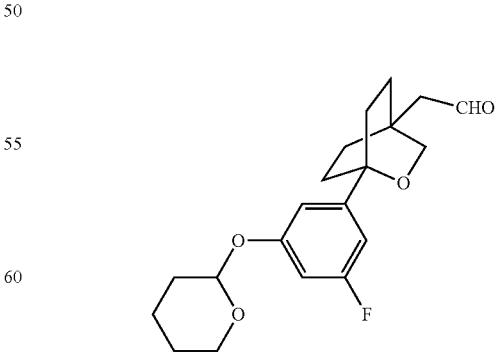

To a −78° C. solution of 2-(1-(3-fluoro-5-(tetrahydro-2H-pyran-2-yloxy)phenyl)-2-oxabicyclo[2.2.2]octan-4-yl)acetonitrile (520 mg, 1.51 mmol) in DCM (5 mL) under N$_2$ was added DIBAL-H (1.66 mL of a 1.0 M solution in DCM, 1.66 mmol) dropwise. The reaction mixture was stirred at −78° C. for 2 h and then quenched with sat. aq. NH₄Cl. The mixture was extracted with EtOAc. The organic layer was washed with brine and dried (Na₂SO₄), and concentrated in vacuo. The crude oil was purified by flash chromatography (SiO₂) using a gradient of 0% to 30% EtOAc/hexane (10 min) to give the title compound (424 mg, 1.22 mmol, 81% yield) as a white solid. ¹H NMR (CDCl₃) δ: 9.85 (t, J=2.7 Hz, 1H), 7.29 (s, 1H), 6.88-6.85 (m, 1H), 6.78-6.73 (m, 1H), 6.70 (dt, J=10.5, 2.3 Hz, 1H), 5.41 (t, J=3.1 Hz, 1H), 4.01-3.84 (m, 3H), 3.68-3.58 (m, 1H), 2.28 (d, J=2.7 Hz, 2H), 2.13-1.94 (m, 5H), 1.96-1.79 (m, 6H), 1.78-1.57 (m, 3H); ¹⁹F NMR (CDCl₃) δ: −111.9 (s).

36G. 2-(1-(3-Fluoro-5-(tetrahydro-2H-pyran-2-yloxy)phenyl)-2-oxabicyclo[2.2.2]octan-4-yl) ethanol

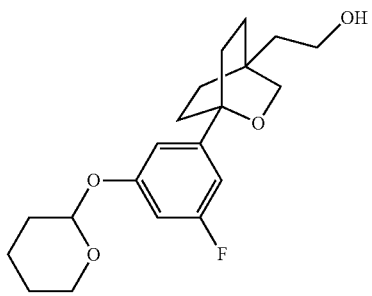 [SMILES: OCCC12CCC(c3cc(F)cc(OC4CCCCO4)c3)(CC1)OC2]

To a −78° C. solution of 2-(1-(3-fluoro-5-(tetrahydro-2H-pyran-2-yloxy)phenyl)-2-oxabicyclo[2.2.2]octan-4-yl) acetaldehyde (424 mg, 1.22 mmol) in DCM (5 mL) under N₂ was added DIBAL-H (1.34 mL of a 1.0 M solution in DCM, 1.34 mmol) dropwise. The reaction mixture was stirred at −78° C. for 2 h; CELITE® (500 mg) was then added and the reaction was quenched with sat. aq. NH₄Cl (0.5 mL). The mixture was stirred at rt for 30 min, MgSO₄ (500 mg) was added, and the mixture was stirred at rt for 30 min. The mixture was filtered and the residual solid was washed with DCM (3×). The combined filtrates were concentrated in vacuo. The crude oil was purified by flash chromatography (SiO₂) using a gradient of 0% to 50% EtOAc/hexane (10 min) to give the title compound (350 mg, 1.00 mmol, 82% yield) as a clear oil. ¹H NMR (CDCl₃) δ: 6.85 (t, J=1.7 Hz, 1H), 6.73 (ddd, J=10.1, 2.3, 1.5 Hz, 1H), 6.66 (dt, J=10.6, 2.3 Hz, 1H), 5.38 (t, J=3.1 Hz, 1H), 3.94-3.81 (m, 3H), 3.70 (td, J=7.2, 4.1 Hz, 2H), 3.60 (dtd, J=11.3, 4.0, 1.2 Hz, 1H), 2.04-1.92 (m, 5H), 1.90-1.77 (m, 2H), 1.76-1.52 (m, 8H), 1.45 (t, J=7.3 Hz, 2H); ¹⁹F NMR (CDCl₃) δ: −112.1 (s).

36H. tert-Butyl 2-(2-(1-(3-fluoro-5-(tetrahydro-2H-pyran-2-yloxy)phenyl)-2-oxabicyclo [2.2.2]octan-4-yl)ethoxy)acetate

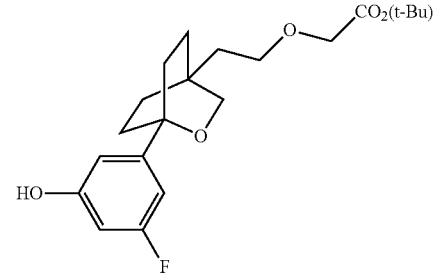

To a solution of 2-(1-(3-fluoro-5-(tetrahydro-2H-pyran-2-yloxy)phenyl)-2-oxabicyclo[2.2.2]octan-4-yl) ethanol (350 mg, 1.00 mmol) in toluene (1 mL) was added Bu₄NCl.H₂O (89 mg, 0.300 mmol). The reaction mixture was cooled to 0° C. after which aqueous 35% NaOH (10 mL) and tert-butyl bromoacetate (295 μL, 1.99 mmol) were successively added. The reaction was stirred at rt for 18 h. The organic layer was separated, washed with H₂O (5×15 mL) and brine (15 mL) until the pH=7, and then was concentrated in vacuo. The residual crude oil was purified by flash chromatography (SiO2) using a gradient from 0% to 30% EtOAc/hexane (10 min) to give the title compound (400 mg, 0.861 mmol, 86% yield) as a clear oil. ¹H NMR (500 MHz, CDCl₃) δ: 6.86 (t, J=1.7 Hz, 1H), 6.77-6.72 (m, 1H), 6.67 (d, J=10.5 Hz, 1H), 5.39 (s, 1H), 3.94 (s, 2H), 3.87 (s, 3H), 3.57 (t, J=6.9 Hz, 3H), 2.04-1.95 (m, 5H), 1.84 (d, J=5.0 Hz, 2H), 1.77-1.57 (m, 7H), 1.55-1.50 (m, 11H); ¹⁹F NMR (471 MHz, CDCl₃) δ: −112.2 (s, 1F).

36I. tert-Butyl 2-(2-(1-(3-fluoro-5-hydroxyphenyl)-2-oxabicyclo[2.2.2]octan-4-yl)ethoxy)acetate A mixture of tert-butyl 2-(2-(1-(3-fluoro-5-(tetrahydro-2H-pyran-2-yloxy)phenyl)-2-oxabicyclo[2.2.2]octan-4-yl) ethoxy)acetate (400 mg, 0.861 mmol) and PPTS (65 mg, 0.258 mmol) in MeOH (10 mL) was stirred at 50° C. for 3 h. The reaction was cooled to rt, then concentrated in vacuo. The residual crude oil was purified by flash chromatography (SiO₂) using a gradient from 0% to 30% EtOAc/hexane (10 min) to give the title compound (292 mg, 0.768 mmol, 89% yield) as a clear oil. ¹H NMR (500 MHz, CDCl₃) δ: 6.71-6.66 (m, 1H), 6.66-6.61 (m, 1H), 6.42 (d, J=10.2 Hz, 1H), 5.96 (s, 1H), 3.96 (s, 2H), 3.88 (s, 2H), 3.58 (t, J=6.9 Hz, 2H), 2.04-

1.92 (m, 4H), 1.80-1.70 (m, 4H), 1.57-1.49 (m, 11H); $^{19}$F NMR (471 MHz, CDCl$_3$) δ: −112.25 (s, 1F).

Example 36

A mixture of 361 (25 mg, 0.066 mmol), K$_2$CO$_3$ (45.4 mg, 0.329 mmol) and 1-iodo-2-methylpropane (0.014 ml, 0.121 mmol) in DMF (0.5 mL) was stirred at 70° C. for 18 h. The reaction was cooled to rt and partitioned between EtOAc (5 mL) and water. The organic layer was concentrated in vacuo to give the corresponding crude alkylated t-butyl ester product. This material was dissolved in THF (2 mL) and aq. NaOH (0.657 mL of a 1M solution, 0.657 mmol) was added. The reaction was stirred at rt for 1 h, then was concentrated in vacuo. The residue was dissolved in EtOAc (3 mL) and washed with 1N aq. HCl, water, and concentrated in vacuo. The residue was purified by preparative HPLC (PHENOMENEX® Axia 5μ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (16 mg, 0.040 mmol, 60.8% yield) as a clear oil. LCMS [M−H]$^+$=379.3. $^1$H NMR (CDCl$_3$) δ: 6.77-6.73 (t, J=1.9 Hz, 1H), 6.70-6.65 (ddd, J=10.1, 2.3, 1.4 Hz, 1H), 6.51-6.45 (dt, J=10.6, 2.3 Hz, 1H), 4.13 (s, 2H), 3.89 (s, 2H), 3.73-3.68 (d, J=6.5 Hz, 2H), 3.65-3.59 (t, J=6.9 Hz, 2H), 2.14-1.95 (m, 5H), 1.79-1.68 (t, J=7.8 Hz, 4H), 1.61-1.51 (t, J=6.9 Hz, 2H), 1.07-0.99 (d, J=6.7 Hz, 6H); $^{19}$F NMR (CDCl$_3$) δ: −112.18 (s).

Example 37

2-(2-(1-(2-Phenoxyphenyl)-2-oxabicyclo[2.2.2]octan-4-yl)ethoxy)acetic acid

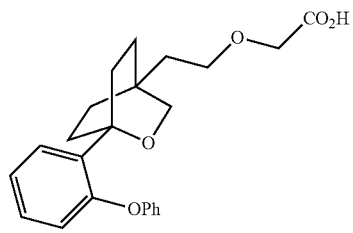 [SMILES: O=C(O)COCCC12CCC(c3ccccc3Oc3ccccc3)(CC1)OC2]

37A. (1-(2-Phenoxyphenyl)-2-oxabicyclo[2.2.2]octan-4-yl)methyl 4-methylbenzenesulfonate

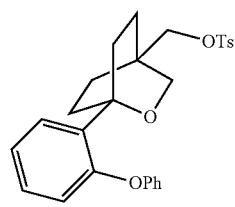 [SMILES: Cc1ccc(S(=O)(=O)OCC23CCC(c4ccccc4Oc4ccccc4)(CC2)OC3)cc1]

To a −78° C. solution of 1-bromo-2-phenoxybenzene (283 mg, 1.136 mmol) in anhydrous THF (5 mL) was added dropwise n-BuLi (545 μL of a 2.5 M solution in hexane, 1.363 mmol). The reaction was stirred at −78° C. for 0.5 h, after which a solution of 4-oxocyclohexane-1,1-diyl)bis(methylene)bis(4-methylbenzenesulfonate (1E; 530 mg, 1.14 mmol) in THF (4 mL) was added dropwise. The reaction mixture was slowly warmed to rt and stirred at rt for 2 h. Analytical HPLC showed the reaction was complete. Powdered NaOH (91 mg, 2.27 mmol) was added and the mixture was stirred under reflux for 18 h. The reaction was cooled to rt, diluted with water and extracted with EtOAc (2×). The organic layer was dried (MgSO$_4$) and concentrated in vacuo. The crude oil purified by flash chromatography (SiO$_2$) using a gradient from 0% to 40% EtOAc/hexane (15 min) to give the title compound (230 mg, 0.495 mmol, 44% yield) as a white solid. LCMS [M+H]$^+$=465.1; $^1$H NMR (CDCl$_3$) δ: 7.85-7.77 (m, 2H), 7.76-7.69 (dd, J=7.9, 1.9 Hz, 1H), 7.41-7.30 (m, 4H), 7.20-7.14 (td, J=7.6, 1.9 Hz, 1H), 7.14-7.06 (m, 2H), 6.98-6.92 (dd, J=7.6, 1.5 Hz, 2H), 6.83-6.76 (dd, J=8.1, 1.4 Hz, 1H), 3.87 (s, 2H), 3.75 (s, 2H), 2.59-2.50 (ddd, J=13.5, 11.3, 4.1 Hz, 2H), 2.48 (s, 3H), 1.98-1.87 (m, 2H), 1.75-1.64 (td, J=11.3, 10.8, 2.7 Hz, 2H), 1.60-1.51 (m, 2H).

37B. 2-(1-(2-Phenoxyphenyl)-2-oxabicyclo[2.2.2]octan-4-yl)acetonitrile

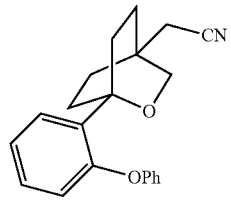 [SMILES: N#CCC12CCC(c3ccccc3Oc3ccccc3)(CC1)OC2]

A mixture of (1-(2-phenoxyphenyl)-2-oxabicyclo[2.2.2]octan-4-yl)methyl 4-methylbenzene-sulfonate (230 mg, 0.495 mmol), Bu$_4$NI (2 mg, 4.95 μmol), and NaCN (73 mg, 1.49 mmol) in DMSO (10 mL) was stirred at 135° C. under N$_2$ for 20 h, then cooled to rt. The reaction was diluted with EtOAc (10 ml) and washed with water (20 ml×4). The organic layer was concentrated in vacuo to give a crude brown oil, which was purified by flash chromatography (SiO$_2$) using a gradient from 0% to 30% EtOAc/hexane (20 min) to give the title compound (150 mg, 0.470 mmol, 95% yield) as a clear oil. LCMS [M+Na]$^+$=342.1. $^1$H NMR (CDCl$_3$) δ: 7.77-7.72 (dd, J=7.7, 1.9 Hz, 1H), 7.38-7.33 (m, 2H), 7.22-7.16 (m, 1H), 7.15-7.10 (m, 2H), 7.01-6.95 (m, 2H), 6.83-6.79 (dd, J=8.0, 1.3 Hz, 1H), 3.98 (s, 2H), 2.70-2.58 (m, 2H), 2.22 (s, 2H), 2.05-1.94 (m, 2H), 1.88-1.74 (m, 4H).

37C. 2-(1-(2-Phenoxyphenyl)-2-oxabicyclo[2.2.2]octan-4-yl)acetaldehyde

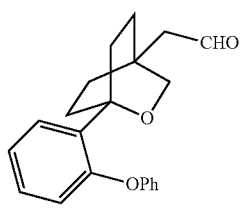 [SMILES: O=CCC12CCC(c3ccccc3Oc3ccccc3)(CC1)OC2]

To a −78° C. solution of 2-(1-(2-phenoxyphenyl)-2-oxabicyclo[2.2.2]octan-4-yl)acetonitrile (150 mg, 0.470 mmol) in DCM (5 mL) under N$_2$ was added dropwise DIBAL-H (0.564 mL of a 1 M solution in DCM, 0.564 mmol). The reaction mixture was stirred at −78° C. for 2 h, after which CELITE® (3500 mg) was added. The reaction was then quenched at −78° C. with sat. aq. NH$_4$Cl (2 mL). The mixture was stirred at rt for 30 min, after which MgSO$_4$ (1000 mg) was added. Stirring was continued at rt for 1 h, after which the mixture was filtered. The solid was washed with DCM (4×). The combined filtrates were concentrated in vacuo to give a crude oil, which was purified by flash chromatography (SiO$_2$) using a gradient from 0% to 30% EtOAc/hexane (20 min) to give the title compound (150 mg, 0.465 mmol, 99% yield) as a clear oil. $^1$H NMR (CDCl$_3$) δ: 9.86-9.82 (t, J=2.8 Hz, 1H), 7.80-7.70 (m, 1H), 7.40-7.31 (tt, J=7.1, 2.0 Hz, 2H), 7.21-7.07 (m, 3H), 7.02-6.94 (m, 2H), 6.85-6.77 (dd, J=8.0, 1.4 Hz, 1H), 4.00 (s, 1H), 2.67-2.55 (m, 2H), 2.30-2.24 (d, J=2.8 Hz, 2H), 2.05-1.93 (m, 2H), 1.92-1.76 (m, 4H).

37D. 2-(1-(2-Phenoxyphenyl)-2-oxabicyclo[2.2.2]octan-4-yl)ethanol

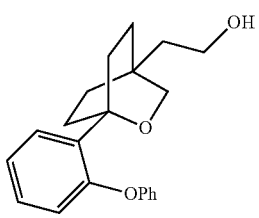 [SMILES: OCCC12CCC(c3ccccc3Oc3ccccc3)(CC1)OC2]

To a −78° C. solution of 2-(1-(2-phenoxyphenyl)-2-oxabicyclo[2.2.2]octan-4-yl)acetaldehyde (150 mg, 0.465 mmol) in DCM (5 mL) under N$_2$ was added dropwise DIBAL-H (0.558 mL of a 1 M solution in DCM, 0.558 mmol). The reaction mixture was stirred at −78° C. for 2 h, after which CELITE® (3500 mg) was added. The reaction was then quenched at −78° C. with sat. aq. NH$_4$Cl (2 mL). The mixture was stirred at rt for 30 min, after which MgSO$_4$ (1000 mg) was added. Stirring was continued at rt for 1 h, after which the mixture was filtered. The solid was washed with DCM (4×). The combined filtrates were concentrated in vacuo to give a crude oil, which was purified by flash chromatography (SiO$_2$) using a gradient from 0% to 50% EtOAc/hexane (10 min) to give the title compound (135 mg, 0.416 mmol, 89% yield) as a clear oil. $^1$H NMR (CDCl$_3$) δ: 7.78-7.73 (dd, J=7.9, 1.9 Hz, 1H), 7.38-7.32 (m, 2H), 7.20-7.07 (m, 3H), 7.01-6.95 (m, 2H), 6.83-6.78 (dd, J=8.0, 1.4 Hz, 1H), 3.96-3.84 (s, 2H), 3.75-3.66 (t, J=7.4 Hz, 2H), 2.61-2.50 (m, 2H), 1.98-1.88 (m, 2H), 1.75-1.61 (m, 4H), 1.51-1.42 (t, J=7.4 Hz, 2H), 1.33 (s, 1H).

Example 37

The title compound was synthesized from 2-(1-(2-phenoxyphenyl)-2-oxabicyclo[2.2.2]octan-4-yl)ethanol using the same reaction sequence as the synthesis of Example 6 from 6B. The title compound was purified as a clear oil (29 mg, 0.074 mmol, 96% yield). LCMS [M−H]$^+$=381.3; $^1$H NMR (CDCl$_3$) δ: 7.77-7.72 (dd, J=7.8, 1.9 Hz, 1H), 7.38-7.31 (m, 2H), 7.20-7.07 (m, 3H), 7.00-6.94 (m, 2H), 6.83-6.77 (dd, J=8.0, 1.3 Hz, 1H), 4.12 (s, 2H), 3.91 (s, 2H), 3.65-3.57 (t, J=7.0 Hz, 2H), 2.62-2.48 (dt, J=13.6, 7.5 Hz, 2H), 2.00-1.89 (m, 2H), 1.71-1.63 (t, J=8.0 Hz, 4H), 1.58-1.50 (t, J=7.0Hz, 2H).

Example 38

2-(2-(1-(3-(Phenylthio)phenyl)-2-oxabicyclo[2.2.2]octan-4-yl)ethoxy)acetic acid

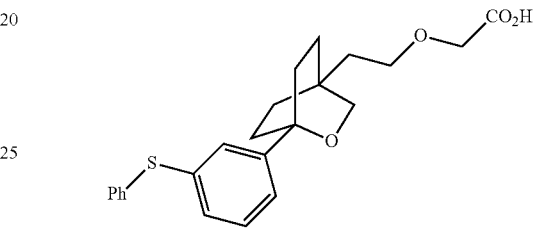

38A. tert-Butyl 2-(2-(1-(3-(((trifluoromethyl)sulfonyl)oxy)phenyl)-2-oxabicyclo[2.2.2]octan-4-yl)ethoxy)acetate

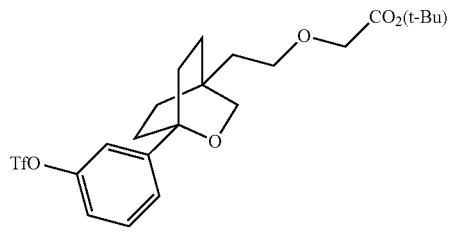

To a −78° C. mixture of tert-butyl 2-(2-(1-(3-hydroxyphenyl)-2-oxabicyclo[2.2.2]octan-4-yl) ethoxy)acetate (414 mg, 1.14 mmol) and TEA (0.64 mL, 4.57 mmol) in CH$_2$Cl$_2$ (1 mL) under N$_2$ was added triflic anhydride (1.37 mL of a 1M solution in DCM, 1.37 mmol) dropwise. After 10 min at −78° C., the reaction was stirred at rt for 30 min, then was concentrated in vacuo. The residue was dissolved in EtOAc (5 mL) and washed with water, dried (MgSO$_4$), and concentrated in vacuo. The residual crude oil was purified by flash chromatography (SiO$_2$) using a gradient from 0% to 30% EtOAc/hexane (10 min) to give the title compound (540 mg, 1.09 mmol, 96% yield) as a light yellowish oil. LCMS [M+Na]$^+$= 517.1; $^1$H NMR (CDCl$_3$) δ: 7.40-7.35 (m, 2H), 7.34 (dt, J=3.2, 1.5 Hz, 1H), 7.11 (dt, J=6.2, 2.7 Hz, 1H), 3.93 (s, 2H), 3.88 (s, 2H), 3.56 (t, J=6.8 Hz, 2H), 2.05-1.94 (m, 4H), 1.74 (t, J=7.9 Hz, 4H), 1.53 (t, J=6.8 Hz, 2H), 1.49 (s, 9H); $^{19}$F NMR (CDCl$_3$) δ: −73.0.

38B. tert-Butyl 2-(2-(1-(3-(4,4,5,5-tetramethyl-1,3,2-dioxaborolan-2-yl)phenyl)-2-oxabicyclo[2.2.2]octan-4-yl)ethoxy)acetate

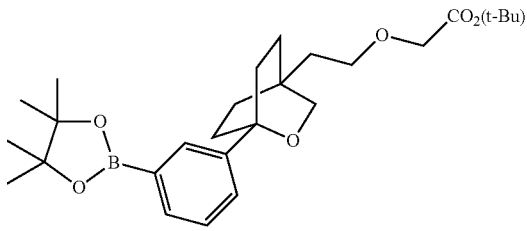

A mixture of methyl 2-(2-(1-(3-(((trifluoromethyl)sulfonyl)oxy)phenyl)-2-oxabicyclo[2.2.2]octan-4-yl)ethoxy)acetate (109 mg, 0.241 mmol), bis(pinacolato)diboron (153 mg, 0.602 mmol), and KOAc (59 mg, 0.602 mmol) in 1,4-dioxane (5 mL) was degassed under Ar for 3 min in a sonicator and then [1,1'-bis(diphenylphosphine)ferrocene]Pd(II)Cl$_2$ (10 mg, 0.014 mmol) was added. The reaction was stirred at 80° C. under Ar for 18 h, then was cooled to rt and concentrated in vacuo. The residue was dissolved in EtOAc (5 mL) and washed with water, dried (MgSO$_4$), and concentrated in vacuo. The residual crude oil was chromatographed (SiO$_2$) using a gradient from 0% to 20% EtOAc/hexane (10 min) to give the title compound (81 mg, 0.188 mmol, 78% yield) as a light yellowish oil. [M+NH$_4$]$^+$=490.0; $^1$H NMR (CDCl$_3$) δ: 7.81 (s, 1H), 7.66 (d, J=7.2 Hz, 1H), 7.51 (d, J=7.6 Hz, 1H), 7.31 (t, J=7.6 Hz, 1H), 4.07 (s, 2H), 3.87 (s, 2H), 3.76 (s, 3H), 3.57 (t, J=7.0 Hz, 2H), 2.05 (qt, J=13.0, 7.0 Hz, 4H), 1.71 (t, J=8.0 Hz, 4H), 1.52 (t, J=7.0 Hz, 2H), 1.33 (s, 12H); $^{11}$B NMR (CDCl$_3$) δ: 31.45.

38C. tert-Butyl 2-(2-(1-(3-(phenylthio)phenyl)-2-oxabicyclo[2.2.2]octan-4-yl)ethoxy)acetate

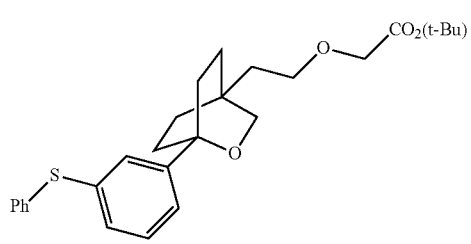

A solution of tert-butyl 2-(2-(1-(3-(((trifluoromethyl)sulfonyl)oxy)phenyl)-2-oxabicyclo[2.2.2]octan-4-yl)ethoxy) acetate (80 mg, 0.162 mmol), thiophenol (0.025 mL, 0.243 mmol), XantPhos (18.72 mg, 0.032 mmol), and Pd$_2$(dba)$_3$ (14.8 mg, 0.016 mmol) in 1,4-dioxane (1 mL) was degassed with low vacuum under Ar five times using a sonicator. DIPEA (0.085 mL, 0.485 mmol) pre-degassed in the same way was added under an atmosphere of Ar. The mixture was heated to reflux for 2 h, then was cooled to rt, filtered, and the filtrate was concentrated in vacuo. The crude oil was chromatographed (SiO$_2$) using a gradient from 0% to 50% EtOAc/hexane (10 min) to give the title compound (70 mg, 0.154 mmol, 95% yield) as a clear oil. LCMS: [M+Na]$^+$=477.1. $^1$H NMR (CDCl$_3$) δ: 7.48 (t, J=1.8 Hz, 1H), 7.35-7.27 (m, 6H), 7.26-7.18 (m, 2H), 3.96 (s, 2H), 3.88 (s, 2H), 3.58 (t, J=6.9 Hz, 2H), 2.06-1.97 (m, 4H), 1.73 (dd, J=9.1, 6.8 Hz, 4H), 1.51 (s, 11H).

Example 38

A mixture of tert-butyl 2-(2-(1-(3-(phenylthio)phenyl)-2-oxabicyclo[2.2.2]octan-4-yl)ethoxy) acetate (70 mg, 0.154 mmol) and aq. NaOH (1.54 mL of a 1 M solution, 1.54 mmol) in MeOH (1 mL) was stirred at rt for 18 h, then was concentrated in vacuo. The residue was acidified to pH=2 with 1N aq. HCl, then was extracted with EtOAc (1 mL×3). The combined organic extracts were washed with water and concentrated in vacuo. The residue was purified on preparative HPLC (PHENOMENEX® Axia 5μ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (60 mg, 0.143 mmol, 93% yield) as a light yellowish oil. LCMS [M−H]$^+$=397.2; $^1$H NMR (CDCl$_3$) δ: 7.44 (t, J=1.8 Hz, 1H), 7.32-7.23 (m, 6H), 7.24-7.14 (m, 2H), 4.10 (s, 2H), 3.86 (s, 2H), 3.59 (t, J=6.9 Hz, 2H), 2.08-1.92 (m, 4H), 1.70 (dd, J=9.3, 6.6 Hz, 4H), 1.53 (t, J=6.9 Hz, 2H).

Examples 39-45

A mixture of tert-butyl 2-(2-(1-(3-hydroxyphenyl)-2-oxabicyclo[2.2.2]octan-4-yl)ethoxy)acetate (7F; 25 mg, 69 μmol), (4-fluorophenyl)boronic acid (17 mg, 0.124 mmol), Cu(OAc)$_2$ (13 mg, 0.069 mmol), TEA (70 mg, 0.7 mmol), pyridine (6 mg, 0.07 mmol) and 4A molecular sieves (30 mg) in DCM (1 mL) was stirred under air at rt overnight. LCMS analysis of the reaction mixture showed that the desired O-arylation product had been formed. The sample was concentrated using a stream of N$_2$; the residue was dissolved in MeOH (1 mL) and NaOH (11 mg, 0.28 mmol) in H$_2$O (200 μL) was added. The reaction mixture was stirred for 2 h, after which volatiles were removed by a stream of N$_2$. The crude material was purified by preparative HPLC/MS (Column: Waters XBridge C18, 19×200 mm, 5-μm particles; Mobile Phase A: water with 20-mM NH$_4$OAc; Mobile Phase B: 95:5 MeCN:water with 20-mM NH$_4$OAc; Gradient: 10-100% B over 20 min, then a 5-min hold at 100% B; Flow rate: 20 mL/min) to give Example 39 as an oil. Examples 40-45 were synthesized using the same protocol as for Example 39 with the appropriate corresponding substituted phenylboronic acid.

| Example No | Name | Structure | Observed [M + H]+ |
|---|---|---|---|
| 39 | 2-(2-(1-(3-(4-fluorophenoxy)phenyl)-2-oxabicyclo[2.2.2]octan-4-yl)ethoxy)acetic acid | 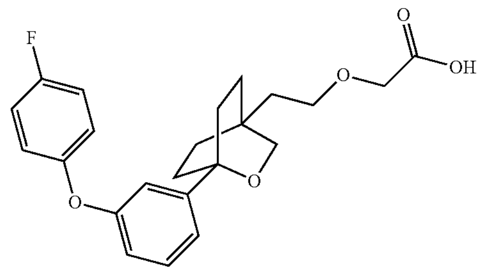 [SMILES: O=C(O)COCCC12CCC(c3cccc(Oc4ccc(F)cc4)c3)(CC1)OC2] | 401.16 |
| 40 | 2-(2-(1-(3-(4-chlorophenoxy)phenyl)-2-oxabicyclo[2.2.2]octan-4-yl)ethoxy)acetic acid | 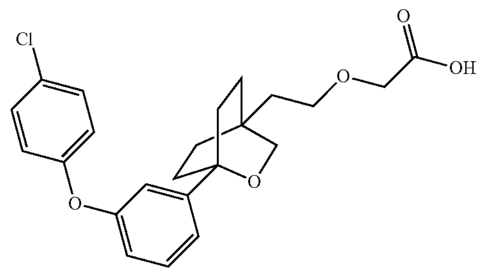 [SMILES: O=C(O)COCCC12CCC(c3cccc(Oc4ccc(Cl)cc4)c3)(CC1)OC2] | 417.13 |
| 41 | 2-(2-(1-(3-(p-tolyloxy)phenyl)-2-oxabicyclo[2.2.2]octan-4-yl)ethoxy)acetic acid | 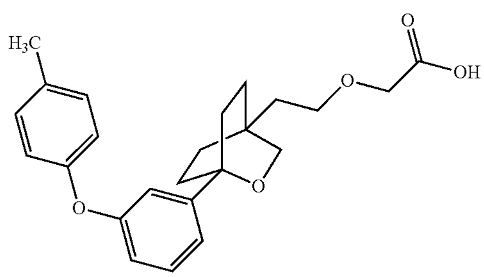 [SMILES: Cc1ccc(Oc2cccc(C34CCC(CCOCC(=O)O)(CC3)CO4)c2)cc1] | 397.19 |
| 42 | 2-(2-(1-(3-(4-methoxyphenoxy)phenyl)-2-oxabicyclo[2.2.2]octan-4-yl)ethoxy)acetic acid | 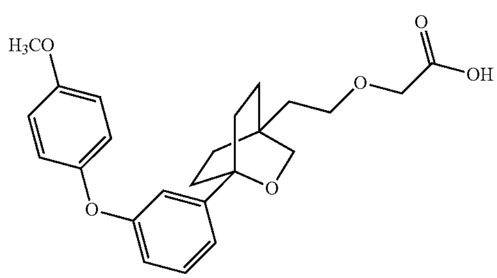 [SMILES: COc1ccc(Oc2cccc(C34CCC(CCOCC(=O)O)(CC3)CO4)c2)cc1] | 413.18 |
| 43 | 2-(2-(1-(3-(m-tolyloxy)phenyl)-2-oxabicyclo[2.2.2]octan-4-yl)ethoxy)acetic acid | 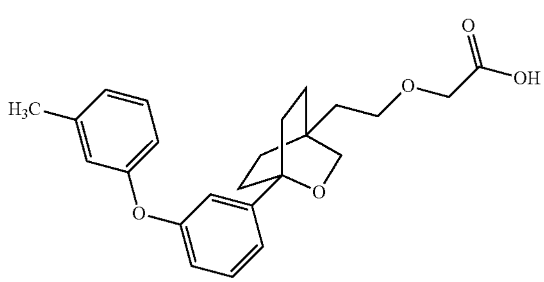 [SMILES: Cc1cccc(Oc2cccc(C34CCC(CCOCC(=O)O)(CC3)CO4)c2)c1] | 397.19 |

-continued

| Example No | Name | Structure | Observed [M + H]+ |
|---|---|---|---|
| 44 | 2-(2-(1-(3-(3-chlorophenoxy)phenyl)-2-oxabicyclo[2.2.2]octan-4-yl)ethoxy)acetic acid | 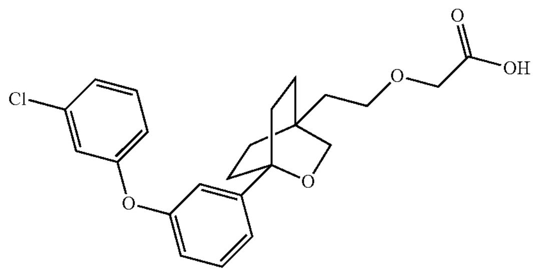 [SMILES: O=C(O)COCCC12CCC(c3cccc(Oc4cccc(Cl)c4)c3)(CC1)OC2] | 417.13 |
| 45 | 2-(2-(1-(3-(3-fluorophenoxy)phenyl)-2-oxabicyclo[2.2.2]octan-4-yl)ethoxy)acetic acid | 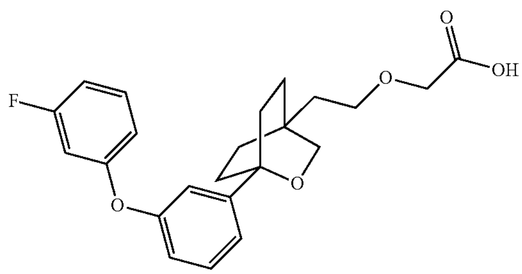 [SMILES: O=C(O)COCCC12CCC(c3cccc(Oc4cccc(F)c4)c3)(CC1)OC2] | 401.16 |

Example 46

2-(2-(1-(3-(3-Cyanophenoxy)phenyl)-2-oxabicyclo[2.2.2]octan-4-yl)ethoxy)acetic acid

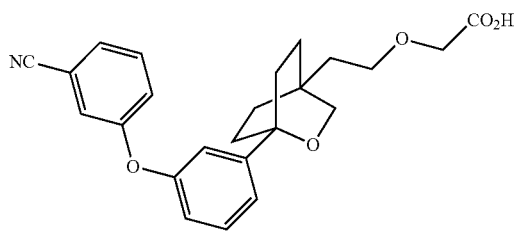 [SMILES: N#Cc1cccc(Oc2cccc(C34CCC(CCOCC(=O)O)(CC3)CO4)c2)c1]

A mixture of tert-butyl 2-(2-(1-(3-hydroxyphenyl)-2-oxabicyclo[2.2.2]octan-4-yl)ethoxy)acetate (7F; 29 mg, 0.080 mmol), (3-cyanophenyl)boronic acid (24 mg, 0.160 mmol), TEA (0.2 mL, 1.44 mmol), pyridine (0.2 mL, 2.473 mmol), Cu(OAc)$_2$ (16 mg, 0.088 mmol), 4A Molecular sieves (200 mg) in DCM (1 mL) was stirred under air at rt for 3 days. The reaction was filtered and the filtrate was concentrated in vacuo. The residue was partitioned between EtOAc (5 mL) and 1N aq. HCl (5 mL). The organic phase was washed with water (5 mL×5), dried (MgSO$_4$), and concentrated in vacuo to provide the crude 3-cyanophenoxyphenyl t-butyl ester intermediate. This material was taken up in 1N aq. NaOH in MeOH (1 mL) and stirred at rt for 2 h, then was concentrated in vacuo. The residue was acidified to pH=5 with 1N aq. HCl and extracted with EtOAc. The organic layer was washed with brine and concentrated in vacuo. The crude material was purified by preparative LC/MS (Column: Waters XBridge C18, 19×200 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 40-80% B over 20 minutes, then a 5-minute hold at 100% B; Flow: 20 mL/min) to give the title compound (17 mg, 0.040 mmol, 50% yield) as a clear oil. LCMS [M–H]+=406.1; $^1$H NMR (DMSO-d$_6$) δ: 7.62-7.55 (m, 2H), 7.47 (d, J=2.6 Hz, 1H), 7.36 (t, J=7.9 Hz, 1H), 7.30 (dt, J=5.9, 2.8 Hz, 1H), 7.21 (d, J=7.8 Hz, 1H), 7.09 (s, 1H), 6.92 (dd, J=8.0, 2.4 Hz, 1H), 3.96 (s, 2H), 3.75 (s, 2H), 3.49 (t, J=6.8 Hz, 2H), 2.12-1.99 (m, 2H), 1.87-1.74 (m, 2H), 1.72-1.57 (m, 4H), 1.40 (t, J=6.8 Hz, 2H).

Example 47

2-(2-(1-(3-(Trifluoromethylsulfonyloxy)phenyl)-2-oxabicyclo[2.2.2]octan-4-yl)ethoxy)acetic acid

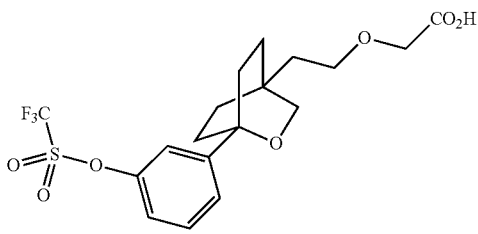 [SMILES: O=C(O)COCCC12CCC(c3cccc(OS(=O)(=O)C(F)(F)F)c3)(CC1)OC2]

A mixture of tert-butyl 2-(2-(1-(3-(((trifluoromethyl)sulfonyl)oxy)phenyl)-2-oxabicyclo[2.2.2]octan-4-yl)ethoxy)acetate (28 mg, 0.057 mmol) and formic acid (0.022 mL, 0.57 mmol) in CH$_2$Cl$_2$ (0.5 mL) was stirred at rt for 18 h, then was concentrated in vacuo. The crude material was purified by preparative LC/MS (Column: Waters XBridge C18, 19×100 mm, 5-nm particles; Mobile Phase A: 5:95 MeCN:water with 0.1% TFA; Mobile Phase B: 95:5 MeCN:water with 0.1% TFA; Gradient: 40-80% B over 10 min, then a 5-min hold at 100% B; Flow rate: 20 mL/min) to give the title compound (19 mg, 0.043 mmol, 76% yield) as a clear oil. LCMS [M–H]+=437.0; $^1$H NMR (DMSO-d$_6$) δ: 7.53-7.48 (m, 2H), 7.42 (d, J=2.7 Hz, 1H), 7.34 (dt, J=7.3, 2.3 Hz, 1H), 3.96 (s, 2H), 3.80 (s, 2H), 3.50 (t, J=6.7 Hz, 2H), 2.16-2.05 (m, 2H), 1.89-1.74 (m, 2H), 1.73-1.59 (m, 4H), 1.42 (t, J=6.8 Hz, 2H).

Example 48

2-(2-(1-(3-(5-Methyl-1,2,4-oxadiazol-3-yl)phenyl)-2-oxabicyclo[2.2.2]octan-4-yl)ethoxy)acetic acid

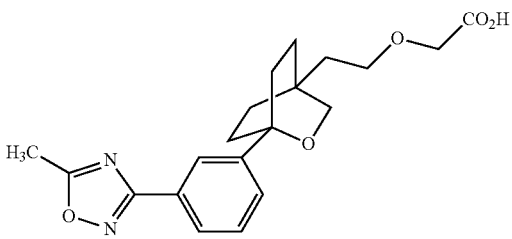 [SMILES: Cc1nc(-c2cccc(C34CCC(CCOCC(=O)O)(CC3)CO4)c2)no1]

48A. (Z)-tert-Butyl 2-(2-(1-(3-(1-amino-2-hydroxyvinyl)phenyl)-2-oxabicyclo[2.2.2]octan-4-yl)ethoxy)acetate

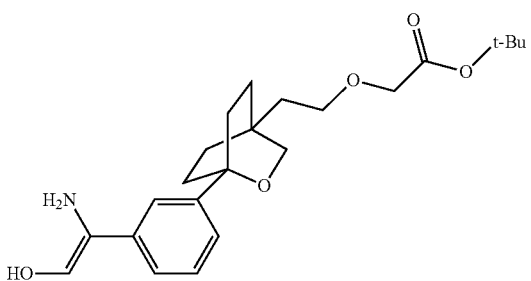 [SMILES: CC(C)(C)OC(=O)COCCC12CCC(c3cccc(/C(N)=C/O)c3)(CC1)OC2]

A mixture of tert-butyl 2-(2-(1-(3-cyanophenyl)-2-oxabicyclo[2.2.2]octan-4-yl)ethoxy)acetate (Example 46 penultimate intermediate; 89 mg, 0.240 mmol) and 50% hydroxylamine in water (0.025 mL, 0.41 mmol) in EtOH (1 mL) was stirred at rt for 3 days. The reaction was concentrated in vacuo, and the residual crude oil was chromatographed (SiO$_2$) using a gradient from 0% to 100% EtOAc/hexane (10 min) to give the title compound (76 mg, 0.19 mmol, 78% yield) as a clear oil. LCMS [M+H]$^+$=405.3; $^1$H NMR (CDCl$_3$) δ: 7.69 (t, J=1.8 Hz, 1H), 7.50 (dt, J=7.7, 1.5 Hz, 1H), 7.49-7.45 (m, 1H), 7.35 (t, J=7.8 Hz, 1H), 4.92 (s, 2H), 3.96 (s, 2H), 3.90 (s, 2H), 3.58 (t, J=6.9 Hz, 2H), 2.12-1.98 (m, 4H), 1.75 (t, J=8.0 Hz, 4H), 1.54 (t, J=7.0 Hz, 2H), 1.51 (s, 9H).

Example 48

A mixture of (Z)-tert-butyl 2-(2-(1-(N'-hydroxycarbamimidoyl)-2-oxabicyclo[2.2.2]octan-4-yl)ethoxy) acetate (76 mg, 0.188 mmol), HOAc (0.012 mL, 0.21 mmol), HOBT (35 mg, 0.23 mmol), and EDC (43 mg, 0.23 mmol) in DMF (1 mL) was stirred at rt for 18 h. LC-MS showed that the first step of the reaction sequence was complete at this point. The mixture was concentrated in vacuo, and the residue was partitioned between EtOAc and water, washed with brine, dried (MgSO$_4$) and concentrated in vacuo. The residue was dissolved in DMF (1 mL) and heated to 120° C. for 3 h. LC-MS showed that the second reaction was complete. The mixture was cooled at rt was concentrated in vacuo. The residue was diluted with EtOAc, washed with water and brine, dried (MgSO$_4$), and concentrated in vacuo. The residue was stirred with formic acid (0.72 mL, 18.8 mmol) at rt for 18 h. LC-MS showed that the reaction was complete, and the mixture was concentrated in vacuo. The residual crude oil was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (18 mg, 0.047 mmol, 25% yield) as a clear oil. LCMS [M−H]$^+$=371.2; $^1$H NMR (CDCl$_3$) δ: 8.00 (t, J=1.8 Hz, 1H), 7.84 (dt, J=7.8, 1.4 Hz, 1H), 7.49 (dt, J=7.9, 1.5 Hz, 1H), 7.35 (t, J=7.8 Hz, 1H), 4.04 (s, 2H), 3.82 (s, 2H), 3.54 (t, J=6.9 Hz, 2H), 2.58 (s, 3H), 2.09-1.94 (m, 4H), 1.66 (t, J=7.9 Hz, 4H), 1.48 (t, J=6.9 Hz, 2H).

Example 49

2-(2-(1-(3-(Trifluoromethyl)phenyl)-2-oxabicyclo[2.2.2]octan-4-yl)ethoxy)acetic acid

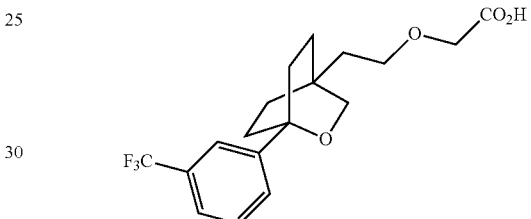

49A. 3-(4-(2-(2-tert-Butoxy-2-oxoethoxy)ethyl)-2-oxabicyclo[2.2.2]octan-1-yl)phenyl boronic acid

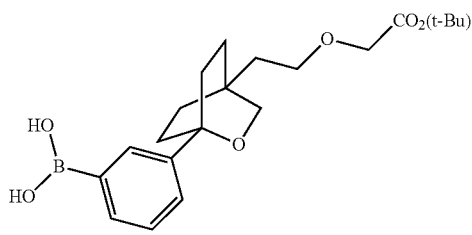

To a mixture of tert-butyl 2-(2-(1-(3-(4,4,5,5-tetramethyl-1,3,2-dioxaborolan-2-yl)phenyl)-2-oxabicyclo[2.2.2]octan-4-yl)ethoxy)acetate (38B; 400 mg, 0.847 mmol) and NH$_4$OAc (392 mg, 5.08 mmol) in acetone (5 mL) and water (5 mL) was added NaIO$_4$ (543 mg, 2.54 mmol) with stirring. The reaction was stirred at rt for 18 h, then was concentrated in vacuo. The residue was dissolved in EtOAc (5 mL) and washed with 1N aq. HCl and water. The organic layer was concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (201 mg, 0.505 mmol, 59.6% yield) as a clear oil. LCMS [M+NH$_4$]$^+$=408.0.

49B. tert-Butyl 2-(2-(1-(3-(trifluoromethyl)phenyl)-2-oxabicyclo[2.2.2]octan-4-yl)ethoxy) acetate

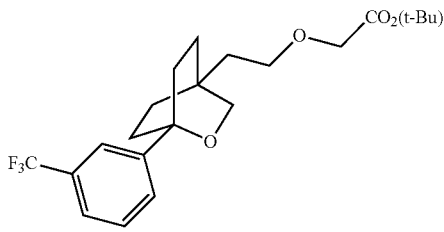

To a mixture of 3-(4-(2-(2-tert-butoxy-2-oxoethoxy)ethyl)-2-oxabicyclo[2.2.2]octan-1-yl)phenylboronic acid (50 mg, 0.128 mmol), sodium trifluoromethanesulfinate (60 mg, 0.38 mmol) and Cu (I) Cl (13 mg, 0.13 mmol) in DCM (0.5 mL)/MeOH (0.5 mL)/water (0.2 mL) was added 70% aq. t-BuOOH solution (0.088 mL, 0.64 mmol) dropwise over 30 min. The reaction was stirred at rt for 18 h, then was filtered. The filtrate was concentrated in vacuo and then purified by preparative HPLC (PHENOMENEX® Axia 5µ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (40 mg, 0.097 mmol, 75% yield) as a clear oil. $^1$H NMR (CDCl$_3$) δ: 7.70 (t, J=1.8 Hz, 1H), 7.58 (dt, J=7.7, 1.5 Hz, 1H), 7.49 (d, J=7.7 Hz, 1H), 7.43 (t, J=7.7 Hz, 1H), 3.97 (s, 2H), 3.92 (s, 2H), 3.59 (t, J=6.9 Hz, 2H), 2.16-1.99 (m, 4H), 1.77 (t, J=8.0 Hz, 4H), 1.56 (t, J=6.8 Hz, 2H), 1.51 (s, 9H); $^{19}$F NMR (CDCl$_3$) δ: −62.5.

Example 49

A mixture of tert-butyl 2-(2-(1-(3-(trifluoromethyl)phenyl)-2-oxabicyclo[2.2.2]octan-4-yl) ethoxy)acetate (40 mg, 0.097 mmol) and formic acid (185 µl, 4.83 mmol) was stirred at rt for 2 days, then was concentrated in vacuo. The residue was purified by preparative HPLC (PHENOMENEX® Axia 5µ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (26 mg, 0.071 mmol, 74% yield) as a clear oil. LCMS [M+H]$^+$=359.0; $^1$H NMR (CDCl$_3$) δ: 7.70 (t, J=1.7 Hz, 1H), 7.58 (dt, J=7.8, 1.4 Hz, 1H), 7.52-7.47 (m, 1H), 7.43 (t, J=7.7 Hz, 1H), 4.13 (s, 2H), 3.92 (s, 2H), 3.64 (t, J=6.8 Hz, 2H), 2.15-1.99 (m, 4H), 1.76 (t, J=7.9 Hz, 4H), 1.57 (t, J=6.8 Hz, 2H); $^{19}$F NMR (CDCl$_3$) δ: −62.5.

Example 50

2-(2-(1-(3-Benzylphenyl)-2-oxabicyclo[2.2.2]octan-4-yl)ethoxy)acetic acid

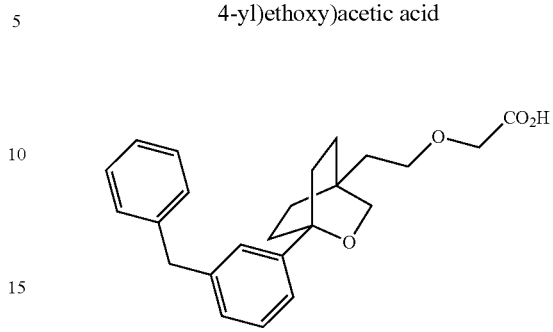

50A. tert-Butyl 2-(2-(1-(3-benzylphenyl)-2-oxabicyclo[2.2.2]octan-4-yl)ethoxy)acetate A mixture of (3-(4-(2-(2-(tert-butoxy)-2-oxoethoxy)ethyl)-2-oxabicyclo[2.2.2]octan-1-yl)phenyl)boronic acid (49A; 20 mg, 0.051 mmol), benzyl bromide (0.012 mL, 0.102 mmol), and Na$_2$CO$_3$ (16 mg, 0.15 mmol) in 1,4-dioxane (1 mL)/water (0.2 mL) was degassed under Ar for 3 min using an ultrasonicator and then (Ph$_3$P)$_4$Pd (59 mg, 0.051 mmol) was added. The reaction was stirred at 100° C. under Ar for 18 h, then was cooled to rt and partitioned between EtOAc (5 mL) and water, dried (MgSO$_4$), and concentrated in vacuo to give the crude product as a yellow oil, which was used in the next reaction without further purification.

Example 50

A mixture of tert-butyl 2-(2-(1-(3-benzylphenyl)-2-oxabicyclo[2.2.2]octan-4-yl)ethoxy)acetate (22 mg, 0.051 mmol) and formic acid (2.0 µL, 0.051 mmol) was stirred at rt for 2 h and then concentrated in vacuo. The crude product was purified by preparative LC/MS (Column: Waters XBridge C18, 19×100 mm, 5-µm particles; Mobile Phase A: 5:95 MeCN:water with 0.1% formic acid; Mobile Phase B: 95:5 MeCN:water with 0.1% formic acid; Gradient: 40-85% B over 10 min, then a 5-min hold at 100% B; Flow rate: 20 mL/min) to give the title compound (3.2 mg, 8.2 µmol, 16% yield) as a white solid. LCMS [M−H]$^+$=379.1; $^1$H NMR (DMSO-d$_6$) δ: 7.31-7.25 (m, 3H), 7.24-7.14 (m, 5H), 7.06-7.02 (m, 1H), 3.93 (s, 2H), 3.91 (s, 2H), 3.75 (s, 2H), 3.48 (t, J=6.8 Hz, 2H), 2.01 (ddd, J=13.0, 10.8, 4.7 Hz, 2H), 1.78 (dtd, J=13.9, 7.9, 2.9 Hz, 2H), 1.71-1.55 (m, 4H), 1.39 (t, J=6.8 Hz, 2H).

Example 51

2-(2-(1-(3-(Cyclobutylmethoxy)phenyl)-2-oxabicyclo[2.2.2]octan-4-yl)ethoxy)acetic acid

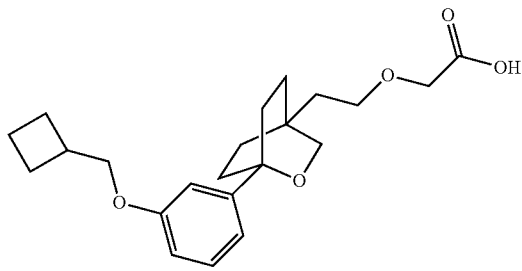 [SMILES: O=C(O)COCCC12CCC(c3cccc(OCC4CCC4)c3)(CC1)OC2]

A mixture of tert-butyl 2-(2-(1-(3-hydroxyphenyl)-2-oxabicyclo[2.2.2]octan-4-yl)ethoxy)acetate (7F; 15 mg, 0.041 mmol), (bromomethyl)cyclobutane (9.25 mg, 0.062 mmol) and Cs$_2$CO$_3$ (41 mg, 0.124 mmol) in MeCN (1.0 mL) was heated to ~60° C. for 10 h. The reaction was then cooled to rt, filtered and the filtrates were concentrated in vacuo. The crude alkylated phenol ester product was dissolved in THF/MeOH (1 mL of a 1:1 mixture) and aq. NaOH (90 μL of a 1 N solution, 0.090 mmol) and the mixture was stirred at rt for 3 h, then was concentrated in vacuo. The residue was dissolved in EtOAc (3 mL) and washed with 1 N aq. HCl, water, brine, then dried (MgSO$_4$), and concentrated in vacuo. The crude product was purified by preparative HPLC/MS (Column: Waters XBridge C18, 19×200 mm, 5-μm particles; Mobile Phase A: 5:95 MeCN:water with 0.1% HCO$_2$H; Mobile Phase B: 95:5 MeCN:water with 0.1% HCO$_2$H; Gradient: 45-85% B over 20 min, then a 5-min hold at 100% B; Flow rate: 20 mL/min) to give the title compound (7.7 mg, 67% yield; 99% purity by LC/MS) as a light yellow oil. LCMS [M−H]$^-$=373; $^1$H NMR (500 MHz, DMSO-d$_6$) δ 7.18 (t, J=8.3 Hz, 1H), 6.97-6.86 (m, 2H), 6.75 (dd, J=8.1, 1.2 Hz, 1H), 3.95 (s, 2H), 3.92 (d, J=6.6 Hz, 2H), 3.77 (s, 2H), 3.53-3.48 (m, 2H), 2.74-2.65 (m, 1H), 2.14-1.98 (m, 4H), 1.97-1.74 (m, 6H), 1.72-1.58 (m, 4H), 1.41 (t, J=6.6 Hz, 2H).

Example 52

2-(2-(1-(3-(Cyclohexylmethoxy)phenyl)-2-oxabicyclo[2.2.2]octan-4-yl)ethoxy)acetic acid

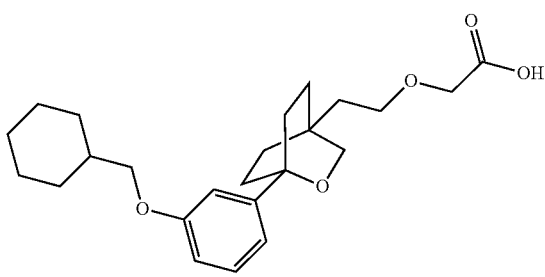 [SMILES: O=C(O)COCCC12CCC(c3cccc(OCC4CCCCC4)c3)(CC1)OC2]

The title compound was prepared by an analogous sequence to that used to synthesize Example 51 from 7F (tert-butyl 2-(2-(1-(3-hydroxyphenyl)-2-oxabicyclo[2.2.2]octan-4-yl)ethoxy)acetate) except that (bromomethyl)cyclohexane was used instead of (bromomethyl)cyclobutane as the alkylating agent. The crude product was purified by preparative LC/MS (Column: Waters XBridge C18, 19×200 mm, 5-nm particles; Mobile Phase A: 5:95 MeCN:water with 10-mM NH$_4$OAc; Mobile Phase B: 95:5 MeCN:water with 10-mM NH$_4$OAc; Gradient: 30-70% B over 20 min, then a 5-min hold at 100% B; Flow rate: 20 mL/min) to give the title compound (8 mg, 65% yield; 100% purity by LC/MS) as a light yellow oil. LCMS, [M−H]$^-$=401. $^1$H NMR (500 MHz, DMSO-d$_6$) δ 7.96 (s, 1H), 7.17 (t, J=8.1 Hz, 1H), 6.96-6.85 (m, 2H), 6.78-6.68 (m, 1H), 3.95 (s, 2H), 3.79-3.70 (m, 4H), 3.50 (t, J=6.7 Hz, 3H), 2.08-1.98 (m, 2H), 1.86-1.57 (m, 12H), 1.40 (t, J=6.7 Hz, 2H), 1.32-1.12 (m, 3H), 1.10-0.99 (m, 2H).

Example 53

2-(2-(1-(3-(Pentan-2-yloxy)phenyl)-2-oxabicyclo[2.2.2]octan-4-yl)ethoxy)acetic acid (racemate)

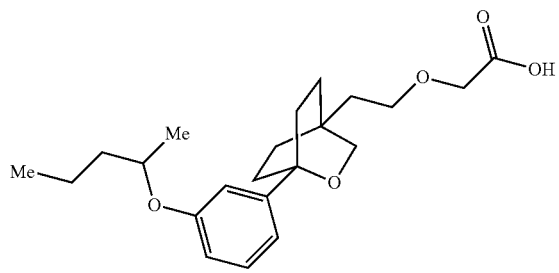 [SMILES: CCCC(C)Oc1cccc(C23CCC(CCOCC(=O)O)(CC2)CO3)c1]

The title compound was prepared by an analogous sequence to that used to synthesize Example 51 from 7F (tert-butyl 2-(2-(1-(3-hydroxyphenyl)-2-oxabicyclo[2.2.2]octan-4-yl)ethoxy)acetate) except that 2-bromopentane instead of (bromomethyl)cyclobutane was used as the alkylating agent. The crude product was purified by preparative LC/MS (Column: Waters XBridge C18, 19×200 mm, 5-μm particles; Mobile Phase A: 5:95 MeCN:water with 10 mM NH$_4$OAc; Mobile Phase B: 95:5 MeCN:water with 10 mM NH$_4$OAc; Gradient: 30-70% B over 20 min, then a 5-min hold at 100% B; Flow rate: 20 mL/min) to give the title compound (11.5 mg, 88% yield; 96% purity by LC/MS) as a light yellow oil. LCMS, [M−H]$^-$=375. $^1$H NMR (500 MHz, DMSO-d$_6$) δ 7.96 (s, 1H), 7.17 (t, J=8.0 Hz, 1H), 6.96-6.83 (m, 2H), 6.74 (d, J=8.3 Hz, 1H), 4.41 (sxt, J=5.9 Hz, 1H), 3.95 (s, 2H), 3.76 (s, 2H), 3.50 (t, J=6.7 Hz, 3H), 2.09-1.96 (m, 2H), 1.87-1.75 (m, 2H), 1.71-1.57 (m, 5H), 1.56-1.47 (m, 1H), 1.46-1.32 (m, 3H), 1.21 (d, J=6.1 Hz, 3H), 0.90 (t, J=7.2 Hz, 3H).

Example 54

2-(2-(1-(3-Fluoro-5-(2,2,2-trifluoroethoxy)phenyl)-2-oxabicyclo[2.2.2]octan-4-yl)ethoxy)acetic acid

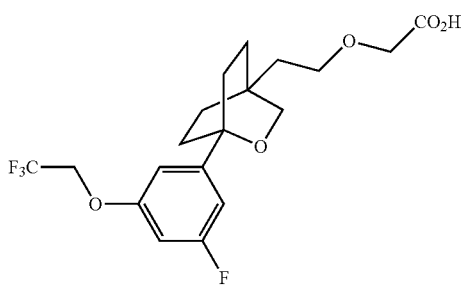 [SMILES: O=C(O)COCCC12CCC(c3cc(F)cc(OCC(F)(F)F)c3)(CC1)OC2]

54A. tert-Butyl 2-(2-(1-(3-fluoro-5-(2,2,2-trifluoroethoxy)phenyl)-2-oxabicyclo[2.2.2]octan-4-yl)ethoxy)acetate

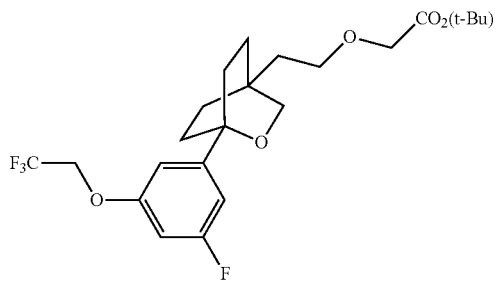

A mixture of tert-butyl 2-(2-(1-(3-fluoro-5-hydroxyphenyl)-2-oxabicyclo[2.2.2]octan-4-yl)ethoxy)acetate (36I; 17 mg, 0.045 mmol), 2,2,2-trifluoroethyl trifluoromethane-sulfonate (10.0 µL, 0.067 mmol), and $K_2CO$ (12.4 mg, 0.089 mmol) in acetone (1 mL) was stirred at rt for 18 h, after which the reaction was concentrated in vacuo. The residue was taken up in DCM (2 mL) and the filtrate was concentrated in vacuo. The residue was stirred with formic acid (0.5 mL) at rt for 2 h and then concentrated in vacuo. The crude product (oil) was purified by preparative HPLC (PHENOMENEX® Axia 5µ C18 30×100 mm column; detection at 220 nm; flow rate=40 mL/min; continuous gradient from 50% B to 100% B over 10 min+2 min hold time at 100% B, where A=90:10:0.1 $H_2O$:MeOH:TFA and B=90:10:0.1 MeOH:$H_2O$:TFA) to give (16 mg, 0.039 mmol, 86% yield) as clear oil. LCMS [M−H]$^+$=405.2; $^1$H NMR (CDCl$_3$) δ: 6.85-6.82 (m, 1H), 6.79 (ddd, J=9.9, 2.2, 1.3 Hz, 1H), 6.54 (dt, J=9.9, 2.3 Hz, 1H), 4.36 (q, J=8.1 Hz, 2H), 4.13 (s, 2H), 3.89 (s, 2H), 3.63 (t, J=6.8 Hz, 2H), 2.06-1.94 (m, 4H), 1.79-1.69 (m, 4H), 1.56 (t, J=6.8 Hz, 2H); $^{19}$F NMR (CDCl$_3$) δ: −74.0, −111.1.

Example 55

2-(2-(1-(3-Fluoro-5-(3-fluorophenoxy)phenyl)-2-oxabicyclo[2.2.2]octan-4-yl)ethoxy) acetic acid

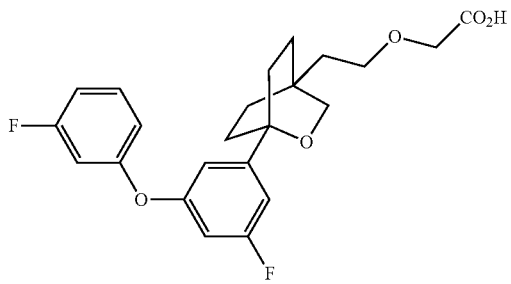 [SMILES: O=C(O)COCCC12CCC(c3cc(F)cc(Oc4cccc(F)c4)c3)(CC1)OC2]

A mixture of tert-butyl 2-(2-(1-(3-fluoro-5-hydroxyphenyl)-2-oxabicyclo[2.2.2]octan-4-yl)ethoxy)acetate (36I; 17 mg, 0.045 mmol), (3-fluorophenyl)boronic acid (7.5 mg, 0.054 mmol), Cu(OAc)$_2$ (9.7 mg, 0.054 mmol), TEA (0.062 mL, 0.45 mmol), pyridine (0.036 mL, 0.45 mmol), and 4A Molecular Sieves (0.2 g) in DCM (1 mL) was stirred under air at rt for 3 days. The reaction mixture was filtered, and the filtrate was concentrated in vacuo. The residual crude oil was dissolved in EtOAc (5 mL) and washed with aq. 1N HCl and water, dried (MgSO$_4$), and concentrated in vacuo. The crude 3-fluorophenoxy ether ester product was stirred with formic acid (0.5 mL) for 3 h and then volatiles were removed in vacuo. The residue was purified by preparative HPLC (PHENOMENEX® Axia 5µ C18 30×100 mm column; detection at 220 nm; flow rate=40 mL/min; continuous gradient from 50% B to 100% B over 10 min+5 min hold time at 100% B, where A=90:10:0.1 $H_2O$:MeOH:TFA and B=90:10:0.1 MeOH:$H_2O$:TFA) to give the title compound (14 mg, 0.033 mmol, 73% yield) as a light brown oil. LCMS [M+Na]$^+$=441.0; $^1$H NMR (CDCl$_3$) δ: 7.32-7.23 (m, 1H), 6.93-6.75 (m, 4H), 6.70 (dt, J=10.1, 2.4 Hz, 1H), 6.56 (dt, J=9.5, 2.3 Hz, 1H), 4.10 (s, 2H), 3.85 (s, 2H), 3.60 (t, J=6.8 Hz, 2H), 2.07-1.90 (m, 4H), 1.71 (t, J=7.9 Hz, 4H), 1.53 (t, J=6.8 Hz, 2H); $^{19}$F NMR (CDCl$_3$) δ: −110.69, −110.74.

Example 56

4-(1-(3-Phenoxyphenyl)-2-oxabicyclo[2.2.2]octan-4-yl)butane-1,2-diol

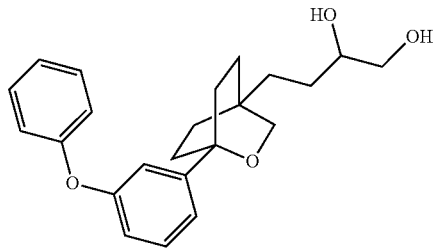 [SMILES: OCC(O)CCC12CCC(c3cccc(Oc4ccccc4)c3)(CC1)OC2]

56A. 4-(Iodomethyl)-1-(3-phenoxyphenyl)-2-oxabicyclo[2.2.2]octane

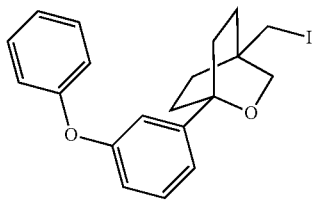 [SMILES: ICC12CCC(c3cccc(Oc4ccccc4)c3)(CC1)OC2]

A mixture of (1-(3-phenoxyphenyl)-2-oxabicyclo[2.2.2]octan-4-yl)methyl 4-methylbenzenesulfonate (1G; 950 mg, 2.05 mmol) and NaI (3.07 g, 20.45 mmol) in MeCN (10 mL) was heated to 70° C. for 72 h. The reaction mixture was cooled to rt, filtered and concentrated in vacuo. The residual crude product was purified by flash chromatography to give the title compound (745 mg, 1.77 mmol; 87% yield) as a white solid. LCMS, [M+H]$^+$=421; $^1$H NMR (400M Hz, CDCl$_3$) δ 7.38-7.23 (m, 3H), 7.19-7.08 (m, 3H), 7.04-6.98 (m, 2H), 6.87 (ddd, J=8.0, 2.3, 1.0 Hz, 1H), 3.88 (s, 2H), 3.07 (s, 2H), 2.18-1.95 (m, 4H), 1.87-1.68 (m, 4H).

56B. 4-(But-3-enyl)-1-(3-phenoxyphenyl)-2-oxabicyclo[2.2.2]octane

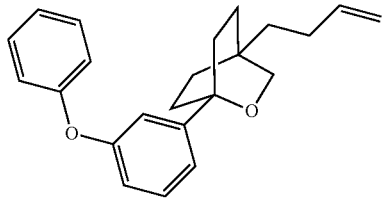 [SMILES: C=CCCC12CCC(c3cccc(Oc4ccccc4)c3)(CC1)OC2]

A solution of 4-(iodomethyl)-1-(3-phenoxyphenyl)-2-oxabicyclo[2.2.2]octane (70 mg, 0.17 mmol) in diisopropyl ether (1.0 mL) was added to a flask containing Cu(OTf)$_2$ (3.0 mg, 8.3 μmol), followed by allylmagnesium bromide (500 μL of a 1M solution in Et$_2$O, 0.50 mmol). The reaction mixture was stirred at rt for 4 h, then was quenched by slow addition of satd aq. NH$_4$Cl and extracted with EtOAc. The organic layer was washed with brine, dried (MgSO$_4$), and concentrated in vacuo. The residual crude oil was first purified by flash chromatography (0 to 50% gradient in EtOAc:hexanes), then underwent a final purification by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H$_2$O:MeOH:TFA and B=90:10:0.1 MeOH:H$_2$O:TFA) to afford the title compound (11 mg, 19% yield; 95% purity by LC/MS) as a white solid. $^1$H NMR (400 MHz, CDCl$_3$) δ 7.34-7.27 (m, 2H), 7.24 (s, 1H), 7.16-7.10 (m, 2H), 7.10-7.04 (m, 1H), 7.01-6.96 (m, 2H), 6.84 (dd, J=8.5, 3.0 Hz, 1H), 5.80 (ddt, J=17.0, 10.3, 6.5 Hz, 1H), 5.01 (dq, J=17.1, 1.7 Hz, 1H), 4.94 (dq, J=10.1, 1.5 Hz, 1H), 3.81 (s, 2H), 2.05-1.96 (m, 6H), 1.70-1.62 (m, 4H), 1.28-1.21 (m, 2H).

Example 56

To a solution of 4-(but-3-en-1-yl)-1-(3-phenoxyphenyl)-2-oxabicyclo[2.2.2]octane (9 mg, 0.027 mmol) in THF (0.5 mL) was added N-methyl morpholine N-oxide (5 mg, 0.040 mmol) followed by OsO$_4$ (3.8 μL of a 4.5% solution in water, 0.54 μmol). The reaction mixture was stirred at rt for 18 h, then was quenched with Na$_2$SO$_3$ and partitioned between water and EtOAc. The organic layer was washed with brine, dried (MgSO$_4$), and concentrated in vacuo. The crude product was purified by preparative HPLC (PHENOMENEX® Axia 5μ C18 30×100 mm column; detection at 220 nm; flow rate=40 mL/min; continuous gradient from 10% B to 100% B over 10 min+5 min hold time at 100% B, where A=90:10:0.1 H$_2$O:MeOH:TFA and B=90:10:0.1 MeOH:H$_2$O:TFA) to afford the title compound as a white solid. (9 mg, 88% yield; 99% purity by LC/MS). LCMS, [M–H$_2$O]$^+$=351, $^1$H NMR (500 MHz, CDCl$_3$) δ 7.37-7.31 (m, 2H), 7.30-7.26 (m, 1H), 7.18-7.15 (m, 1H), 7.14-7.12 (m, 1H), 7.12-7.08 (m, 1H), 7.03-6.99 (m, 2H), 6.86 (ddd, J=8.1, 2.5, 1.0 Hz, 1H), 3.83 (s, 2H), 3.73-3.63 (m, 2H), 3.53-3.44 (m, 1H), 2.09-1.99 (m, 4H), 1.72-1.63 (m, 4H), 1.45-1.39 (m, 3H), 1.24-1.14 (m, 1H).

Example 57

4-(1-(3-Phenoxyphenyl)-2-oxabicyclo[2.2.2]octan-4-yl)butan-1-ol

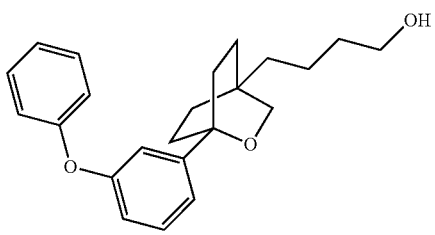 [SMILES: OCCCCC12CCC(c3cccc(Oc4ccccc4)c3)(CC1)OC2]

57A. Methyl 4-(1-(3-phenoxyphenyl)-2-oxabicyclo[2.2.2]octan-4-yl)butanoate

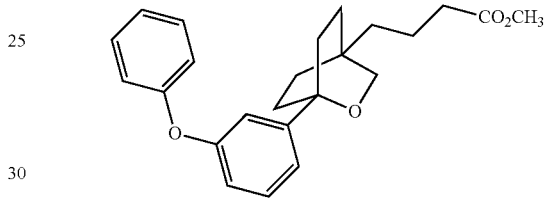

A mixture of Zn (622 mg, 9.52 mmol), anhydrous pyridine (5 mL) and methyl acrylate (0.95 mL, 9.52 mmol) was warmed to 50° C., after which NiCl$_2$.6H$_2$O (283 mg, 1.19 mmol) was added. The resulting mixture was heated to 65° C. for 1 h and stirred until the color of the solution became reddish-brown, then was cooled to 0° C., after which a solution of 4-(iodomethyl)-1-(3-phenoxyphenyl)-2-oxabicyclo[2.2.2]octane (500 mg, 1.190 mmol) in pyridine (2 mL) was added. The reaction mixture was allowed to warm to rt overnight, then was diluted with EtOAc (10 mL) and the resulting mixture was filtered off through a pad of CELITE®. The filtrate was washed with 1 N aq. HCl and brine, dried (MgSO$_4$), and concentrated in vacuo. The residual crude oil was purified by flash chromatography (SiO$_2$; gradient from 0 to 50% EtOAc:hexanes) to afford the title compound as a colorless oil (318 mg, 73% yield). LCMS, [M+H]$^+$=381, $^1$H NMR (400M Hz, CDCl$_3$) δ 7.39-7.24 (m, 3H), 7.19-7.06 (m, 3H), 7.04-6.98 (m, 2H), 6.86 (ddd, J=8.1, 2.4, 0.9 Hz, 1H), 3.82 (s, 2H), 3.70 (s, 3H), 2.31 (t, J=7.3 Hz, 2H), 2.10-1.98 (m, 4H), 1.76-1.57 (m, 6H), 1.22-1.12 (m, 2H).

Example 57

To a 0° C. solution of methyl 4-(1-(3-phenoxyphenyl)-2-oxabicyclo[2.2.2]octan-4-yl)butanoate (250 mg, 0.66 mmol) was added LiAlH$_4$ (0.657 mL of a 1 M solution in DCM, 0.657 mmol) dropwise. The reaction mixture was allowed to warm to rt and stirred at rt for 2 h, then was cooled to 0° C. and quenched by dropwise addition of EtOAc followed by satd aq. NaSO$_4$ (1 mL). The mixture was filtered and the filtrate was concentrated in vacuo. The residual crude oil was purified by flash chromatography (SiO$_2$; gradient from 0 to 100% EtOAc:hexanes) to afford the title compound as a colorless oil (230 mg, 99% yield). LCMS, [M+Na]$^+$=375; $^1$H NMR (400 MHz, CDCl$_3$) δ 7.37-7.30 (m, 2H), 7.28-7.25 (m, 1H), 7.19-

7.06 (m, 3H), 7.01 (dd, J=8.6, 1.0 Hz, 2H), 6.86 (ddd, J=8.1, 2.5, 1.0 Hz, 1H), 3.82 (s, 2H), 3.68 (t, J=6.4 Hz, 2H), 2.03 (dd, J=9.3, 5.1 Hz, 4H), 1.77-1.61 (m, 4H), 1.57 (dt, J=14.2, 6.9 Hz, 3H), 1.39-1.27 (m, 2H), 1.22-1.16 (m, 1H).

Example 58

5-(1-(3-Phenoxyphenyl)-2-oxabicyclo[2.2.2]octan-4-yl)pentane-1,2-diol

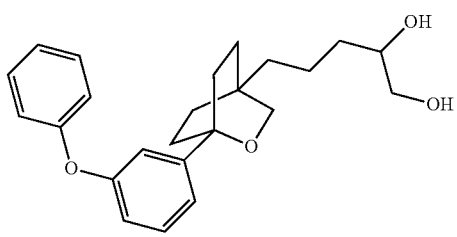 [SMILES: OCC(O)CCCC12CCC(c3cccc(Oc4ccccc4)c3)(CC1)OC2]

58A. 4-(1-(3-Phenoxyphenyl)-2-oxabicyclo[2.2.2]octan-4-yl)butanal

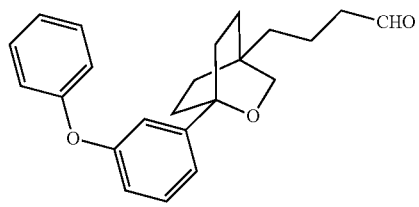 [SMILES: O=CCCCC12CCC(c3cccc(Oc4ccccc4)c3)(CC1)OC2]

To a 0° C. solution of 4-(1-(3-phenoxyphenyl)-2-oxabicyclo[2.2.2]octan-4-yl)butan-1-ol (150 mg, 0.426 mmol) in DCM (3 mL) was added Dess-Martin periodinane (217 mg, 0.511 mmol) over 5 min. The reaction mixture was slowly warmed up to rt and stirred for 2 h. An aq. solution of saturated NaHCO$_3$-Na$_2$S$_2$O$_3$ was added, and the mixture was stirred at rt for 5 min. The organic layer was washed with brine, dried (MgSO$_4$), and concentrated in vacuo. The crude product was purified by flash chromatography (SiO$_2$; gradient from 0 to 40% EtOAc:hexanes) to afford the title compound as a white solid (120 mg, 80% yield). $^1$H NMR (400 MHz, CDCl$_3$) δ 9.77 (t, J=1.5 Hz, 1H), 7.35-7.27 (m, 2H), 7.24 (s, 1H), 7.16-7.03 (m, 3H), 7.01-6.94 (m, 2H), 6.84 (ddd, J=8.0, 2.4, 1.0 Hz, 1H), 3.80 (s, 2H), 2.42 (td, J=7.3, 1.5 Hz, 2H), 2.07-1.96 (m, 4H), 1.76-1.55 (m, 6H), 1.23-1.10 (m, 2H).

58B. 4-(Pent-4-enyl)-1-(3-phenoxyphenyl)-2-oxabicyclo[2.2.2]octane

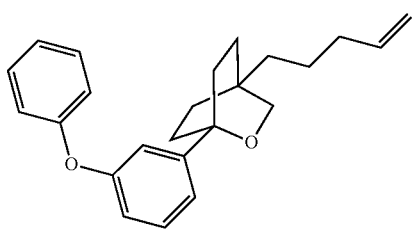 [SMILES: C=CCCCC12CCC(c3cccc(Oc4ccccc4)c3)(CC1)OC2]

To a 0° C. mixture of methyl triphenylphosphonium bromide (236 mg, 0.66 mmol) in THF (8 mL) was added dropwise n-BuLi (0.27 mL of a 2.5 M solution in hexane, 0.66 mmol). The reaction mixture was stirred at 0° C. for 30 min, and a solution of 4-(1-(3-phenoxyphenyl)-2-oxabicyclo[2.2.2]octan-4-yl)butanal (116 mg, 0.33 mmol) in THF (2 mL) was added at 0° C. The reaction mixture was warmed to rt and stirred for 2 h, then was quenched with sat'd aq. NH$_4$Cl, and extracted with EtOAc. The organic layer was washed with brine, dried (MgSO$_4$), and concentrated in vacuo. The crude material was purified by flash chromatography (SiO$_2$; gradient from 0 to 30% EtOAc:hexanes) to afford the title compound as a colorless oil (94 mg; 81% yield). $^1$H NMR (400 MHz, CDCl$_3$) δ 7.34-7.23 (m, 4H), 7.16-7.05 (m, 2H), 6.98 (dd, J=8.7, 1.0 Hz, 2H), 6.83 (ddd, J=8.0, 2.4, 1.0 Hz, 1H), 5.79 (ddt, J=17.0, 10.3, 6.6 Hz, 1H), 5.03-4.93 (m, 1H), 3.79 (s, 2H), 2.06-1.93 (m, 5H), 1.70-1.52 (m, 6H), 1.48-1.22 (m, 3H), 1.21-1.03 (m, 2H).

Example 58

To a solution of 4-(pent-4-en-1-yl)-1-(3-phenoxyphenyl)-2-oxabicyclo[2.2.2]octane (27 mg, 0.077 mmol) in THF (1 mL) was added N-methylmorpholine-N-oxide (13.61 mg, 0.116 mmol) followed by OsO$_4$ (11 μL of a 4.5% solution in water, 1.6 μmol). The reaction mixture was stirred at rt for 18 h, then was quenched with addition of saturated aq. Na$_2$SO$_3$, then was partitioned between water and EtOAc. The organic layer was washed with brine, dried (MgSO$_4$) and concentrated in vacuo. The crude material was purified by preparative HPLC (PHENOMENEX® Axia 5μ C18 30×100 mm column; detection at 220 nm; flow rate=40 mL/min; continuous gradient from 25% B to 100% B over 10 min+5 min hold time at 100% B, where A=90:10:0.1 H$_2$O:MeOH:TFA and B=90:10:0.1 MeOH:H$_2$O:TFA). The resulting purified product (but contaminated by trifluoroacetate ester from reaction with the TFA) was dissolved in THF (1 mL) followed by addition of 1N aq. NaOH (0.5 mL). The reaction mixture was stirred at rt for 2 h, then was concentrated in vacuo. The residue was dissolved in EtOAc (3 mL) and washed with 1 N aq. HCl, water and brine, dried (MgSO$_4$), and concentrated in vacuo. The crude material was purified by flash chromatography (SiO$_2$; gradient from 0 to 100% EtOAc:hexanes) to afford the title compound as a colorless oil (13 mg, 43% yield). $^1$H NMR (400 MHz, CDCl$_3$) δ 7.35-7.24 (m, 3H), 7.18-7.04 (m, 3H), 7.01-6.96 (m, 2H), 6.83 (ddd, J=8.0, 2.5, 0.9 Hz, 1H), 3.79 (s, 2H), 3.75-3.62 (m, 2H), 3.44 (dd, J=10.9, 7.6 Hz, 1H), 2.00 (dd, J=9.4, 5.2 Hz, 4H), 1.83 (br. s., 1H), 1.70-1.61 (m, 4H), 1.47-1.36 (m, 3H), 1.26 (s, 2H), 1.20-1.12 (m, 2H).

Examples 59 and 60

S-5-(1-(3-Phenoxyphenyl)-2-oxabicyclo[2.2.2]octan-4-yl)pentane-1,2-diol and R-5-(1-(3-phenoxyphenyl)-2-oxabicyclo[2.2.2]octan-4-yl)pentane-1,2-diol

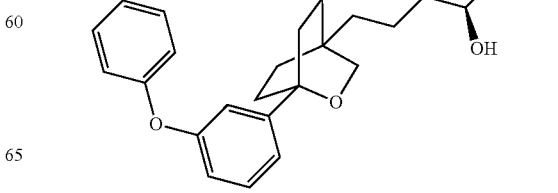

-continued

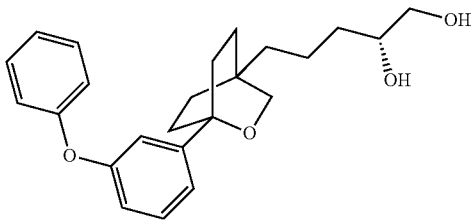

Example 58 (racemate) was separated by chiral preparative HPLC (CHIRALCEL® OD-H, 21×250 mm, 5 μm column; detection at 210 nm; flow rate=40 mL/min, 120 Bar, 40° C.; Mobile Phase: 20% EtOH, 80% $CO_2$; Injection: 0.5 mL of 12 mg/mL to afford Example 59 as the faster moving isomer on chiral preparative HPLC. Analysis for Example 59: CHIRALPAK® AD-H, 4.6×250 mm, 5μ. Mobile Phase: 30% EtOH-heptane (1:1)/70% $CO_2$,Flow rate=40 mL/min, 100 Bar, 35° C.; Wavelength: 220 nm. LCMS Purity=99.5%, 99.0% ee; $^1$H NMR (400 MHz, $CDCl_3$) δ 7.35-7.24 (m, 3H), 7.18-7.04 (m, 3H), 7.01-6.96 (m, 2H), 6.83 (ddd, J=8.0, 2.5, 0.9 Hz, 1H), 3.79 (s, 2H), 3.75-3.62 (m, 2H), 3.44 (dd, J=10.9, 7.6 Hz, 1H), 2.00 (dd, J=9.4, 5.2 Hz, 4H), 1.83 (br. s., 1H), 1.70-1.61 (m, 4H), 1.47-1.36 (m, 3H), 1.26 (s, 2H), 1.20-1.12 (m, 2H). Example 60 was isolated as the slower moving isomer on chiral preparative HPLC. Analysis for Example 60: CHIRALPAK® AD-H, 4.6×250 mm, 5 μm. Mobile Phase: 30% EtOH-heptane (1:1)/70% $CO_2$, Flow rate=40 mL/min, 100 Bar, 35° C.; Wavelength: 220 nm. Purity=99.5%, 99.0% ee. $^1$H NMR (400 MHz, CDC δ 7.35-7.24 (m, 3H), 7.18-7.04 (m, 3H), 7.01-6.96 (m, 2H), 6.83 (ddd, J=8.0, 2.5, 0.9 Hz, 1H), 3.79 (s, 2H), 3.75-3.62 (m, 2H), 3.44 (dd, J=10.9, 7.6 Hz, 1H), 2.00 (dd, J=9.4, 5.2 Hz, 4H), 1.83 (br. s., 1H), 1.70-1.61 (m, 4H), 1.47-1.36 (m, 3H), 1.26 (s, 2H), 1.20-1.12 (m, 2H).

Example 61

2-(2-(1-(3-(Tetrahydro-2H-pyran-2-yloxy)phenyl)-2-oxabicyclo[2.2.2]octan-4-yl)ethyl) cyclopropanecarboxylic acid

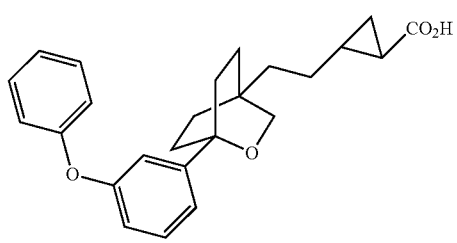 [SMILES: O=C(O)C1CC1CCC12CCC(c3cccc(Oc4ccccc4)c3)(CC1)OC2]

61A. Methyl 2-(2-(1-(3-(tetrahydro-2H-pyran-2-yloxy)phenyl)-2-oxabicyclo[2.2.2]octan-4-yl)ethyl) cyclopropanecarboxylate

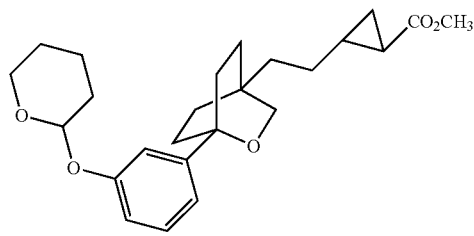 [SMILES: COC(=O)C1CC1CCC12CCC(c3cccc(OC4CCCCO4)c3)(CC1)OC2]

To a vigorously stirred mixture of $Et_2O$ (80 mL), 40% aq. KOH (20 mL, 140 mmol) and water (10 mL) with was added N-methyl-N'-nitro-N-nitrosoguanidine (6.0 g, 20.4 mmol) portionwise over 15 min at 0° C. Upon completion of the addition, stirring was stopped and the aq. layer was separated. The ethereal layer was dried with KOH pellets (2×). ~Half of the diazomethane solution in $Et_2O$ (40 mL) was mixed with a 0° C. solution of (E)-methyl 5-(1-(3-((tetrahydro-2H-pyran-2-yl)oxy)phenyl)-2-oxabicyclo [2.2.2]octan-4-yl) pent-2-enoate (2.5 g, 6.24 mmol) in THF (20 mL). A mixture of $Pd(OAc)_2$ (0.08 g, 0.36 mmol) in THF (2 mL) was added slowly and the reaction was stirred at 0° C. for 15 min and then the remainder of the ethereal diazomethane solution (40 mL) was added slowly. The reaction was allowed to warm to rt and stirred for 1 h at rt, then was filtered and then concentrated in vacuo to give the crude title compound. The combined crude products from 4 such reactions were chromatographed ($SiO_2$; gradient from 0% to 50% EtOAc/hexane) to give the title compound (8.3 g, 20.0 mmol, 99% yield) as a clear oil. $^1$H NMR ($CDCl_3$-$d_6$) δ: 7.23 (t, J=8.0 Hz, 1H), 7.15-7.08 (m, 1H), 7.01 (dt, J=7.8, 1.3 Hz, 1H), 6.94 (ddd, J=8.1, 2.5, 1.0 Hz, 1H), 5.44 (t, J=3.3 Hz, 1H), 3.94 (ddd, J=11.3, 9.7, 3.1 Hz, 1H), 3.85-3.77 (m, 2H), 3.69 (s, 3H), 3.61 (dtd, J=11.4, 4.1, 1.4 Hz, 1H), 2.12-1.96 (m, 5H), 1.94-1.82 (m, 2H), 1.78-1.55 (m, 7H), 1.44-1.14 (m, 7H), 0.73 (ddd, J=8.1, 6.2, 4.1 Hz, 1H).

Example 61

A mixture of methyl 2-(2-(1-(3-((tetrahydro-2H-pyran-2-yl)oxy)phenyl)-2-oxabicyclo[2.2.2]octan-4-yl)ethyl)cyclopropanecarboxylate (120 mg, 0.29 mmol) and 1N aq. NaOH (1.45 mL, 1.45 mmol) in MeOH (3 mL) was stirred at rt for 18 h. The reaction was diluted with EtOAc (5 mL), washed with 1N aq. HCl and water. The organic layer was dried ($MgSO_4$) and concentrated in vacuo to give the title compound (110 mg, 0.26 mmol, 90% yield) as a white solid. LCMS [M−H]$^+$=339.3; $^1$H NMR ($CDCl_3$) δ: 7.23 (t, J=8.0 Hz, 1H), 7.12 (t, J=2.1 Hz, 1H), 7.04-6.99 (m, 1H), 6.94 (dd, J=8.0, 2.4 Hz, 1H), 5.45 (t, J=3.2 Hz, 1H), 3.94 (ddd, J=11.3, 9.8, 3.1 Hz, 1H), 3.81 (d, J=1.4 Hz, 2H), 3.66-3.57 (m, 1H), 2.07-1.98 (m, 5H), 1.89-1.83 (m, 2H), 1.73-1.57 (m, 7H), 1.39 (ddt, J=20.5, 8.4, 4.3 Hz, 2H), 1.34-1.21 (m, 5H), 0.80 (ddd, J=8.1, 6.4, 4.2 Hz, 1H).

Example 62

N-((1H-1,2,4-Triazol-5-yl)methyl)-2-(2-(1-(3-phenoxyphenyl)-2-oxabicyclo[2.2.2]octan-4-yl)ethyl)cyclopropanecarboxamide (single enantiomer; absolute stereochemistry shown is arbitrary)

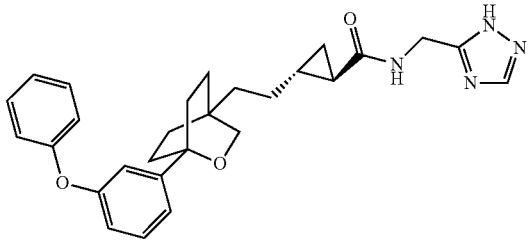 [SMILES: O=C(NCc1ncn[nH]1)[C@@H]1C[C@H]1CCC12CCC(c3cccc(Oc4ccccc4)c3)(CC1)OC2]

To a solution of 2-(2-(1-(3-phenoxyphenyl)-2-oxabicyclo[2.2.2]octan-4-yl)ethyl)cyclopropanecarboxylic acid (Example 15; 10 mg, 0.025 mmol) in DMF (1 mL) added 3H-[1,2,3]-triazolo[4,5-b]pyridin-3-ol (8.3 mg, 0.061 mmol), followed by EDC (10 mg, 0.051 mmol). The reaction was stirred at rt for 5 min, after which 4-DMAP (0.3 mg, 2.6 µmol) and iPr$_2$NEt (0.018 mL, 0.10 mmol) were added. The reaction mixture was stirred at rt overnight. More 3H-[1,2,3]-triazolo[4,5-b]pyridin-3-ol (8 mg, 0.061 mmol) and EDC (10 mg, 0.051 mmol) were added and the reaction was stirred overnight, then was purified by preparative HPLC (PHENOMENEX® Axia 5µ C18 30×100 mm column; detection at 220 nm; flow rate=40 mL/min; continuous gradient from 25% B to 100% B over 20 min+5 min hold time at 100% B, where A=90:10:0.1 H$_2$O:MeOH:TFA and B=90:10:0.1 MeOH:H$_2$O:TFA) to afford the title compound (4.9 mg, 40% yield; 96.7% purity by LC/MS) as a colorless oil. LCMS, [M+H]$^+$=473; $^1$H NMR (400 MHz, CDCl$_3$) δ: 8.36 (s, 1H), 8.19 (d, J=4.8 Hz, 1H), 8.13 (s, 1H), 7.38-7.30 (m, 2H), 7.27 (s, 1H), 7.19-7.07 (m, 3H), 7.01 (dd, J=8.6, 0.9 Hz, 2H), 6.88 (dd, J=8.0, 1.7 Hz, 1H), 4.89-4.76 (m, 2H), 3.81 (s, 2H), 2.14-1.94 (m, 4H), 1.64 (t, J=7.5 Hz, 4H), 1.44-1.16 (m, 7H), 0.85-0.77 (m, 1H).

Example 63

2-(2-(1-(3-Fluoro-5-phenoxyphenyl)-2-oxabicyclo[2.2.2]octan-4-yl)ethyl)cyclopropanecarboxylic acid

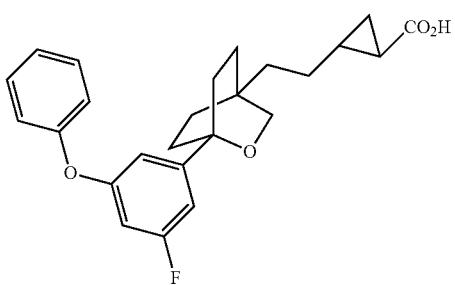 [SMILES: O=C(O)C1CC1CCC12CCC(c3cc(F)cc(Oc4ccccc4)c3)(CC1)OC2]

63A. 2-(1-(3-Fluoro-5-(tetrahydro-2H-pyran-2-yloxy)phenyl)-2-oxabicyclo[2.2.2]octan-4-yl)ethyl methanesulfonate

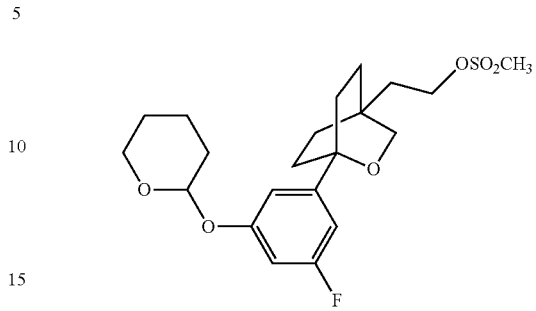

Methanesulfonyl chloride (0.100 mL, 1.28 mmol) was added to a solution of 2-(1-(3-fluoro-5-((tetrahydro-2H-pyran-2-yl)oxy)phenyl)-2-oxabicyclo[2.2.2]octan-4-yl)ethanol (36G; 0.373 g, 1.06 mmol) and TEA (0.46 mL. 3.19 mmol) in DCM (5 mL) at 0° C. and the reaction was stirred at 0° C. for 2 h and then concentrated in vacuo. The residue was dissolved in EtOAc (50 mL), washed with 1 N aq. HCl and water, sat. aq. NaHCO$_3$, and water again. The organic layer was dried (MgSO$_4$) and filtered. The filtrate was concentrated in vacuo to give the crude title compound (0.456 g, 1.06 mmol, 100% yield) as a clear oil.

63B. 3-(1-(3-Fluoro-5-((tetrahydro-2H-pyran-2-yl)oxy)phenyl)-2-oxabicyclo[2.2.2]octan-4-yl)propanenitrile

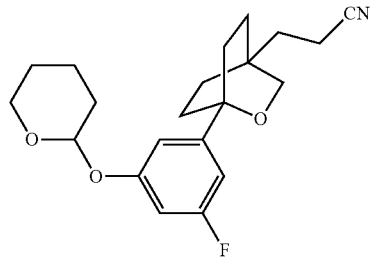 [SMILES: N#CCCC12CCC(c3cc(F)cc(OC4CCCCO4)c3)(CC1)OC2]

A mixture of 2-(1-(3-fluoro-5-((tetrahydro-2H-pyran-2-yl)oxy)phenyl)-2-oxabicyclo[2.2.2]octan-4-yl)ethyl methanesulfonate (0.45 g, 1.05 mmol), NaCN (0.309 g, 6.30 mmol), and Bu$_4$NI (0.039 g, 0.105 mmol) in DMSO (10 mL) was stirred at 85° C. for 18 h, then was cooled to rt and diluted with EtOAc (10 mL). The organic phase was washed with water (3×), dried (MgSO$_4$), filtered, and concentrated in vacuo. The residual crude oil was chromatographed (SiO$_2$; gradient from 0% to 30% EtOAc/hexane over 10 min) to give the title compound (0.348 g, 0.968 mmol, 92% yield) as a clear oil. $^1$H NMR (CDCl$_3$) δ: 6.86 (t, J=1.8 Hz, 1H), 6.74 (dt, J=10.1, 1.9 Hz, 1H), 6.69 (dt, J=10.6, 2.3 Hz, 1H), 5.40 (t, J=3.2 Hz, 1H), 3.93-3.86 (m, 1H), 3.85-3.81 (m, 2H), 3.62 (dtd, J=11.4, 4.1, 1.4 Hz, 1H), 2.32 (dd, J=8.6, 7.3 Hz, 2H), 2.07-1.96 (m, 4H), 1.88-1.80 (m, 2H), 1.79-1.55 (m, 10H); $^{19}$F NMR (CDCl$_3$) δ: −111.9.

63C. 3-(1-(3-Fluoro-5-((tetrahydro-2H-pyran-2-yl)oxy)phenyl)-2-oxabicyclo[2.2.2]octan-4-yl)propanal

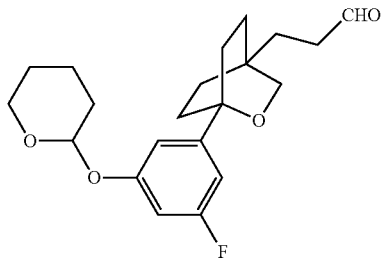 [SMILES: O=CCCC12CCC(c3cc(F)cc(OC4CCCCO4)c3)(CC1)OC2]

DIBAL-H, (1.45 mL of a 1.0 M solution in heptane, 1.452 mmol) was added dropwise to a −78° C. solution of 3-(1-(3-fluoro-5-((tetrahydro-2H-pyran-2-yl)oxy)phenyl)-2-oxabicyclo[2.2.2]octan-4-yl) propanenitrile (0.348 g, 0.968 mmol) in DCM (100 mL) and the reaction was then stirred at −78° C. for 2 h. CELITE® (50 g) was then added and the reaction was quenched with sat. aq. NH₄Cl (15 mL) at −78° C. The mixture was warmed to rt and stirred for 30 min, after which MgSO₄ (30 g) was added and the mixture was stirred at rt for another 1 h and then filtered. The solid was washed with DCM (4×). The combined filtrates were concentrated in vacuo. The crude oil was chromatographed (SiO₂; gradient from 0% to 50% EtOAc/hexane over 15 min) to give the title compound (0.33 g, 0.911 mmol, 94% yield) as a clear oil. ¹H NMR (CDCl₃) δ: 9.81 (t, J=1.6 Hz, 1H), 6.87 (t, J=1.8 Hz, 1H), 6.75 (dt, J=10.0, 2.0 Hz, 1H), 6.69 (dt, J=10.5, 2.3 Hz, 1H), 5.40 (t, J=3.2 Hz, 1H), 3.94-3.85 (m, 1H), 3.83-3.81 (m, 2H), 3.62 (dtd, J=11.4, 4.1, 1.4 Hz, 1H), 2.43 (ddd, J=9.6, 6.5, 1.6 Hz, 2H), 2.05-1.97 (m, 4H), 1.88-1.82 (m, 2H), 1.76-1.59 (m, 8H), 1.56-1.50 (m, 2H); ¹⁹F NMR (CDCl₃) δ: −112.0.

63D. (E)-Methyl 5-(1-(3-fluoro-5-((tetrahydro-2H-pyran-2-yl)oxy)phenyl)-2-oxabicyclo[2.2.2]octan-4-yl)pent-2-enoate

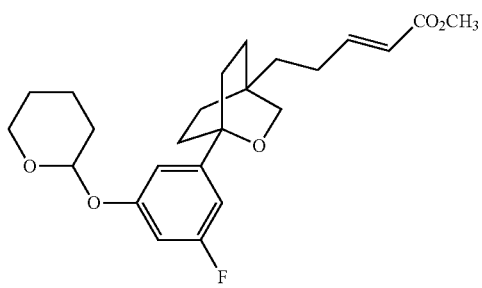 [SMILES: COC(=O)/C=C/CCC12CCC(c3cc(F)cc(OC4CCCCO4)c3)(CC1)OC2]

A 0° C. mixture of trimethyl phosphonoacetate (0.209 mL, 1.45 mmol), DBU (0.218 mL, 1.45 mmol) and LiCl (0.061 g, 1.45 mmol) in MeCN (5 mL) was stirred for 30 min under N₂, after which 3-(1-(3-fluoro-5-((tetrahydro-2H-pyran-2-yl)oxy)phenyl)-2-oxabicyclo[2.2.2]octan-4-yl)propanal (0.35 g, 0.966 mmol) in MeCN (5 mL) was added. The reaction was stirred for 2 h at rt, then was concentrated in vacuo. The residue was diluted with Et₂O, and then washed successively with 1N aq. HCl, sat. aq. NaHCO₃, and brine, dried (MgSO₄), and concentrated in vacuo. The residual crude oil was chromatographed (SiO₂; gradient from 0% to 50% EtOAc/hexane over 20 min) to give the title compound (0.30 g, 0.717 mmol, 74.2% yield) as a white solid. ¹H NMR (CDCl₃) δ: 6.97 (dt, J=15.6, 6.8 Hz, 1H), 6.87 (t, J=1.8 Hz, 1H), 6.75 (ddd, J=10.1, 2.3, 1.4 Hz, 1H), 6.68 (dt, J=10.5, 2.3 Hz, 1H), 5.85 (dt, J=15.6, 1.6 Hz, 1H), 5.40 (t, J=3.2 Hz, 1H), 3.89 (ddd, J=11.3, 10.0, 3.1 Hz, 1H), 3.84-3.81 (m, 2H), 3.75 (s, 3H), 3.62 (dtd, J=11.4, 4.1, 1.4 Hz, 1H), 2.22-2.14 (m, 2H), 2.05-1.98 (m, 4H), 1.88-1.82 (m, 2H), 1.75-1.59 (m, 8H), 1.36-1.30 (m, 2H); ¹⁹F NMR (CDCl₃) δ: −112.1.

63E. Methyl 2-(2-(1-(3-fluoro-5-((tetrahydro-2H-pyran-2-yl)oxy)phenyl)-2-oxabicyclo[2.2.2]octan-4-yl)ethyl)cyclopropanecarboxylate

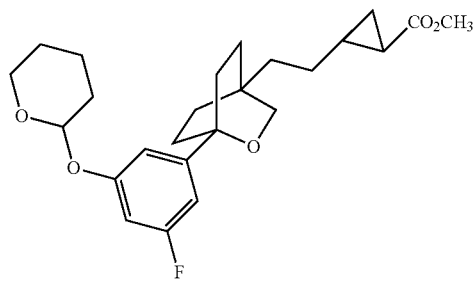 [SMILES: COC(=O)C1CC1CCC12CCC(c3cc(F)cc(OC4CCCCO4)c3)(CC1)OC2]

To a vigorously stirred 0° C. biphasic solution of Et₂O (10 mL), 40% aq. KOH (2 mL, 14.0 mmol) and water (2 mL) was added portionwise N-methyl-N'-nitro-N-nitrosoguanidine (0.844 g, 2.87 mmol) over 15 min. When addition had been completed, the ether layer was separated and dried with KOH pellets. The contents were allowed to stand for 5 min, then redried over fresh KOH pellets. To 5 mL of the diazomethane solution (~50% of total volume) was added a 0° C. solution of (E)-methyl 5-(1-(3-fluoro-5-((tetrahydro-2H-pyran-2-yl)oxy)phenyl)-2-oxabicyclo[2.2.2]octan-4-yl)pent-2-enoate (0.3 g, 0.717 mmol) in THF (2 mL). A mixture of PdOAc₂ (0.016 g, 0.072 mmol) in THF (2 mL) was added slowly and the reaction was stirred at 0° C. for 15 min and then the remainder of the diazomethane solution (~5 mL) was added slowly. The reaction was allowed to warm to rt and stirred for 1 h, then was filtered and then concentrated in vacuo. The residual crude oil was chromatographed (SiO₂; gradient from 0% to 30% EtOAc/hexane over 10 min) to give the title compound (0.26 g, 0.601 mmol, 84% yield) as a clear oil. ¹H NMR (CDCl₃) δ: 6.86 (t, J=1.8 Hz, 1H), 6.74 (ddd, J=10.1, 2.4, 1.5 Hz, 1H), 6.68 (dt, J=10.5, 2.3 Hz, 1H), 5.40 (t, J=3.2 Hz, 1H), 3.93-3.84 (m, 1H), 3.83-3.76 (m, 2H), 3.68 (s, 3H), 3.62 (dtt, J=11.4, 4.1, 1.9 Hz, 1H), 2.03-1.94 (m, 5H), 1.88-1.81 (m, 2H), 1.75-1.56 (m, 7H), 1.43-1.16 (m, 7H), 0.75-0.68 (m, 1H); ¹⁹F NMR (CDCl₃) δ: −112.1.

63F. Methyl 2-(2-(1-(3-fluoro-5-hydroxyphenyl)-2-oxabicyclo[2.2.2]octan-4-yl)ethyl) cyclopropane carboxylate

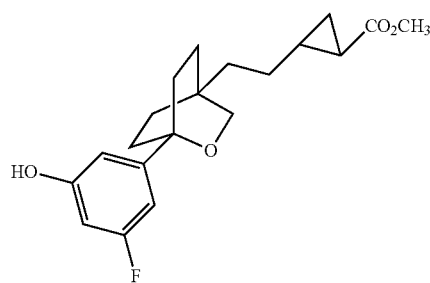 [SMILES: COC(=O)C1CC1CCC12CCC(c3cc(O)cc(F)c3)(CC1)OC2]

A mixture of methyl 2-(2-(1-(3-fluoro-5-((tetrahydro-2H-pyran-2-yl)oxy)phenyl)-2-oxabicyclo[2.2.2]octan-4-yl)ethyl)cyclopropanecarboxylate (260 mg, 0.601 mmol) and PPTS (30.2 mg, 0.120 mmol) in MeOH (5 mL) was stirred at 50° C. for 3 h and then concentrated in vacuo. The residual crude oil was chromatographed (SiO$_2$; gradient from 0% to 30% EtOAc/hexane over 10 min) to give the title compound (160 mg, 0.459 mmol, 76% yield) as a white solid. LCMS [M+H]$^+$=349.1; $^1$H NMR (CDCl$_3$) δ: 7.36-7.07 (m, 1H), 6.66 (d, J=2.3 Hz, 1H), 6.61 (dt, J=10.2, 1.8 Hz, 1H), 6.37 (dt, J=10.1, 2.1 Hz, 1H), 3.78 (s, 2H), 3.69 (s, 3H), 2.03-1.84 (m, 4H), 1.70-1.52 (m, 4H), 1.44-1.12 (m, 7H), 0.73 (ddd, J=8.0, 6.3, 4.2 Hz, 1H); $^{19}$F NMR (CDCl$_3$) δ: −112.2.

The 2 enantiomers of racemic 63F were separated by chiral separation (Instrument: Berger Multigram II; Column: CHIRALPAK® AD-H, 30×250 mm, 5 μm; Mobile Phase: 30% MeOH/70% CO$_2$; Flow Conditions: 85 mL/min, 150 Bar, 40° C.; Detector Wavelength: 220 nm; Injection Details: 0.5 mL of 51 mg/mL in MeOH-MeCN) to give the individual enantiomers A (75 mg, 0.215 mmol, 46.9% yield) and B (71 mg, 0.204 mmol, 44.4% yield) as clear oil. 1st Eluting enantiomer: A [α]=+84.68° (0.035% w/v in MeOH) @589; 2$^{nd}$ Eluting enantiomer B: [α]=−62.17° (0.0017% w/v in MeOH) @589 nm.

Example 63

Single Enantiomer; Absolute Stereochemistry not Determined

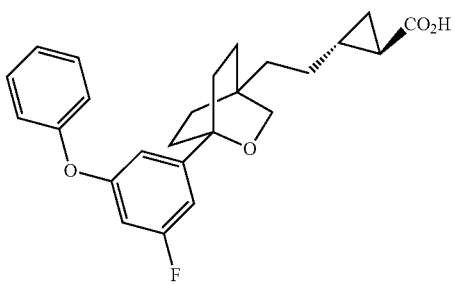 [SMILES: O=C(O)[C@@H]1C[C@H]1CCC12CCC(c3cc(F)cc(Oc4ccccc4)c3)(CC1)OC2]

A mixture of methyl 2-(2-(1-(3-fluoro-5-hydroxyphenyl)-2-oxabicyclo[2.2.2]octan-4-yl)ethyl)cyclopropane carboxylate (63G enantiomer A; 35 mg, 0.100 mmol), phenylboronic acid (12.3 mg, 0.100 mmol), Cu(OAc)$_2$ (21.9 mg, 0.121 mmol), TEA (0.140 mL, 1.01 mmol), pyridine (0.081 mL, 1.01 mmol), and 4A Molecular Sieves (5 g) in DCM (3 mL) was stirred under air at rt for 18 h. The reaction was filtered, and the filtrate was concentrated in vacuo. The residual crude oil was dissolved in EtOAc (5 mL) and washed with 1N aq. HCl and water. The organic layer was concentrated in vacuo. To the residual crude product phenyl ether ester was added a solution of 1N aq. NaOH (1.01 mL, 1.01 mmol) in THF (2 mL) and the reaction was stirred at rt for 18 h. The reaction was then acidified to pH=2 with 1N aq. HCl and extracted with EtOAc (5 mL). The organic layer was concentrated in vacuo. The residual crude oil was purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H$_2$O:MeOH:TFA and B=90:10:0.1 MeOH:H$_2$O:TFA) to give the title compound (41 mg, 0.092 mmol, 91% yield) as a yellowish oil. LCMS [M−H]$^+$=409.1; $^1$H NMR (CDCl$_3$) δ: 7.38-7.30 (m, 2H), 7.15-7.09 (m, 1H), 7.03-6.98 (m, 2H), 6.89-6.83 (m, 2H), 6.51 (dt, J=9.8, 2.3 Hz, 1H), 3.76 (s, 2H), 2.02-1.88 (m, 4H), 1.68-1.52 (m, 4H), 1.45-1.17 (m, 7H), 0.82-0.72 (m, 1H); $^{19}$F NMR (CDCl$_3$) δ: −111.2.

Example 64

2-(2-(1-(3-Fluoro-5-(3-fluorophenoxy)phenyl)-2-oxabicyclo[2.2.2]octan-4-yl)ethyl) cyclopropanecarboxylic acid (single enantiomer; absolute stereochemistry not determined)

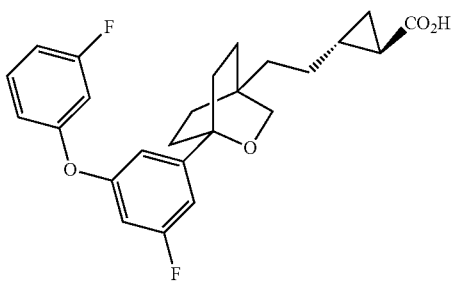 [SMILES: O=C(O)[C@@H]1C[C@H]1CCC12CCC(c3cc(F)cc(Oc4cccc(F)c4)c3)(CC1)OC2]

The title compound was prepared using the same sequence as for the synthesis of Example 63 from 63F Enantiomer A, except that (3-fluorophenyl)boronic acid was used instead of phenylboronic acid to give the title compound (41 mg, 0.088 mmol, 88% yield) as a yellowish oil. LCMS [M−H]$^+$=427.1; $^1$H NMR (CDCl$_3$) δ: 7.31-7.23 (m, 1H), 6.93-6.75 (m, 4H), 6.70 (dt, J=10.0, 2.3 Hz, 1H), 6.56 (dt, J=9.5, 2.3 Hz, 1H), 3.77 (s, 2H), 2.03-1.89 (m, 4H), 1.69-1.52 (m, 4H), 1.45-1.18 (m, 7H), 0.84-0.73 (m, 1H); $^{19}$F NMR (CDCl$_3$) δ: −110.67, −110.77.

Example 65

2-(2-(1-(3-(3-Fluorophenoxy)phenyl)-2-oxabicyclo[2.2.2]octan-4 yl)ethyl)cyclopropane carboxylic acid

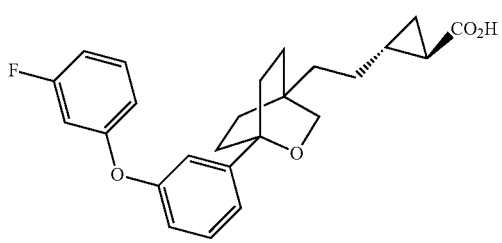 [SMILES: O=C(O)[C@@H]1C[C@H]1CCC12CCC(c3cccc(Oc4cccc(F)c4)c3)(CC1)OC2]

65A and 65B: Methyl 2-(2-(1-(3-hydroxyphenyl)-2-oxabicyclo[2.2.2]octan-4-yl)ethyl)cyclopropane carboxylate (enantiomers 1 and 2; absolute stereochemistry drawn in arbitrary manner)

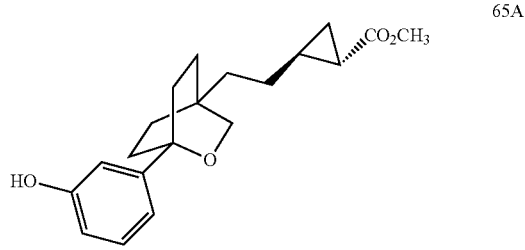

65A

65B

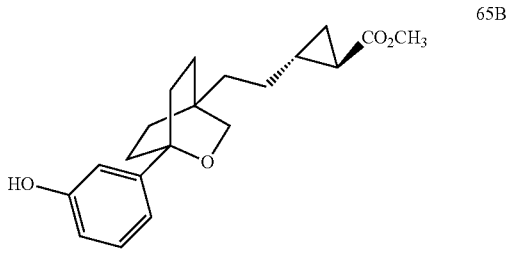

A mixture of methyl 2-(2-(1-(3-((tetrahydro-2H-pyran-2-yl)oxy)phenyl)-2-oxabicyclo[2.2.2]octan-4-yl)ethyl)cyclopropanecarboxylate (61A; 8.8 g, 21.2 mmol), and PPTS (1.07 g, 4.25 mmol) in MeOH (50 mL) was stirred at 50° C. for 3 h, then was cooled to rt and concentrated in vacuo. The residual crude oil was chromatographed ($SiO_2$; gradient with 0% to 30% EtOAc/hexane over 20 min to give methyl 2-(2-(1-(3-hydroxyphenyl)-2-oxabicyclo[2.2.2]octan-4-yl)ethyl)cyclopropanecarboxylate (racemate; 7.0 g, 21.2 mmol, 100% yield) as a white solid. LCMS $[M+H]^+$=331.1; $^1$H NMR ($CDCl_3$) δ: 7.18 (t, J=7.9 Hz, 1H), 6.99-6.86 (m, 2H), 6.69 (ddd, J=8.0, 2.6, 1.0 Hz, 1H), 5.32 (s, 1H), 3.82 (d, J=1.1 Hz, 2H), 3.69 (s, 3H), 2.07-1.95 (m, 4H), 1.71-1.57 (m, 4H), 1.45-1.14 (m, 7H), 0.73 (ddd, J=8.1, 6.3, 4.2 Hz, 1H). This racemate was separated by chiral preparative HPLC (Instrument=Berger Multigram II SFC; Column: CHIRALPAK® AD-H, 30×250 mm, 5μ; Mobile Phase: 20% MeOH/80% $CO_2$; Flow Conditions: 85 mL/min, 150 Bar, 40° C.; Detector Wavelength: 220 nm; Injection Details: 1.0 mL of ~150 mg/mL) to give Example 65A (2.35 g, 7.11 mmol, 45% yield; [α]=+60.6° (1.8% in DCM) @589 nm) and Example 65B (2.34 g, 7.08 mmol, 45% yield; [α]=−72.2° (1.0% in DCM) @589 nm) as oils.

Example 65

A mixture of methyl 2-(2-(1-(3-hydroxyphenyl)-2-oxabicyclo[2.2.2]octan-4-yl)ethyl)cyclo-propanecarboxylate (Example 65B; 27 mg, 0.082 mmol), (3-fluorophenyl)boronic acid (11 mg, 0.082 mmol), $Cu(OAc)_2$ (18 mg, 0.098 mmol), TEA (0.11 mL, 0.82 mmol), pyridine (0.066 mL, 0.82 mmol), and 4A molecular sieves (5 g) in DCM (2 mL) was stirred under air at rt for 18 h. The reaction was filtered, and the filtrate was concentrated in vacuo. The residual crude oil was dissolved in EtOAc (5 mL) and washed with 1N aq. HCl and water, then was concentrated in vacuo. The crude 3-fluorophenyl ether ester product was dissolved in THF (2 mL) and stirred with 1N aq. NaOH (1.23 mL, 1.23 mmol) at rt for 18 h. The reaction mixture was then acidified to pH=2 with 1N aq. HCl and then extracted with EtOAc (5 mL). The organic layer was concentrated in vacuo. The residual crude oil was purified by preparative HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 $H_2O$:MeOH:TFA and B=90:10:0.1 MeOH:$H_2O$:TFA) to give the title compound (27 mg, 0.064 mmol, 78% yield) as a clear oil. LC/MS $[M-H]^+$=409.1; $^1$H NMR ($CDCl_3$) δ: 7.32-7.20 (m, 2H), 7.17 (dt, J=7.8, 1.3 Hz, 1H), 7.14-7.09 (m, 1H), 6.89-6.84 (m, 1H), 6.79-6.71 (m, 2H), 6.66 (dt, J=10.3, 2.4 Hz, 1H), 3.78 (s, 2H), 2.08-1.92 (m, 4H), 1.61 (dp, J=8.6, 3.3, 2.8 Hz, 4H), 1.45-1.16 (m, 7H), 0.83-0.73 (m, 1H); $^{19}$F NMR ($CDCl_3$) δ: −111.1.

Example 66

2-(2-(1-(3-Isobutoxyphenyl)-2-oxabicyclo[2.2.2]octan-4-yl)ethyl)cyclopropanecarboxylic acid (single enantiomer)

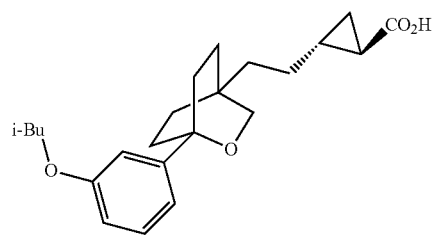

A mixture of methyl 2-(2-(1-(3-hydroxyphenyl)-2-oxabicyclo[2.2.2]octan-4-yl)ethyl)cyclo-propane carboxylate (Example 65B; 28 mg, 0.085 mmol), 1-iodo-2-methylpropane (0.020 mL, 0.17 mmol), and $K_2CO_3$ (59 mg, 0.42 mmol) in DMF (1 mL) was stirred at 70° C. for 18 h. The reaction was cooled to rt, EtOAc (5 mL) was added, and the mixture was washed with water. The organic layer was concentrated in vacuo. The residual crude isobutyl ether ester product was dissolved in THF (1 mL) and stirred with 1M aq. LiOH (0.85 mL, 0.85 mmol) at rt for 3 days. The reaction was then acidified to pH=2 with 1N aq. HCl and the aqueous layer was extracted with EtOAc (3×). The combined organic extracts were concentrated in vacuo. The residual crude oil was purified by preparative HPLC (PHENOMENEX® Axia 5μ C18 30×100 mm column; detection at 220 nm; flow rate=40 mL/min; continuous gradient from 50% B to 100% B over 10 min+4 min hold time at 100% B, where A=90:10:0.1 $H_2O$:MeOH:TFA and B=90:10:0.1 MeOH:$H_2O$:TFA) to give the title compound (22 mg, 0.058 mmol, 68% yield) as a white solid. LCMS $[M-H]^+$=371.2; [α]=−62.5° (1.9% w/v in DCM) @589 nm; $^1$H NMR ($CDCl_3$) δ: 7.19 (t, J=8.0 Hz, 1H), 7.01-6.95 (m, 1H), 6.91 (d, J=7.8 Hz, 1H), 6.74 (dd, J=8.3, 2.6 Hz, 1H), 3.79 (s, 2H), 3.71 (d, J=6.5 Hz, 2H), 2.13-1.91 (m, 5H), 1.69-1.53 (m, 4H), 1.46-1.15 (m, 7H), 1.01 (d, J=6.7 Hz, 6H), 0.78 (ddd, J=8.1, 6.3, 4.2 Hz, 1H).

Example 67

2-(2-(1-(3-(3-Methoxyphenoxy)phenyl)-2-oxabicyclo[2.2.2]octan-4-yl)ethyl)cyclopropanecarboxylic acid (single enantiomer)

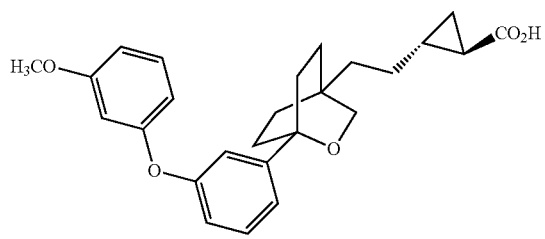 [SMILES: COc1cccc(Oc2cccc(C34CCC(CC[C@@H]5C[C@H]5C(=O)O)(CC3)CO4)c2)c1]

Example 67 was prepared from methyl 2-(2-(1-(3-hydroxyphenyl)-2-oxabicyclo[2.2.2]octan-4-yl)ethyl) cyclopropanecarboxylate (Example 65B; 25 mg, 0.076 mmol) and (3-methoxyphenyl)boronic acid (12 mg, 0.076 mmol) using the same 2-step sequence as used for the synthesis of Example 65. The crude product was purified by preparative HPLC (PHENOMENEX® Axia 5μ C18 30×100 mm column; detection at 220 nm; flow rate=40 mL/min; continuous gradient from 50% B to 100% B over 10 min+4 min hold time at 100% B, where A=90:10:0.1 H$_2$O:MeOH:TFA and B=90:10:0.1 MeOH:H$_2$O:TFA) to give the title compound (27 mg, 0.063 mmol, 84% yield) as a light brownish oil. LCMS [M−H]$^+$=421.2; $^1$H NMR (CDCl$_3$) δ: 10.03 (s, 1H), 7.32-7.27 (m, 1H), 7.23 (t, J=8.5 Hz, 1H), 7.17 (dt, J=7.8, 1.3 Hz, 1H), 7.15-7.13 (m, 1H), 6.89 (ddd, J=8.1, 2.4, 1.0 Hz, 1H), 6.66 (ddd, J=8.3, 2.3, 1.0 Hz, 1H), 6.61-6.56 (m, 2H), 3.81 (s, 2H), 3.80 (s, 3H), 2.11-1.96 (m, 4H), 1.73-1.57 (m, 4H), 1.48-1.20 (m, 7H), 0.87-0.78 (m, 1H).

Example 68

N-((1H-1,2,4-Triazol-5-yl)methyl)-2-(2-(1-(3-phenoxyphenyl)-2-oxabicyclo[2.2.2]octan-4-yl)ethyl)cyclopropanecarboxamide (single enantiomer; absolute stereochemistry shown is arbitrary)

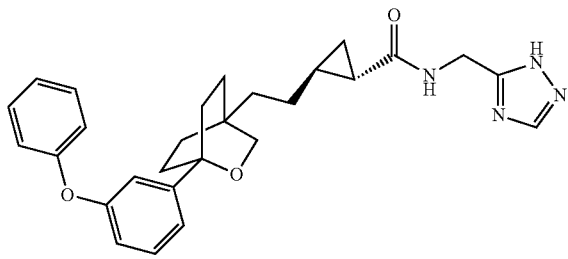 [SMILES: O=C(NCc1ncn[nH]1)[C@H]1C[C@@H]1CCC12CCC(c3cccc(Oc4ccccc4)c3)(CC1)OC2]

The title compound (8 mg; colorless oil) was synthesized as described for Example 62 except that the opposite enantiomer of the α,β-cyclopropyl acid was used (i.e., Example 14; 10 mg; 0.025 mmol). LCMS [M+H]$^+$=473; $^1$H NMR (400 MHz, CDCl$_3$) δ: 8.32 (s, 1H), 8.09 (t, J=6.1 Hz, 1H), 7.38-7.27 (m, 3H), 7.20-7.07 (m, 3H), 7.05-6.97 (m, 2H), 6.87 (ddd, J=8.1, 2.5, 0.9 Hz, 1H), 4.89-4.73 (m, 2H), 3.80 (s, 2H), 2.13-1.94 (m, 4H), 1.64 (t, J=7.0 Hz, 4H), 1.44-1.13 (m, 8H), 0.87-0.76 (m, 1H).

Example 69

N-Ethyl-2-(2-(1-(3-phenoxyphenyl)-2-oxabicyclo[2.2.2]octan-4-yl)ethyl) cyclopropanecarboxamide (single enantiomer; absolute stereochemistry shown is arbitrary)

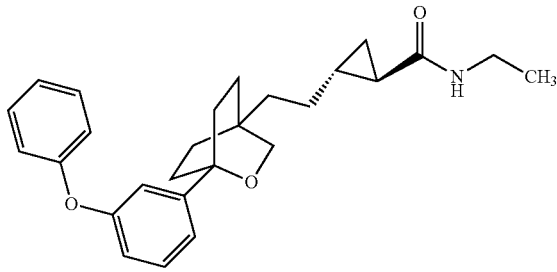 [SMILES: CCNC(=O)[C@@H]1C[C@H]1CCC12CCC(c3cccc(Oc4ccccc4)c3)(CC1)OC2]

The title compound (8 mg; colorless oil) was synthesized as described for Example 62 except that the opposite enantiomer of the α,β-cyclopropyl acid was used (i.e., Example 14; 10 mg; 0.025 mmol) along with ethylamine (0.025 mL of a 2 M solution in THF; 0.05 mmol). $^1$H NMR (400 MHz, CDCl$_3$) δ: 7.38-7.23 (m, 3H), 7.17-7.04 (m, 3H), 7.03-6.94 (m, 2H), 6.84 (ddd, J=8.0, 2.4, 1.0 Hz, 1H), 5.51 (br. s., 1H), 3.78 (s, 2H), 3.38-3.25 (m, 2H), 2.00 (dd, J=9.8, 4.7 Hz, 4H), 1.62 (dd, J=9.7, 6.2 Hz, 4H), 1.35-1.10 (m, 9H), 1.05 (dt, J=8.0, 4.1 Hz, 1H), 0.57 (ddd, J=8.0, 5.8, 4.0 Hz, 1H).

Example 70

2-(2-(1-(3-(3-Hydroxyphenoxy)phenyl)-2-oxabicyclo[2.2.2]octan-4-yl)ethyl) cyclopropanecarboxylic acid (single enantiomer; absolute stereochemistry shown is arbitrary)

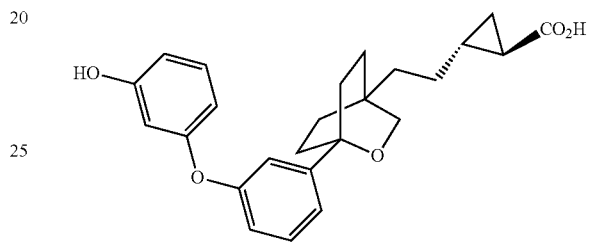

70A. Methyl 2-(2-(1-(3-(3-(tert-butyldimethylsilyloxy)phenoxy)phenyl)-2-oxabicyclo [2.2.2]octan-4-yl)ethyl)cyclopropanecarboxylate

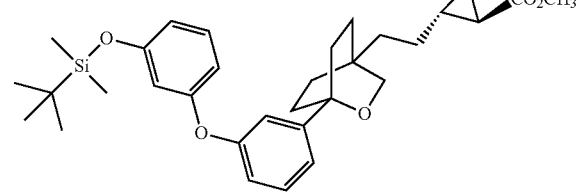

A mixture of methyl 2-(2-(1-(3-hydroxyphenyl)-2-oxabicyclo[2.2.2]octan-4-yl)ethyl)cyclopropane-carboxylate (65B; 360 mg, 1.09 mmol), (3-((tert-butyldimethylsilyl)oxy)phenyl)boronic acid (340 mg, 1.348 mmol), Cu(OAc)$_2$ (237 mg, 1.31 mmol), TEA (1.52 mL, 10.9 mmol), pyridine (0.88 mL, 10.9 mmol), and 4A molecular sieves (5 g) in DCM (10 mL) was stirred under air at rt for 3 days. The reaction was then filtered, and the filtrate was concentrated in vacuo. The residual crude oil was dissolved in EtOAc (15 mL) and washed with 1N aq. HCl and water, dried (MgSO$_4$), and filtered. The filtrate was concentrated in vacuo. The residual crude oil was chromatographed (SiO$_2$; gradient from 0% to 30% over 10 min EtOAc/hexane) to give the title compound (570 mg, 1.06 mmol, 97% yield) as a clear oil. LCMS [M+H]$^+$=537.3; $^1$H NMR (CDCl$_3$) δ: 7.26 (t, J=7.9 Hz, 1H), 7.18-7.11 (m, 2H), 7.09 (dd, J=2.5, 1.7 Hz, 1H), 6.85 (ddd, J=8.1, 2.5, 1.0 Hz, 1H), 6.58 (dd, J=8.2, 2.3 Hz, 2H), 6.49 (t, J=2.3 Hz, 1H), 3.78 (d, J=1.1 Hz, 2H), 3.68 (s, 3H), 2.00 (dt, J=11.4, 4.1 Hz, 4H), 1.62 (dtd, J=8.1, 4.1, 3.5, 2.0 Hz, 4H), 1.41-1.14 (m, 7H), 0.97 (s, 9H), 0.71 (ddd, J=8.1, 6.3, 4.1 Hz, 1H), 0.18 (s, 6H).

Example 70

A mixture of methyl 2-(2-(1-(3-(3-((tert-butyldimethylsilyl)oxy)phenoxy)phenyl)-2-oxabicyclo[2.2.2]octan-4-yl)ethyl)cyclopropanecarboxylate (70A; 32 mg, 0.060 mmol) and 1M aq. NaOH (0.060 mL, 0.060 mmol) in MeOH (1 mL)/THF (1 mL) was stirred at rt for 3 days, after which the reaction was concentrated in vacuo. The residual crude oil was dissolved in EtOAc (5 mL) and washed with 1N aq. HCl and water. The organic layer was concentrated in vacuo. The residual crude oil was purified by preparative HPLC (Column: XBridge C18, 19×100 mm, 5-μm particles; Mobile Phase A: 5:95 MeCN: water with 0.1% TFA; Mobile Phase B: 95:5 MeCN: water with 0.1% TFA; Gradient:25-65% B over 10 min, then a 5-min hold at 100% B; Flow: 20 mL/min) to give the title compound (19 mg, 0.046 mmol, 76% yield) as a light brown oil. LCMS [M−H]$^+$=407.1; $^1$H NMR (DMSO-d$_6$) δ: 9.60 (s, 1H), 7.31 (t, J=7.9 Hz, 1H), 7.19-7.09 (m, 2H), 7.03 (s, 1H), 6.85 (dd, J=8.0, 2.4 Hz, 1H), 6.53 (dd, J=8.1, 2.2 Hz, 1H), 6.40 (dd, J=8.3, 2.2 Hz, 1H), 6.34 (s, 1H), 3.68 (s, 2H), 2.09-1.97 (m, 2H), 1.85-1.74 (m, 2H), 1.68-1.48 (m, 4H), 1.33-1.11 (m, 6H), 1.00-0.90 (m, 1H), 0.72-0.65 (m, 1H).

Examples 71-74 were synthesized according to the same protocol as for Example 65 from intermediate phenol 65B and an appropriate corresponding substituted aryl boronic acid.

| Example No | Name | Structure | Observed [M − H]$^+$ |
|---|---|---|---|
| 71 | (1R,2R)-2-(2-(1-(3-(4-methoxy-phenoxy)phenyl)-2-oxabicyclo[2.2.2]octan-4-yl)ethyl)cyclo-propane carboxylic acid | 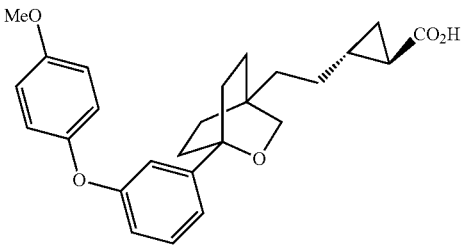 [SMILES: COc1ccc(Oc2cccc(C34CCC(CC[C@@H]5C[C@H]5C(=O)O)(CC3)CO4)c2)cc1] | 421.05 |
| 72 | (1R,2R)-2-(2-(1-(3-(3,5-difluorophenoxy)phenyl)-2-oxabicyclo[2.2.2]octan-4-yl)ethyl)cyclopropanecarboxylic acid | 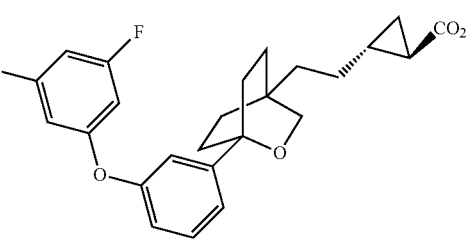 | 427.10 |
| 73 | (1R,2R)-2-(2-(1-(3-(3,4-difluorophenoxy)phenyl)-2-oxabicyclo[2.2.2]octan-4-yl)ethyl)cyclopropanecarboxylic acid | 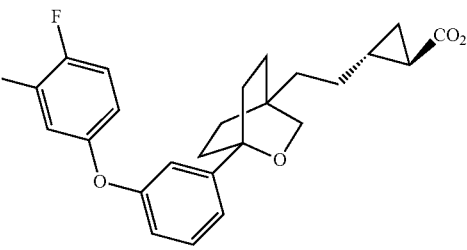 | 427.05 |
| 74 | (1R,2R)-2-(2-(1-(3-(4-hydroxy-phenoxy)phenyl)-2-oxabicyclo[2.2.2]octan-4-yl)ethyl)cyclo-propanecarboxylic acid | 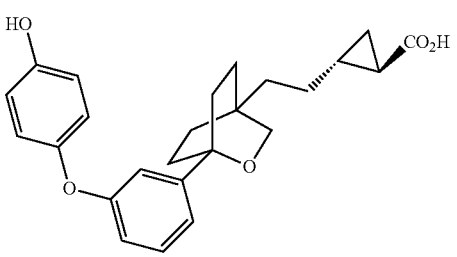 [SMILES: O=C(O)[C@@H]1C[C@H]1CCC12CCC(c3cccc(Oc4ccc(O)cc4)c3)(CC1)OC2] | 407.00 |

Examples 75-78 were synthesized according to the same protocol as for Examples 39-45 from intermediate phenol 7F and an appropriate corresponding substituted aryl boronic acid.

| Example No | Name | Structure | Observed [M − H]+ = |
|---|---|---|---|
| 75 | 2-(2-(1-(3-(3,4-difluoro-phenoxy)phenyl)-2-oxabicyclo[2.2.2]octan-4-yl)ethoxy)acetic acid | 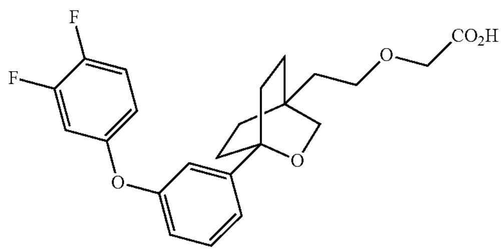 [SMILES: O=C(O)COCCC12CCC(c3cccc(Oc4ccc(F)c(F)c4)c3)(CC1)OC2] | 417.05 |
| 76 | 2-(2-(1-(3-(3,5-difluorophenoxy)phenyl)-2-oxabicyclo[2.2.2]octan-4-yl)ethoxy)acetic acid | 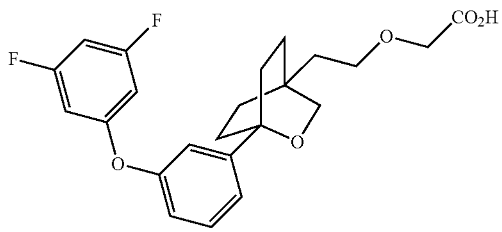 [SMILES: O=C(O)COCCC12CCC(c3cccc(Oc4cc(F)cc(F)c4)c3)(CC1)OC2] | 417.05 |
| 77 | 2-(2-(1-(3-(3-fluoro-4-methylphenoxy)phenyl)-2-oxabicyclo[2.2.2]octan-4-yl)ethoxy)acetic acid | 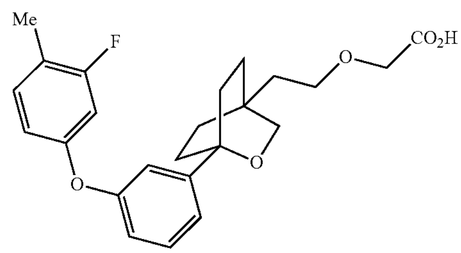 [SMILES: Cc1ccc(Oc2cccc(C34CCC(CCOCC(=O)O)(CC3)CO4)c2)cc1F] | 413.5 |
| 78 | 2-(2-(1-(3-(4-fluoro-3-methylphenoxy)phenyl)-2-oxabicyclo[2.2.2]octan-4-yl)ethoxy)acetic acid | 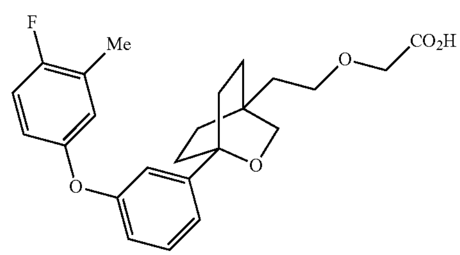 [SMILES: Cc1cc(Oc2cccc(C34CCC(CCOCC(=O)O)(CC3)CO4)c2)ccc1F] | 413.5 |

Examples 79-86 were synthesized according to the same protocol as for Example 55 from intermediate phenol 361 and an appropriate corresponding substituted aryl boronic acid.

| Example No | Name | Structure | Observed |
|---|---|---|---|
| 79 | 2-(2-(1-(3-(3,4-difluorophenoxy)-5-fluorophenyl)-2-oxabicyclo[2.2.2]octan-4-yl)ethoxy)acetic acid | 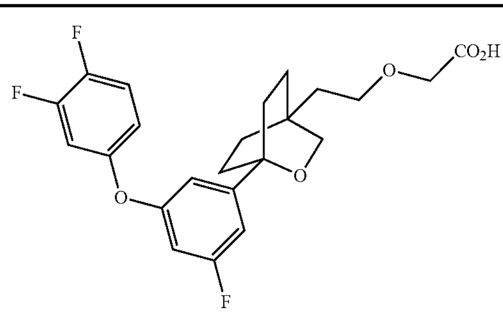 | [M − H]+ = 435.4 |

-continued

| Example No | Name | Structure | Observed |
|---|---|---|---|
| 80 | 2-(2-(1-(3-fluoro-5-(3-fluoro-4-methylphenoxy)phenyl)-2-oxabicyclo[2.2.2]octan-4-yl)ethoxy)acetic acid | 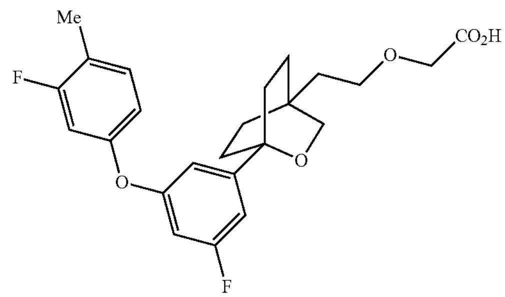 [SMILES: Cc1ccc(Oc2cc(F)cc(C34CCC(CCOCC(=O)O)(CC3)CO4)c2)cc1F] | [M − H]+ = 431.4 |
| 81 | 2-(2-(1-(3-fluoro-5-(4-fluoro-3-methylphenoxy)phenyl)-2-oxabicyclo[2.2.2]octan-4-yl)ethoxy)acetic acid | 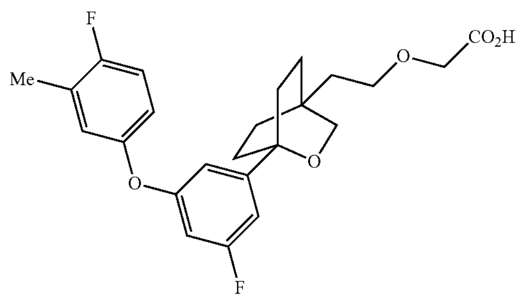 [SMILES: Cc1cc(Oc2cc(F)cc(C34CCC(CCOCC(=O)O)(CC3)CO4)c2)ccc1F] | [M − H]+ = 431.5 |
| 82 | 2-(2-(1-(3-fluoro-5-(3-methoxyphenoxy)phenyl)-2-oxabicyclo[2.2.2]octan-4-yl)ethoxy)acetic acid | 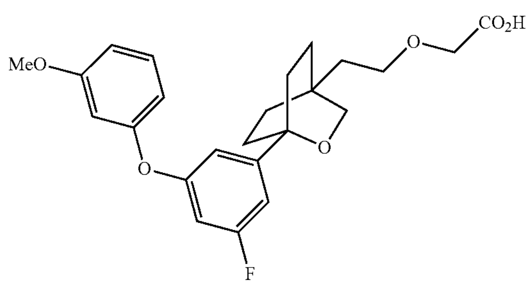 [SMILES: COc1cccc(Oc2cc(F)cc(C34CCC(CCOCC(=O)O)(CC3)CO4)c2)c1] | [M + Na]+ = 453.2 |
| 83 | 2-(2-(1-(3-fluoro-5-(p-tolyloxy)phenyl)-2-oxabicyclo[2.2.2]octan-4-yl)ethoxy)acetic acid | 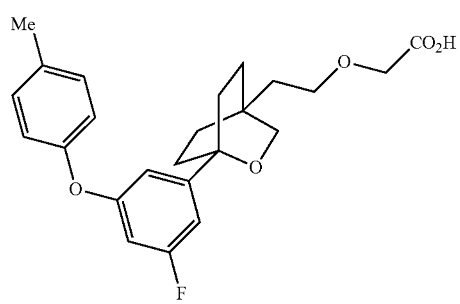 [SMILES: Cc1ccc(Oc2cc(F)cc(C34CCC(CCOCC(=O)O)(CC3)CO4)c2)cc1] | [M − H]+ = 413.5 |
| 84 | 2-(2-(1-(3-fluoro-5-(3-fluoro-5-methoxyphenoxy)phenyl)-2-oxabicyclo[2.2.2]octan-4-yl)ethoxy)acetic acid | 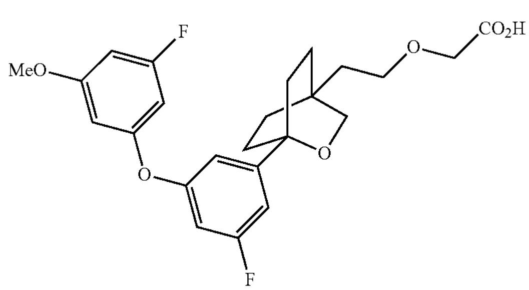 [SMILES: COc1cc(F)cc(Oc2cc(F)cc(C34CCC(CCOCC(=O)O)(CC3)CO4)c2)c1] | [M − H]+ = 447.5 |

| Example No | Name | Structure | Observed |
|---|---|---|---|
| 85 | 2-(2-(1-(3-fluoro-5-(4-fluorophenoxy)phenyl)-2-oxabicyclo[2.2.2]octan-4-yl)ethoxy)acetic acid | 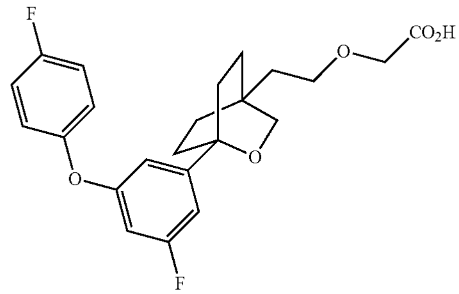 [SMILES: O=C(O)COCCC12CCC(c3cc(F)cc(Oc4ccc(F)cc4)c3)(CC1)OC2] | [M − H]+ = 417.4 |
| 86 | 2-(2-(1-(3-fluoro-5-(4-fluoro-3-methoxyphenoxy)phenyl)-2-oxabicyclo[2.2.2]octan-4-yl)ethoxy)acetic acid | 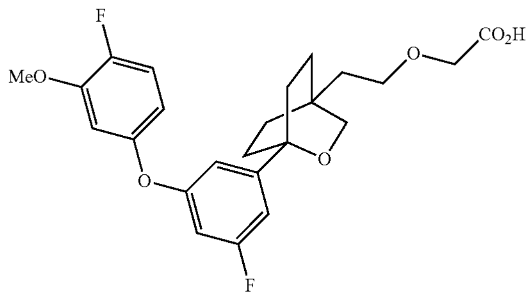 [SMILES: COc1cc(Oc2cc(F)cc(C34CCC(CCOCC(=O)O)(CC3)CO4)c2)ccc1F] | [M − H]+ = 447.4 |

Examples 87-89 were synthesized according to the same protocol as for Example 65. The phenol intermediate used for these syntheses was tert-butyl 2-(2-(1-(4-fluoro-3-hydroxyphenyl)-2-oxabicyclo[2.2.2]octan-4-yl)ethoxy)acetate in combination with an appropriate corresponding substituted aryl boronic acid. tert-Butyl 2-(2-(1-(4-fluoro-3-hydroxyphenyl)-2-oxabicyclo[2.2.2]octan-4-yl)ethoxy)acetate was synthesized from 2-(5-bromo-2-fluorophenoxy)tetrahydro-2H-pyran using the same synthetic sequence as for the synthesis of 36I.

| Example No | Name | Structure | Observed |
|---|---|---|---|
| 87 | 2-(2-(1-(4-fluoro-3-phenoxyphenyl)-2-oxabicyclo[2.2.2]octan-4-yl)ethoxy)acetic acid | 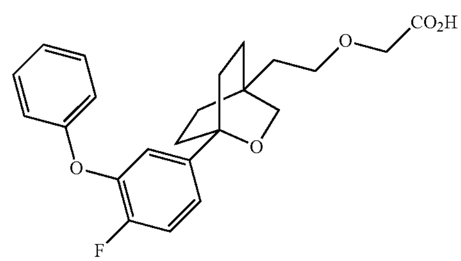 [SMILES: O=C(O)COCCC12CCC(c3ccc(F)c(Oc4ccccc4)c3)(CC1)OC2] | [M + H]+ = 401.3 |
| 88 | 2-(2-(1-(4-fluoro-3-(4-fluorophenoxy)phenyl)-2-oxabicyclo[2.2.2]octan-4-yl)ethoxy)acetic acid | 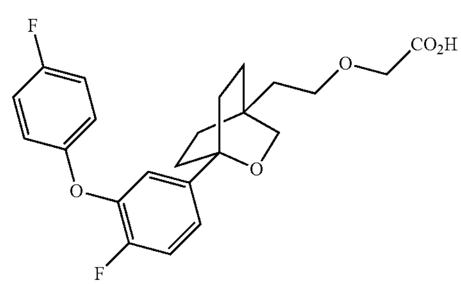 [SMILES: O=C(O)COCCC12CCC(c3ccc(F)c(Oc4ccc(F)cc4)c3)(CC1)OC2] | [M − H]+ = 417.4 |

-continued

| Example No | Name | Structure | Observed |
|---|---|---|---|
| 89 | 2-(2-(1-(4-fluoro-3-(3-fluoro-4-methylphenoxy)phenyl)-2-oxabicyclo[2.2.2]octan-4-yl)ethoxy)acetic acid | 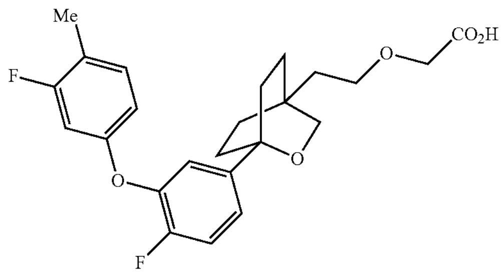 [SMILES: Cc1ccc(Oc2cc(C34CCC(CCOCC(=O)O)(CC3)CO4)ccc2F)cc1F] | $[M - H]^+ =$ 431.4 |

Examples 90-93 were synthesized according to the same protocol as for Example 65. The phenol intermediate used for these syntheses was tert-butyl 2-(2-(1-(3-hydroxy-5-methoxyphenyl)-2-oxabicyclo[2.2.2]octan-4-yl)ethoxy)acetate in combination with an appropriate corresponding substituted aryl boronic acid. tert-Butyl 2-(2-(1-(3-hydroxy-5-methoxyphenyl)-2-oxabicyclo[2.2.2]octan-4-yl)ethoxy)acetate was synthesized from 2-(3-bromo-5-methoxyphenoxy)tetrahydro-2H-pyran using the same synthetic sequence as for the synthesis of 36I.

| Example No | Name | Structure | Observed |
|---|---|---|---|
| 90 | 2-(2-(1-(3-methoxy-5-phenoxyphenyl)-2-oxabicyclo[2.2.2]octan-4-yl)ethoxy)acetic acid | 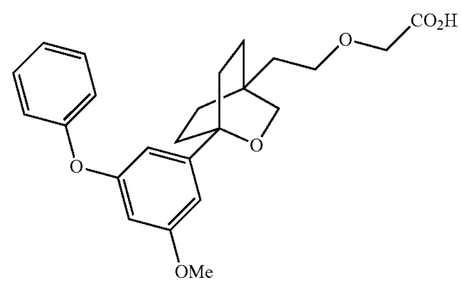 [SMILES: COc1cc(Oc2ccccc2)cc(C23CCC(CCOCC(=O)O)(CC2)CO3)c1] | $[M - H]^+ =$ 411.4 |
| 91 | 2-(2-(1-(3-(3,4-difluorophenoxy)-5-methoxyphenyl)-2-oxabicyclo[2.2.2]octan-4-yl)ethoxy)acetic acid | 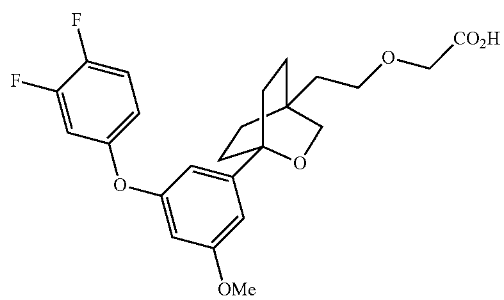 [SMILES: COc1cc(Oc2ccc(F)c(F)c2)cc(C23CCC(CCOCC(=O)O)(CC2)CO3)c1] | $[M - H]^+ =$ 447.4 |
| 92 | 2-(2-(1-(3-(4-fluorophenoxy)-5-methoxyphenyl)-2-oxabicyclo[2.2.2]octan-4-yl)ethoxy)acetic acid | 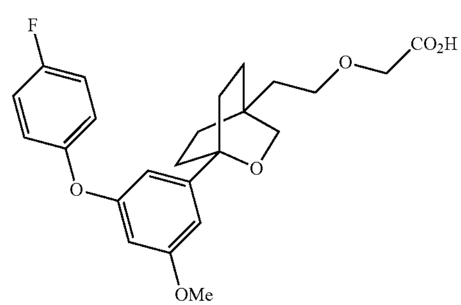 [SMILES: COc1cc(Oc2ccc(F)cc2)cc(C23CCC(CCOCC(=O)O)(CC2)CO3)c1] | $[M - H]^+ =$ 429.4 |

| Example No | Name | Structure | Observed |
|---|---|---|---|
| 93 | 2-(2-(1-(3-fluoro-4-methylphenoxy)-5-methoxyphenyl)-2-oxabicyclo[2.2.2]octan-4-yl)ethoxy)acetic acid | 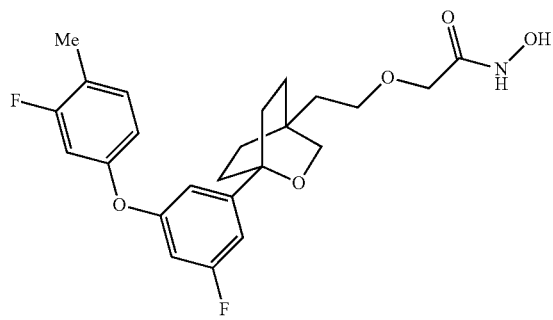 [SMILES: Cc1ccc(Oc2cc(F)cc(C34CCC(CCOCC(=O)NO)(CC3)CO4)c2)cc1F] | $[M + H]^+ =$ 445.5 |

Example 94

2-(2-(1-(3-Fluoro-5-(3-fluoro-4-methylphenoxy) phenyl)-2-oxabicyclo[2.2.2]octan-4-yl)ethoxy)-N-hydroxyacetamide

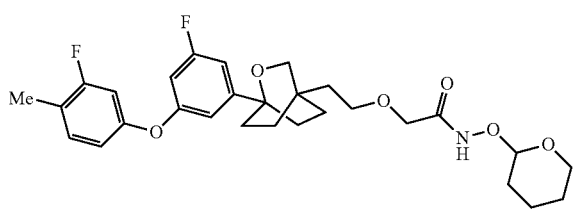 [SMILES: Cc1ccc(Oc2cc(F)cc(C34CCC(CCOCC(=O)NOC5CCCCO5)(CC3)CO4)c2)cc1F]

94A. 2-(2-(1-(3-Fluoro-5-(3-fluoro-4-methylphenoxy)phenyl)-2-oxabicyclo[2.2.2]octan-4-yl) ethoxy)-N-(tetrahydro-2H-pyran-2-yloxy)acetamide To a mixture of 2-(2-(1-(3-fluoro-5-(3-fluoro-4-methylphenoxy)phenyl)-2-oxabicyclo[2.2.2]octan-4-yl)ethoxy) acetic acid (23 mg, 0.053 mmol), HOBT (10 mg, 0.064 mmol), EDC (12 mg, 0.064 mmol) in THF (1 mL)/DMF (1 mL) was added 0-(tetrahydro-2H-pyran-2-yl)hydroxylamine (7.5 mg, 0.064 mmol) and TEA (0.074 mL, 0.53 mmol). The reaction mixture was stirred at rt overnight. After volatiles were removed in vacuo, the residue was dissolved in EtOAc (5 mL), then successively washed with 10% aq. citric acid (5 mL), sat'd aq. NaHCO$_3$ (5 mL) and water (5 mL). The organic layer was dried (Na$_2$SO$_4$), filtered and concentrated in vacuo. The crude product (oil) was chromatographed [SiO$_2$; gradient of EtOAc/hexanes (0% to 50% over 10 min)] to give the title compound (27 mg, 0.051 mmol, 96% yield) as a clear oil. [M+Na]$^+$=554.4; $^1$H NMR (CDCl$_3$) δ: 8.92 (s, 1H), 7.13 (t, J=8.7 Hz, 1H), 6.91-6.81 (m, 2H), 6.74-6.65 (m, 2H), 6.53 (dt, J=9.7, 2.3 Hz, 1H), 4.99 (t, J=3.0 Hz, 1H), 4.06-3.91 (m, 3H), 3.83 (s, 2H), 3.66 (dtd, J=11.3, 4.0, 1.7 Hz, 1H), 3.54 (t, J=6.9 Hz, 2H), 2.25 (d, J=2.0 Hz, 3H), 2.03-1.94 (m, 4H), 1.91-1.77 (m, 3H), 1.76-1.55 (m, 7H), 1.50 (t, J=6.8 Hz, 2H); $^{19}$F NMR (CDCl$_3$) δ: -110.95, -114.13.

94. 2-(2-(1-(3-Fluoro-5-(3-fluoro-4-methylphenoxy) phenyl)-2-oxabicyclo[2.2.2]octan-4-yl)ethoxy)-N-hydroxyacetamide

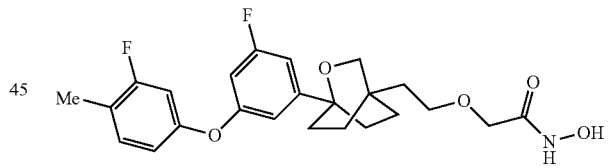

A mixture of Part A compound (27 mg, 0.051 mmol) and formic acid (1 mL, 26.1 mmol) was stirred at 40° C. for 2 h, then cooled to rt and concentrated in vacuo. The crude oil was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O: MeOH:TFA and B=90:10:0.1 MeOH:H$_2$O:TFA) to give the title compound (13 mg, 0.028 mmol, 56% yield) as a white solid. [M+H]$^+$=448.3; [M-H]$^+$=446.5; $^1$H NMR (CDCl$_3$) δ: 7.14 (t, J=8.6 Hz, 1H), 6.91-6.81 (m, 2H), 6.75-6.65 (m, 2H), 6.53 (dt, J=9.8, 2.4 Hz, 1H), 4.07 (s, 2H), 3.83 (s, 2H), 3.55 (t, J=6.9 Hz, 2H), 2.25 (d, J=1.8 Hz, 3H), 2.10-1.90 (m, 4H), 1.69 (t, J=7.9 Hz, 4H), 1.50 (t, J=6.8 Hz, 2H), 0.97-0.75 (m, 2H); $^{19}$F NMR (CDCl$_3$) δ: -110.90, -114.12.

Example 95

2-(2-(1-(3,4-Difluoro-5-(4-fluorophenoxy)phenyl)-2-oxabicyclo[2.2.2]octan-4-yl)ethoxy) acetic acid

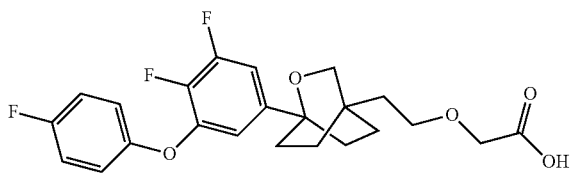 [SMILES: O=C(O)COCCC12CCC(c3cc(F)c(F)c(Oc4ccc(F)cc4)c3)(CC1)OC2]

95A.
2-(5-Bromo-2,3-difluorophenoxy)tetrahydro-2H-pyran

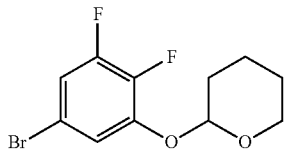 [SMILES: Fc1cc(Br)cc(OC2CCCCO2)c1F]

A solution of 5-bromo-2,3-difluorophenol (2.75 g, 13.16 mmol), 3,4-dihydro-2H-pyran (2.39 mL, 26.3 mmol) and PPTS (0.165 g, 0.658 mmol) in DCM (10 mL) was stirred for 1 h at rt. At this time, analytical HPLC showed that the reaction was complete. The reaction was concentrated in vacuo. The crude oily product was chromatographed [SiO$_2$; continuous gradient of EtOAc/hexane (0% to 20% over 15 min)] to give the title compound (2.5 g, 8.5 mmol, 65% yield) as a clear oil. $^1$H NMR (CDCl$_3$) δ: 7.17 (dt, J=6.4, 2.2 Hz, 1H), 6.99 (ddd, J=8.8, 6.2, 2.4 Hz, 1H), 5.45 (t, J=3.0 Hz, 1H), 3.88 (td, J=11.0, 3.0 Hz, 1H), 3.72-3.62 (m, 1H), 2.11-1.82 (m, 3H), 1.80-1.59 (m, 3H); $^{19}$F NMR (CDCl$_3$) δ: −135.00, −158.84.

95B. (3,4-Difluoro-5-((tetrahydro-2H-pyran-2-yl)oxy)phenyl)magnesium bromide

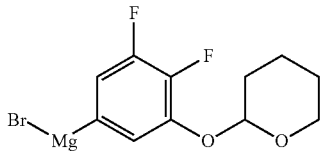

A mixture of Example 95A [2-(5-bromo-2,3-difluorophenoxy)tetrahydro-2H-pyran] (600 mg, 2.047 mmol), Mg (60 mg, 2.456 mmol), and I$_2$ (5 mg, 0.020 mmol) in THF (10 mL) was stirred at reflux under N$_2$ for 5 h to give the title compound (2.05 mmol, 100% yield) as a brown solution which was used to next reaction directly.

95C. (1-(3,4-Difluoro-5-((tetrahydro-2H-pyran-2-yl)oxy)phenyl)-2-oxabicyclo[2.2.2]octan-4-yl)methyl 4-methylbenzenesulfonate

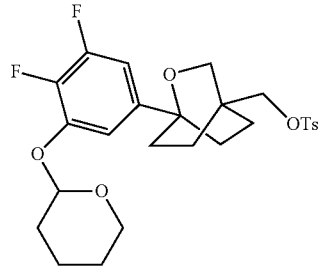 [SMILES: Cc1ccc(S(=O)(=O)OCC23CCC(c4cc(F)c(F)c(OC5CCCCO5)c4)(CC2)OC3)cc1]

To a solution of crude Example 95B (3,4-difluoro-5-((tetrahydro-2H-pyran-2-yl)oxy)phenyl)magnesium bromide (2.05 mmol) in THF (10 mL) at −78° C. was added a solution of Example 1E (4-oxocyclohexane-1,1-diyl)bis(methylene) bis(4-methylbenzenesulfonate) (0.70 g, 1.50 mmol) in THF (10 mL) over 15 min. The resulting mixture was stirred at rt for 18 h. Powdered NaOH (0.60 g, 15.0 mmol) was added and the reaction was stirred under reflux for 24 h, then was cooled to rt and partitioned between ice water and EtOAc (10 mL). The aqueous phase was extracted with EtOAc (2×10 mL). The combined organic extracts were washed with water (20 mL×3), dried (MgSO$_4$), filtered, and concentrated in vacuo. The crude product was chromatographed [SiO$_2$; continuous gradient of EtOAc/hexane (0% to 30% over 14 min)] to give the title compound (0.20 g, 0.39 mmol, 26% yield) as a clear oil. [M+Na]$^+$=531.2; $^1$H NMR (CDCl$_3$) δ: 7.78 (d, J=8.3 Hz, 2H), 7.37 (d, J=8.1 Hz, 2H), 6.98 (dt, J=6.8, 1.9 Hz, 1H), 6.87-6.78 (m, 1H), 5.47 (t, J=3.0 Hz, 1H), 3.92 (td, J=11.0, 3.0 Hz, 1H), 3.83-3.77 (m, 2H), 3.75 (s, 2H), 3.62 (dtd, J=11.4, 3.9, 1.5 Hz, 1H), 2.47 (s, 3H), 2.07-1.82 (m, 6H), 1.77-1.58 (m, 8H); $^{19}$F NMR (CDCl$_3$) δ: −137.20 (d, J=20 Hz), −160.08 (d, J=20 Hz).

95D. 2-(1-(3,4-Difluoro-5-((tetrahydro-2H-pyran-2-yl)oxy)phenyl)-2-oxabicyclo[2.2.2]octan-4-yl)acetonitrile

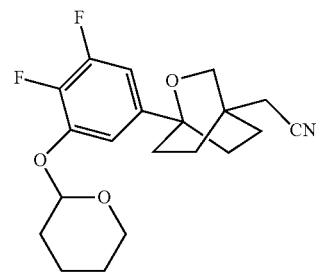 [SMILES: N#CCC12CCC(c3cc(F)c(F)c(OC4CCCCO4)c3)(CC1)OC2]

The title compound was prepared using a procedure analogous to the synthesis of Example 37B from 37A. The title compound was obtained (0.137 g, 0.377 mmol, 96% yield) as a clear oil. $^1$H NMR (CDCl$_3$) δ: 7.00 (dt, J=6.8, 2.0 Hz, 1H), 6.84 (ddd, J=11.4, 6.7, 2.2 Hz, 1H), 5.48 (t, J=3.0 Hz, 1H), 3.98-3.85 (m, 3H), 3.63 (dtd, J=11.5, 3.9, 1.5 Hz, 1H), 2.22 (s, 2H), 2.09-1.57 (m, 14H); $^{19}$F NMR (CDCl$_3$) δ: −137.09 (d, J=20.1 Hz), −159.94 (d, J=20.0 Hz).

95E. 2-(1-(3,4-Difluoro-5-((tetrahydro-2H-pyran-2-yl)oxy)phenyl)-2-oxabicyclo[2.2.2]octan-4-yl)acetaldehyde

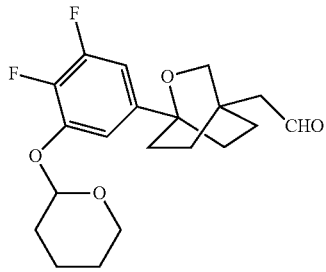 [SMILES: O=CCC12CCC(c3cc(F)c(F)c(OC4CCCCO4)c3)(CC1)OC2]

The title compound was prepared using a procedure analogous to the synthesis of Example 37C from 37B. The title compound was obtained (0.12 g, 0.33 mmol, 87% yield) as a clear oil. $^1$H NMR (CDCl$_3$) δ: 9.75 (s, 1H), 6.93 (dt, J=6.9, 2.0 Hz, 1H), 6.82-6.72 (m, 1H), 5.40 (t, J=3.0 Hz, 1H), 3.92-3.81 (m, 3H), 3.56 (dtd, J=11.5, 3.9, 1.6 Hz, 1H), 2.19 (d, J=2.7 Hz, 2H), 1.99-1.50 (m, 14H); $^{19}$F NMR (CDCl$_3$) δ: −137.26 (d, J=20.1 Hz), −160.18 (d, J=21.0 Hz).

95F. 2-(1-(3,4-Difluoro-5-((tetrahydro-2H-pyran-2-yl)oxy)phenyl)-2-oxabicyclo[2.2.2]octan-4-yl)ethanol

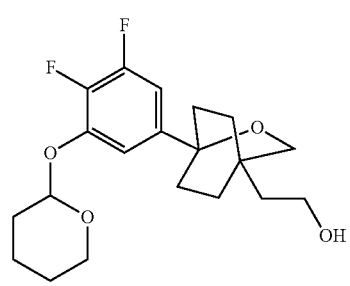 [SMILES: OCCC12CCC(c3cc(F)c(F)c(OC4CCCCO4)c3)(CC1)OC2]

The title compound was prepared using a procedure analogous to the synthesis of Example 37D from 37C. The title compound was obtained (0.081 g, 0.22 mmol, 67% yield) as a clear oil. $^1$H NMR (CDCl$_3$) δ: 7.00 (dt, J=6.8, 2.0 Hz, 1H), 6.85 (ddd, J=11.4, 6.8, 2.2 Hz, 1H), 5.47 (t, J=2.9 Hz, 1H), 3.93 (td, J=10.9, 3.0 Hz, 1H), 3.83 (s, 2H), 3.68 (t, J=7.2 Hz, 2H), 3.62 (dtd, J=11.4, 4.0, 1.6 Hz, 1H), 2.04-1.81 (m, 7H), 1.76-1.58 (m, 8H), 1.44 (t, J=7.2 Hz, 2H); $^{19}$F NMR (CDCl$_3$) δ: −137.44 (d, J=20.7 Hz), −160.44 (d, J=21.1 Hz).

95G. tert-Butyl 2-(2-(1-(3,4-difluoro-5-((tetrahydro-2H-pyran-2-yl)oxy)phenyl)-2-oxabicyclo[2.2.2]octan-4-yl)ethoxy)acetate

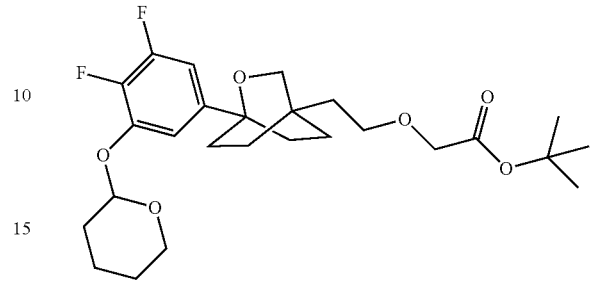

The title compound was prepared using a procedure analogous to the synthesis of tert-butyl 2-(2-(1-(3-phenoxyphenyl)-2-oxabicyclo[2.2.2]octan-4-yl)ethoxy)acetate from 6B (the penultimate step of the synthesis of Example 6). The title compound was obtained (74 mg, 0.15 mmol, 70% yield) as a clear oil. $^1$H NMR (CDCl$_3$) δ: 7.00 (dt, J=7.0, 1.9 Hz, 1H), 6.85 (ddt, J=11.5, 6.8, 2.5 Hz, 1H), 5.48 (t, J=3.1 Hz, 1H), 3.98-3.91 (m, 3H), 3.88-3.83 (m, 2H), 3.63 (dtd, J=11.6, 3.9, 1.5 Hz, 1H), 3.55 (t, J=6.9 Hz, 2H), 2.02-1.90 (m, 6H), 1.75-1.66 (m, 6H), 1.54-1.47 (m, 13H); $^{19}$F NMR (CDCl$_3$) δ: −137.51 (d, J=20.1 Hz), −160.53 (d, J=20.1 Hz).

95H. tert-Butyl 2-(2-(1-(3,4-difluoro-5-hydroxyphenyl)-2-oxabicyclo[2.2.2]octan-4-yl)ethoxy)acetate

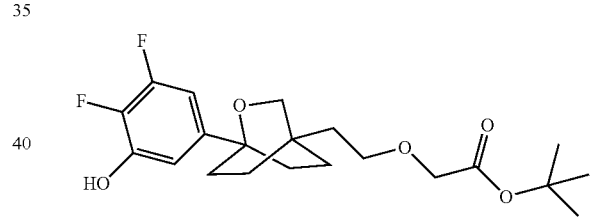

The title compound was prepared using a procedure analogous to the synthesis of Example 7F. The title compound was obtained (41 mg, 0.10 mmol, 67% yield) as a clear oil. [M−H]$^+$=397.4; $^1$H NMR (CDCl$_3$) δ: 6.81-6.71 (m, 2H), 5.98 (s, 1H), 3.94 (s, 2H), 3.85 (s, 2H), 3.56 (t, J=6.8 Hz, 2H), 1.99-1.89 (m, 4H), 1.71 (dd, J=9.3, 6.6 Hz, 4H), 1.54-1.47 (m, 11H); $^{19}$F NMR (CDCl$_3$) δ: −137.67 (d, J=20.6 Hz), −166.10 (d, J=20.9 Hz).

95. 2-(2-(1-(3,4-Difluoro-5-(4-fluorophenoxy)phenyl)-2-oxabicyclo[2.2.2]octan-4-yl)ethoxy)acetic acid

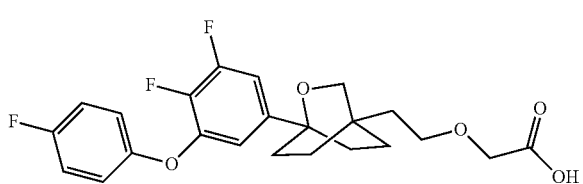 [SMILES: O=C(O)COCCC12CCC(c3cc(F)c(F)c(Oc4ccc(F)cc4)c3)(CC1)OC2]

The title compound was prepared using a procedure analogous to the synthesis of Example 21 except that (4-fluorophenyl)boronic acid was used instead of pyridine-3-boronic acid. The title compound was obtained (29 mg, 0.065 mmol, 65% yield) as a light yellowish oil. [M−H]+=435.4; 1H NMR (CDCl3) δ: 8.14 (brs, 1H), 7.07-6.90 (m, 5H), 6.81 (dt, J=6.8, 2.0 Hz, 1H), 4.09 (s, 2H), 3.82 (s, 2H), 3.58 (t, J=6.8 Hz, 2H), 2.00-1.84 (m, 4H), 1.69 (t, J=7.8 Hz, 4H), 1.51 (t, J=6.8 Hz, 2H); 19F NMR (CDCl3) δ: −119.92, −135.68 (d, J=20.4 Hz), −157.59 (d, J=20.5 Hz).

Example 96

2-(((1-(3-Phenoxyphenyl)-2-oxabicyclo[2.2.2]octan-4-yl)oxy)methyl) cyclopropanecarboxylic acid

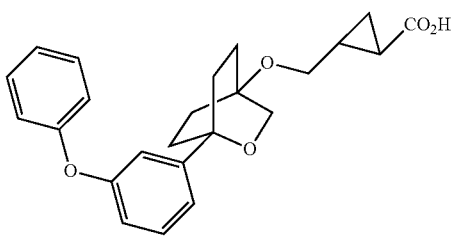 [SMILES: O=C(O)C1CC1COC12CCC(c3cccc(Oc4ccccc4)c3)(CC1)OC2]

96A. 1-(3-Phenoxyphenyl)-2-oxabicyclo[2.2.2]octane-4-carbaldehyde

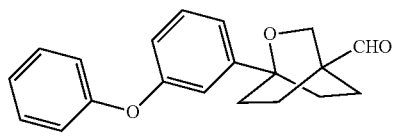 [SMILES: O=CC12CCC(c3cccc(Oc4ccccc4)c3)(CC1)OC2]

DMSO (0.50 mL, 7.04 mmol) was added dropwise to oxalyl chloride (1.76 mL of a 2M solution in DCM, 3.52 mmol) at −78° C. After stirring at −78° C. for 15 min, a solution of Example 5A [(1-(3-phenoxyphenyl)-2-oxabicyclo[2.2.2]octan-4-yl)methanol] (0.91 g, 2.93 mmol) in DCM (10 mL) was added dropwise. After 15 min, TEA (2.04 mL, 14.7 mmol) was added dropwise. Th reaction was allowed to warm to rt over 2 h, then was concentrated in vacuo. The crude product was dissolved in EtOAc (10 mL) and washed with 1N aq HCl (3×10 mL), water (10 mL), sat'd aq. NaHCO3, and brine. The organic layer was dried (Na2SO4) and concentrated in vacuo. The crude product was chromatographed [SiO2; continuous gradient of EtOAc/hexane (0% to 50% over 12 min)] to give the title compound (0.89 g, 2.89 mmol, 98% yield) as a clear oil. [M+H]+=309.09; 1H NMR (CDCl3) δ: 9.55 (s, 1H), 7.39-7.26 (m, 3H), 7.20-7.08 (m, 3H), 7.06-6.99 (m, 2H), 6.93-6.87 (m, 1H), 4.12 (t, J=1.5 Hz, 2H), 2.22-1.99 (m, 6H), 1.98-1.88 (m, 2H).

96B. 2,2,6,6-Tetramethyl-1-((1-(3-phenoxyphenyl)-2-oxabicyclo[2.2.2]octan-4-yl)oxy) piperidin-4-ol

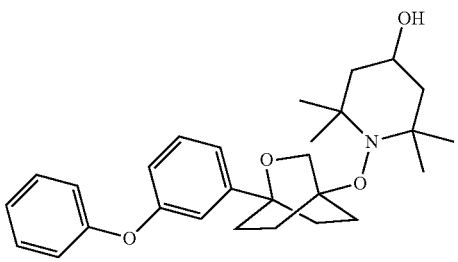 [SMILES: CC1(C)CC(O)CC(C)(C)N1OC12CCC(c3cccc(Oc4ccccc4)c3)(CC1)OC2]

A mixture of 96A [1-(3-phenoxyphenyl)-2-oxabicyclo[2.2.2]octane-4-carbaldehyde] (452 mg, 1.47 mmol), 4-hydroxy-TEMPO (252 mg, 1.47 mmol), Cu (I) Cl (15 mg, 0.15 mmol) in iPrOH (7 mL)/water (0.6 mL) was added dropwise 30% aq H2O2 (0.299 mL, 2.93 mmol) over 5 h at rt. The reaction was then stirred at rt for 18 h and filtered. The filtrate was diluted with EtOAc (5 mL), washed with water (3 mL×3), and concentrated in vacuo. The residue was purified on prep. HPLC (PHENOMENEX® Axia 5μ C18 30×100 mm column; detection at 220 nm; flow rate=40 mL/min; continuous gradient from 50% B to 100% B over 10 min+5 min hold time at 100% B, where A=90:10:0.1 H2O:MeOH:TFA and B=90:10:0.1 MeOH:H2O:TFA) to give the title compound (107 mg, 0.237 mmol, 16% yield) as a clear oil. A by-product 1-(3-phenoxyphenyl)-2-oxabicyclo[2.2.2]octane-4-carboxylic acid (117 mg, 0.361 mmol, 25% yield) was also recovered. [M+H]+=452.2; 1H NMR (CDCl3) δ: 7.35-7.30 (m, 2H), 7.29-7.24 (m, 1H), 7.12-7.03 (m, 3H), 7.00-6.95 (m, 2H), 6.89-6.84 (m, 1H), 4.20-4.06 (m, 3H), 2.42-2.19 (m, 11H), 2.10 (t, J=17.0 Hz, 2H), 1.56 (s, 6H), 1.45 (s, 6H).

96C. 1-(3-Phenoxyphenyl)-2-oxabicyclo[2.2.2]octan-4-ol

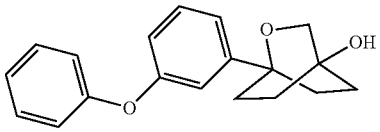 [SMILES: OC12CCC(c3cccc(Oc4ccccc4)c3)(CC1)OC2]

A mixture of 96B [2,2,6,6-tetramethyl-1-((1-(3-phenoxyphenyl)-2-oxabicyclo[2.2.2]octan-4-yl)oxy)piperidin-4-ol] (140 mg, 0.310 mmol), activated zinc dust (203 mg, 3.10 mmol), and HOAc (3.55 mL, 62.0 mmol) in THF (1 mL)/water (0.5 mL) was stirred at rt for 3 days, then was filtered. The filtrate was dissolved in EtOAc (5 mL) and washed with water. The organic layer was dried (MgSO4) and concentrated in vacuo. The crude product was chromatographed [SiO2; continuous gradient of EtOAc/hexane (0% to 50% over 10 min)] to give the title compound (62 mg, 0.209 mmol, 68% yield) as a clear oil. [M+Na]+=319.1; 1H NMR (CDCl3) δ: 7.38-7.27 (m, 3H), 7.20-7.09 (m, 3H), 7.06-6.99 (m, 2H), 6.92-6.86 (m, 1H), 3.88 (t, J=1.6 Hz, 2H), 2.24-2.12 (m, 4H), 2.01-1.84 (m, 4H), 1.70 (s, 1H).

96D. (E)-Methyl 4-((1-(3-phenoxyphenyl)-2-oxabicyclo[2.2.2]octan-4-yl)oxy)but-2-enoate

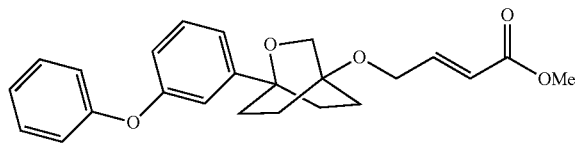 [SMILES: COC(=O)/C=C/COC12CCC(c3cccc(Oc4ccccc4)c3)(CC1)OC2]

A mixture of 96C [1-(3-phenoxyphenyl)-2-oxabicyclo[2.2.2]octan-4-ol] (63 mg, 0.213 mmol), methyl 4-bromocrotonate (0.075 mL, 0.64 mmol), 2,6-di-tert-butylpyridine (0.334 mL, 1.49 mmol), and AgOTf (164 mg, 0.64 mmol) in DCM (0.5 mL) was stirred at rt in the dark for 3 days. LC-MS showed the presence of the product, and the reaction was filtered. The filtrate was concentrated in vacuo. The crude product was chromatographed [SiO$_2$; continuous gradient of EtOAc/hexane (0% to 10% over 10 min)] to give the title compound (42 mg, 0.106 mmol, 50% yield) as an oil. $^1$H NMR (CDCl$_3$) δ: 7.28-7.17 (m, 3H), 7.07-6.98 (m, 3H), 6.94-6.86 (m, 3H), 6.78 (ddd, J=8.1, 2.4, 1.0 Hz, 1H), 6.02 (dt, J=15.6, 2.2 Hz, 1H), 4.07 (dd, J=4.2, 2.1 Hz, 2H), 3.84 (t, J=1.4 Hz, 2H), 3.67 (s, 3H), 2.11-2.03 (m, 4H), 1.97-1.88 (m, 2H), 1.86-1.77 (m, 2H).

96. 2-(((1-(3-Phenoxyphenyl)-2-oxabicyclo[2.2.2]octan-4-yl)oxy)methyl) cyclopropanecarboxylic acid

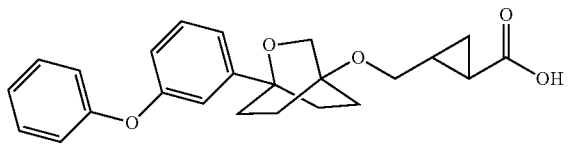 [SMILES: O=C(O)C1CC1COC12CCC(c3cccc(Oc4ccccc4)c3)(CC1)OC2]

To a mixture of trimethylsulfoxonium iodide (297 mg, 1.35 mmol) and 60% NaH in mineral oil (54 mg, 1.35 mmol) in DMSO (3 mL) at 0° C. was added a solution of Example 96D [(E)-methyl 4-((1-(3-phenoxyphenyl)-2-oxabicyclo[2.2.2]octan-4-yl)oxy) but-2-enoate] (41 mg, 0.10 mmol) in dry DMSO (1 mL) under Ar. After 2 h, the reaction was quenched with water and extracted with ether, washed with brine, dried (Na$_2$SO$_4$) and concentrated in vacuo. The crude product was purified by preparative HPLC (PHENOMENEX® Axia 5µ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (1.9 mg, 4.34 µmol, 4% yield) as an oil. [M−H]$^+$=393.3; $^1$H NMR (CDCl$_3$) δ: 7.38-7.31 (m, 2H), 7.32-7.26 (m, 1H), 7.17-7.09 (m, 3H), 7.03-6.98 (m, 2H), 6.87 (ddd, J=8.1, 2.5, 1.0 Hz, 1H), 3.89 (s, 2H), 3.45 (dd, J=9.8, 5.6 Hz, 1H), 3.36 (dd, J=9.7, 6.1 Hz, 1H), 2.19-2.10 (m, 4H), 2.03-1.80 (m, 4H), 1.77-1.67 (m, 1H), 1.62-1.54 (m, 1H), 1.30-1.24 (m, 1H), 1.03-0.93 (m, 1H).

Example 97

Trans-2-(((1-(3-phenoxyphenyl)-2-oxabicyclo[2.2.2]octan-4-yl)methoxy)methyl) cyclopropane carboxylic acid

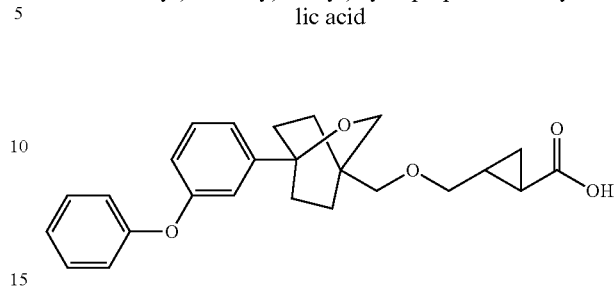

97A. Trans-methyl 2-(((1-(3-phenoxyphenyl)-2-oxabicyclo[2.2.2]octan-4-yl)methoxy)methyl) cyclopropanecarboxylate

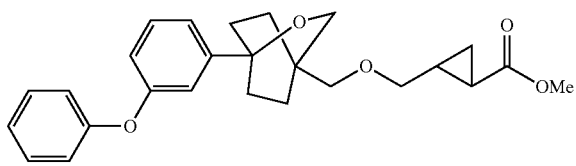 [SMILES: COC(=O)C1CC1COCC12CCC(c3cccc(Oc4ccccc4)c3)(CC1)OC2]

To a 0° C. of Example 5A compound (30 mg, 0.068 mmol) in CH$_2$Cl$_2$ (0.6 mL) were successively added 2,6-di-tert-butylpyridine (0.046 mL, 0.20 mmol) and AgOTf (52 mg, 0.20 mmol). The mixture was stirred at 0° C. under N$_2$ for 30 min. Trans-methyl 2-(bromomethyl)cyclopropane carboxylate (39 mg, 0.20 mmol) was added. The mixture was stirred at 0° C. for 2 h, and then at rt for 70 h. The reaction was diluted with CH$_2$Cl$_2$ (10 mL) and filtered through a plug of CELITE®. The filtrate was concentrated in vacuo to give the title compound, which was used directly without further purification. LCMS, [M+H]$^+$=423.2.

97B. Trans-methyl 2-(((1-(3-phenoxyphenyl)-2-oxabicyclo[2.2.2]octan-4-yl)methoxy)methyl) cyclopropanecarboxylate

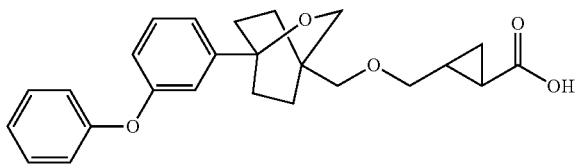 [SMILES: O=C(O)C1CC1COCC12CCC(c3cccc(Oc4ccccc4)c3)(CC1)OC2]

To the crude 97B compound was added THF (0.5 mL), MeOH (1 mL), water (0.5 mL) and KOH (0.19 g, 3.40 mmol). The reaction mixture was stirred at rt for 2 h, then was concentrated in vacuo. The residue was neutralized with 1N aq. HCl to pH=~2-3. The mixture was extracted with EtOAc (3×5 mL). The combined organic extracts were washed with brine (5 mL), dried (MgSO$_4$), filtered and concentrated in vacuo. The crude product was purified via preparative HPLC with the following conditions: Column: XBridge Shield RP18, 19×200 mm, 5-nm particles; Mobile Phase A: 5:95 acetonitrile: water with 10-mM ammonium acetate; Mobile Phase B:

95:5 acetonitrile: water with 10-mM NH₄OAc; Gradient: 10-100% B over 20 min, then a 5-min hold at 100% B; Flow: 20 mL/min. The fractions containing the desired product were combined and concentrated via centrifugal evaporation (white solid, 11 mg, 38% yield from Example 5A compound). LCMS, [M-H]⁺=407.2; ¹H NMR (500 MHz, DMSO-$d_6$) δ 7.38 (t, J=7.7 Hz, 2H), 7.30 (t, J=8.0 Hz, 1H), 7.12 (d, J=7.5 Hz, 2H), 7.02 (s, 1H), 6.97 (d, J=7.9 Hz, 2H), 6.82 (d, J=8.1 Hz, 1H), 3.76 (s, 2H), 3.41-3.33 (m, 1H), 3.22 (dd, J=10.9, 6.5 Hz, 1H), 3.12 (s, 2H), 2.06-2.0 (m, 2H), 1.84-1.74 (m, 2H), 1.69-1.61 (m, 2H), 1.60-1.50 (m, 2H), 1.49-1.38 (m, 2H), 0.96 (d, J=6.6 Hz, 1H), 0.82-0.75 (br s, 1H). HPLC: RT=1.62 min, purity=98%; analytical LC/MS conditions: Column: Waters Acquity UPLC BEH C18, 2.1×50 mm, 1.7-μm particles; Mobile Phase A: 5:95 acetonitrile:water with 10 mM NH₄OAc; Mobile Phase B: 95:5 MeCN:H₂O with 10 mM NH₄OAc; Temperature: 50° C.; Gradient: 0-100% B over 3 minutes, then a 0.75-minute hold at 100% B; Flow: 1.11 mL/min; Detection: UV at 220 nm.

Example 98

Single Enantiomer; Absolute Stereochemistry not Determined, Arbitrarily Drawn

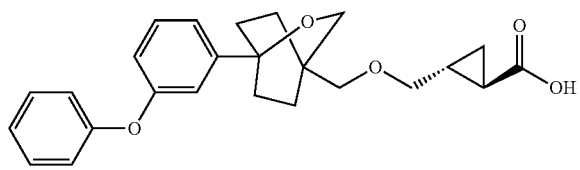 [SMILES: O=C(O)[C@@H]1C[C@H]1COCC12CCC(c3cccc(Oc4ccccc4)c3)(CC1)OC2]

Example 99

Single Enantiomer; Absolute Stereochemistry not Determined, Arbitrarily Drawn

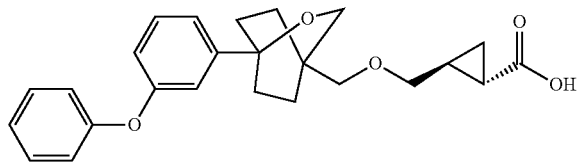 [SMILES: O=C(O)[C@H]1C[C@@H]1COCC12CCC(c3cccc(Oc4ccccc4)c3)(CC1)OC2]

The two individual enantiomers of racemic Example 97 were separated by chiral preparative HPLC (Instrument: PIC Solution 200 SFC; Column: CHIRALPAK® OJ-H, 21×250 mm, 5μ; Mobile Phase: 15% IPA-0.1% FA/85% CO₂; Flow Conditions: 45 mL/min, 150 Bar, 40° C.; Detector Wavelength: 220 nm; Injection Details: 0.5 mL of 4 mg/mL in ACN:EtOH(1:1)). The first eluting enantiomer was designated as Example 98, (2.3 mg, purity=96%): >99% ee. The second eluting enantiomer was designated as Example 99 (2.9 mg, purity=96%): 98.2% ee.

Example 100

2-(2-(4-(3-(3-Fluoro-4-methoxyphenoxy)phenyl)-2-oxabicyclo[2.2.2]octan-1-yl)ethoxy) acetic acid

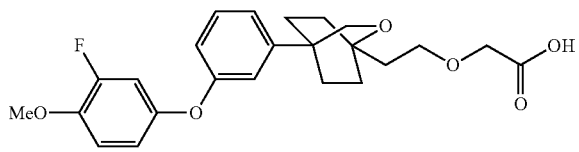 [SMILES: COc1ccc(Oc2cccc(C34CCC(CCOCC(=O)O)(CC3)OC4)c2)cc1F]

100A. Ethyl 4-methylene-1-(3-((2-(trimethylsilyl)ethoxy)methoxy)phenyl) cyclohexanecarboxylate

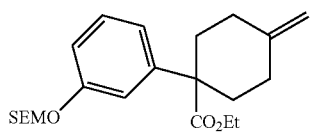

n-BuLi (3.33 mL of a 2.5 M solution in hexanes; 8.32 mmol) was added slowly at 0° C. to a solution of dicyclohexylamine (1.65 mL, 8.32 mmol) in toluene (20 mL) and stirred for 30 min. Then, a solution of ethyl 4-methylenecyclohexanecarboxylate (Example 30A compound; 1.18 g, 7.04 mmol) in toluene (2 mL) was added slowly to the solution of lithium dicyclohexylamide and the reaction was stirred at 0° C. for 30 min. In a separate flask, di-μ-bromobis(tri-tert-butylphosphino)dipalladium (I) (25 mg, 0.032 mmol) in toluene (1 mL) was purged with N₂ and added to the reaction mixture. Finally, a solution of 2-(3-bromophenoxy)tetrahydro-2H-pyran (2.0 g, 7.78 mmol) in toluene (5 mL) was added, and the reaction mixture was allowed to warm to rt and stirred overnight. The reaction was quenched with satd aq. NH₄Cl, filtered through a pad of CELITE®, diluted with EtOAc (25 mL), washed with water, dried (MgSO₄), and concentrated in vacuo. The crude was chromatographed (SiO₂; continuous gradient of hexanes/EtOAc from 100:0 to 60:40) to afford the title compound (2.4 g, 86% yield) as a yellow oil. LCMS [M+H₂O]⁺=408.4. ¹H NMR (400 MHz, CDCl₃) δ 7.24 (t, J=8.0 Hz, 1H), 7.08-7.06 (m, 1H), 7.05-7.01 (m, 1H), 6.94 (dt, J=8.1, 1.2 Hz, 1H), 5.21 (s, 2H), 4.66 (br. s, 2H), 4.16 (q, J=7.1 Hz, 2H), 3.79-3.73 (m, 2H), 2.61-2.52 (m, 2H), 2.36-2.18 (m, 4H), 1.87-1.77 (m, 2H), 1.21 (t, J=7.2 Hz, 3H), 1.01-0.92 (m, 2H), 0.01 (s, 9H).

100B. (4-Methylene-1-(3-((2-(trimethylsilyl)ethoxy)methoxy)phenyl)cyclohexyl) methanol

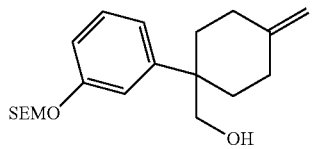

LiAlH₄ (7.22 mL of a 1.0 M solution in THF, 7.22 mmol) was added dropwise at 0° C. to a solution of Part A compound (2.35 g, 6.02 mmol) in THF (30 mL). The reaction was warmed to rt and stirred for 1 h, then was cooled to 0° C. and quenched carefully with water (5 mL) and MeOH (3 mL) and stirred for 10 min. The mixture was filtered through a pad of CELITE®, diluted with EtOAc, washed with 1N aq HCl, dried (MgSO₄), and concentrated in vacuo. The crude product was chromatographed (SiO₂; continuous gradient from hexanes/EtOAc 100:0 to 60:40) to afford the title compound (1.79 g, 85% yield) as a colorless oil. $^1$H NMR (400 MHz, CDCl₃) δ 7.34-7.28 (m, 1H), 7.10-7.04 (m, 2H), 6.97 (ddd, J=8.2, 2.4, 0.9 Hz, 1H), 5.25-5.22 (m, 2H), 4.61 (s, 2H), 3.82-3.74 (m, 2H), 3.53 (s, 2H), 2.33-2.18 (m, 4H), 2.17-2.07 (m, 2H), 1.72-1.63 (m, 2H), 1.00-0.94 (m, 2H), 0.03-0.00 (m, 9H).

100C. (6-(3-((2-(Trimethylsilyl)ethoxy)methoxy)phenyl)-1-oxaspiro[2.5]octan-6-yl)methanol

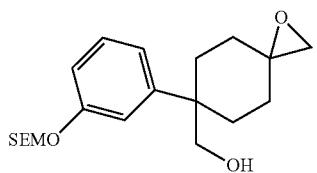

To a solution of Part B compound in acetone (12 mL) and water (12 mL) was added N-bromo succinimide (0.911 g, 5.12 mmol) in 3 portions over 30 min. The reaction was stirred at rt for 1 h, then was diluted with DCM, washed with water, and concentrated in vacuo. The crude bromohydrin product was dissolved in MeOH (5 mL) and a few drops of water, after which solid NaOH (0.195 g, 4.88 mmol) was added and the reaction mixture was stirred for 20 min at rt. The mixture was concentrated in vacuo to remove the MeOH, then was diluted with DCM (20 mL), washed with water, dried (MgSO₄), and concentrated in vacuo. The crude material was chromatographed (SiO₂; continuous gradient of hexanes/EtOAc from 100:0 to 0:100) to afford the title compound (0.84 g, 47% yield) as a colorless oil. This material was a ~70:30 mixture of diastereomers.

100D. (4-(3-((2-(Trimethylsilyl)ethoxy)methoxy)phenyl)-2-oxabicyclo[2.2.2]octan-1-yl)methanol

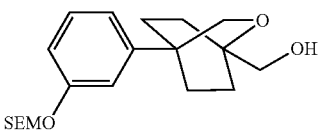

A mixture of Part C compound (0.84 g, 2.30 mmol) and TsOH.H₂O (0.022 g, 0.12 mmol) in DCM (10 mL) was stirred at rt for 1.5 h. The reaction was diluted with DCM, washed with sat'd aq NaHCO₃, dried (MgSO₄), and concentrated in vacuo. The crude product was chromatographed (SiO₂; continuous gradient of hexanes/EtOAc from 100:0 to 0:100) to afford the title compound (0.588 g, 70% yield) as a colorless oil. $^1$H NMR (400 MHz, CDCl₃) δ 7.25 (s, 1H), 6.98-6.89 (m, 3H), 5.22 (s, 2H), 4.02 (d, J=1.3 Hz, 2H), 3.80-3.74 (m, 2H), 3.47 (d, J=6.4 Hz, 2H), 2.15-2.02 (m, 4H), 2.01-1.93 (m, 2H), 1.65 (br. s., 2H), 1.01-0.93 (m, 2H), 0.01 (s, 9H).

100E. 4-(3-((2-(Trimethylsilyl)ethoxy)methoxy)phenyl)-2-oxabicyclo[2.2.2]octane-1-carbaldehyde

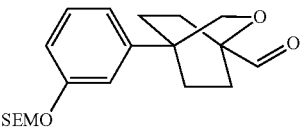

To a 0° C. mixture of Part D compound (0.60 g, 1.65 mmol) and NaHCO₃ (1.38 g, 16.5 mmol) in DCM (8 mL) was added Dess-Martin periodinane (0.838 g, 1.96 mmol). The reaction was warmed to rt and stirred for 2.5 h, then was filtered through a pad of CELITE®, diluted with DCM, washed with water, dried (MgSO₄), and concentrated in vacuo. The crude product was chromatographed (SiO₂; continuous gradient of hexanes/EtOAc from 100:0 to 40:60) to afford the title compound (0.41 g, 69% yield) as a light yellow oil. $^1$H NMR (400 MHz, CDCl₃) δ 9.64 (s, 1H), 7.29-7.22 (m, 1H), 6.97-6.90 (m, 3H), 5.22 (s, 2H), 4.10 (s, 2H), 3.81-3.74 (m, 2H), 2.17-1.87 (m, 8H), 1.01-0.93 (m, 2H), 0.01 (s, 9H).

100F. Trimethyl(2-((3-(1-vinyl-2-oxabicyclo[2.2.2]octan-4-yl)phenoxy)methoxy)ethyl) silane

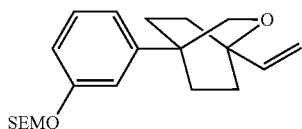

n-BuLi (0.66 mL of a 2.5M solution in hexanes; 1.66 mmol) was added at 0° C. to a suspension of methyltriphenylphosphonium bromide (0.591 g, 1.66 mmol) in THF (7 mL) and the reaction mixture was stirred for 30 min at 0° C. A solution of Part E compound (0.40 g, 1.10 mmol) in THF (2 mL) was then added. The reaction mixture was allowed to warm to rt and stirred at rt for 3 h, then was diluted with DCM, washed with water, dried (MgSO₄), and concentrated in vacuo. The crude product was chromatographed (SiO₂; continuous gradient of hexanes/EtOAc from 100:0 to 60:40) to afford the title compound (0.241 g, 54.5% yield) as a yellow oil. $^1$H NMR (400 MHz, CDCl₃) δ 7.26-7.21 (m, 1H), 6.94 (td, J=8.0, 1.9 Hz, 3H), 5.95-5.84 (m, 1H), 5.25-5.17 (m, 3H), 5.07 (dd, J=10.9, 1.4 Hz, 1H), 4.07 (d, J=1.3 Hz, 2H), 3.81-3.74 (m, 2H), 2.18-1.79 (m, 8H), 1.00-0.93 (m, 2H), 0.04-−0.02 (m, 9H).

100G. 2-(4-(3-((2-(Trimethylsilyl)ethoxy)methoxy)phenyl)-2-oxabicyclo[2.2.2]octan-1-yl)ethanol

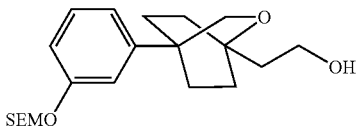

To a 0° C. solution of Part F compound (200 mg, 0.555 mmol) in THF (3 mL) was added borane dimethyl sulfide complex (0.56 mL of a 2.0 M solution in THF, 1.11 mmol).

The reaction was allowed to warm to rt and stirred at rt for 2 h, then was cooled to 0° C. Aq. NaOH (1.7 mL of a 1 N solution, 1.7 mmol) and 30% aq H₂O₂ (0.23 mL, 2.22 mmol) were added and the reaction was stirred at rt overnight, then was diluted with DCM, washed with water, dried (MgSO₄), and concentrated in vacuo. The crude product was chromatographed (SiO₂; continuous gradient of hexanes/EtOAc from 100:0 to 50:50) to afford the title compound (110 mg, 52% yield) as a yellow oil. LCMS [M+H]⁺=379.4. ¹H NMR (400 MHz, CDCl₃) δ 7.25-7.21 (m, 1H), 6.97-6.89 (m, 3H), 5.22 (s, 2H), 3.99 (t, J=1.3 Hz, 2H), 3.86-3.73 (m, 4H), 2.18-1.88 (m, 6H), 1.75-1.63 (m, 4H), 1.00-0.92 (m, 2H), 0.01 (s, 9H).

100H. tert-Butyl 2-(2-(4-(3-((2-(trimethylsilyl)ethoxy)methoxy)phenyl)-2-oxabicyclo [2.2.2]octan-1-yl)ethoxy)acetate

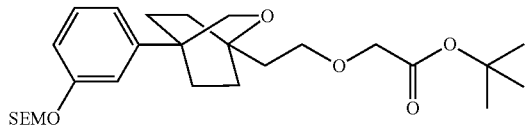

KOtBu (0.79 g, 7.04 mmol) was added at 0° C. to a solution of Part G compound (0.533 g, 1.41 mmol) in toluene (10 mL) and the reaction was stirred for 5 min at 0° C. t-Butyl 2-bromoacetate (0.62 mL, 4.22 mmol) was then added and the reaction was warmed to rt and stirred for 3 h, then was diluted with EtOAc, washed with water, dried (MgSO₄), and concentrated in vacuo. The crude product was chromatographed (SiO₂; continuous gradient of hexanes/EtOAc from 100:0 to 50:50) to afford the title compound (0.403 g, 58% yield) as a colorless oil. LCMS [M+H]⁺=493.5.

100I. tert-Butyl 2-(2-(4-(3-hydroxyphenyl)-2-oxabicyclo[2.2.2]octan-1-yl)ethoxy)acetate

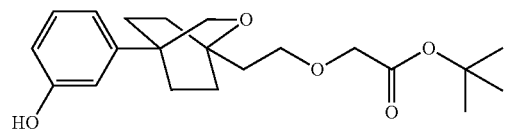 [SMILES: CC(C)(C)OC(=O)COCCC12CCC(c3cccc(O)c3)(CC1)CO2]

HCl (0.41 mL of a 4N solution in dioxane; 1.64 mmol) was added to a solution of Part H compound (0.40 g, 0.81 mmol) in DCM (2 mL) and the reaction was stirred at rt for 20 min, then was concentrated in vacuo, diluted with DCM, washed with sat.aq. NaHCO₃, dried (MgSO₄), and concentrated in vacuo to afford the title compound (0.253 g. 86% yield). LCMS [M+H]⁺=363.3. ¹H NMR (400 MHz, CDCl₃) δ 7.19 (t, J=7.9 Hz, 1H), 6.84 (d, J=7.7 Hz, 1H), 6.75 (t, J=2.0 Hz, 1H), 6.72-6.66 (m, 1H), 3.99 (s, 2H), 3.97 (s, 2H), 3.66 (t, J=6.8 Hz, 2H), 2.09-1.87 (m, 6H), 1.85-1.74 (m, 4H), 1.49 (s, 9H).

100J. tert-Butyl 2-(2-(4-(3-(3-fluoro-4-methoxyphenoxy)phenyl)-2-oxabicyclo[2.2.2]octan-1-yl)ethoxy)acetate

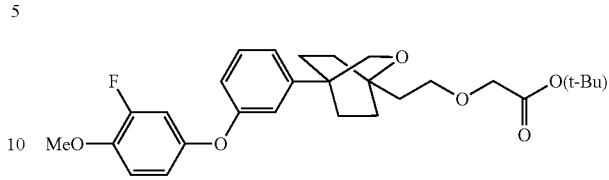

A mixture of Part I compound (17 mg, 0.05 mmol), 3-fluoro-4-methoxyphenyl boronic acid (16 mg, 0.09 mmol), Cu (II) OAc₂ (26 mg, 0.14 mmol), pyridine (38 μL, 0.47 mmol), Et₃N (19.6 μL, 0.14 mmol), and 4A molecular sieves (60 mg) in DCM (1.5 mL) was stirred at rt under air for 3 days. The reaction mixture was filtered through a pad of CELITE®, diluted with DCM, washed with 1N aq HCl, dried (MgSO₄), and concentrated in vacuo. The crude product was purified using preparative HPLC (PHENOMENEX® Luna Axia C18 5μ; 30×100 mm Column; detection at 220 nM; flow rate=40 mL/min; continuous gradient from 40% B to 100% B over 10 min+5 min hold at 100% B, where A=10:90:0.1 MeOH—H₂O-TFA and B=90:10:0.1 MeOH—H₂O-TFA) to afford the title compound (12 mg, 53% yield) as a brown oil. LCMS [M+H]⁺=487.3. ¹H NMR (400 MHz, CDCl₃) δ 7.29-7.23 (m, J=8.0, 8.0 Hz, 1H), 7.00 (d, J=7.9 Hz, 1H), 6.96-6.90 (m, 2H), 6.83-6.77 (m, 2H), 6.76-6.71 (m, 1H), 3.99-3.94 (m, 4H), 3.90 (s, 3H), 3.65 (t, J=6.8 Hz, 2H), 2.09-1.86 (m, 6H), 1.84-1.73 (m, 4H), 1.49 (s, 9H).

Example 100

2-(2-(4-(3-(3-Fluoro-4-methoxyphenoxy)phenyl)-2-oxabicyclo[2.2.2]octan-1-yl)ethoxy)acetic acid

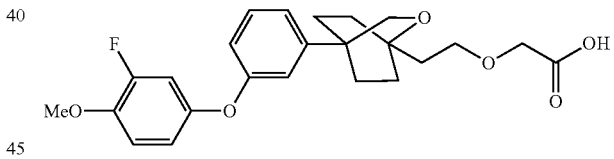

A mixture of Part J compound (12 mg, 0.03 mmol) and TFA (0.2 mL, 2.60 mmol) in DCM (1 mL) was stirred at rt for 1 h, then was concentrated in vacuo. The crude product was purified using preparative HPLC (PHENOMENEX® Luna Axia C18 5μ; 30×100 mm Column; detection at 220 nM; flow rate=40 mL/min; continuous gradient from 40% B to 100% B over 10 min+5 min hold at 100% B, where A=10:90:0.1 MeOH—H₂O-TFA and B=90:10:0.1 MeOH—H₂O-TFA) to afford the title compound (8.5 mg, 23% yield) as an off-white gum. LCMS [M+H]⁺=431.4. ¹H NMR (400 MHz, CDCl₃) δ 7.27 (d, J=15.9 Hz, 1H), 7.00 (d, J=7.7 Hz, 1H), 6.97-6.91 (m, 2H), 6.84-6.78 (m, 2H), 6.77-6.72 (m, 1H), 4.09 (s, 2H), 4.04 (s, 2H), 3.90 (s, 3H), 3.74 (t, J=5.3 Hz, 2H), 2.18-2.04 (m, 4H), 2.02-1.90 (m, 2H), 1.80 (t, J=5.4 Hz, 2H), 1.74-1.63 (m, 2H). HPLC-1: RT=12.5 min, purity=99.0%; HPLC-2: RT=11.7 min, purity=98%.

Examples 101-107 were synthesized using the same general 2-step protocol as for the synthesis of Example 100 from intermediate phenol Example 100I (via Chan-Lam coupling with the appropriate corresponding substituted aryl or heteroaryl boronic acid, followed by ester deprotection).

| Example No. | Structure and Name | Analytical Data |
|---|---|---|
| 101 | 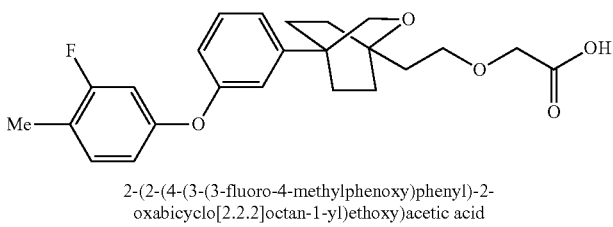 [SMILES: Cc1ccc(Oc2cccc(C34CCC(CCOCC(=O)O)(CC3)OC4)c2)cc1F]<br>2-(2-(4-(3-fluoro-4-methylphenoxy)phenyl)-2-oxabicyclo[2.2.2]octan-1-yl)ethoxy)acetic acid | $^1$H NMR (400 MHz, CDCl$_3$) δ 7.32-7.28 (m, 1H), 7.12 (t, J = 8.7 Hz, 1H), 7.05-7.00 (m, 1H), 6.95 (t, J = 2.0 Hz, 1H), 6.88-6.83 (m, 1H), 6.72-6.64 (m, 2H), 4.09 (s, 2H), 4.04 (s, 2H), 3.77-3.71 (m, 2H), 2.25 (d, J = 1.7 Hz, 3H), 2.18-2.04 (m, 4H), 2.02-1.91 (m, 2H), 1.82-1.77 (m, 2H), 1.73-1.63 (m, 2H). LCMS [M + H]$^+$ = 415.4. |
| 102 | 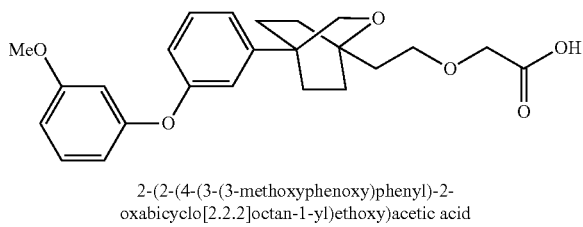 [SMILES: COc1cccc(Oc2cccc(C34CCC(CCOCC(=O)O)(CC3)OC4)c2)c1]<br>2-(2-(4-(3-methoxyphenoxy)phenyl)-2-oxabicyclo[2.2.2]octan-1-yl)ethoxy)acetic acid | $^1$H NMR (400 MHz, CDCl$_3$) δ 7.31-7.19 (m, 2H), 7.04-6.99 (m, 1H), 6.98 (t, J = 2.0 Hz, 1H), 6.87 (ddd, J = 8.1, 2.4, 0.8 Hz, 1H), 6.67 (ddd, J = 8.3, 2.2, 1.0 Hz, 1H), 6.59-6.54 (m, 2H), 4.09 (s, 2H), 4.04 (s, 2H), 3.79 (s, 3H), 3.74 (t, J = 5.3 Hz, 2H), 2.18-2.04 (m, 4H), 2.02-1.91 (m, 2H), 1.80 (t, J = 5.3 Hz, 2H), 1.73-1.61 (m, 2H). LCMS [M + H]$^+$ = 413.3. |
| 103 | 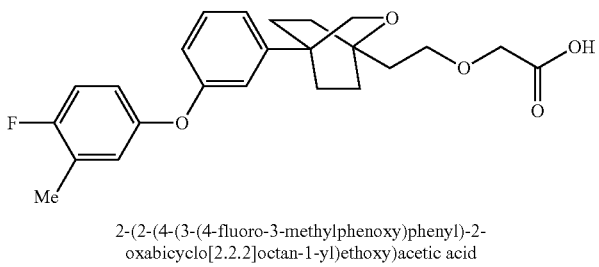 [SMILES: Cc1cc(Oc2cccc(C34CCC(CCOCC(=O)O)(CC3)OC4)c2)ccc1F]<br>2-(2-(4-(3-(4-fluoro-3-methylphenoxy)phenyl)-2-oxabicyclo[2.2.2]octan-1-yl)ethoxy)acetic acid | $^1$H NMR (500 MHz, DMSO-d$_6$) δ 7.29 (t, J = 7.7 Hz, 1H), 7.14 (t, J = 8.9 Hz, 1H), 7.06 (d, J = 7.4 Hz, 1H), 6.99-6.89 (m, 2H), 6.87-6.79 (m, 1H), 6.73 (d, J = 7.7 Hz, 1H), 3.95 (br. s., 2H), 3.82 (br. s., 2H), 3.64-3.47 (m, 2H), 2.21 (br. s., 3H), 1.96-1.87 (m, J = 7.4 Hz, 2H), 1.86-1.77 (m, J = 8.1 Hz, 4H), 1.75-1.66 (m, J = 8.1 Hz, 2H), 1.63 (t, J = 6.2 Hz, 2H). LCMS [M + H]$^+$ = 415.3. |
| 104 | 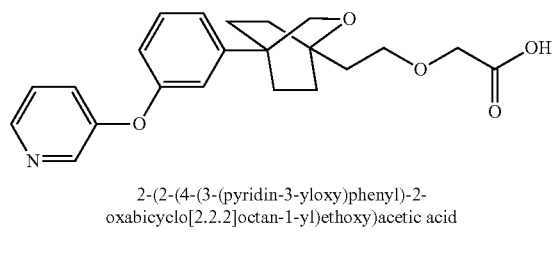 [SMILES: O=C(O)COCCC12CCC(c3cccc(Oc4cccnc4)c3)(CC1)CO2]<br>2-(2-(4-(3-(pyridin-3-yloxy)phenyl)-2-oxabicyclo[2.2.2]octan-1-yl)ethoxy)acetic acid | $^1$H NMR (400 MHz, CDCl$_3$) δ 8.57 (dd, J = 5.3, 1.0 Hz, 1H), 8.46 (d, J = 2.6 Hz, 1H), 7.85-7.80 (m, 1H), 7.79-7.73 (m, 1H), 7.44 (t, J = 1.0 Hz, 1H), 7.26-7.22 (m, 1H), 7.03 (t, J = 2.0 Hz, 1H), 6.97 (dd, J = 8.0, 1.7 Hz, 1H), 4.09 (s, 2H), 4.04 (s, 2H), 3.73 (t, J = 5.4 Hz, 2H), 2.19-2.05 (m, 4H), 2.04-1.93 (m, 2H), 1.81 (t, J = 5.4 Hz, 2H), 1.76-1.65 (m, 2H). LCMS [M + H]$^+$ = 384.3. |
| 105 | 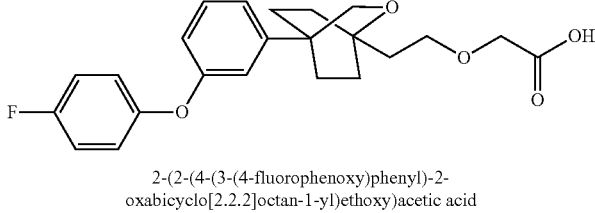 [SMILES: O=C(O)COCCC12CCC(c3cccc(Oc4ccc(F)cc4)c3)(CC1)CO2]<br>2-(2-(4-(3-(4-fluorophenoxy)phenyl)-2-oxabicyclo[2.2.2]octan-1-yl)ethoxy)acetic acid | $^1$H NMR (500 MHz, DMSO-d$_6$) δ 7.34-7.28 (m, 1H), 7.26-7.19 (m, 2H), 7.11-7.03 (m, 3H), 6.96 (br. s., 1H), 6.80-6.73 (m, 1H), 3.84 (br. s., 2H), 3.75 (br. s, 2H), 3.48-3.31 (m, 2H), 2.00-1.59 (m, 10H). LCMS [M + H]$^+$ = 397.4. |
| 106 | 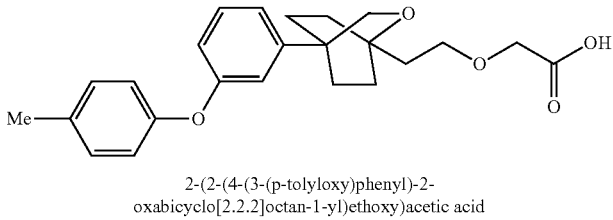 [SMILES: Cc1ccc(Oc2cccc(C34CCC(CCOCC(=O)O)(CC3)OC4)c2)cc1]<br>2-(2-(4-(3-(p-tolyloxy)phenyl)-2-oxabicyclo[2.2.2]octan-1-yl)ethoxy)acetic acid | $^1$H NMR (500 MHz, DMSO-d$_6$) δ 7.27 (t, J = 8.1 Hz, 1H), 7.18 (d, J = 8.1 Hz, 2H), 7.04 (d, J = 7.7 Hz, 1H), 6.95-6.86 (m, 3H), 6.73 (d, J = 6.4 Hz, 1H), 3.82 (d, J = 7.7 Hz, 4H), 3.53-3.37 (m, 2H), 2.28 (s, 3H), 1.96-1.86 (m, 2H), 1.81 (d, J = 7.7 Hz, 4H), 1.74-1.66 (m, 2H), 1.61 (t, J = 7.1 Hz, 2H). LCMS [M + H]$^+$ = 397.5. |

| Example No. | Structure and Name | Analytical Data |
|---|---|---|
| 107 | 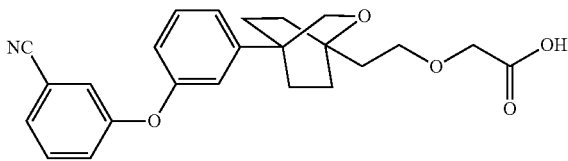<br>2-(2-(4-(3-(3-cyanophenoxy)phenyl)-2-oxabicyclo[2.2.2]octan-1-yl)ethoxy)acetic acid | $^1$H NMR (400 MHz, CDCl$_3$) δ 7.47-7.40 (m, 1H), 7.40-7.32 (m, 2H), 7.25-7.18 (m, 2H), 7.14-7.09 (m, 1H), 6.97 (t, J = 2.0 Hz, 1H), 6.88 (dt, J = 8.1, 1.2 Hz, 1H), 4.10 (s, 2H), 4.05 (s, 2H), 3.77-3.70 (m, 2H), 2.21-2.05 (m, 4H), 2.04-1.91 (m, 2H), 1.81 (t, J = 5.4 Hz, 2H), 1.76-1.62 (m, 2H). LCMS [M + H]$^+$ = 408.4. |

Example 108

2-(2-(4-(3-Fluoro-5-(3-fluoro-4-methylphenoxy)phenyl)-2-oxabicyclo[2.2.2]octan-1-yl)ethoxy)acetic acid

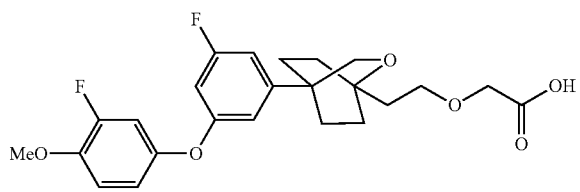 [SMILES: COc1ccc(Oc2cc(F)cc(C34CCC(CCOCC(=O)O)(CC3)OC4)c2)cc1F]

Example 108 was synthesized using the same reaction sequence as for the conversion of Example 100A to Example 100 (except that 2-(3-bromo-5-fluoro-phenoxy)tetrahydro-2H-pyran was used instead of 2-(3-bromophenoxy)tetrahydro-2H-pyran). LCMS [M+H]$^+$=433.3. $^1$H NMR (400 MHz, CDCl$_3$) δ 7.16 (t, J=8.6 Hz, 1H), 6.76-6.67 (m, 4H), 6.53 (dt, J=9.7, 2.1 Hz, 1H), 4.09 (s, 2H), 4.00 (s, 2H), 3.73 (t, J=5.3 Hz, 2H), 2.27 (d, J=1.7 Hz, 3H), 2.16-2.00 (m, 4H), 1.98-1.88 (m, 2H), 1.80 (t, J=5.3 Hz, 2H), 1.73-1.64 (m, 2H). HPLC-1: RT=14.0 min, purity=96.0%; HPLC-2: RT=12.6 min, purity=97%.

Example 109

2-(2-(4-(3-(Pyridin-2-yloxy)phenyl)-2-oxabicyclo[2.2.2]octan-1-yl)ethoxy)acetic acid

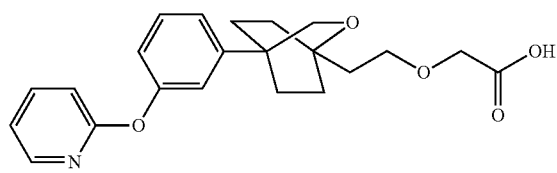 [SMILES: O=C(O)COCCC12CCC(c3cccc(Oc4ccccn4)c3)(CC1)CO2]

Example 109 was prepared from Example 5 Part 1 compound using a procedure analogous to that used to synthesize Example 14, except that 2-iodopyridine was used instead of 4-iodopyridine. LCMS [M+H]$^+$=384.2. $^1$H NMR (400 MHz, CDCl$_3$) δ 8.35 (d, J=4.2 Hz, 1H), 7.84 (ddd, J=8.6, 7.1, 1.9 Hz, 1H), 7.42-7.35 (m, 1H), 7.20-7.13 (m, 2H), 7.07 (t, J=2.0 Hz, 1H), 7.04-6.98 (m, 1H), 6.89 (d, J=8.3 Hz, 1H), 4.09 (s, 2H), 4.05 (s, 2H), 3.74 (t, J=5.3 Hz, 2H), 2.17-2.05 (m, 4H), 2.04-1.93 (m, 2H), 1.80 (t, J=5.4 Hz, 2H), 1.74-1.63 (m, 2H).

Example 110

2-(3-(4-(3-Phenoxyphenyl)-2-oxabicyclo[2.2.2]octan-1-yl)propoxy)acetic acid

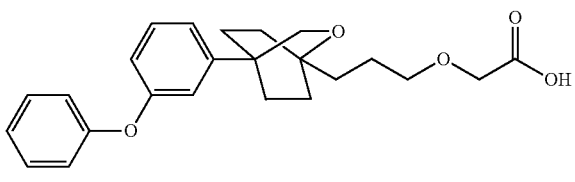 [SMILES: O=C(O)COCCCC12CCC(c3cccc(Oc4ccccc4)c3)(CC1)CO2]

110A. 2-(4-(3-Phenoxyphenyl)-2-oxabicyclo[2.2.2]octan-1-yl)ethyl methanesulfonate

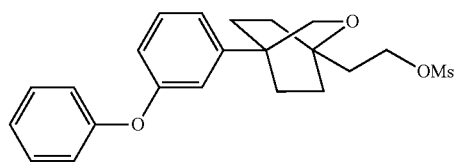 [SMILES: CS(=O)(=O)OCCC12CCC(c3cccc(Oc4ccccc4)c3)(CC1)CO2]

To a 0° C. solution of Example 31 Part C compound (82 mg, 0.253 mmol) and Et$_3$N (0.11 mL, 0.76 mmol) in DCM (2 mL) was added methanesulfonyl chloride (0.024 mL, 0.30 mmol) dropwise and the reaction was stirred at rt for 1 h. The mixture was diluted with DCM, washed with 1N aq HCl, water, dried (MgSO$_4$), and concentrated in vacuo to afford the title compound (100 mg, 100% yield). LCMS [M+H]$^+$=403.3.

110B. 3-(4-(3-Phenoxyphenyl)-2-oxabicyclo[2.2.2]octan-1-yl)propanenitrile

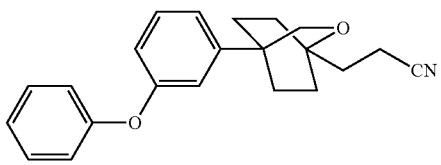 [SMILES: N#CCCC12CCC(c3cccc(Oc4ccccc4)c3)(CC1)CO2]

A mixture of 110A compound (100 mg, 0.25 mmol) and NaCN (61 mg, 1.2 mmol) in DMSO (3 mL) was stirred at 80° C. overnight. The mixture was cooled to rt, diluted with DCM, washed with 1N aq HCl, dried (MgSO$_4$), and concentrated in vacuo. The crude was chromatographed (SiO$_2$; continuous gradient of hexanes/EtOAc from 100:0 to 50:50) to afford the title compound (62 mg, 75% yield) as a colorless oil. LCMS [M+H]$^+$=334.3. $^1$H NMR (400 MHz, CDCl$_3$) δ 7.38-7.32 (m, 2H), 7.31-7.25 (m, J=7.9, 7.9 Hz, 1H), 7.14-7.09 (m, 1H), 7.00 (dd, J=8.6, 1.1 Hz, 3H), 6.96 (t, J=2.0 Hz, 1H), 6.84 (ddd, J=8.1, 2.4, 0.9 Hz, 1H), 3.96 (s, 2H), 2.47-2.41 (m, 2H), 2.12-2.03 (m, 2H), 2.00-1.89 (m, 4H), 1.84-1.78 (m, 2H), 1.74-1.64 (m, 2H).

110C. 3-(4-(3-Phenoxyphenyl)-2-oxabicyclo[2.2.2]octan-1-yl)propanal

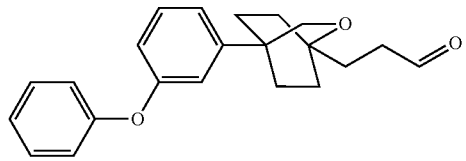 [SMILES: O=CCCC12CCC(c3cccc(Oc4ccccc4)c3)(CC1)CO2]

To a −78° C. solution of 110B compound (62 mg, 0.19 mmol) in DCM (2 mL) was added DIBAL-H (0.24 mL of a 1M solution in toluene; 0.24 mmol) and the reaction was stirred at −78° C. for 2 h. CELITE® (300 mg) was added and the reaction was quenched with sat'd aq NH$_4$Cl. The mixture was stirred at rt for 30 min, then was filtered through a 1:1 mixture of CELITE® and MgSO$_4$ and the filtrate was concentrated in vacuo. The crude product was chromatographed (SiO$_2$; continuous gradient of hexanes/EtOAc from 100:0 to 0:100) to afford the title compound (34 mg, 54% yield) as a light yellow oil. $^1$H NMR (400 MHz, CDCl$_3$) δ 9.78 (t, J=1.8 Hz, 1H), 7.38-7.32 (m, 2H), 7.30-7.24 (m, 1H), 7.14-7.08 (m, 1H), 7.03-6.95 (m, 4H), 6.87-6.82 (m, 1H), 4.01-3.90 (m, 2H), 2.56-2.50 (m, 2H), 2.12-1.87 (m, 6H), 1.82-1.76 (m, 2H), 1.75-1.60 (m, 2H).

110D. 3-(4-(3-Phenoxyphenyl)-2-oxabicyclo[2.2.2]octan-1-yl)propan-1-ol

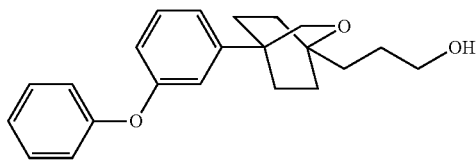 [SMILES: OCCCC12CCC(c3cccc(Oc4ccccc4)c3)(CC1)CO2]

To a −78° C. solution of 110C compound (35 mg, 0.10 mmol) in DCM (2 mL) was added DIBAL-H (0.16 mL of a 1M solution in toluene; 16 mmol) and the solution was stirred at −78° C. for 2 h. The reaction was quenched with sat'd aq. NaH$_4$Cl and CELITE® (200 mg) was added. The mixture was stirred at rt for 30 min, then was filtered through a 1:1 mixture of CELITE® and MgSO$_4$ and concentrated in vacuo to give the title compound (22 mg, 77% yield). LCMS [M+H]$^+$=339.4.

110E. tert-Butyl 2-(3-(4-(3-phenoxyphenyl)-2-oxabicyclo[2.2.2]octan-1-yl)propoxy) acetate

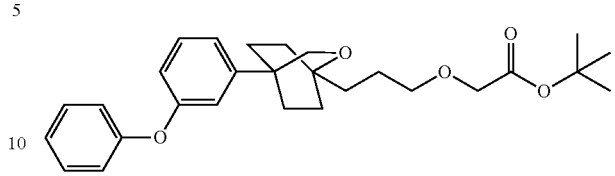

tert-Butyl 2-bromoacetate (0.026 mL, 0.18 mmol) was added to a mixture of 110D compound (20 mg, 0.06 mmol) and KOtBu (33 mg, 0.30 mmol) in toluene (1 mL) and the reaction mixture was sonicated for 5 min, then was stirred for 30 min. The mixture was diluted with DCM, washed with 1N aq. HCl, dried (MgSO$_4$), and concentrated in vacuo. The crude product was purified using preparative HPLC (PHENOMENEX® Luna Axia C18 5μ; 30×100 mm Column; detection at 220 nM; flow rate=40 mL/min; continuous gradient from 40% B to 100% B over 10 min+5 min hold at 100% B, where A=10:90:0.1 MeOH—H$_2$O-TFA and B=90:10:0.1 MeOH—H$_2$O-TFA) to afford the title compound (11 mg, 39% yield) as a colorless oil. $^1$H NMR (400 MHz, CDCl$_3$) δ 7.37-7.31 (m, 2H), 7.27 (d, J=15.9 Hz, 1H), 7.13-7.08 (m, 1H), 7.04-6.96 (m, 4H), 6.83 (ddd, J=8.1, 2.4, 0.8 Hz, 1H), 3.98 (s, 2H), 3.96 (s, 2H), 3.53 (t, J=6.5 Hz, 2H), 2.09-2.01 (m, 2H), 1.98-1.86 (m, 4H), 1.74-1.64 (m, 4H), 1.55-1.44 (m, 11H).

Example 110

2-(3-(4-(3-Phenoxyphenyl)-2-oxabicyclo[2.2.2]octan-1-yl)propoxy)acetic acid

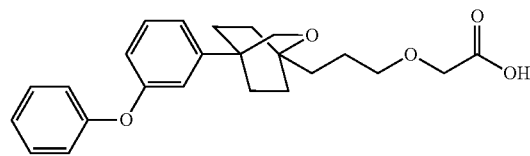 [SMILES: O=C(O)COCCCC12CCC(c3cccc(Oc4ccccc4)c3)(CC1)CO2]

A mixture of 110E compound (10.5 mg, 0.02 mmol) and TFA (0.5 mL, 6.49 mmol) in DCM (1.5 mL) was stirred at rt for 1 h, then was concentrated in vacuo. The crude product was purified using preparative HPLC (PHENOMENEX® Luna Axia C18 5μ; 30×100 mm Column; detection at 220 nM; flow rate=40 mL/min; continuous gradient from 0% B to 100% B over 10 min+5 min hold at 100% B, where A=10:90:0.1 ACN—H$_2$O-TFA and B=90:10:0.1 ACN—H$_2$O-TFA) to afford the title compound (7.5 mg, 79% yield) as a white solid. LCMS [M+H]$^+$=397.4. $^1$H NMR (400 MHz, CDCl$_3$) δ 7.37-7.31 (m, 2H), 7.27 (d, J=15.9 Hz, 1H), 7.14-7.08 (m, 1H), 7.03-6.96 (m, 4H), 6.84 (ddd, J=8.1, 2.4, 0.9 Hz, 1H), 4.10 (s, 2H), 3.98 (s, 2H), 3.61 (t, J=6.3 Hz, 2H), 2.11-1.87 (m, 6H), 1.78-1.62 (m, 4H), 1.58-1.52 (m, 2H). HPLC-1: RT=13.2 min, purity=98.0%; HPLC-2: RT=12.2 min, purity=97%.

Example 111

2-(2-(4-(3-(Cyclohexyloxy)phenyl)-2-oxabicyclo[2.2.2]octan-1-yl)ethoxy) acetic acid

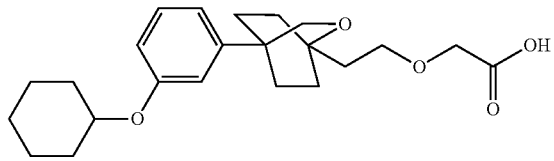 [SMILES: O=C(O)COCCC12CCC(c3cccc(OC4CCCCC4)c3)(CC1)CO2]

111A. tert-Butyl 2-(2-(4-(3-(cyclohexyloxy)phenyl)-2-oxabicyclo[2.2.2]octan-1-yl)ethoxy)acetate

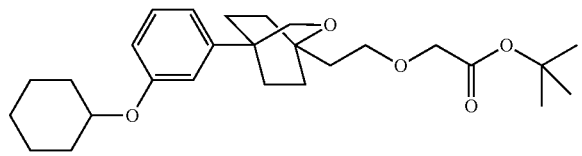 [SMILES: CC(C)(C)OC(=O)COCCC12CCC(c3cccc(OC4CCCCC4)c3)(CC1)CO2]

To a stirred solution of Example 5 Part 1 compound (20 mg, 0.06 mmol) and iodocyclohexane (116 mg, 0.55 mmol) in DMF (0.8 mL) was added NaH (4.4 mg, 0.11 mmol) and the mixture was heated to 50° C. and stirred for 4 h, then cooled to rt and quenched with few drops of water. The crude product was purified by preparative HPLC (PHENOMENEX® Luna Axia C18 5 μm; 30×100 mm Column; detection at 220 nM; flow rate=40 mL/min; continuous gradient from 0% B to 100% B over 10 min+5 min hold at 100% B, where A=10:90:0.1 ACN—H$_2$O-TFA and B=90:10:0.1 ACN—H$_2$O-TFA) to afford the title compound (7 mg, 29% yield) as a brown oil. LCMS [M+H]$^+$=445.5. $^1$H NMR (400 MHz, CDCl$_3$) δ 7.21 (t, J=7.9 Hz, 1H), 6.86-6.80 (m, 2H), 6.78-6.72 (m, 1H), 4.27-4.18 (m, 1H), 3.99 (s, 2H), 3.96 (s, 2H), 3.65 (t, J=6.8 Hz, 2H), 2.12-1.87 (m, 8H), 1.86-1.70 (m, 6H), 1.63-1.24 (m, 15H).

Example 111

2-(2-(4-(3-(Cyclohexyloxy)phenyl)-2-oxabicyclo[2.2.2]octan-1-yl)ethoxy)acetic acid A solution of 111A compound (7 mg, 0.016 mmol) and TFA (0.2 mL, 2.60 mmol) in DCM (1 mL) was stirred at rt for 1 h, then was concentrated in vacuo. The crude product was purified by preparative HPLC (PHENOMENEX® Luna Axia C18 5μ; 30×100 mm Column; detection at 220 nM; flow rate=40 mL/min; continuous gradient from 0% B to 100% B over 10 min+5 min hold at 100% B, where A=10:90:0.1 ACN—H$_2$O-TFA and B=90:10:0.1 ACN—H$_2$O-TFA) to afford the title compound (4.5 mg, 71% yield) as a white solid. LCMS [M+H]$^+$=389.4. $^1$H NMR (400 MHz, CDCl$_3$) δ 7.25-7.19 (m, 1H), 6.85-6.75 (m, 3H), 4.27-4.19 (m, 1H), 4.09 (s, 2H), 4.05 (s, 2H), 3.74 (t, J=5.3 Hz, 2H), 2.17-2.05 (m, 4H), 2.03-1.90 (m, 4H), 1.87-1.74 (m, 4H), 1.73-1.64 (m, 1H), 1.62-1.47 (m, 3H), 1.44-1.24 (m, 4H).

Examples 112-114 were synthesized using the same synthetic route as used for the preparation of Example 100 from Example 100A compound, except that 2-(3-bromo-6-fluorophenoxy)tetrahydro-2H-pyran was used instead of 2-(3-bromophenoxy) tetrahydro-2H-pyran).

| Example No. | Structure and Name | Analytical Data |
|---|---|---|
| 112 | 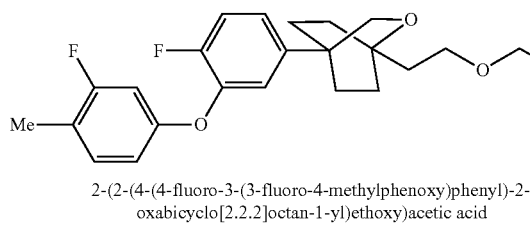<br>2-(2-(4-(4-fluoro-3-(3-fluoro-4-methylphenoxy)phenyl)-2-oxabicyclo[2.2.2]octan-1-yl)ethoxy)acetic acid | $^1$H NMR (400 MHz, CDCl$_3$) δ 7.12 (td, J = 10.2, 8.5 Hz, 2H), 7.06-6.97 (m, 2H), 6.67-6.59 (m, 2H), 4.08 (s, 2H), 3.99 (s, 2H), 3.73 (t, J = 5.4 Hz, 2H), 2.24 (d, J = 1.8 Hz, 3H), 2.16-2.00 (m, 4H), 1.99-1.87 (m, 2H), 1.79 (t, J = 5.4 Hz, 2H), 1.73-1.63 (m, 2H). LCMS [M + H]$^+$ = 433.4. |
| 113 | 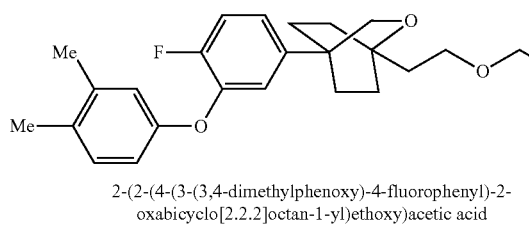<br>2-(2-(4-(3-(3,4-dimethylphenoxy)-4-fluorophenyl)-2-oxabicyclo[2.2.2]octan-1-yl)ethoxy)acetic acid | $^1$H NMR (400 MHz, CDCl$_3$) δ 7.15-7.04 (m, 2H), 7.01-6.94 (m, 2H), 6.77 (d, J = 2.4 Hz, 1H), 6.67 (dd, J = 8.3, 2.5 Hz, 1H), 4.08 (s, 2H), 3.98 (s, 2H), 3.72 (t, J = 5.4 Hz, 2H), 2.24 (d, J = 2.2 Hz, 6H), 2.14-1.99 (m, 4H), 1.95-1.85 (m, 2H), 1.79 (t, J = 5.4 Hz, 2H), 1.71-1.62 (m, 2H). LCMS [M + H]$^+$ = 429.4. |

| Example No. | Structure and Name | Analytical Data |
|---|---|---|
| 114 | 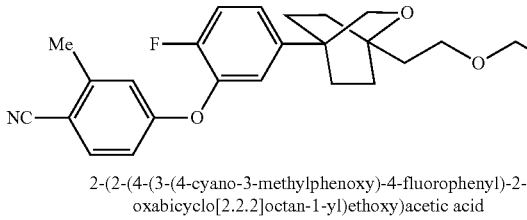<br>2-(2-(4-(3-(4-cyano-3-methylphenoxy)-4-fluorophenyl)-2-oxabicyclo[2.2.2]octan-1-yl)ethoxy)acetic acid | $^1$H NMR (400 MHz, CDCl$_3$) δ 7.54 (d, J = 8.6 Hz, 1H), 7.21-7.10 (m, 2H), 7.06 (dd, J = 7.5, 2.2 Hz, 1H), 6.83 (d, J = 2.0 Hz, 1H), 6.76 (dd, J = 8.5, 2.3 Hz, 1H), 4.09 (s, 2H), 4.02 (s, 2H), 3.77-3.70 (m, 2H), 2.52 (s, 3H), 2.18-2.03 (m, 4H), 2.02-1.90 (m, 2H), 1.81 (t, J = 5.4 Hz, 2H), 1.75-1.64 (m, 2H). LCMS [M + H]$^+$ = 440.4. |

Example 115

2-(2-(1-(3-(6-methylpyridin-3-yloxy)phenyl)-2-oxabicyclo[2.2.2]octan-4-yl)ethoxy)acetic acid

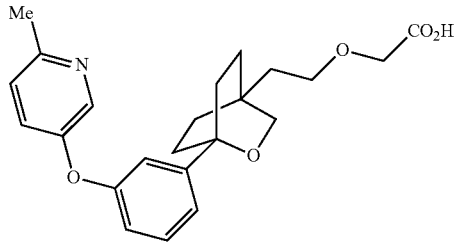 [SMILES: Cc1ccc(Oc2cccc(C34CCC(CCOCC(=O)O)(CC3)CO4)c2)cn1]

Example 115 was synthesized using the same 2-step protocol as for the syntheses of Examples 39-45 from intermediate phenol 7F, but with 6-methylpyridin-3-ylboronic acid. LCMS, [M−H]$^+$=396.2. $^1$H NMR (500 MHz, DMSO-d$_6$) δ=8.18 (br. s, 1H), 7.35-7.25 (m, 3H), 7.11 (d, J=7.3 Hz, 1H), 7.00 (br. s, 1H), 6.83 (d, J=7.6 Hz, 1H), 3.95 (s, 2H), 3.58-3.43 (m, 2H), 2.44 (s, 3H), 2.06-1.96 (m, 2H), 1.81-1.72 (m, 2H), 1.68-1.54 (m, 4H), 1.40-1.34 (m, 2H), 1.28-1.20 (m, 2H).

Example 116

2-(2-(1-(6-(3,4-Difluorophenoxy)pyridin-2-yl)-2-oxabicyclo[2.2.2]octan-4-yl)ethoxy) acetic acid

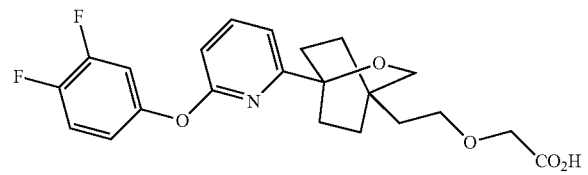 [SMILES: O=C(O)COCCC12CCC(c3cccc(Oc4ccc(F)c(F)c4)n3)(CC1)OC2]

116A. 2-Bromo-6-(3,4-difluorophenoxy)pyridine

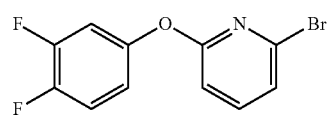 [SMILES: Fc1ccc(Oc2cccc(Br)n2)cc1F]

A mixture of 3,4-difluorophenol (1.55 g, 11.9 mmol), 2,6-dibromopyridine (2.82 g, 11.9 mmol), and Cs$_2$CO$_3$ (3.88 g, 11.9 mmol) in N-Methyl-2-pyrrolidinone (10 mL) was stirred at 100° C. for 18 h, then was cooled to rt. EtOAc (10 mL) and 1N aq. NaOH (20 mL) were added to the reaction mixture. The organic layer was separated and washed with water (3×) and brine, dried (MgSO$_4$), and filtered. The filtrate was concentrated in vacuo. The crude product was chromatographed (SiO$_2$; continuous gradient of EtOAc/hexanes from 0% to 10% over 12 min) to give the title compound (2.90 g, 10.1 mmol, 85% yield) as a clear oil, which eventually became a white solid. $^1$H NMR (CDCl$_3$) δ: 7.56 (t, J=7.8 Hz, 1H), 7.24 (d, J=7.5 Hz, 1H), 7.18 (q, J=9.1 Hz, 1H), 7.06-7.00 (m, 1H), 6.92-6.87 (m, 1H), 6.85 (d, J=8.1 Hz, 1H); $^{19}$F NMR (CDCl$_3$) δ: −134.55 (d, J=21.4 Hz), −142.14 (d, J=21.3 Hz).

116B. (1-(6-(3,4-Difluorophenoxy)pyridin-2-yl)-2-oxabicyclo[2.2.2]octan-4-yl)methyl 4-methylbenzene-sulfonate

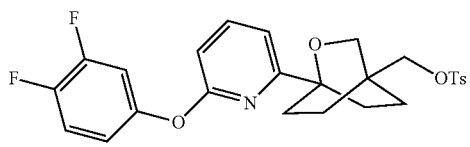 [SMILES: Cc1ccc(S(=O)(=O)OCC23CCC(c4cccc(Oc5ccc(F)c(F)c5)n4)(CC2)OC3)cc1]

(1-(6-(3,4-Difluorophenoxy)pyridin-2-yl)-2-oxabicyclo[2.2.2]octan-4-yl)methyl 4-methylbenzene sulfonate was prepared from compound 116A and 4-oxocyclohexane-1,1-diyl)bis(methylene)bis(4-methylbenzenesulfonate using a procedure analogous to the synthesis of Example 37A. The title compound was obtained (0.078 g, 0.156 mmol, 8% yield) as a light yellowish oil. [M+H]$^+$=502.4; $^1$H NMR (CDCl$_3$) δ: 8.18 (ddd, J=4.9, 2.0, 0.8 Hz, 1H), 7.78 (d, J=8.3 Hz, 2H), 7.70 (ddd, J=8.3, 7.2, 2.0 Hz, 1H), 7.40-7.32 (m, 2H), 7.13 (ddd, J=5.3, 3.0, 2.0 Hz, 1H), 7.01 (ddd, J=7.2, 5.0, 0.9 Hz, 1H), 6.94-6.85 (m, 2H), 3.79 (t, J=1.4 Hz, 2H), 3.74 (s, 2H), 2.46 (s, 3H), 2.37-2.26 (m, 2H), 2.01-1.90 (m, 2H), 1.77-1.54 (m, 4H); $^{19}$F NMR (CDCl$_3$) δ: −135.92 (d, J=20.8 Hz), −143.57 (d, J=20.7 Hz).

116C. 2-(1-(6-(3,4-Difluorophenoxy)pyridin-2-yl)-2-oxabicyclo[2.2.2]octan-4-yl)acetonitrile

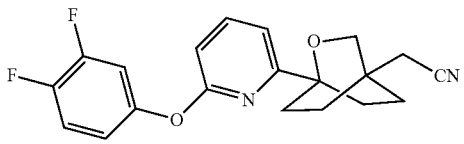 [SMILES: N#CCC12CCC(c3cccc(Oc4ccc(F)c(F)c4)n3)(CC1)OC2]

2-(1-(6-(3,4-Difluorophenoxy)pyridin-2-yl)-2-oxabicyclo[2.2.2]octan-4-yl)acetonitrile was prepared from Compound 116B using a procedure analogous to that used for the synthesis of Example 37B. The title compound was obtained (55 mg, 0.15 mmol, 99% yield) as a light brownish oil. [M+H]$^+$=357.1; (CDCl$_3$) δ: 8.18 (dd, J=4.9, 1.9 Hz, 1H), 7.70 (ddd, J=8.2, 7.1, 2.0 Hz, 1H), 7.15 (ddd, J=5.3, 3.0, 2.0 Hz, 1H), 7.02 (ddd, J=7.3, 5.0, 1.0 Hz, 1H), 6.94-6.88 (m, 2H), 3.90 (t, J=1.4 Hz, 2H), 2.49-2.34 (m, 2H), 2.22 (s, 2H), 2.09-1.99 (m, 2H), 1.91-1.75 (m, 4H); $^{19}$F NMR (CDCl$_3$) δ: −135.79 (d, J=21.0 Hz), −143.58 (d, J=21.1 Hz).

116D. 2-(1-(6-(3,4-Difluorophenoxy)pyridin-2-yl)-2-oxabicyclo[2.2.2]octan-4-yl)acetaldehyde

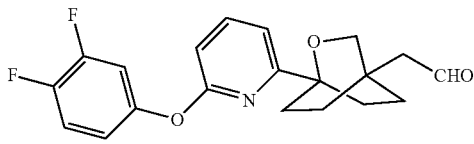 [SMILES: O=CCC12CCC(c3cccc(Oc4ccc(F)c(F)c4)n3)(CC1)OC2]

2-(1-(6-(3,4-Difluorophenoxy)pyridin-2-yl)-2-oxabicyclo[2.2.2]octan-4-yl)acetaldehyde was prepared from compound 116C using a procedure analogous to that used for the synthesis of Example 37C. The title compound was obtained (54 mg, 0.150 mmol, 97% yield) as a clear oil. [M+Na]$^+$=392.1; $^1$H NMR (CDCl$_3$) δ: 9.83 (t, J=2.6 Hz, 1H), 8.19 (dd, J=5.2, 1.9 Hz, 1H), 7.70 (ddd, J=8.3, 7.2, 2.1 Hz, 1H), 7.15 (ddd, J=5.4, 2.9, 1.9 Hz, 1H), 7.01 (ddd, J=7.3, 4.9, 0.9 Hz, 1H), 6.95-6.85 (m, 2H), 3.93 (t, J=1.4 Hz, 2H), 2.47-2.33 (m, 2H), 2.27 (d, J=2.7 Hz, 2H), 2.07-1.96 (m, 2H), 1.96-1.78 (m, 4H); $^{19}$F NMR (CDCl$_3$) δ: −135.95 (d, J=20.5 Hz), −143.59 (d, J=20.8 Hz).

116E. 2-(1-(6-(3,4-Difluorophenoxy)pyridin-2-yl)-2-oxabicyclo[2.2.2]octan-4-yl)ethanol

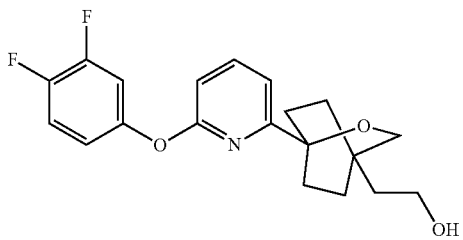 [SMILES: OCCC12CCC(c3cccc(Oc4ccc(F)c(F)c4)n3)(CC1)OC2]

2-(1-(6-(3,4-Difluorophenoxy)pyridin-2-yl)-2-oxabicyclo[2.2.2]octan-4-yl)ethanol was prepared from compound 116D using a procedure analogous to that used for the synthesis of Example 37D. The title compound was obtained (42 mg, 0.116 mmol, 77% yield) as a clear oil. [M+H]$^+$=362.1; $^1$H NMR (CDCl$_3$) δ: 8.18 (dd, J=5.3, 1.9 Hz, 1H), 7.68 (ddd, J=8.4, 7.2, 2.0 Hz, 1H), 7.15 (ddd, J=5.3, 3.0, 2.0 Hz, 1H), 7.00 (ddd, J=7.2, 5.0, 1.0 Hz, 1H), 6.92-6.84 (m, 2H), 3.82 (t, J=1.3 Hz, 2H), 3.69 (t, J=7.2 Hz, 2H), 2.39-2.28 (m, 2H), 2.01-1.91 (m, 2H), 1.78-1.63 (m, 4H), 1.45 (t, J=7.2 Hz, 2H); $^{19}$F NMR (CDCl$_3$) δ: −136.08 (d, J=21.3 Hz), −143.49 (d, J=20.6 Hz).

Example 116

To a solution of 2-(1-(6-(3,4-difluorophenoxy)pyridin-2-yl)-2-oxabicyclo[2.2.2]octan-4-yl)ethanol (42 mg, 0.116 mmol) in toluene (1 mL) was added Bu$_4$NCl.H$_2$O (10.3 mg, 0.035 mmol). The reaction mixture was cooled to 0° C., after which aq. 35% aq. NaOH (0.15 mL) was added, followed by the addition of tert-butyl bromoacetate (0.021 mL, 0.139 mmol). The reaction was stirred at rt for 18 h, after which the organic layer was separated, washed with H$_2$O (5×15 mL) and brine (15 mL) until pH ~7 and concentrated in vacuo. The crude tert-butyl ester product was stirred with HCO$_2$H (0.5 mL) at rt for 18 h and then concentrated in vacuo. The crude carboxylic acid product was purified by preparative HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound as its TFA salt (27 mg, 0.050 mmol, 43% yield) as oil. [M−H]$^+$=418.2; $^1$H NMR (CDCl$_3$) δ: 9.14 (s, 1H), 8.29 (dd, J=5.3, 1.9 Hz, 1H), 7.79 (ddd, J=8.8, 7.3, 2.0 Hz, 1H), 7.20-7.07 (m, 2H), 6.94-6.83 (m, 2H), 4.09 (s, 2H), 3.83 (d, J=1.4 Hz, 2H), 3.59 (t, J=6.8 Hz, 2H), 2.40-2.25 (m, 2H), 2.01-1.89 (m, 2H), 1.78-1.64 (m, 4H), 1.52 (t, J=6.8 Hz, 2H); $^{19}$F NMR (CDCl$_3$) δ: −75.91, −135.20 (d, J=21 Hz), −142.33 (d, J=21 Hz).

Example 117

2-(2-(1-(3-(3-Hydroxyphenoxy)phenyl)-2-oxabicyclo[2.2.2]octan-4-yl)ethoxy)acetic acid

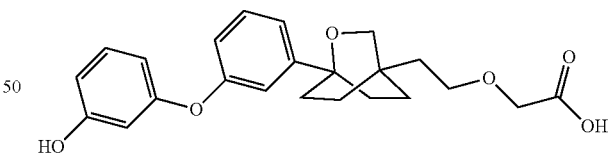

117A. tert-Butyl 2-(2-(1-(3-(3-(tert-butyldimethylsilyloxy)phenoxy)phenyl)-2-oxabicyclo[2.2.2]octan-4-yl)ethoxy)acetate

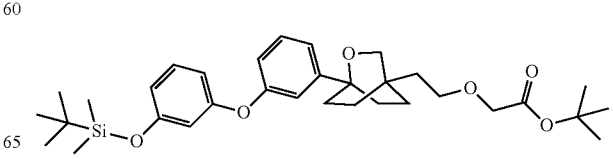

A mixture of Example 7F compound [tert-butyl 2-(2-(1-(3-hydroxyphenyl)-2-oxabicyclo[2.2.2]octan-4-yl)ethoxy)acetate] (350 mg, 0.97 mmol), (3-((tert-butyldimethylsilyl)oxy)phenyl)boronic acid (244 mg, 0.97 mmol), Cu(OAc)$_2$ (144 mg, 0.97 mmol), Et$_3$N (98 mg, 0.97 mmol) and pyridine (76 mg, 0.97 mmol) with 4A molecular sieves (1 g) in DCM (10 mL) was stirred at rt for 4 days. The reaction was then filtered, and the filtrate was concentrated in vacuo. The crude product was dissolved in EtOAc (5 mL) and washed with 1N aq. HCl and water, dried (MgSO$_4$), and filtered. The filtrate was concentrated in vacuo and chromatographed (SiO$_2$; continuous gradient of EtOAc/hexanes from 0-40%) to afford the title compound as a light yellow oil (380 mg, 69%). $^1$H NMR (400 MHz, CDCl$_3$) δ 7.08-7.05 (m, 1H), 7.01-6.93 (m, 2H), 6.93-6.89 (m, 1H), 6.66 (ddd, J=8.1, 2.5, 1.1 Hz, 1H), 6.43-6.37 (m, 2H), 6.31 (t, J=2.3 Hz, 1H), 3.76 (s, 2H), 3.67 (s, 2H), 3.38 (t, J=7.0 Hz, 2H), 1.87 (s, 2H), 1.83 (dd, J=10.7, 5.4 Hz, 4H), 1.62-1.49 (m, 4H), 1.31 (s, 9H), 0.81-0.77 (m, 9H), 0.02--0.02 (m, 6H).

Example 117

To a solution of Example 117A [tert-Butyl 2-(2-(1-(3-(3-((tert-butyldimethylsilyl)oxy)phenoxy)phenyl)-2-oxabicyclo[2.2.2]octan-4-yl)ethoxy)acetate] (12 mg, 0.021 mmol) in 1 mL MeOH was added 1N aq. NaOH (0.105 mL, 0.105 mmol). The reaction mixture was stirred at rt for 18 h, then was concentrated in vacuo. The residue was acidified to pH ~2 with 1 N aq. HCl and extracted with EtOAc. The organic layer was washed with water and concentrated in vacuo. The residue was purified via preparative LC/MS with the following conditions: Column: Waters XBridge C18, 19×200 mm, 5-µm particles; Mobile Phase A: 5:95 MeCN:water with 0.1% TFA; Mobile Phase B: 95:5 MeCN:water with 0.1% TFA; Gradient: 20-55% B over 15 min, then a 5-min hold at 100% B; Flow: 20 mL/min. Fractions containing the desired product were combined and dried via centrifugal evaporation. The yield of the title product was 4.4 mg (51%) and its estimated purity by LCMS analysis was 96%. Two analytical LC/MS injections were used to determine the final purity. Injection 1 conditions: Column: Waters Acquity UPLC BEH C18, 2.1× 50 mm, 1.7-nm particles; Mobile Phase A: 5:95 MeCN:water with 10 mM aq. NH$_4$OAc; Mobile Phase B: 95:5 MeCN:water with 10 mM aq. NH$_4$OAc; Temperature: 50° C.; Gradient: 0-100% B over 3 min, then a 0.75-min hold at 100% B; Flow: 1.11 mL/min; Detection: UV at 220 nm. Injection 2 conditions: Column: Waters Acquity UPLC BEH C18, 2.1× 50 mm, 1.7-nm particles; Mobile Phase A: 5:95 MeCN:water with 0.1% TFA; Mobile Phase B: 95:5 MeCN:water with 0.1% TFA; Temperature: 50° C.; Gradient: 0-100% B over 3 min, then a 0.75-min hold at 100% B; Flow: 1.11 mL/min; Detection: UV at 220 nm. LCMS, [M+Na]$^+$=421 $^1$H NMR (500 MHz, DMSO-d$_6$) δ 7.96 (s, 1H), 7.36-7.23 (m, 1H), 7.20-7.10 (m, 2H), 7.03 (s, 1H), 6.85 (dd, J=8.0, 2.5 Hz, 1H), 6.52 (dd, J=8.1, 2.1 Hz, 1H), 6.40 (dd, J=8.1, 2.1 Hz, 1H), 6.34 (t, J=2.2 Hz, 1H), 3.90 (s, 2H), 3.75 (s, 2H), 3.48 (t, J=1.0 Hz, 2H), 2.09-1.98 (m, 2H), 1.80 (td, J=10.9, 5.4 Hz, 2H), 1.71-1.57 (m, 4H), 1.39 (t, J=6.9 Hz, 2H).

Example 118

(1R,2R)-2-(2-(1-(3-(3-Ethylphenoxy)phenyl)-2-oxabicyclo[2.2.2]octan-4-yl)ethyl)cyclo-propane carboxylic acid

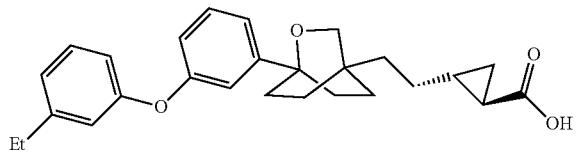

118A. (1R,2R)-Methyl 2-(2-(1-(3-(3-ethylphenoxy)phenyl)-2-oxabicyclo[2.2.2]octan-4-yl)ethyl)cyclopropanecarboxylate

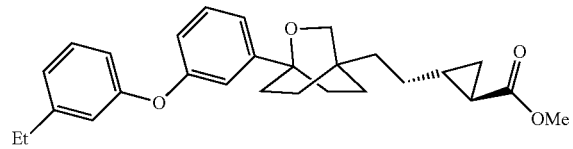

A mixture of Example 65B [(1R,2R)-methyl 2-(2-(1-(3-hydroxyphenyl)-2-oxabicyclo[2.2.2]octan-4-yl)ethyl)cyclopropanecarboxylate] (25 mg, 0.076 mmol), (3-ethylphenyl)boronic acid (15 mg, 0.098 mmol), Cu(OAc)$_2$ (14 mg, 0.091 mmol), Et$_3$N (0.105 mL, 0.757 mmol), pyridine (0.061 mL, 0.76 mmol) and 4A molecular sieves (0.5 g) in DCM (3 mL) was stirred under an atmosphere of air for 3 days. The reaction was filtered and the filtrate was concentrated in vacuo. The crude oil was dissolved in EtOAc (5 mL) and washed with 1N aq. HCl and water, dried (MgSO$_4$) and filtered. The filtrate was concentrated in vacuo and chromatographed (SiO$_2$; continuous gradient of EtOAc/hexane from 0-40%) to give the title compound as a colorless oil (22 mg, 67%). [M+Na]$^+$= 457, $^1$H NMR (400 MHz, CDCl$_3$) δ 7.28 (s, 1H), 7.28-7.20 (m, 1H), 7.19-7.10 (m, 2H), 6.95 (dd, J=7.6, 0.6 Hz, 1H), 6.90-6.78 (m, 3H), 3.80 (s, 2H), 3.70 (s, 3H), 2.65 (q, J=7.7 Hz, 2H), 2.07-1.98 (m, 4H), 1.74-1.61 (m, 4H), 1.33-1.20 (m, 10H), 0.80-0.68 (m, 1H).

Example 118

To a solution of Example 65B compound [(1R,2R)-methyl 2-(2-(1-(3-(3-ethylphenoxy)phenyl)-2-oxabicyclo[2.2.2]octan-4-yl)ethyl)cyclopropanecarboxylate] (22 mg, 0.051 mmol) in 1 mL MeOH was added 1N aq. NaOH (0.5 mL; 0.5 mmol). The reaction was stirred at rt for 18 h, then was concentrated in vacuo. The residue was acidified to pH ~2 with 1 N aq. HCl and extracted with EtOAc. The organic layer was washed with water and brine, then dried (MgSO$_4$). The filtrate was concentrated in vacuo and the crude product was purified via preparative LC/MS using the following conditions: Column: Waters XBridge C18, 19×100 mm, 5-µm particles; Mobile Phase A: 5:95 MeCN: water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation. The yield of the product was 12.3 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 MeCN:water with 10 mM aq. NH₄OAc; Mobile Phase B: 95:5 MeCN:water with 10 mM aq. NH₄OAc; Temperature: 50° C.; Gradient: 0-100% B over 3 min then a 0.75-min hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 MeCN:water with 0.1% TFA; Mobile Phase B: 95:5 MeCN:water with 0.1% TFA; Temperature: 50° C.; Gradient: 0-100% B over 3 min, then a 0.75-min hold at 100% B; Flow: 1.11 mL/min; Detection: UV at 220 nm. $[M-1]^+$=419, ¹H NMR (500 MHz, DMSO-d₆) δ 8.01-7.95 (m, 1H), 7.29 (td, J=7.8, 5.5 Hz, 2H), 7.12 (d, J=8.0 Hz, 1H), 7.03 (s, 1H), 6.99 (d, J=7.7 Hz, 1H), 6.86 (s, 1H), 6.82 (dd, J=8.0, 1.9 Hz, 1H), 6.77 (dd, J=8.1, 2.1 Hz, 1H), 3.68 (s, 2H), 2.60 (q, J=7.7 Hz, 2H), 2.08-1.95 (m, 2H), 1.79 (td, J=11.1, 4.7 Hz, 2H), 1.65-1.48 (m, 4H), 1.31-1.12 (m, 9H), 0.95 (dt, J=8.1, 4.2 Hz, 1H), 0.74-0.64 (m, 1H).

Example 119

2-(2-(1-(3-(3-Ethylphenoxy)phenyl)-2-oxabicyclo [2.2.2]octan-4-yl)ethoxy)acetic acid

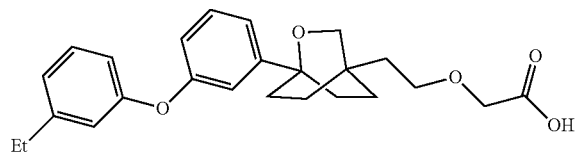 [SMILES: CCc1cccc(Oc2cccc(C34CCC(CCOCC(=O)O)(CC3)CO4)c2)c1]

The title compound was prepared using the same reaction sequence as for the synthesis of Examples 39-45 from intermediate phenol 7F [tert-butyl 2-(2-(1-(3-hydroxyphenyl)-2-oxabicyclo[2.2.2]octan-4-yl)ethoxy)acetate]. The title compound was obtained as a light yellow oil (13 mg, 66%) and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 MeCN:water with 10 mM aq. NH₄OAc; Mobile Phase B: 95:5 MeCN:water with 10 mM aq. NH₄OAc; Temperature: 50° C.; Gradient: 0-100% B over 3 min, then a 0.75-min hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 MeCN:water with 0.1% TFA; Mobile Phase B: 95:5 MeCN: water with 0.1% TFA; Temperature: 50° C.; Gradient: 0-100% B over 3 min, then a 0.75-min hold at 100% B; Flow: 1.11 mL/min; Detection: UV at 220 nm. $[M+Na]^+$=433, ¹H NMR (500 MHz, DMSO-d₆) δ 7.35-7.23 (m, 2H), 7.12 (d, J=7.4 Hz, 1H), 7.04 (br. s., 1H), 6.99 (d, J=7.4 Hz, 1H), 6.87 (s, 1H), 6.84-6.72 (m, 2H), 3.74 (s., 2H), 3.51-3.41 (s, 2H), 3.32-3.23 (m, 2H), 2.60 (q, J=7.4 Hz, 2H), 2.51-2.47 (m, 2H), 2.04 (s., 2H), 1.90-1.55 (m, 6H), 1.17 (t, J=7.7 Hz, 3H).

Example 120

2-(3-(1-(3-Phenoxyphenyl)-2-oxabicyclo[2.2.2]octan-4-yl)propyl) cyclopropane carboxylic acid

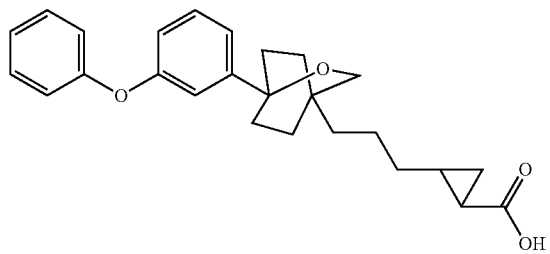 [SMILES: O=C(O)C1CC1CCCC12CCC(c3cccc(Oc4ccccc4)c3)(CC1)OC2]

120A. 4-(1-(3-Phenoxyphenyl)-2-oxabicyclo[2.2.2] octan-4-yl)butanal

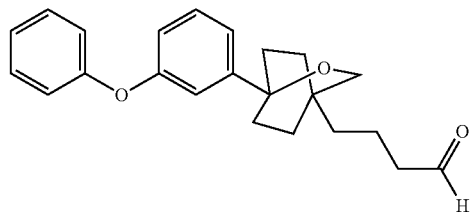 [SMILES: O=CCCCC12CCC(c3cccc(Oc4ccccc4)c3)(CC1)OC2]

To a 0° C. solution of Example 57 compound [4-(1-(3-phenoxyphenyl)-2-oxabicyclo[2.2.2]octan-4-yl)butan-1-ol] (110 mg, 0.312 mmol) in DCM (3 mL) was added Dess-Martin periodinane (159 mg, 0.375 mmol) over 5 min. The reaction mixture was slowly warmed up to rt and stirred at rt for 2 h. Sat'd aq. NaHCO₃—Na₂S₂O₃ was then added, and the reaction mixture was stirred at rt for 5 min. The layers were separated, and the organic layer was washed with water and brine, dried (MgSO₄), filtered and concentrated in vacuo. The crude product was chromatographed (SiO₂; continuous gradient of EtOAc/hexanes from 0 to 40%) to give the title compound as a white solid. (60 mg, 55% yield and 98% purity) ¹H NMR (400 MHz, CDCl₃) δ 9.80 (s, 1H), 7.41-7.32 (m, 3H), 7.32-7.27 (m, J=15.8 Hz, 1H), 7.20-7.07 (m, 1H), 7.05-6.98 (m, 1H), 6.87 (ddd, J=8.1, 2.5, 1.1 Hz, 1H), 3.83 (s, 2H), 2.46 (td, J=7.3, 1.5 Hz, 2H), 2.09-1.95 (m, 5H), 1.81-1.58 (m, 7H), 1.23-1.14 (m, 2H).

120B. (E)-Methyl 6-(1-(3-phenoxyphenyl)-2-oxabicyclo[2.2.2]octan-4-yl)hex-2-enoate

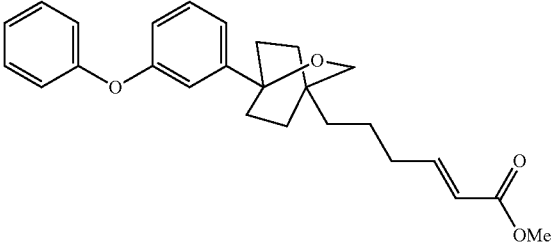 [SMILES: COC(=O)/C=C/CCCC12CCC(c3cccc(Oc4ccccc4)c3)(CC1)OC2]

Trimethyl phosphonoacetate (47 mg, 0.26 mmol) and DBU (39 mg, 0.26 mmol) were successively added to a 0° C. solution of LiCl (11 mg; 0.26 mmol) in MeCN (0.6 mL) under argon. The reaction mixture was stirred at 0° C. for 30 min, after which a solution of 120A compound [4-(1-(3-phenoxyphenyl)-2-oxabicyclo[2.2.2]octan-4-yl)butanal] (60 mg, 0.171 mmol) in MeCN (0.5 mL) was added. The reaction mixture was stirred at rt for 2 h, then was concentrated in vacuo. The residue was diluted with ether and successively washed with 1N aq. HCl, sat'd aq. NaHCO$_3$, water and brine, dried (MgSO$_4$), filtered and concentrated in vacuo. The crude product was chromatographed (SiO$_2$; continuous gradient of EtOAc/hexanes from 0 to 40%) to give the title compound as a white solid (65 mg, 89%). [MS+H]$^+$=407, $^1$H NMR (400 MHz, CDCl$_3$) δ 7.29-7.19 (m, 3H), 7.10-6.97 (m, 3H), 6.95-6.88 (m, 2H), 6.87-6.83 (m, 1H), 6.77 (ddd, J=8.0, 2.5, 0.9 Hz, 1H), 5.75 (dt, J=15.6, 1.5 Hz, 1H), 3.72 (s, 2H), 3.66 (s, 3H), 2.11 (qd, J=7.2, 1.5 Hz, 2H), 1.93 (dd, J=9.5, 5.3 Hz, 4H), 1.67-1.51 (m, 4H), 1.40-1.25 (m, 2H), 1.14-1.02 (m, 2H).

120C. Methyl 2-(3-(1-(3-phenoxyphenyl)-2-oxabicyclo[2.2.2]octan-4-yl)propyl)cyclopropane carboxylate

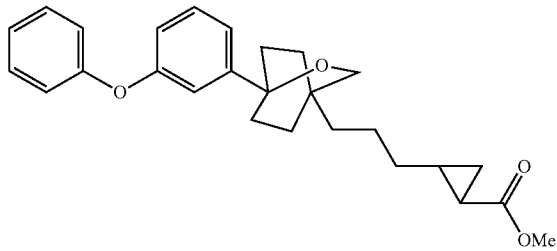 [SMILES: COC(=O)C1CC1CCCC12CCC(c3cccc(Oc4ccccc4)c3)(CC1)OC2]

To a vigorously stirred mixture of Et$_2$O (5 mL) and 40% aq. KOH (3 mL) was added N-methyl-N'-nitro-N-nitrosoguanidine (470 mg, 1.60 mmol) portionwise over 10 min at 0° C. Upon complete addition of MNNG, stirring was ceased and the aqueous layer was separated. The ether layer was dried twice with KOH pellets for 5 min, then was poured onto a solution of Example 120B compound [(E)-methyl 6-(1-(3-phenoxyphenyl)-2-oxabicyclo[2.2.2]octan-4-yl)hex-2-enoate] (65 mg, 0.160 mmol) in THF (1 mL). Pd(OAc)$_2$ (3.6 mg, 0.016 mmol) in THF (0.2 mL) was subsequently added and the reaction was allowed to warm to rt and stirred at rt for 1 h. Volatiles were removed in vacuo and the crude product was chromatographed (SiO$_2$; continuous gradient of EtOAc/hexanes from 0 to 40%) to give the title compound as a colorless oil (66 mg, 94%). [MS+H]$^+$=421. $^1$H NMR (400 MHz, CDCl$_3$) δ 7.32 (dd, J=8.6, 7.5 Hz, 2H), 7.29-7.24 (m, 1H), 7.18-7.13 (m, 1H), 7.13-7.11 (m, 1H), 7.11-7.05 (m, 1H), 6.99 (dd, J=8.7, 1.0 Hz, 2H), 6.85 (ddd, J=8.0, 2.5, 1.1 Hz, 1H), 3.80 (s, 2H), 3.68 (s, 3H), 2.08-1.94 (m, 4H), 1.73-1.59 (m, 4H), 1.48-1.21 (m, 6H), 1.22-1.07 (m, 3H), 0.71 (td, J=7.2, 4.2 Hz, 1H).

Example 120

To a solution of Example 120C compound [methyl 2-(3-(1-(3-phenoxyphenyl)-2-oxabicyclo[2.2.2]octan-4-yl)propyl)cyclopropane carboxylate] (65 mg, 0.155 mmol) in 1:1 THF:water (2 mL) and MeOH (0.3 mL) was added LiOH.H$_2$O (33 mg, 0.77 mmol). The reaction mixture was stirred at rt for 18 h, then THF was removed in vacuo. The aq. layer was acidified to pH ~2 with 1N aq. HCl and extracted with EtOAc (5 mL). The organic layer was washed with water and brine, dried (MgSO$_4$), filtered and concentrated in vacuo. The crude product was purified by preparative HPLC (PHENOMENEX® Axia 5μ C18 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA) to give the title compound (58 mg, 90%) as a colorless oil. [MS−H]$^+$=405 HPLC1:RT=12.9 min, purity=98%; HPLC-2: RT=10.7 min, purity=98%. $^1$H NMR (400 MHz, CDCl$_3$) δ 7.39-7.31 (m, 2H), 7.30-7.27 (m, 1H), 7.20-7.08 (m, 3H), 7.05-6.99 (m, 2H), 6.88 (ddd, J=8.1, 2.5, 0.9 Hz, 1H), 3.84 (s, 2H), 2.08-1.96 (m, 4H), 1.77-1.61 (m, 4H), 1.56-1.25 (m, 7H), 1.23-1.14 (m, 2H), 0.85 (ddd, J=8.0, 6.5, 4.2 Hz, 1H).

What is claimed is:

1. A compound of Formula (I):

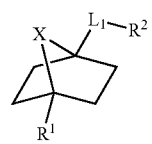

or a stereoisomer, a tautomer, or a pharmaceutically acceptable salt thereof, wherein:

X is independently CH$_2$O or OCH$_2$;

L$_1$ is independently a hydrocarbon linker substituted with 0-2 R$^c$, a hydrocarbon-heteroatom linker substituted with 0-2 R$^c$, or —(CH$_2$)$_{1-3}$—(C$_{3-4}$ cycloalkyl substituted with 0-2 R$^c$)—(CH$_2$)$_{0-2}$—; wherein said hydrocarbon linker has one to six carbon atoms and may be straight or branched, saturated or unsaturated; and said hydrocarbon-heteroatom linker has one to four carbon atoms and one group selected from O, CO, S(O)$_p$, NH, N(C$_{1-4}$ alkyl), CONH, NHCO and NHCO$_2$;

R$^1$ is independently selected from: C$_{6-10}$ carbocycle and a 5- to 10-membered heterocycle comprising: carbon atoms and 1-4 heteroatoms selected from N, NR$^b$, O, and S(O)$_p$; wherein said carbocycle and heterocycle are substituted with 0-4 R$^3$ and R$^4$;

R$^2$ independently selected from: OH, CO$_2$H, —CONHSO$_2$R$^e$, and —CONH—(CH$_2$)$_{0-3}$-(5-membered heteroaryl comprising: carbon atoms and 1-4 heteroatoms selected from N, NR$^b$, O, and S(O)$_p$;);

R$^3$, at each occurrence, is independently selected from: halogen, C$_{1-6}$ alkyl, C$_{1-4}$ alkoxy, C$_{1-4}$ alkylthio, C$_{1-4}$ haloalkyl, C$_{1-4}$ haloalkoxy, C$_{1-4}$ haloalkylthio, and NO$_2$;

R$^4$ is independently -L$_2$-R$^5$;

L$_2$ is independently selected from: O, S, CH$_2$, C(=O), and —OSO$_2$;

R$^5$ is independently selected from: C$_{1-6}$ alkyl, C$_{2-6}$ alkenyl, C$_{1-6}$ haloalkyl, —(CH$_2$)$_n$—C$_{3-6}$ carbocycle and a 5- to 6-membered heterocycle comprising: carbon atoms and 1-4 heteroatoms selected from N, NR$^b$, O, and S(O)$_p$; wherein each ring moiety is substituted with 0-2 R$^a$;

R$^a$, at each occurrence, is independently selected from: halogen, C$_{1-4}$ alkyl, C$_{1-4}$ alkoxy, and C$_{1-4}$ haloalkyl;

R$^b$, at each occurrence, is independently selected from: H, C$_{1-4}$ alkyl, and —(CH$_2$)$_{0-2}$-(phenyl substituted with 0-3 R$^d$);

$R^c$, at each occurrence, is independently selected from: halogen, OH, $C_{1-4}$ alkyl, $C_{1-4}$ haloalkyl, and $C_{1-4}$ alkyoxy;

$R^d$, at each occurrence, is independently selected from: halogen, $C_{1-4}$ alkyl, $C_{1-4}$ alkoxy, and $C_{1-4}$ haloalkyl;

$R^e$ is independently selected from: $C_{1-4}$ alkyl and phenyl;

p is, independently at each occurrence, selected from 0, 1, and 2; and n is, independently at each occurrence, selected from 0, 1, and 2.

2. A compound according to claim 1, wherein:

$L_1$ is independently a hydrocarbon linker substituted with 0-1 $R^c$, a hydrocarbon-heteroatom linker substituted with 0-1 $R^c$, or —$(CH_2)_{1-2}$—$(C_{3-4}$ cycloalkyl substituted with 0-1 $R^c$)—$(CH_2)_{0-1}$—; wherein said hydrocarbon linker has one to six carbon atoms and may be straight or branched, saturated or unsaturated; and said hydrocarbon-heteroatom linker has one to four carbon atoms and one group selected from O, CO, $S(O)_p$, CONH, and $NHCO_2$;

$R^1$ is independently selected from: phenyl, indanyl, naphthyl, and a 5- to 6-membered heterocycle comprising: carbon atoms and 1-4 heteroatoms selected from N, $NR^b$, O, and $S(O)_p$; wherein each ring moiety substituted with 0-4 $R^3$-$R^4$; and $L_2$ is independently selected from: O, S, $CH_2$, and —$OSO_2$;

$R^5$ is independently selected from: $C_{1-6}$ alkyl, $C_{2-6}$ alkenyl, $C_{1-4}$ haloalkyl, tetrahydropyranyl, —$(CH_2)_n$—$(C_{3-6}$ carbocycle substituted with 0-2 $R^a$), and pyridyl substituted with 0-1 $R^a$.

3. A compound of Formula (II):

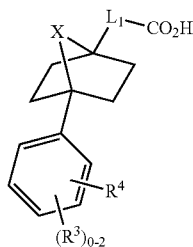

(II)

or a stereoisomer, a tautomer, or a pharmaceutically acceptable salt thereof, wherein:

X is independently $CH_2O$ or $OCH_2$;

$L_1$ is independently a hydrocarbon linker substituted with 0-1 OH, a hydrocarbon-heteroatom linker or —$(CH_2)_{1-2}$-(cyclopropyl)-$(CH_2)_{0-1}$—; wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and one group selected from O, CONH and $NHCO_2$;

$R^3$, at each occurrence, is independently selected from: halogen, $CF_3$, $OCF_3$, $SCF_3$, $NO_2$, $C_{1-4}$ alkyl, $C_{1-4}$ alkoxy, and $C_{1-4}$ alkylthio;

$R^4$ is independently -$L_2$-$R^5$;

$L_2$ is independently: O or S;

$R^5$ is independently selected from: —$(CH_2)_{0-1}$—$C_{4-6}$ cycloalkyl, $C_{5-6}$ cycloalkenyl, tetrahydropyranyl, pyridyl substituted with 0-2 $R^a$, and -$L_3$-(phenyl substituted with 0-2 $R^a$); and $R^a$, at each occurrence, is independently selected from: halogen, $C_{1-4}$ alkyl and $C_{1-4}$ alkoxy.

4. A compound according to claim 3, wherein:

$L_1$ is independently selected from: $(CH_2)_4$, $CH_2CH_2OCH_2$, $CH_2OCH_2CH_2$, $CH_2CH_2CH_2OCH_2$, $CH_2CH_2CH=CH$, $CH_2CH=CHCH_2$, $CH_2CONHCH_2$, $CH_2NHCO_2CH_2$,

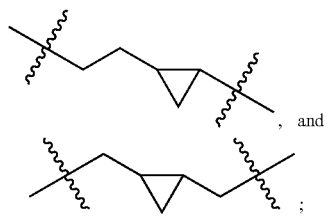

, and

; and $R^4$ is independently selected from: cyclopentenyl, —O—$CH_2$-cyclobutyl, —O-$(CH_2)_{0-1}$-cyclohexyl, —O-tetrahydropyranyl, —O-pyridyl, and -$L_3$-$(CH_2)_{0-1}$-(phenyl substituted with 0-2 $R^a$).

5. A compound according to claim 4, wherein the compound is of Formula (III):

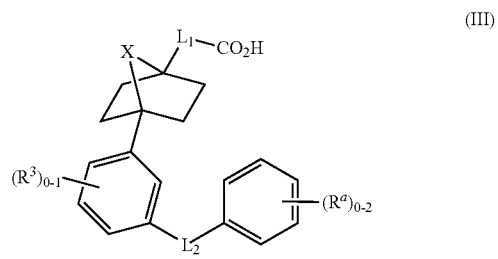

(III)

or a stereoisomer, a tautomer, or a pharmaceutically acceptable salt thereof, wherein:

X is independently $CH_2O$ or $OCH_2$;

$L_1$ is independently selected from: $(CH_2)_4$, $CH_2CH_2OCH_2$, $CH_2OCH_2CH_2$, $CH_2CH_2CH_2OCH_2$, $CH_2CH_2CH=CH$, $CH_2CH=CHCH_2$, $CH_2CONHCH_2$, $CH_2NHCO_2CH_2$,

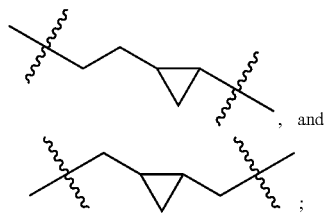

, and

;

$L_2$ is independently O or S;

$R^3$ is independently halogen;

$R^a$, at each occurrence, is independently selected from: halogen, $C_{1-4}$ alkyl and $C_{1-4}$ alkoxy.

6. A compound according to claim 5, wherein:

$L_1$ is independently selected from: $(CH_2)_4$, $CH_2CH_2OCH_2$, $CH_2OCH_2CH_2$, $CH_2CH_2CH_2OCH_2$, $CH_2CH_2CH=CH$, $CH_2CH=CHCH_2$,

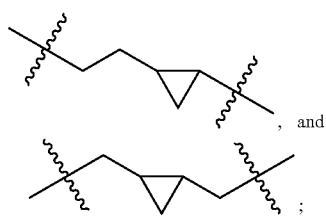

and
L$_2$ is O.

7. A compound selected from the following or a stereoisomer, a tautomer, or a pharmaceutically acceptable salt thereof, 3-(1-(3-phenoxyphenyl)-2-oxabicyclo[2.2.2]octan-4-yl)propanoic acid;
3-(1-(3-phenoxyphenyl)-2-oxabicyclo[2.2.2]octan-4-yl)propanoic acid;
5-(1-(3-methoxyphenyl)-2-oxabicyclo[2.2.2]octan-4-yl)pentanoic acid;
5-(1-(2-methyl-4-phenylthiazol-5-yl)-2-oxabicyclo[2.2.2]octan-4-yl)pentanoic acid;
3-((1-(3-phenoxyphenyl)-2-oxabicyclo[2.2.2]octan-4-yl)methoxy)propanoic acid;
2-(2-(1-(3-phenoxyphenyl)-2-oxabicyclo[2.2.2]octan-4-yl)ethoxy)acetic acid;
2-(2-(1-(3-isopropoxyphenyl)-2-oxabicyclo[2.2.2]octan-4-yl)ethoxy)acetic acid;
2-(2-(1-(3-(cyclohexyloxy)phenyl)-2-oxabicyclo[2.2.2]octan-4-yl)ethoxy)acetic acid;
2-(2-(1-(3-isobutoxyphenyl)-2-oxabicyclo[2.2.2]octan-4-yl)ethoxy)acetic acid;
5-(1-(3-(tetrahydro-2H-pyran-2-yloxy)phenyl)-2-oxabicyclo[2.2.2]octan-4-yl)pentanoic acid;
(E)-5-(1-(3-phenoxyphenyl)-2-oxabicyclo[2.2.2]octan-4-yl)pent-2-enoic acid;
2-(3-(1-(3-phenoxyphenyl)-2-oxabicyclo[2.2.2]octan-4-yl)propoxy)acetic acid;
trans-2-(2-(1-(3-phenoxyphenyl)-2-oxabicyclo[2.2.2]octan-4-yl)ethyl)cyclopropanecarboxylic acid;
(1S,2S)-2-(2-(1-(3-phenoxyphenyl)-2-oxabicyclo[2.2.2]octan-4-yl)ethyl)cyclopropanecarboxylic acid;
(1R,2R)-2-(2-(1-(3-phenoxyphenyl)-2-oxabicyclo[2.2.2]octan-4-yl)ethyl)cyclopropanecarboxylic acid;
2-(2-((1-((3-phenoxyphenyl)-2-oxabicyclo[2.2.2]octan-4-yl)methyl)cyclopropyl)acetic acid (trans);
2-((1R,2R)-2-((1-(3-phenoxyphenyl)-2-oxabicyclo[2.2.2]octan-4-yl) methyl)cyclopropyl)acetic acid;
2-((1S,2S)-2-((1-(3-phenoxyphenyl)-2-oxabicyclo[2.2.2]octan-4-yl) methyl)cyclopropyl)acetic acid;
2-(2-(1-(3-(2-methylallyloxy)phenyl)-2-oxabicyclo[2.2.2]octan-4-yl)ethoxy)acetic acid;
2-(2-(1-(3-(2-methylprop-1-enyloxy)phenyl)-2-oxabicyclo[2.2.2]octan-4-yl)ethoxy)acetic acid;
2-(2-(1-(3-(pyridin-3-yloxy)phenyl)-2-oxabicyclo[2.2.2]octan-4-yl)ethoxy)acetic acid, TFA salt;
2-(2-(1-(3-(3-methoxyphenoxy)phenyl)-2-oxabicyclo[2.2.2]octan-4-yl)ethoxy)acetic acid;
2-(2-(1-(3-fluoro-5-phenoxyphenyl)-2-oxabicyclo[2.2.2]octan-4-yl)ethoxy)acetic acid;
2-(2-(1-(3-cyclopentenylphenyl)-2-oxabicyclo[2.2.2]octan-4-yl)ethoxy)acetic acid;
5-(1-(3-phenoxyphenyl)-2-oxabicyclo[2.2.2]octan-4-yl)-N-(phenylsulfonyl)pentanamide;
N-(methylsulfonyl)-5-(1-(3-phenoxyphenyl)-2-oxabicyclo[2.2.2]octan-4-yl)pentanamide;
2-(2-(1-(3-phenoxyphenyl)-2-oxabicyclo[2.2.2]octan-4-yl)acetamido)acetic acid;
2-((1-(3-phenoxyphenyl)-2-oxabicyclo[2.2.2]octan-4-yl)methylcarbamoyloxy)acetic acid;
3-((1-(3-phenoxyphenyl)-2-oxabicyclo[2.2.2]octan-4-yl)methylsulfonyl)propanoic acid;
3-((4-(3-phenoxyphenyl)-2-oxabicyclo[2.2.2]octan-1-yl)methoxy)propanoic acid;
2-(2-(4-(3-phenoxyphenyl)-2-oxabicyclo[2.2.2]octan-1-yl)ethoxy)acetic acid;
cis-2-(2-(1-(3-phenoxyphenyl)-2-oxabicyclo[2.2.2]octan-4-yl)ethyl)cyclopropanecarboxylic acid (racemic);
3-methoxy-5-(1-(3-phenoxyphenyl)-2-oxabicyclo[2.2.2]octan-4-yl)pentanoic acid;
(E)-5-(1-(3-phenoxyphenyl)-2-oxabicyclo[2.2.2]octan-4-yl)pent-3-enoic acid;
(Z)-5-(1-(3-phenoxyphenyl)-2-oxabicyclo[2.2.2]octan-4-yl)pent-2-enoic acid;
2-(2-(1-(3-fluoro-5-isobutoxyphenyl)-2-oxabicyclo[2.2.2]octan-4-yl)ethoxy)acetic acid;
2-(2-(1-(2-phenoxyphenyl)-2-oxabicyclo[2.2.2]octan-4-yl)ethoxy)acetic acid;
2-(2-(1-(3-(phenylthio)phenyl)-2-oxabicyclo[2.2.2]octan-4-yl)ethoxy)acetic acid;
2-(2-(1-(3-(4-fluorophenoxy)phenyl)-2-oxabicyclo[2.2.2]octan-4-yl)ethoxy)acetic acid;
2-(2-(1-(3-(4-chlorophenoxy)phenyl)-2-oxabicyclo[2.2.2]octan-4-yl)ethoxy)acetic acid;
2-(2-(1-(3-(p-tolyloxy)phenyl)-2-oxabicyclo[2.2.2]octan-4-yl)ethoxy)acetic acid;
2-(2-(1-(3-(4-methoxyphenoxy)phenyl)-2-oxabicyclo[2.2.2]octan-4-yl)ethoxy)acetic acid;
2-(2-(1-(3-(m-tolyloxy)phenyl)-2-oxabicyclo[2.2.2]octan-4-yl)ethoxy)acetic acid;
2-(2-(1-(3-(3-chlorophenoxy)phenyl)-2-oxabicyclo[2.2.2]octan-4-yl)ethoxy)acetic acid;
2-(2-(1-(3-(3-fluorophenoxy)phenyl)-2-oxabicyclo[2.2.2]octan-4-yl)ethoxy)acetic acid;
2-(2-(1-(3-(3-cyanophenoxy)phenyl)-2-oxabicyclo[2.2.2]octan-4-yl)ethoxy)acetic acid;
2-(2-(1-(3-(trifluoromethylsulfonyloxy)phenyl)-2-oxabicyclo[2.2.2]octan-4-yl)ethoxy)acetic acid;
2-(2-(1-(3-(5-methyl-1,2,4-oxadiazol-3-yl)phenyl)-2-oxabicyclo[2.2.2]octan-4-yl)ethoxy)acetic acid;
2-(2-(1-(3-(trifluoromethyl)phenyl)-2-oxabicyclo[2.2.2]octan-4-yl)ethoxy)acetic acid;
2-(2-(1-(3-benzylphenyl)-2-oxabicyclo[2.2.2]octan-4-yl)ethoxy)acetic acid;
2-(2-(1-(3-(cyclobutylmethoxy)phenyl)-2-oxabicyclo[2.2.2]octan-4-yl)ethoxy)acetic acid;
2-(2-(1-(3-(cyclohexylmethoxy)phenyl)-2-oxabicyclo[2.2.2]octan-4-yl)ethoxy)acetic acid;
2-(2-(1-(3-(pentan-2-yloxy)phenyl)-2-oxabicyclo[2.2.2]octan-4-yl)ethoxy)acetic acid (racemate);
2-(2-(1-(3-fluoro-5-(2,2,2-trifluoroethoxy)phenyl)-2-oxabicyclo[2.2.2]octan-4-yl)ethoxy)acetic acid;
2-(2-(1-(3-fluoro-5-(3-fluorophenoxy)phenyl)-2-oxabicyclo[2.2.2]octan-4-yl)ethoxy)acetic acid;
4-(1-(3-phenoxyphenyl)-2-oxabicyclo[2.2.2]octan-4-yl)butane-1,2-diol;
4-(1-(3-phenoxyphenyl)-2-oxabicyclo[2.2.2]octan-4-yl)butan-1-ol;
5-(1-(3-phenoxyphenyl)-2-oxabicyclo[2.2.2]octan-4-yl)pentane-1,2-diol;

S-5-(1-(3-phenoxyphenyl)-2-oxabicyclo[2.2.2]octan-4-yl)pentane-1,2-diol and;
R-5-(1-(3-phenoxyphenyl)-2-oxabicyclo[2.2.2]octan-4-yl)pentane-1,2-diol;
2-(2-(1-(3-(tetrahydro-2H-pyran-2-yloxy)phenyl)-2-oxabicyclo[2.2.2]octan-4-yl)ethyl)cyclopropanecarboxylic acid;
N-((1H-1,2,4-triazol-5-yl)methyl)-2-(2-(1-(3-phenoxyphenyl)-2-oxabicyclo[2.2.2]octan -4-yl)ethyl)cyclopropanecarboxamide;
2-(2-(1-(3-fluoro-5-phenoxyphenyl)-2-oxabicyclo[2.2.2]octan-4-yl)ethyl)cyclopropanecarboxylic acid;
2-(2-(1-(3-fluoro-5-(3-fluorophenoxy)phenyl)-2-oxabicyclo[2.2.2]octan-4-yl)ethyl)cyclopropanecarboxylic acid;
2-(2-(1-(3-(3-fluorophenoxy)phenyl)-2-oxabicyclo[2.2.2]octan-4 yl)ethyl)cyclopropanecarboxylic acid;
2-(2-(1-(3-isobutoxyphenyl)-2-oxabicyclo[2.2.2]octan-4-yl)ethyl)cyclopropanecarboxylic acid (single enantiomer);
2-(2-(1-(3-(3-methoxyphenoxy)phenyl)-2-oxabicyclo[2.2.2]octan-4-yl)ethyl)cyclopropanecarboxylic acid (single enantiomer);
N-((1H-1,2,4-triazol-5-yl)methyl)-2-(2-(1-(3-phenoxyphenyl)-2-oxabicyclo[2.2.2]octan -4-yl)ethyl)cyclopropanecarboxamide;
N-ethyl-2-(2-(1-(3-phenoxyphenyl)-2-oxabicyclo[2.2.2]octan-4-yl)ethyl)cyclopropanecarboxamide;
2-(2-(1-(3-(3-hydroxyphenoxy)phenyl)-2-oxabicyclo[2.2.2]octan-4-yl)ethyl)cyclopropanecarboxylic acid;
(1R,2R)-2-(2-(1-(3-(4-methoxyphenoxy)phenyl)-2-oxabicyclo[2.2.2]octan-4-yl)ethyl)cyclopropanecarboxylic acid;
(1R,2R)-2-(2-(1-(3-(3,5-difluorophenoxy)phenyl)-2-oxabicyclo[2.2.2]octan-4-yl)ethyl)cyclopropanecarboxylic acid;
(1R,2R)-2-(2-(1-(3-(3,4-difluorophenoxy)phenyl)-2-oxabicyclo[2.2.2]octan-4-yl)ethyl)cyclopropanecarboxylic acid;
(1R,2R)-2-(2-(1-(3-(4-hydroxyphenoxy)phenyl)-2-oxabicyclo[2.2.2]octan-4-yl)ethyl)cyclopropanecarboxylic acid;
2-(2-(1-(3-(3,4-difluorophenoxy)phenyl)-2-oxabicyclo[2.2.2]octan-4-yl)ethoxy)acetic acid;
2-(2-(1-(3-(3,5-difluorophenoxy)phenyl)-2-oxabicyclo[2.2.2]octan-4-yl)ethoxy)acetic acid;
2(2(1(3(3fluoro-4-methylphenoxy)phenyl)-2-oxabicyclo[2.2.2]octan-4-yl)ethoxy)acetic acid;
2(2(1(3(4fluoro-3-methylphenoxy)phenyl)-2-oxabicyclo[2.2.2]octan-4-yl)ethoxy)acetic acid;
2-(2-(1-(3-(3,4-difluorophenoxy)-5-fluorophenyl)-2-oxabicyclo[2.2.2]octan-4-yl)ethoxy)acetic acid;
2-(2-(1-(3-fluoro-5-(3-fluoro-4-methylphenoxy)phenyl)-2-oxabicyclo[2.2.2]octan-4-yl)ethoxy)acetic acid;
2-(2-(1-(3-fluoro-5-(4-fluoro-3-methylphenoxy)phenyl)-2-oxabicyclo[2.2.2]octan-4-yl)ethoxy)acetic acid;
2-(2-(1-(3-fluoro-5-(3-methoxyphenoxy)phenyl)-2-oxabicyclo[2.2.2]octan-4-yl)ethoxy)acetic acid;
2-(2-(1-(3-fluoro-5-(p-tolyloxy)phenyl)-2-oxabicyclo[2.2.2]octan-4-yl)ethoxy)acetic acid;
2-(2-(1-(3-fluoro-5-(3-fluoro -5-methoxyphenoxy)phenyl)-2-oxabicyclo[2.2.2]octan-4-yl)ethoxy)acetic acid;
2-(2-(1-(3-fluoro-5-(4-fluorophenoxy)phenyl)-2-oxabicyclo[2.2.2]octan-4-yl)ethoxy)acetic acid;
2-(2-(1-(3-fluoro-5-(4-fluoro-3-methoxyphenoxy)phenyl)-2-oxabicyclo[2.2.2]octan-4-yl)ethoxy)acetic acid;
2-(2-(1-(4-fluoro-3-phenoxyphenyl)-2-oxabicyclo[2.2.2]octan-4-yl)ethoxy)acetic acid;
2-(2-(1-(4-fluoro-3-(4-fluorophenoxy)phenyl)-2-oxabicyclo[2.2.2]octan-4-yl)ethoxy)acetic acid;
2-(2-(1-(4-fluoro-3-(3-fluoro-4-methylphenoxy)phenyl)-2-oxabicyclo[2.2.2]octan-4-yl)ethoxy)acetic acid;
2-(2-(1-(3-methoxy-5-phenoxyphenyl)-2-oxabicyclo[2.2.2]octan-4-yl)ethoxy)acetic acid;
2-(2-(1-(3-(3,4-difluorophenoxy)-5-methoxyphenyl)-2-oxabicyclo[2.2.2]octan-4-yl)ethoxy)acetic acid;
2-(2-(1-(3-(4-fluorophenoxy)-5-methoxyphenyl)-2-oxabicyclo[2.2.2]octan-4-yl)ethoxy)acetic acid;
2-(2-(1-(3-(3-fluoro-4-methylphenoxy)-5-methoxyphenyl)-2-oxabicyclo[2.2.2]octan-4-yl)ethoxy)acetic acid;
2-(2-(1-(3-fluoro-5-(3-fluoro-4-methylphenoxy)phenyl)-2-oxabicyclo[2.2.2]octan-4-yl)ethoxy)-N-hydroxyacetamide;
2-(2-(1-(3,4-difluoro-5-(4-fluorophenoxy)phenyl)-2-oxabicyclo[2.2.2]octan-4-yl)ethoxy)acetic acid;
2-(((1-(3-phenoxyphenyl)-2-oxabicyclo[2.2.2]octan-4-yl)oxy)methyl)cyclopropanecarboxylic acid;
trans-2-(((1-(3-phenoxyphenyl)-2-oxabicyclo[2.2.2]octan-4-yl)methoxy)methyl)cyclopropanecarboxylic acid;
2-(2-(4-(3-(3-fluoro-4-methoxyphenoxy)phenyl)-2-oxabicyclo[2.2.2]octan-1-yl)ethoxy)acetic acid;
2-(2-(4-(3-(3-fluoro-4-methoxyphenoxy)phenyl)-2-oxabicyclo[2.2.2]octan-1-yl)ethoxy)acetic acid;
2-(2-(4-(3-(3-fluoro-4-methylphenoxy)phenyl)-2-oxabicyclo[2.2.2]octan-1-yl)ethoxy)acetic acid;
2-(2-(4-(3-(3-methoxyphenoxy)phenyl)-2-oxabicyclo[2.2.2]octan-1-yl)ethoxy)acetic acid;
2-(2-(4-(3-(4-fluoro-3-methylphenoxy)phenyl)-2-oxabicyclo[2.2.2]octan-1-yl)ethoxy)acetic acid;
2-(2-(4-(3-(pyridin-3-yloxy)phenyl)-2-oxabicyclo[2.2.2]octan-1-yl)ethoxy)acetic acid;
2-(2-(4-(3-(4-fluorophenoxy)phenyl)-2-oxabicyclo[2.2.2]octan-1-yl)ethoxy)acetic acid;
2-(2-(4-(3-(p-tolyloxy)phenyl)-2-oxabicyclo[2.2.2]octan-1-yl)ethoxy)acetic acid;
2-(2-(4-(3-(3-cyanophenoxy)phenyl)-2-oxabicyclo[2.2.2]octan-1-yl)ethoxy)acetic acid;
2-(2-(4-(3-fluoro-5-(3-fluoro-4-methylphenoxy)phenyl)-2-oxabicyclo[2.2.2]octan-1-yl)ethoxy)acetic acid;
2-(2-(4-(3-(pyridin-2-yloxy)phenyl)-2-oxabicyclo[2.2.2]octan-1-yl)ethoxy)acetic acid;
2-(3-(4-(3-phenoxyphenyl)-2-oxabicyclo[2.2.2]octan-1-yl)propoxy)acetic acid;
2-(2-(4-(3-(cyclohexyloxy)phenyl)-2-oxabicyclo[2.2.2]octan-1-yl)ethoxy)acetic acid;
2-(2-(4-(4-fluoro-3-(3-fluoro-4-methylphenoxy)phenyl)-2-oxabicyclo[2.2.2]octan-1-yl)ethoxy)acetic acid;
2-(2-(4-(3-(3,4-dimethylphenoxy)-4-fluorophenyl)-2-oxabicyclo[2.2.2]octan-1-yl)ethoxy)acetic acid;
2(2(4(3(4cyano-3-methylphenoxy)-4-fluorophenyl)-2-oxabicyclo[2.2.2]octan-1-yl)ethoxy)acetic acid;
2-(2-(1-(3-(6-methylpyridin-3-yloxy)phenyl)-2-oxabicyclo[2.2.2]octan-4-yl)ethoxy)acetic acid;
2-(2-(1-(6-(3,4-difluorophenoxy)pyridin-2-yl)-2-oxabicyclo[2.2.2]octan-4-yl)ethoxy)acetic acid;
2-(2-(1-(3-(3-hydroxyphenoxy)phenyl)-2-oxabicyclo[2.2.2]octan-4-yl)ethoxy)acetic acid;
(1R,R)-2-(2-(1-(3-(3-ethylphenoxy)phenyl)-2-oxabicyclo[2.2.2]octan-4-yl)ethyl)cyclopropanecarboxylic acid;
2-(2-(1-(3-(3-ethylphenoxy)phenyl)-2-oxabicyclo[2.2.2]octan-4-yl)ethoxy)acetic acid; and 2-(3-(1-(3-phenoxyphenyl)-2-oxabicyclo[2.2.2]octan-4-yl)propyl)cyclopropanecarboxylic acid.

8. A pharmaceutical composition, comprising: a pharmaceutically acceptable carrier and a compound of claim 1, or a stereoisomer, a tautomer, or a pharmaceutically acceptable salt thereof.

9. The pharmaceutical composition according to claim 8, further comprising one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

10. The pharmaceutical composition according to claim 8, further comprising one or more other suitable therapeutic agents selected from: a dipeptidyl peptidase-IV inhibitor, a sodium-glucose transporter-2 inhibitor and a 11b-HSD-1 inhibitor.

11. A pharmaceutical composition, comprising: a pharmaceutically acceptable carrier and a compound of claim 3.

12. A pharmaceutical composition, comprising: a pharmaceutically acceptable carrier and a compound of claim 7.

* * * * *